United States Patent
Takihana et al.

(10) Patent No.: US 9,182,664 B2
(45) Date of Patent: Nov. 10, 2015

(54) POLYMERIZABLE FLUORINE-CONTAINING SULFONATE, FLUORINE-CONTAINING SULFONATE RESIN, RESIST COMPOSITION AND PATTERN-FORMING METHOD USING SAME

(75) Inventors: Ryozo Takihana, Kawagoe (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 167 days.

(21) Appl. No.: 13/878,597

(22) PCT Filed: Oct. 5, 2011

(86) PCT No.: PCT/JP2011/072931
§ 371 (c)(1),
(2), (4) Date: Apr. 10, 2013

(87) PCT Pub. No.: WO2012/050015
PCT Pub. Date: Apr. 19, 2012

(65) Prior Publication Data
US 2013/0209937 A1    Aug. 15, 2013

(30) Foreign Application Priority Data
Oct. 13, 2010    (JP) ................. 2010-230238

(51) Int. Cl.
| | |
|---|---|
| *G03F 7/004* | (2006.01) |
| *C07C 309/10* | (2006.01) |
| *C07C 381/12* | (2006.01) |
| *C08F 20/38* | (2006.01) |
| *C08F 220/26* | (2006.01) |
| *C08F 232/04* | (2006.01) |
| *C08F 28/02* | (2006.01) |
| *G03F 7/00* | (2006.01) |
| *G03F 7/20* | (2006.01) |
| *G03F 7/038* | (2006.01) |
| *G03F 7/039* | (2006.01) |

(52) U.S. Cl.
CPC ............ *G03F 7/0045* (2013.01); *C07C 309/10* (2013.01); *C07C 381/12* (2013.01); *C08F 20/38* (2013.01); *C08F 28/02* (2013.01); *C08F 220/26* (2013.01); *C08F 232/04* (2013.01); *G03F 7/00* (2013.01); *G03F 7/0046* (2013.01); *G03F 7/0382* (2013.01); *G03F 7/0392* (2013.01); *G03F 7/0397* (2013.01); *G03F 7/20* (2013.01); *G03F 7/2039* (2013.01); *G03F 7/2041* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 5,945,250 A | 8/1999 | Aoai et al. | |
| 5,989,776 A * | 11/1999 | Felter et al. ................ | 430/270.1 |
| 7,569,326 B2 | 8/2009 | Ohsawa et al. | |
| 7,812,105 B2 | 10/2010 | Nagai et al. | |
| 7,897,821 B2 | 3/2011 | Nagai et al. | |
| 7,956,142 B2 | 6/2011 | Nagai et al. | |
| 8,110,711 B2 | 2/2012 | Jodry et al. | |
| 8,222,448 B2 | 7/2012 | Jodry et al. | |
| 2005/0069819 A1* | 3/2005 | Shiobara ...................... | 430/327 |
| 2005/0153232 A1* | 7/2005 | Li et al. ....................... | 430/270.1 |
| 2006/0234164 A1* | 10/2006 | Rhodes et al. ............... | 430/311 |
| 2008/0311507 A1* | 12/2008 | Isono et al. .................. | 430/270.1 |
| 2009/0269696 A1* | 10/2009 | Ohsawa et al. ............. | 430/270.1 |
| 2010/0035185 A1 | 2/2010 | Hagiwara et al. | |
| 2011/0034721 A1 | 2/2011 | Hagiwara et al. | |

(Continued)

FOREIGN PATENT DOCUMENTS

| | | |
|---|---|---|
| CA | 2049772 A1 | 2/1992 |
| JP | 4-230645 A | 8/1992 |

(Continued)

OTHER PUBLICATIONS

Machine translation JP 2006-178317. Jul. 6, 2006.*

(Continued)

*Primary Examiner* — Anca Eoff
*Assistant Examiner* — Alyssa L Cepluch
(74) *Attorney, Agent, or Firm* — Crowell & Moring LLP

(57) ABSTRACT

A sulfonate resin having a repeating unit of the following general formula (3):

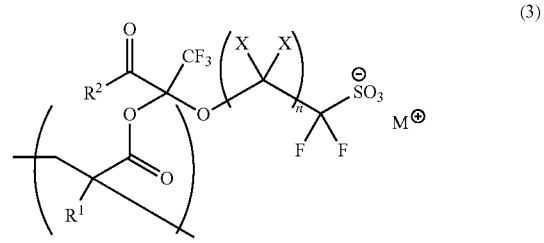

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^AO$ or $R^BR^CN$; and $M^+$ represents a monovalent cation. The sulfonate resin has an onium sulfonate incorporated in a side chain thereof with an anion moiety of the sulfonate salt fixed to the resin and can suitably be used as a resist resin having a high solubility in propylene glycol monomethyl ether acetate.

26 Claims, No Drawings

(56) References Cited

U.S. PATENT DOCUMENTS

| | | |
|---|---|---|
| 2011/0112306 A1 | 5/2011 | Nagamori et al. |
| 2011/0159433 A1* | 6/2011 | Takahashi et al. ......... 430/286.1 |
| 2011/0177453 A1 | 7/2011 | Masubuchi et al. |
| 2013/0209938 A1* | 8/2013 | Takihana et al. .......... 430/285.1 |

FOREIGN PATENT DOCUMENTS

| | | | |
|---|---|---|---|
| JP | 3613491 B2 | | 1/2005 |
| JP | 2005-84365 A | | 3/2005 |
| JP | 2006-178317 A | | 7/2006 |
| JP | 2006178317 A | * | 7/2006 |
| JP | 2007-197718 A | | 8/2007 |
| JP | 2008-133448 A | | 6/2008 |
| JP | 2009-7327 A | | 1/2009 |
| JP | 2009-91351 A | | 4/2009 |
| JP | 2009-275155 A | | 11/2009 |
| JP | 2010-18573 A | | 1/2010 |
| JP | 2010-95643 A | | 4/2010 |
| WO | WO 2006/121096 A1 | | 11/2006 |
| WO | WO 2008/056795 A1 | | 5/2008 |

OTHER PUBLICATIONS

Japanese-language Written Opinion (PCT/ISA/237) dated Nov. 29, 2011 (Four (4) pages).
International Search Report dated Nov. 29, 2011 with English language translation (Five (5) pages.
EPO machine translation for JP 2006-178317, Feb. 19, 2015.

* cited by examiner

POLYMERIZABLE FLUORINE-CONTAINING SULFONATE, FLUORINE-CONTAINING SULFONATE RESIN, RESIST COMPOSITION AND PATTERN-FORMING METHOD USING SAME

FIELD OF THE INVENTION

The present invention relates to a novel polymerizable fluorine-containing sulfonate having an anion structure, a fluorine-containing sulfonate resin as well as a resist composition and a pattern forming method using the same. More particularly, the present invention relates to a resist composition suitable as a chemically amplified resist material for fine processing by high-energy radiation, a novel fluorine-containing sulfonate resin for use in the resist composition and a novel fluorine-containing sulfonate for synthesis of the fluorine-containing sulfonate resin.

BACKGROUND OF THE INVENTION

For lithographic fine patterning in semiconductor manufacturing processes, there has been a demand for resist compositions that can be exposed at shorter wavelengths and show a wide depth of focus tolerance (abbreviated as "DOF"), a small line edge roughness (abbreviated as "LED"), high resolution, high sensitivity, good substrate adhesion and good etching resistance.

It is reported that the introduction of a fluorine atom or an aliphatic moiety into a resist resin would produce a certain effect on the reduction of the exposure wavelength. The use of a fluorine-containing sulfonic acid of high acidity as an anion moiety of an acid generator is being attempted in order for a resist composition to attain a wide depth of focus tolerance and a small pattern line edge roughness. The formation a resist resin with an acid generator function is also being attempted for improvements in resist characteristics. These types of resist resins have been proposed, each containing a sulfonic acid onium salt as an acid generator in a side chain of the resin with an anion moiety of the acid generator fixed to the resin (see Patent Documents 1 to 7). For example, Patent Documents 6 and 7 disclose resist compositions using resins each obtained by polymerization or copolymerization of a methacrylic acid ester containing in a side chain thereof a triphenylsulfonium salt of sulfonic acid having a fluorine atom at its α-position.

However, the sulfonic acid onium salt-containing resins have significantly low solubility in ordinary resist solvents (such as propylene glycol monomethylether acetate). There thus remain various problems, e.g., that it is difficult to incorporate a large amount of sulfonic acid onium salt structure in the resist resin and that the kind of a monomer copolymerizable into the resist resin is considerably limited.

PRIOR ART DOCUMENTS

Patent Documents

Patent Document 1: Japanese Patent No. 3613491
Patent Document 2: International Application No. PCT/JP2006/309446
Patent Document 3: Japanese Laid-Open Patent Publication No. 2006-178317
Patent Document 4: Japanese Laid-Open Patent Publication No. 2007-197718
Patent Document 5: Japanese Laid-Open Patent Publication No. 2008-133448
Patent Document 6: Japanese Laid-Open Patent Publication No. 2009-7327
Patent Document 7: Japanese Laid-Open Patent Publication No. 2010-95643

SUMMARY OF THE INVENTION

Problems to be Solved by the Invention

The resist resins, each containing a sulfonic acid onium salt in a side chain of the resin with an anion moiety of the onium salt fixed to the resin, have been proposed for use in the resist compositions that has high resolution, wide DOF, small LED and high sensitivity and can form good pattern shape by lithography in semiconductor manufacturing processes. These resist resins are however low in solubility in ordinary resist solvents (such as propylene glycol monomethylether acetate) and present the problem that the sulfonic acid onium salt cannot be incorporated in the resist resin in such an amount as to generate a sufficient quantity of acid as mentioned above.

Means for Solving the Problems

The present inventors have found, as a result of extensive researches made to solve the above problems, that: a polymerizable fluorine-containing sulfonic acid onium salt of specific fluorine-containing sulfonate structure shows very high solubility in ordinary resist solvents (such as propylene glycol monomethylether acetate); and, when this polymerizable fluorine containing sulfonic acid salt is subjected to homopolymerization or copolymerization with a resist resin preparation monomer, the resulting resin whose side chain incorporates therein a specific fluorine-containing sulfonate structure shows very high solubility in propylene glycol monomethylether acetate etc. and serve as a sulfonic acid onium salt-type acid generator. The present inventors have further found that a positive or negative resist composition using such a resin has high resolution, wide DOF and small LER and can form a good pattern shape. The present invention has been accomplished based on these findings.

Namely, the present invention includes the following aspects.

[Inventive Aspect 1]

A sulfonate resin having a repeating unit of the following general formula (3):

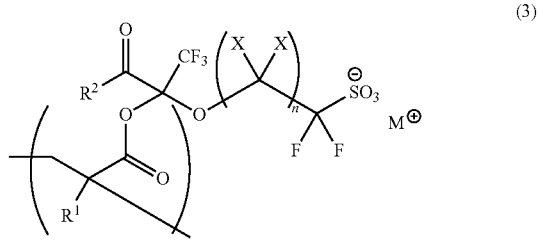

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^AO$ or $R^BR^CN$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with an nitrogen atom (N) in $R^B R^C N$; any of hydrogen atoms on carbons in $R^A$, $R^B$ and $R^C$ may be substituted with a substituent; and $M^+$ represents a monovalent cation.

[Inventive Aspect 2]

The sulfonate resin according to Inventive Aspect 1, wherein the repeating unit is of the following general formula (4):

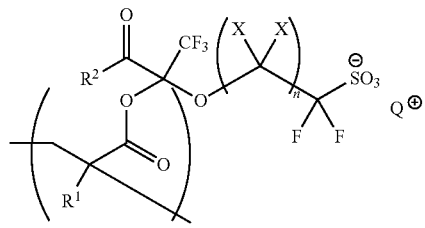

where X, n, $R^1$ and $R^2$ have the same meanings as in the general formula (3); and $Q^+$ represents a sulfonium cation of the general formula (a) or an iodonium cation of the general formula (b):

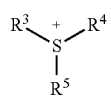

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

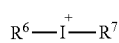

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

[Inventive Aspect 3]

The sulfonate resin according to Inventive Aspect 1, wherein the repeating unit is of the following general formula (5):

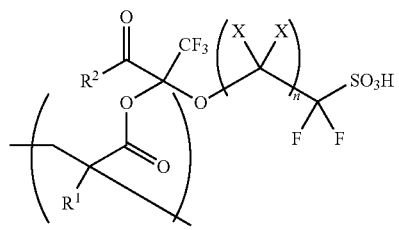

where X, n, $R^1$ and $R^2$ have the same meanings as in the general formula (3).

[Inventive Aspect 4]

The sulfonate resin according to any one of Inventive Aspects 1 to 3, further comprising at least one selected from the group consisting of repeating units formed by cleavage of polymerizable double bonds of olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

[Inventive Aspect 5]

The sulfonate resin according to any one of Inventive Aspects 1 to 4, further comprising a repeating unit of the following general formula (6):

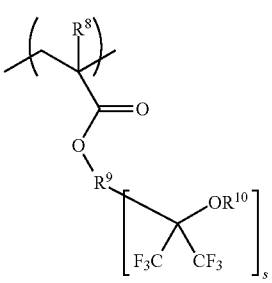

where $R^8$ represents a hydrogen atom, a halogen atom or a $C_1$-$C_3$ alkyl or fluorine-containing alkyl group; $R^9$ represents a substituted or unsubstituted aliphatic hydrocarbon group, a substituted or unsubstituted aromatic group or an organic group in which a plurality of substituted or unsubstituted aliphatic hydrocarbon and/or aromatic groups are bonded to each other; any number of hydrogen atoms in $R^9$ may be substituted with a fluorine atom; $R^{10}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms in $R^{10}$ may be substituted with a fluorine atom; $R^{10}$ may contain an ether bond or a carbonyl group; and s represents an integer of 1 or 2.

[Inventive Aspect 6]

The sulfonate resin according to any one of Inventive Aspects 1 to 5, further comprising a repeating unit of the following general formula (7):

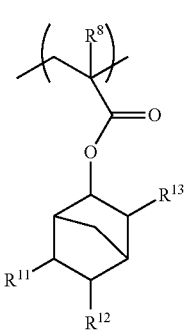

where $R^8$ represents a hydrogen atom, a halogen atom or a $C_1$-$C_3$ alkyl or fluorine-containing alkyl group; one of $R^{11}$, $R^{12}$ and $R^{13}$ represents a $CF_3C(CF_3)(OH)CH_2$— group; and the other two of $R^{11}$, $R^{12}$ and $R^{13}$ each represents a hydrogen atom.

[Inventive Aspect 7]

The sulfonate resin according to any one of Inventive Aspects 1 to 6, further comprising a repeating unit of the following general formula (8):

(8)

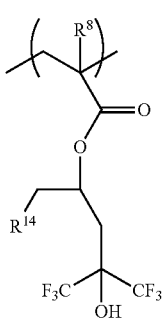

where $R^8$ represents a hydrogen atom, a halogen atom or a $C_1$-$C_3$ alkyl or fluorine-containing alkyl group; and $R^{14}$ represents a hydrogen atom or a $C_1$-$C_4$ alkyl or fluorine-containing alkyl group.

[Inventive Aspect 8]

The sulfonate resin according to any one of Inventive Aspects 1 to 7, further comprising a repeating unit of the following general formula (9):

(9)

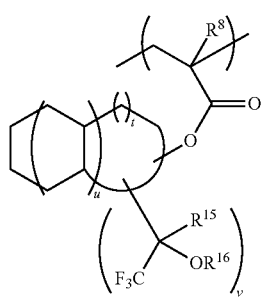

where $R^8$ represents a hydrogen atom, a halogen atom or a $C_1$-$C_3$ alkyl or fluorine-containing alkyl group; $R^{15}$ represents a methyl group or a trifluoromethyl group; $R^{16}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; u represents an integer of 0 to 2; t and v each independently represent an integer of 1 to 8 and satisfy a relationship of $v \leq t+2$; and, when v is 2 to 8, $R^{15}$ and $R^{16}$ can be the same or different.

[Inventive Aspect 9]

The sulfonate resin according to any one of Inventive Aspects 1 to 8, further comprising a repeating unit of the following general formula (10):

(10)

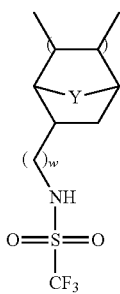

where Y represents either —$CH_2$—, —O— or —S—; and w represents an integer of 2 to 6.

[Inventive Aspect 10]

The sulfonate resin according to any one of Inventive Aspects 1 to 9, further comprising a repeating unit of the following general formula (11) or the following general formula (11-1):

(11)

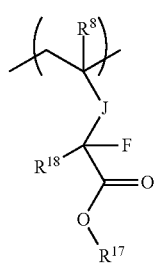

(11-1)

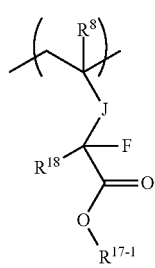

where $R^8$ represents a hydrogen atom, a halogen atom or a $C_1$-$C_3$ alkyl or fluorine-containing alkyl group; $R^{18}$ represents a hydrogen atom, a fluorine atom or a fluorine-containing alkyl group; J represents a divalent linking group; $R^{17}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; and $R^{17-1}$ represents an acid labile group.

[Inventive Aspect 11]

The sulfonate resin according to any one of Inventive Aspects 1 to 10, further comprising a repeating unit of the following general formula (12):

(12)

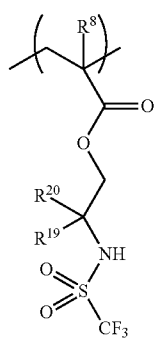

where $R^8$ represents a hydrogen atom, a halogen atom or a $C_1$-$C_3$ alkyl or fluorine-containing alkyl group; $R^{19}$ and $R^{20}$ each independently represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group.

[Inventive Aspect 12]

The sulfonate resin according to any one of Inventive Aspects 1 to 11, wherein, in the formula, —(CX$_2$)$_n$— is represented by —(CH$_2$)$_p$—(CF$_2$)$_q$— where p is an integer of 0 to 10; and q is an integer of 0 to 8.

[Inventive Aspect 13]

The sulfonate resin according to any one of Inventive Aspects 1 to 11, wherein, in the formula, —(CX$_2$)$_n$— is represented by —(CH$_2$)$_p$—(CF$_2$)$_q$— where p is an integer of 0 to 4; and q is 0 or 1.

[Inventive Aspect 14]

A resist composition comprising at least the sulfonate resin according to any one of Inventive Aspects 1 to 13 and a solvent.

[Inventive Aspect 15]

The resist composition according to Inventive Aspect 14, wherein the sulfonate resin has an acid labile group so that the resist composition serves as a chemically amplified positive resist composition.

[Inventive Aspect 16]

The resist composition according to Inventive Aspect 14 or 15, further comprising a resin having an acid labile group.

[Inventive Aspect 17]

The resist composition according to Inventive Aspect 14, wherein the sulfonate resin has an alcoholic hydroxyl group or a carboxyl group so that the resist composition serves as a chemically amplified negative resist composition.

[Inventive Aspect 18]

The resist composition according to Inventive Aspect 14 or 17, further comprising a resin having an alcoholic hydroxyl group or a carboxyl group.

[Inventive Aspect 19]

A pattern forming method, comprising: applying the resist composition according to any one of Inventive Aspects 14 to 18 to a substrate; after heat treating the applied resist composition, exposing the applied resist composition to high-energy radiation of 300 nm or less wavelength through a photomask; and after heat treating the exposed resist composition as needed, developing the exposed resist composition with a developer.

[Inventive Aspect 20]

The pattern forming method according to Inventive Aspect 19, wherein the exposing is performed by liquid immersion lithography using ArF excimer laser radiation of 193 nm wavelength and allowing insertion of water or any other liquid of higher refractive index than that of the air between the substrate to which the resist composition has been applied and projector lens.

[Inventive Aspect 21]

The pattern forming method according to Inventive Aspect 19, wherein the exposing is performed by using soft X-ray radiation (EUV radiation) of 10 to 14 nm wavelength.

[Inventive Aspect 22]

A polymerizable fluorine-containing sulfonic acid or sulfonate having an anion structure of the following general formula (1):

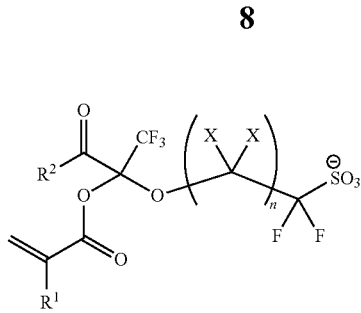

(1)

where X each independently represents a hydrogen atom or a fluorine atom; n represents an integer of 1 to 10; R$^1$ represents a hydrogen atom, a halogen atom, a C$_1$-C$_3$ alkyl group or a C$_1$-C$_3$ fluorine-containing alkyl group; R$^2$ represents either R$^A$O or R$^B$R$^C$N; R$^A$, R$^B$ and R$^C$ each independently represents a hydrogen atom, a C$_1$-C$_{20}$ alkyl group, a C$_2$-C$_{20}$ alkenyl group, a C$_2$-C$_{20}$ oxoalkyl group, a C$_6$-C$_{18}$ aryl group, a C$_6$-C$_{18}$ aralkyl group or a C$_3$-C$_{30}$ lactone group; R$^B$ and R$^C$ may be bonded to each other to form a 3- to 18-membered heterocyclic ring with an nitrogen atom (N) in R$^B$R$^C$N; and any of hydrogen atoms on carbons in R$^A$, R$^B$ and R$^C$ may be substituted with a substituent.

[Inventive Aspect 23]

A polymerizable fluorine-containing sulfonic acid onium salt of the general formula (2):

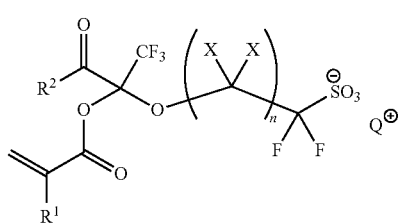

(2)

where X each independently represents a hydrogen atom or a fluorine atom; n represents an integer of 1 to 10; R$^1$ represents a hydrogen atom, a halogen atom, a C$_1$-C$_3$ alkyl group or a C$_1$-C$_3$ fluorine-containing alkyl group; R$^2$ represents either R$^A$O or R$^B$R$^C$N; R$^A$, R$^B$ and R$^C$ each independently represents a hydrogen atom, a C$_1$-C$_{20}$ alkyl group, a C$_2$-C$_{20}$ alkenyl group, a C$_2$-C$_{20}$ oxoalkyl group, a C$_6$-C$_{18}$ aryl group, a C$_6$-C$_{18}$ aralkyl group or a C$_3$-C$_{30}$ lactone group; R$^B$ and R$^C$ may be bonded to each other to form a 3- to 18-membered heterocyclic ring with an nitrogen atom (N) in R$^B$R$^C$N; any of hydrogen atoms on carbons in R$^A$, R$^B$ and R$^C$ may be substituted with a substituent; and Q$^+$ represents a sulfonium cation of the general formula (a) or an iodonium cation of the general formula (b):

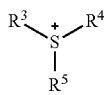

(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

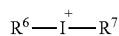
(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

The resin having the repeating unit of specific fluorine-containing sulfonate structure according to the present invention shows high solubility in propylene glycol monomethyl-ether acetate etc. The positive or negative resist composition using such a resin has high resolution, wide DOF, small LER and high sensitivity and can form a good pattern shape. Further, the polymerizable fluorine-containing sulfonate according to the present invention is copolymerizable with a wide variety of monomers for introduction of repeating units into resist resins and thus is advantageous in ease of resin design.

DESCRIPTION OF THE EMBODIMENTS

Hereinafter, exemplary embodiments of the present invention will be described below in detail. It is to be understood that: the following embodiments are illustrative and are not intended to limit the present invention thereto; and various changes and modifications can be made to the following embodiments, without departing from the scope of the present invention, based on the ordinary knowledge of one skilled in the art.

In the present specification, the following terms have the following meanings. The term "base resin" refers to a resin capable of changing its ease of dissolution (sometimes called "solubility") in a developer by exposure. The term "positive resist" refers to a resist whose exposed area is more soluble in a developer, whereas the term "negative resist" refers to a resist whose exposed area is less soluble in a developer. The term "high-energy radiation" refers to an electromagnetic wave or particle beam by which a resist composition is acted on to generate an acid. In general, the high-energy radiation is an electromagnetic wave classified as near-ultraviolet radiation (wavelength: 380 to 200 nm), vacuum-ultraviolet radiation (far-ultraviolet radiation, VUV, wavelength: 200 to 10 nm), extreme-ultraviolet radiation (EUV, wavelength: 10 nm or shorter), soft X-ray, X-ray, γ-ray or the like, or a particle beam classified as electron beam or the like. The names of the above electromagnetic waves are only for the sake of convenience. For example, a radiation of 10 to 14 nm wavelength may sometimes be called EUV, soft X-ray etc.

Unless otherwise specified, the term "salt" includes the case where the cation of the salt is $H^+$.

A material relationship of the present invention is indicated in Scheme (1).

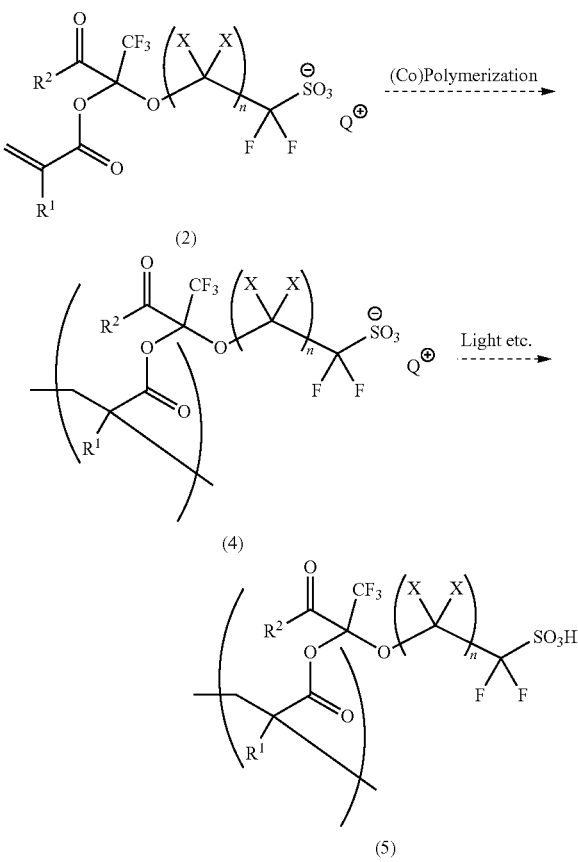

Scheme (1)

A sulfonate resin having a repeating unit of the general formula (4) is obtained by homopolymerization or copolymerization of a polymerizable fluorine-containing sulfonic acid onium salt of the general formula (2) and is converted to a resin having a repeating unit of the general formula (5) by the action of high-energy radiation, heat etc. The resulting fluorine-containing sulfonic acid serves as an acid catalyst.

[Polymerizable Fluorine-Containing Sulfonic Acid or Sulfonate]

A polymerizable fluorine-containing sulfonic acid or sulfonate according to the present invention, which has an anion structure of the general formula (1), will be first described below.

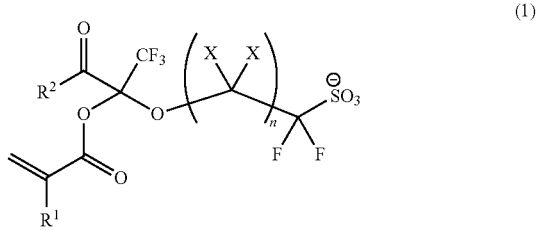
(1)

The polymerizable fluorine-containing sulfonic acid or sulfonate having the structure of the general formula (1) is a polymerizable fluorine-containing sulfonic acid or sulfonate of the general formula (1-1).

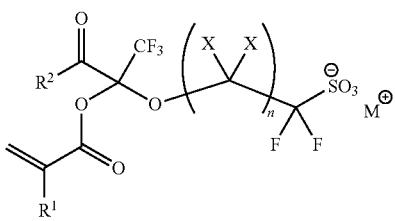

(1-1)

In the general formula (1-1), $M^+$ represents a proton, or a monovalent cation e.g. a metal cation such as lithium ion, sodium ion or potassium ion or an onium ion such as ammonium ion, sulfonium ion, iodonium ion or phosphonium ion.

In the general formula (1) and in the general formula (1-1), X each independently represents a hydrogen atom or a fluorine atom; and n represents an integer of 1 to 10, preferably an integer of 1 to 6.

The structure represented by $—(CX_2)_n—$ in the general formula (1) and in the general formula (1-1) is thus a $C_1$-$C_{10}$ straight alkylene group in which any number of hydrogen atoms may be substituted with a fluorine atom. Among others, preferred are those represented by $—(CH_2)_p—(CF_2)_q—$ where p is an integer of 0 to 10 and q is an integer of 0 to 8. Preferably, p is an integer of 1 to 6; and q is an integer of 0 to 5. It is more preferable that: p is an integer of 1 to 4; and q is 0 or 1. The sulfonic acid onium salt can be fixed to a side chain of a polymer resin so as to serve as a chemically amplified photoacid generator. The resulting polymer resin shows wide DOF and small LER because the length of diffusion of an acid generated from such a photoacid generator is substantially limited. It is however feasible to adjust the ease of diffusion and diffusion length of the acid by specifying the chemical structure of the linking group between the acid moiety and main chain of the polymer resin and the length of the side chain of the polymer resin as mentioned above.

Further, $R^1$ represents a hydrogen atom, a halogen atom or a $C_1$-$C_3$ alkyl or fluorine-containing alkyl group.

Specific examples of the halogen atom as $R^1$ are fluorine, chlorine, bromine and iodine. Specific examples of the $C_1$-$C_3$ alkyl group as $R^1$ are methyl, ethyl, n-propyl and i-propyl. Specific examples of the $C_1$-$C_3$ fluorine-containing alkyl group as $R^1$ are fluoromethyl, difluoromethyl, trifluoromethyl, 2-fluoroethyl, 2,2-difluoroethyl, 2,2,2-trifluoroethyl, pentafluoroethyl, 1-methyl-2,2,2-trifluoroethyl, 1-(trifluoromethyl)-2,2,2-trifluoroethyl and 1-(trifluoromethyl)-1,2,2,2-tetrafluoroethyl. Among others, preferred as $R^1$ are hydrogen, fluorine, methyl and trifluoromethyl.

$R^2$ represents either $R^AO$ or $R^BR^CN$. $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group. The $C_1$-$C_{20}$ alkyl group is either a $C_1$-$C_{20}$ straight alkyl group, a $C_3$-$C_{20}$ branched alkyl group or a $C_3$-$C_{20}$ cyclic alkyl group. The $C_3$-$C_{30}$ lactone group is a $C_3$-$C_{30}$ monocyclic or polycyclic lactone group. $R^B$ and $R^C$ may be bonded to each other to form a 3- to 18-membered heterocyclic ring with a nitrogen atom (N) in $R^BR^CN$. Any of hydrogen atoms on carbons in $R^A$, $R^B$ and $R^C$ may be substituted with a substituent.

$R^A$, $R^B$ and $R^C$ are exemplified as follows. Examples of the $C_1$-$C_{20}$ straight alkyl group are methyl, ethyl, n-propyl, n-butyl, n-pentyl, n-hexyl, n-heptyl, n-octyl, n-nonyl and n-decyl. There can also be used straight alkyl groups with cyclic alkyl substituents, such as cyclopentylmethyl, cyclopentylethyl, cyclohexylmethyl, cyclohexylethyl, adamantylmethyl, adamantylethyl, norbornylmethyl, norbornylethyl, camphoroylmethyl and camphoroylethyl.

Examples of the $C_3$-$C_{20}$ branched alkyl group are i-propyl, sec-butyl, i-butyl and t-butyl.

Examples of the $C_3$-$C_{20}$ cyclic alkyl group are cyclopentyl, cyclohexyl, adamantyl, methylcyclopentyl, methylcyclohexyl, methyladamantyl, ethylcyclopentyl, ethylcyclohexyl, ethyladamantyl, norbornyl and camphoroyl.

Examples of the $C_2$-$C_{20}$ alkenyl group are vinyl, 1-methylethenyl, allyl, 3-butenyl, 1-methylallyl, 2-methylallyl, 4-pentenyl and 5-hexenyl.

Examples of the $C_2$-$C_{20}$ oxoalkyl group are 2-oxo-propyl, 2-oxo-butyl, 2-oxo-3-methylbutyl, 2-oxo-pentyl, 2-oxo-3-methylpentyl, 2-oxo-4-methylpentyl, 2-oxo-3-ethylpentyl, 2-oxo-hexyl, 2-oxo-3-methylhexyl, 2-oxo-4-methylhexyl, 2-oxo-5-methylhexyl, 2-oxo-3-ethylhexyl, 2-oxo-4-ethylhexyl, 2-oxo-heptyl, 2-oxo-3-methylheptyl, 2-oxo-4-methylheptyl, 2-oxo-5-methylheptyl, 2-oxo-6-methylheptyl, 2-oxo-3-ethylheptyl, 2-oxo-4-ethylheptyl, 2-oxo-5-ethylheptyl, 2-oxo-3-propylheptyl, 2-oxo-4-propylheptyl, 2-oxo-octyl, 2-oxo-3-methyloctyl, 2-oxo-4-methyloctyl, 2-oxo-5-methyloctyl, 2-oxo-6-methyloctyl, 2-oxo-7-methyloctyl, 2-oxo-3-ethyloctyl, 2-oxo-4-ethyloctyl, 2-oxo-5-ethyloctyl, 2-oxo-cyclopentyl, 2-oxo-cyclohexyl, 2-oxo-cycloheptyl, 2-oxo-cyclopropylmethyl, 2-oxo-methylcyclohexyl, 2-oxo-cyclohexylmethyl, 2-oxo-norbornyl, 2-oxo-tricyclo[5.2.1.0$^{2,6}$]decyl, 2-cyclo-oxotetracyclo[4.4.0.1$^{2,5}$.1$^{7,10}$]dodecyl and 2-oxo-bornyl.

Examples of the $C_6$-$C_{18}$ aryl group are phenyl, o-tolyl, m-tolyl, p-tolyl, p-hydroxyphenyl, p-trifluoromethylphenyl, 1-naphthyl and 1-anthracenyl.

Examples of the $C_6$-$C_{18}$ aralkyl group are benzyl, 1-phenylethyl, 2-phenylethyl, 1-phenylpropyl, 2-phenylpropyl, 3-phenylpropyl, 1-naphthylmethyl and 2-naphthylmethyl.

Examples of the $C_3$-$C_{30}$ monocyclic or polycyclic lactone group are those obtained by elimination of one hydrogen atom from γ-butyrolactone, γ-valerolactone, Angelica lactone, γ-hexylactone, γ-heptalactone, γ-octalactone, γ-nonalactone, 3-methyl-4-octanolide (Whisky lactone), γ-decalactone, γ-undecalactone, γ-dodecalactone, γ-jasmolactone (7-decenolactone), δ-hexylactone, 4,6,6(4,4,6)-trimethyltetrahydropyrane-2-one, δ-octalactone, δ-nonalactone, δ-decalactone, δ-2-decenolactone, δ-undecalactone, δ-dodecalactone, δ-tridecalactone, δ-tetradecalactone, Lactoscatone, ε-decalactone, ε-dodecalactone, cyclohexyllactone, jasmine lactone, cis-jasmone lactone and methyl-γ-decalactone. There can also be used the following lactone groups. In the respective formulas, the dotted lines each indicate a bonding position.

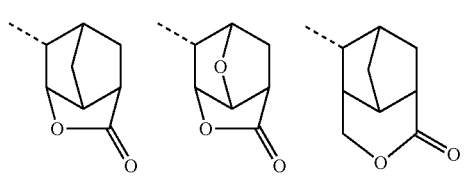

(E-1)

Examples of the 3- to 18-membered heterocyclic ring formed by $R^B$ and $R^C$ are those indicated below. In the respective formulas, the dotted lines each indicate a bonding position.

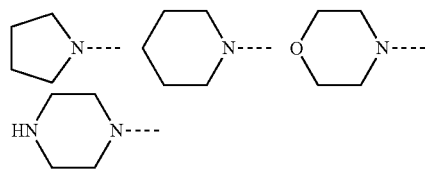
(E-2)

As mentioned above, any number of hydrogen atoms on carbons in $R^A$, $R^B$, $R^C$ may be substituted with a substituent. Examples of such a substituent are a halogen atom such as fluorine, chlorine, bromine or iodine, hydroxyl group, thiol group, aryl group or an organic group having a heteroatom such as oxygen, nitrogen, sulfur, phosphorus or silicon. Two hydrogen atoms on the same carbon in $R^A$, $R^B$, $R^C$ may be replaced by one oxygen atom to form a ketone group. These substituents can exist in any number as long as structurally possible.

Preferred examples of $R^2$ are those indicated below. In the respective formulas, the dotted lines each indicate a bonding position.

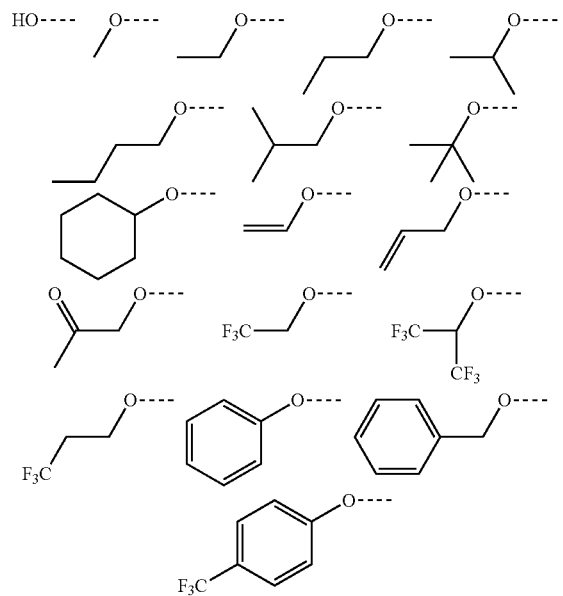
(E-3)

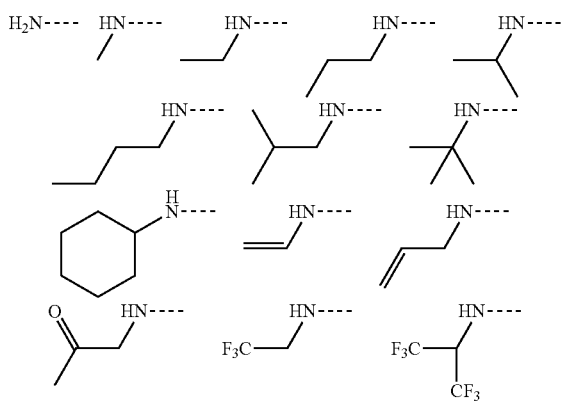
(E-4)

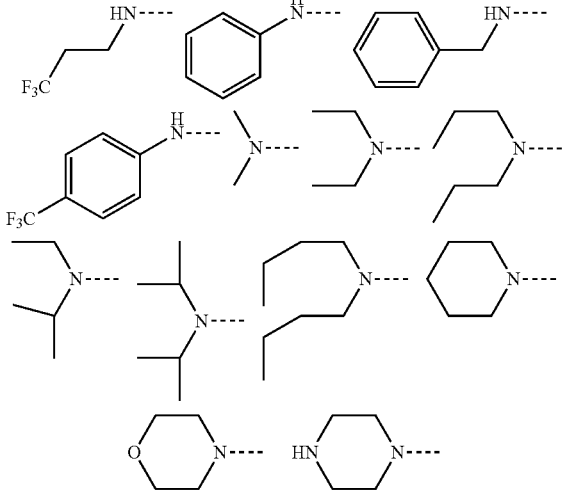

The structure of the general formula (1) is thus exemplified as follows. The fluorine-containing sulfonate of the general formula (1-1) corresponds to those in which a cation $M^+$ is bonded to any of the following anion structures. The fluorine-containing sulfonic acid onium salt of the general formula (2) corresponds to those in which a cation $Q^+$ is bonded to any of the following anion structures.

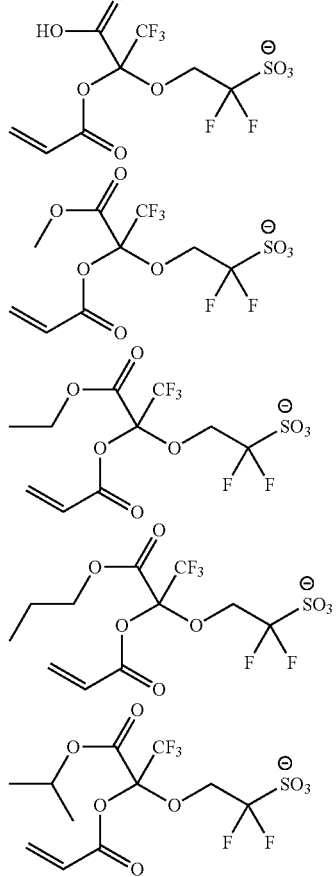
(E-5-1)

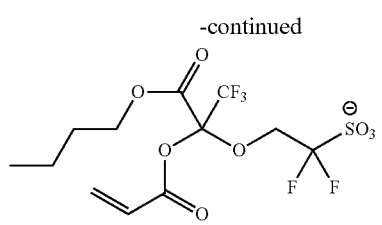
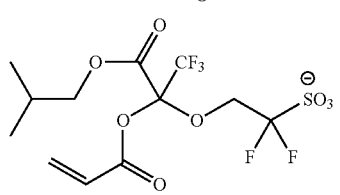
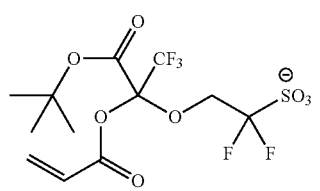
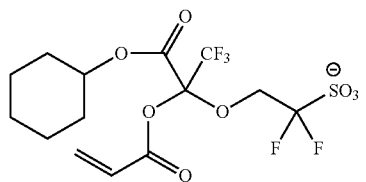
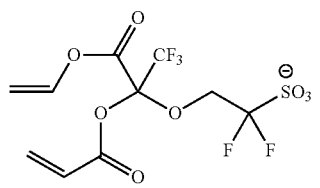
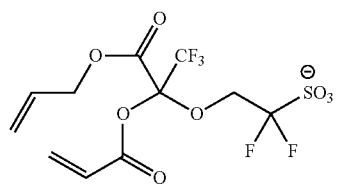
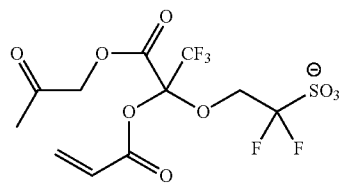
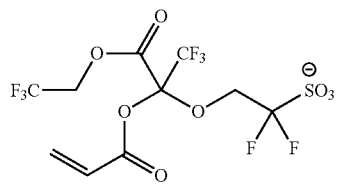
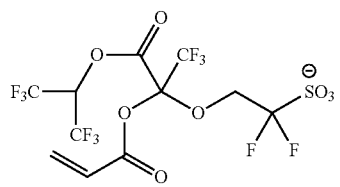
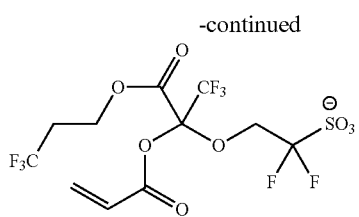
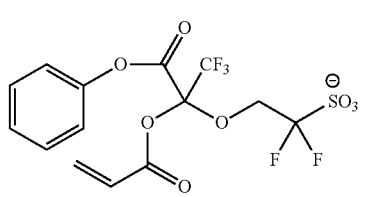
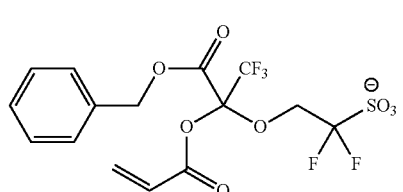
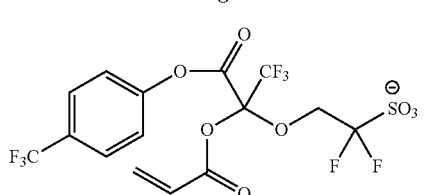
(E-5-2)
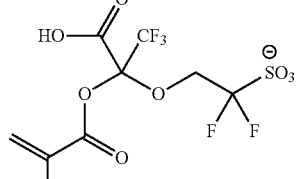
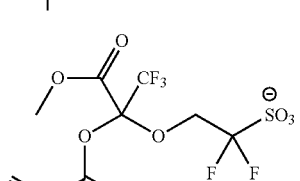
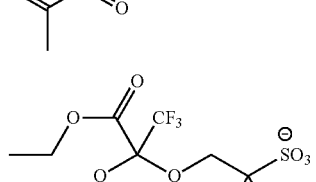
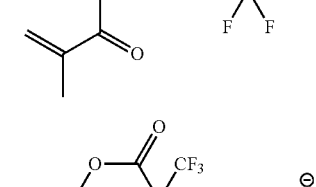
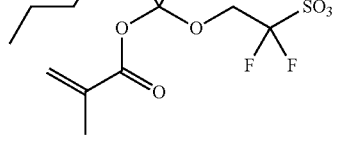

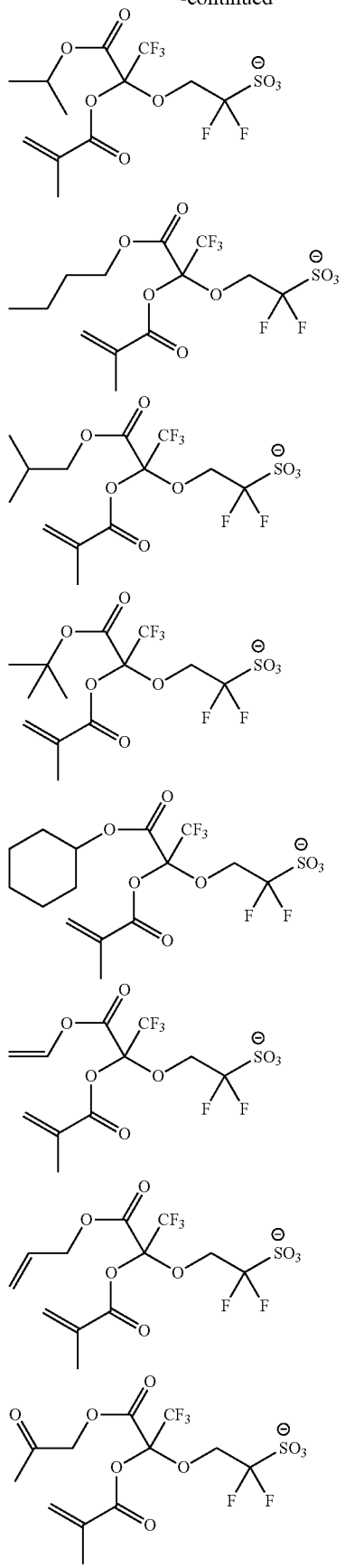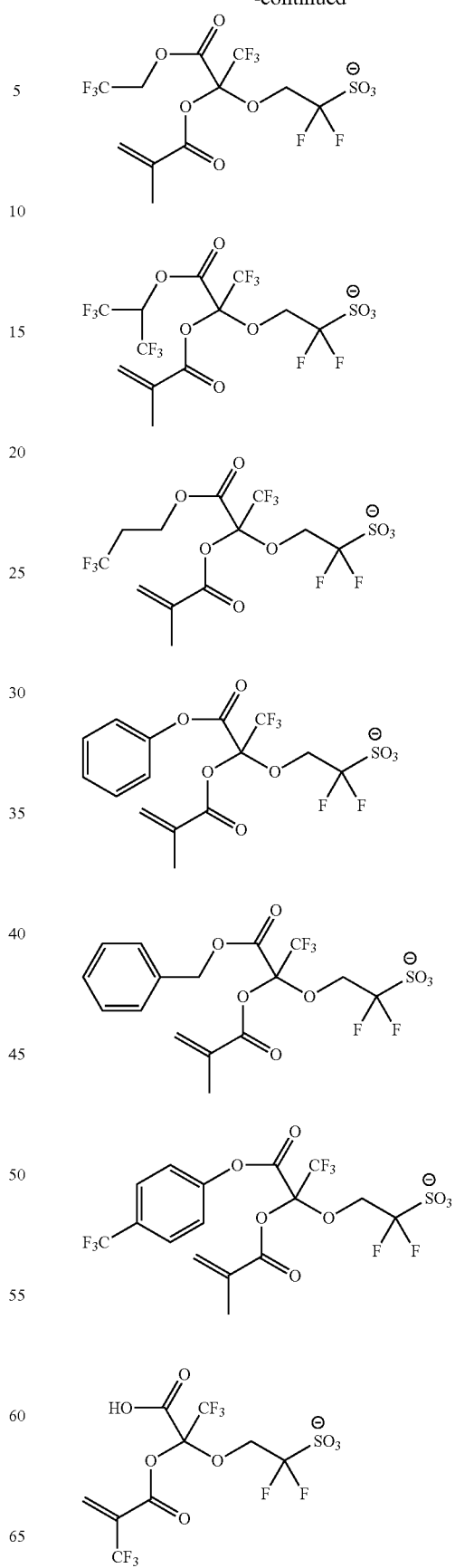
(E-5-3)

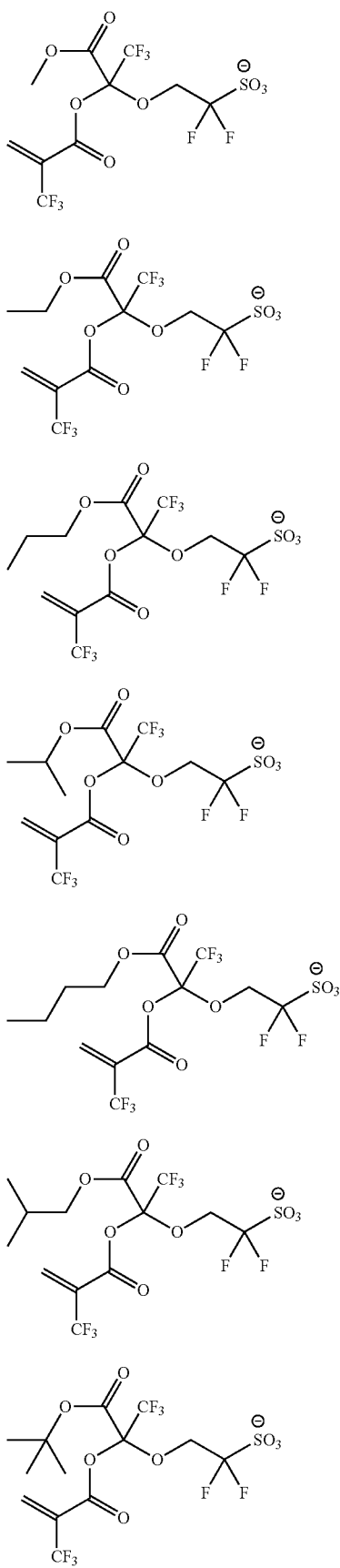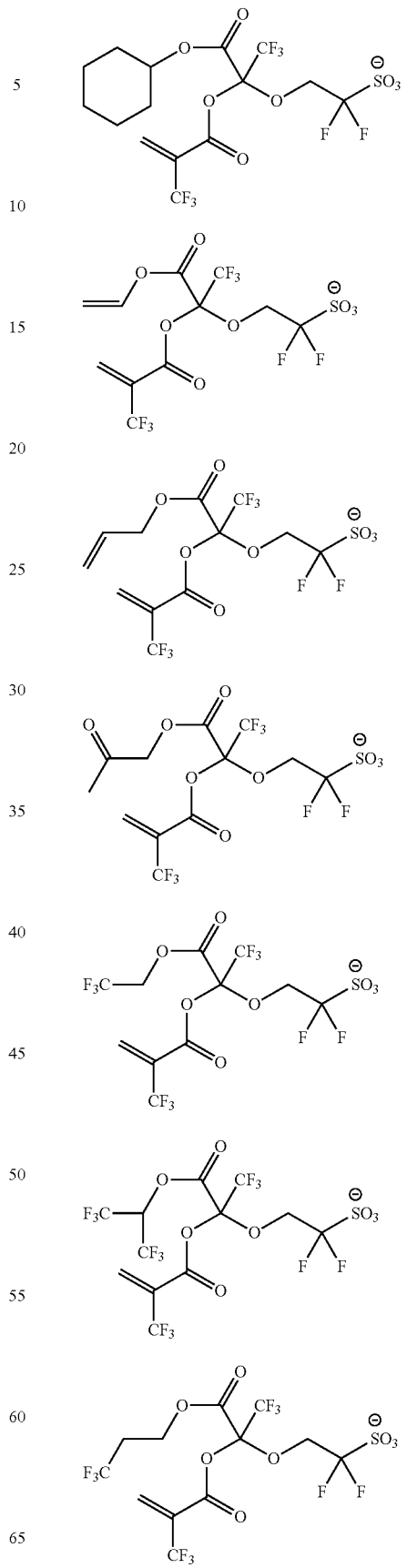

-continued
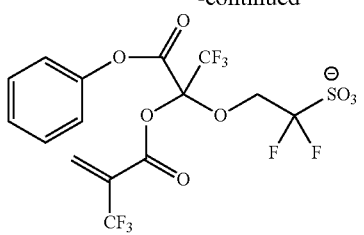
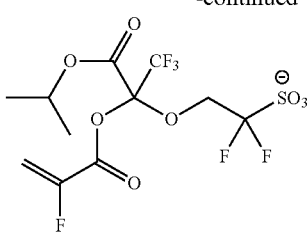
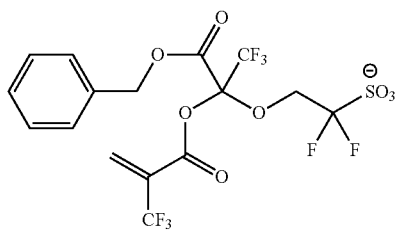
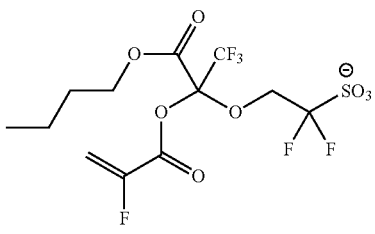
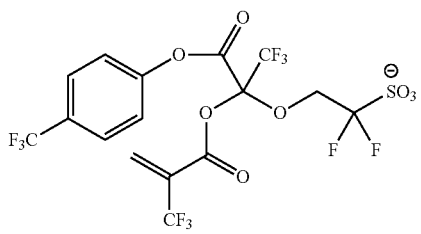
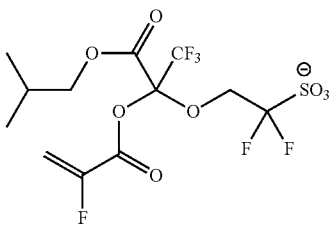
(E-5-4)
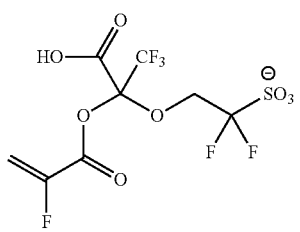
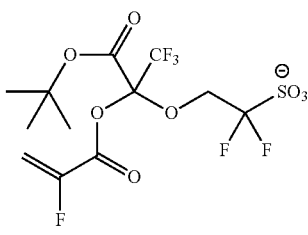
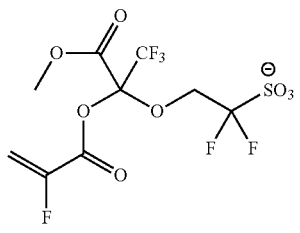
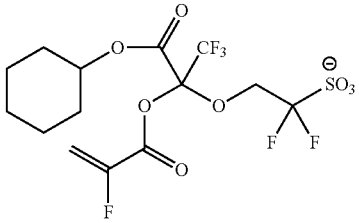
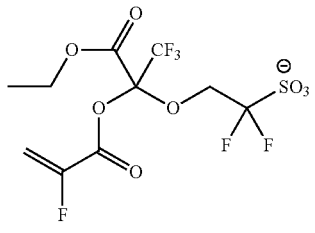
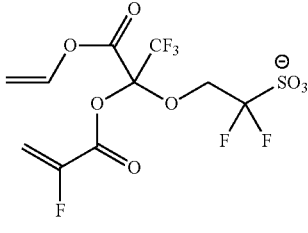
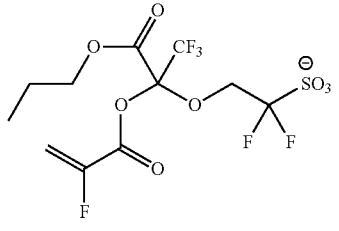
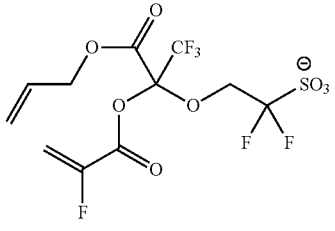

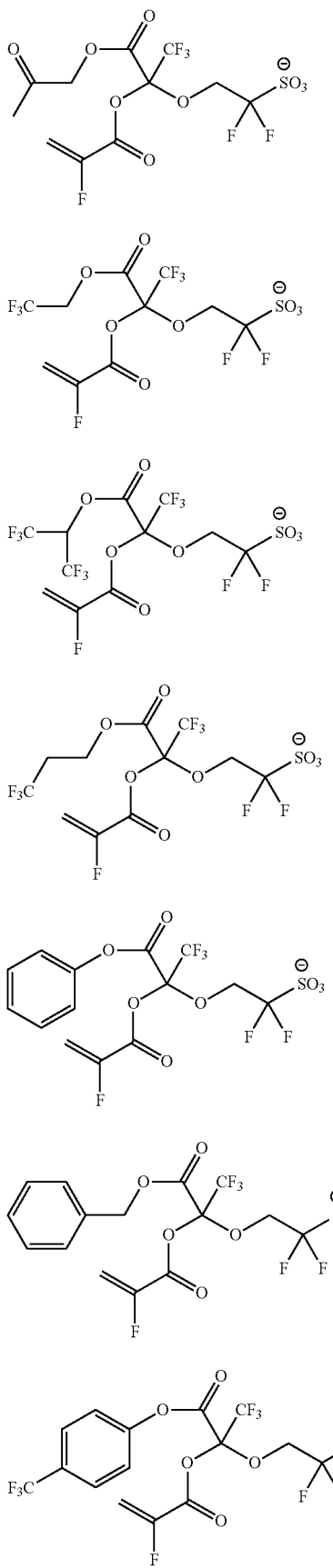
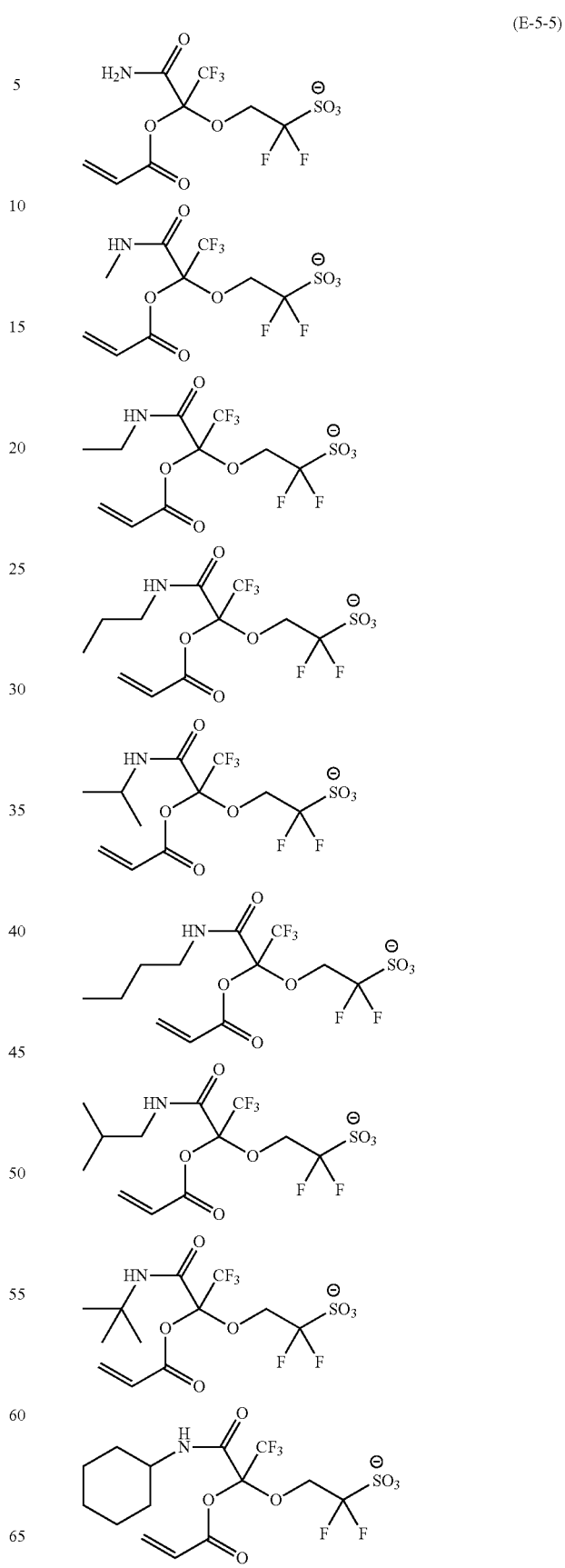
(E-5-5)

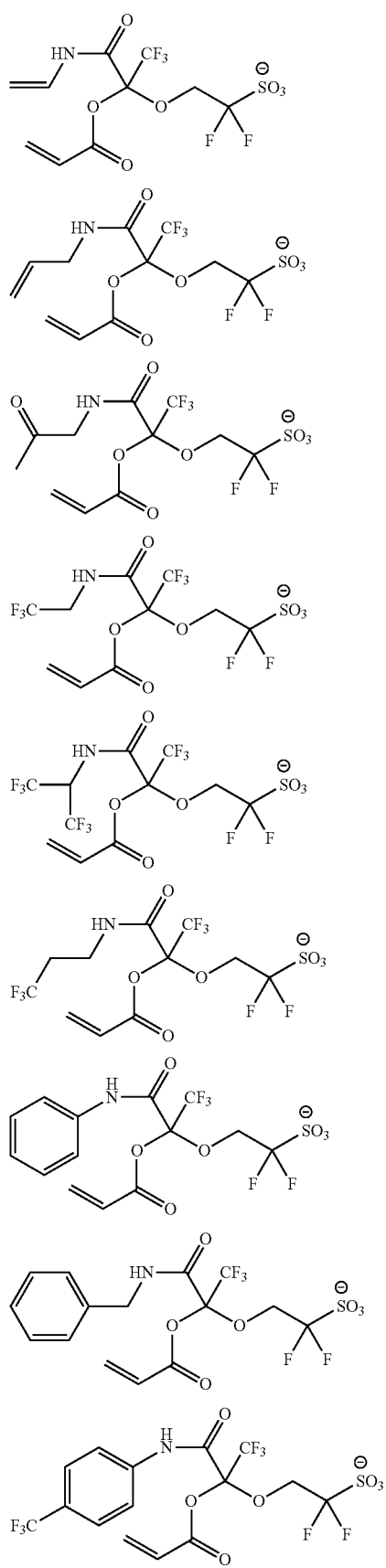
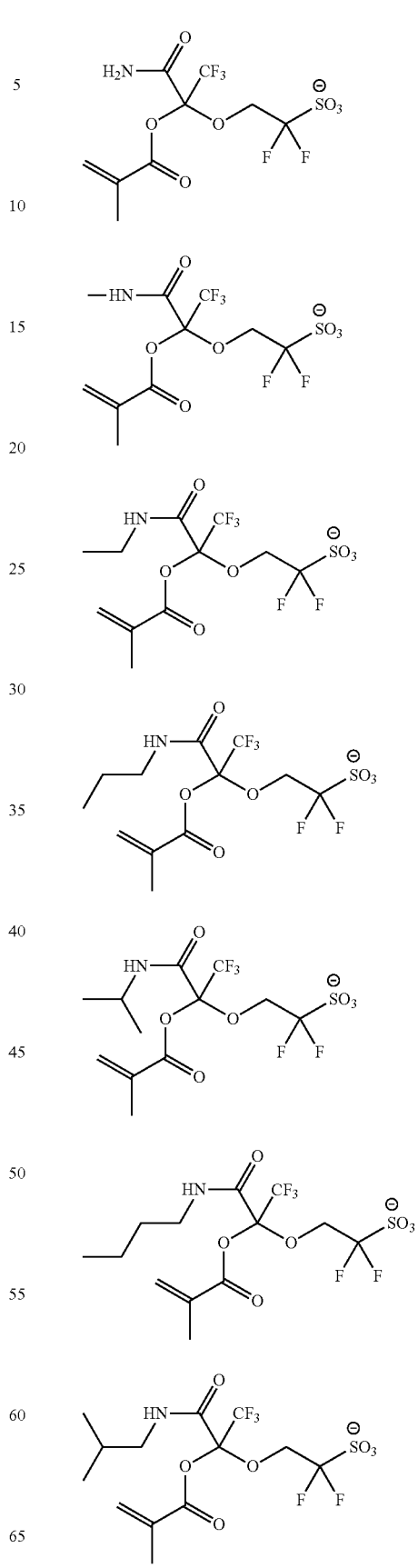
(E-5-6)

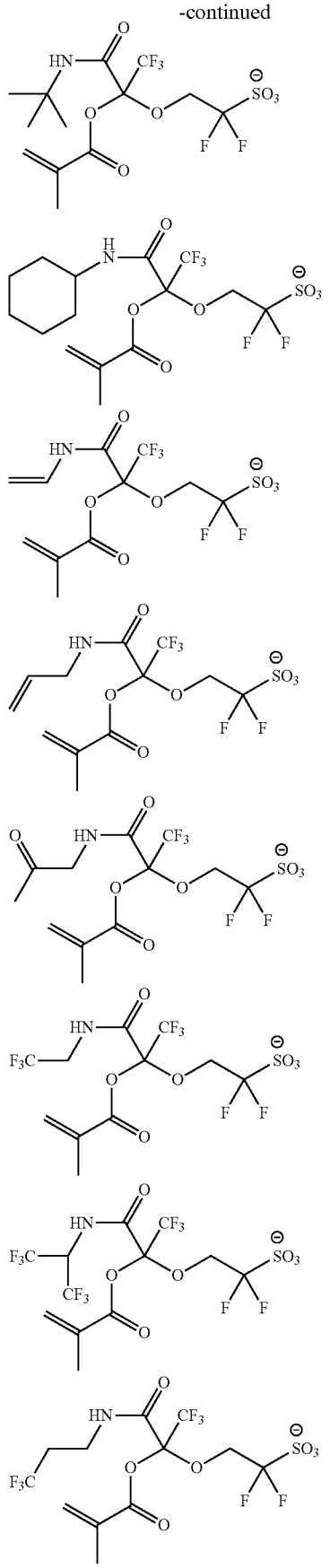
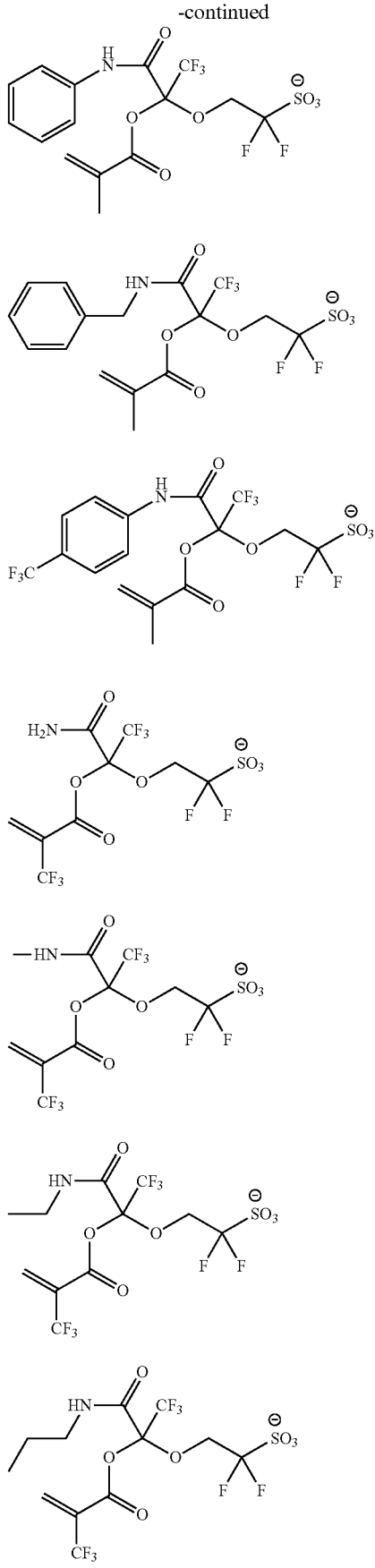
(E-5-7)

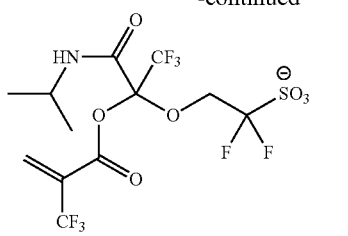
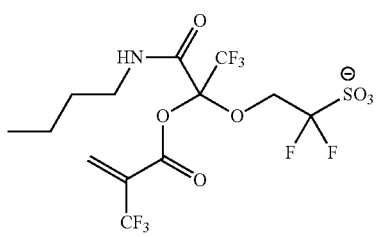
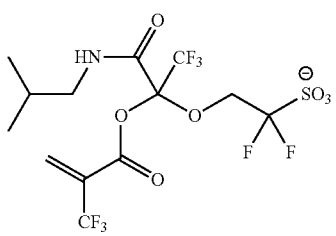
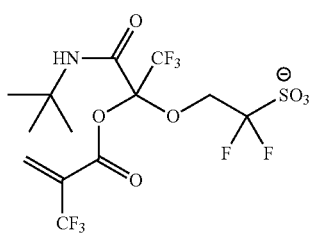
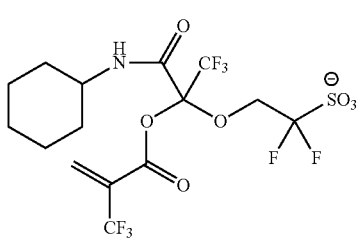
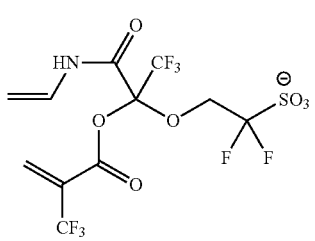
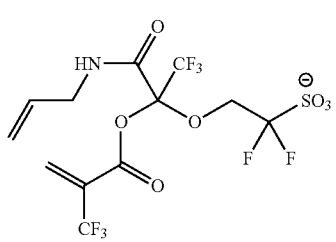
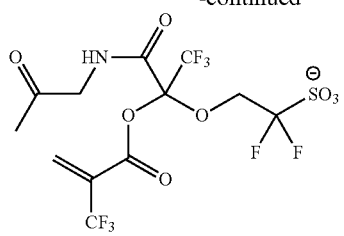
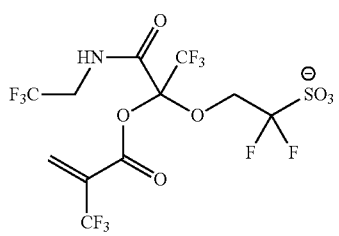
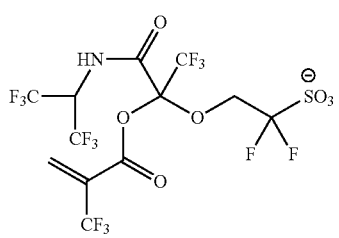
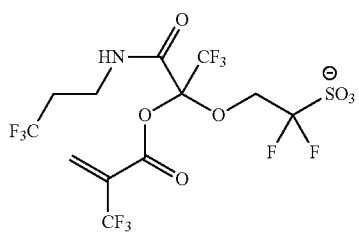
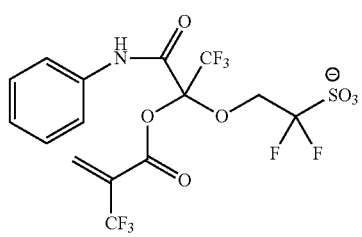
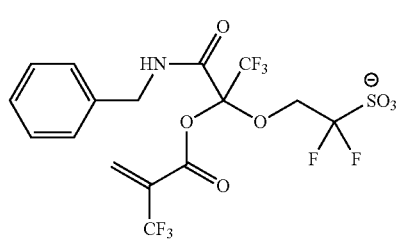
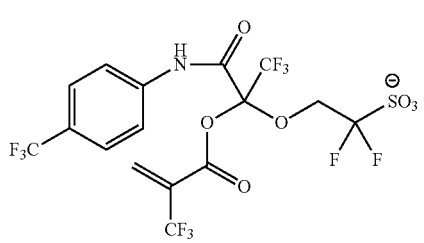

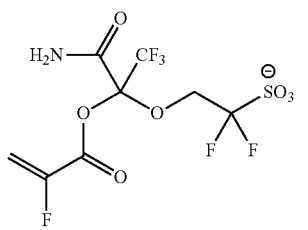
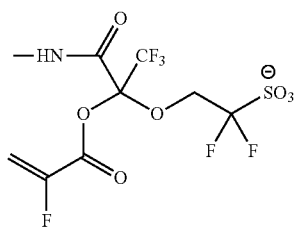
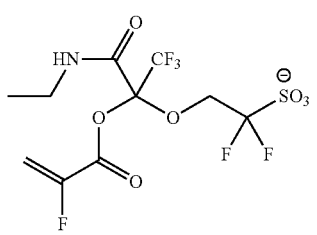
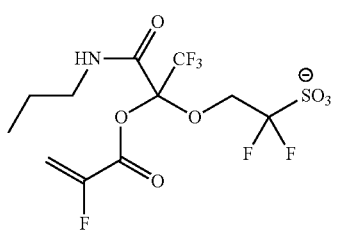
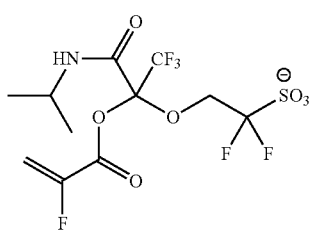
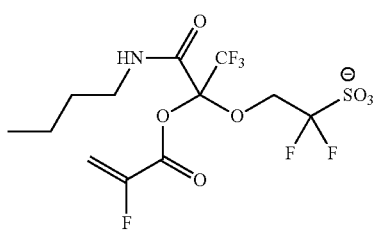
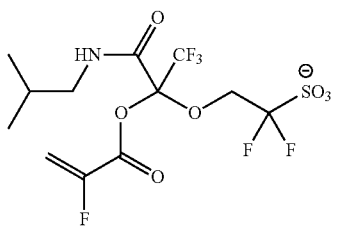
(E-5-8)
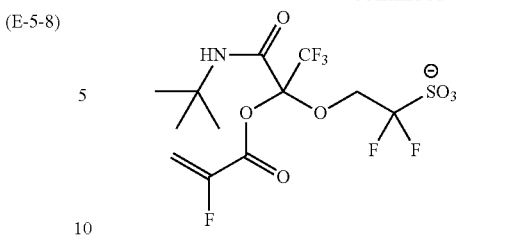
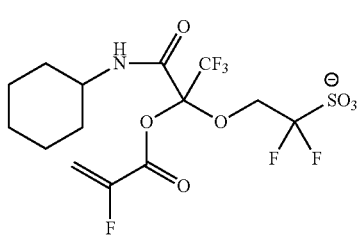
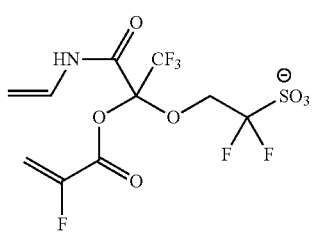
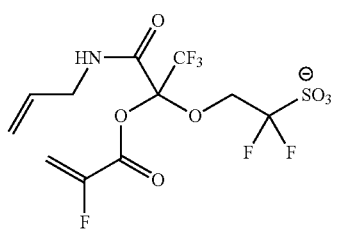
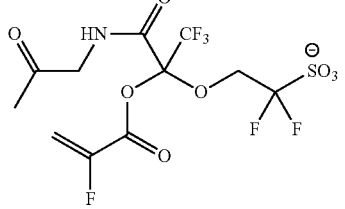
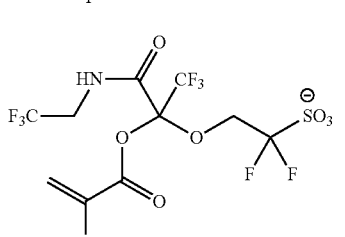
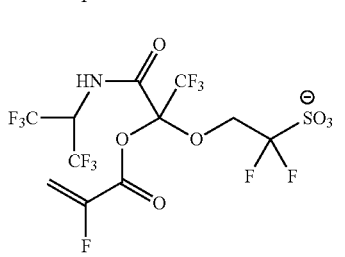

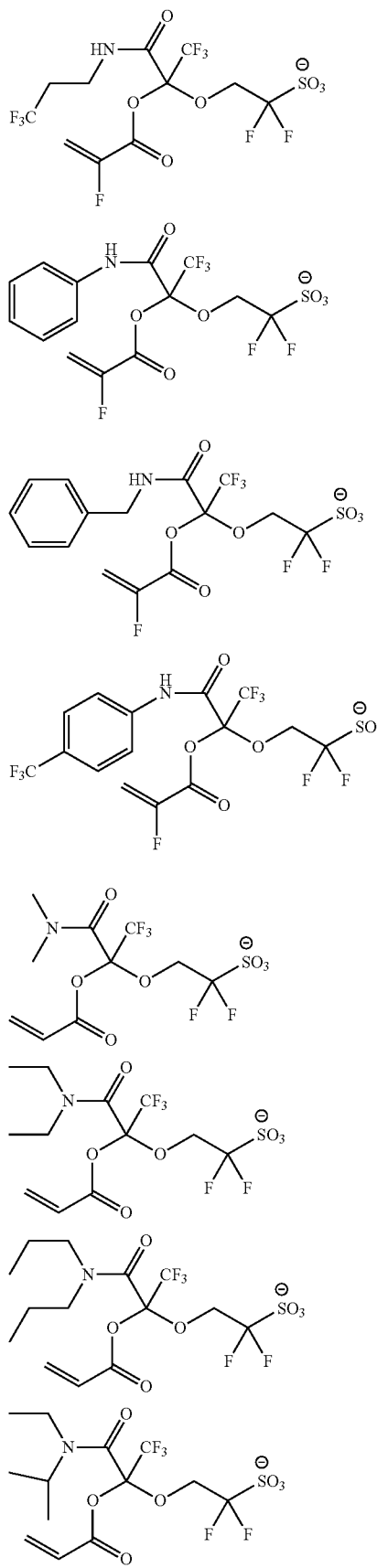
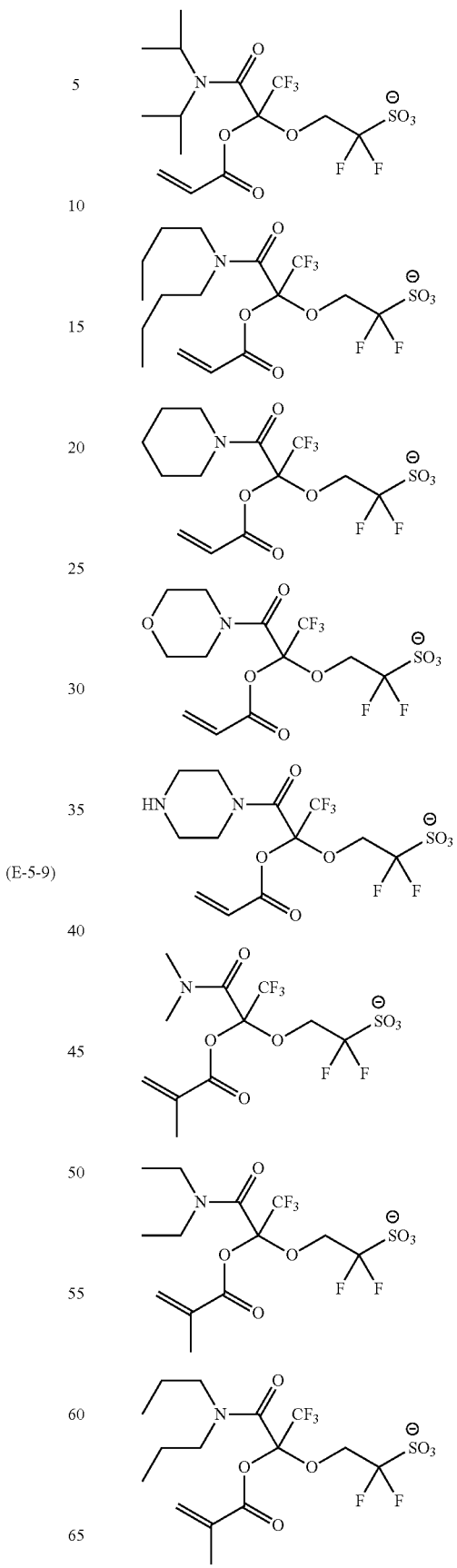
(E-5-9)

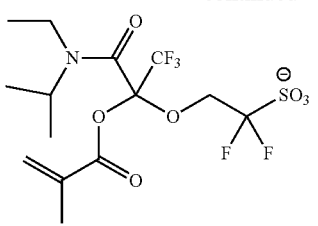
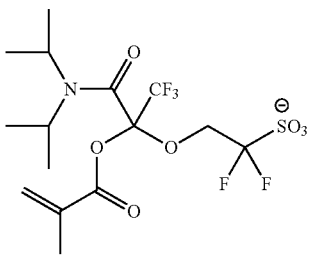
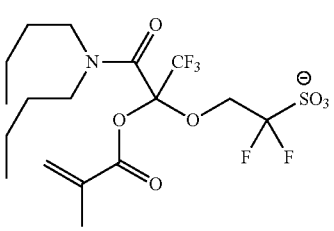
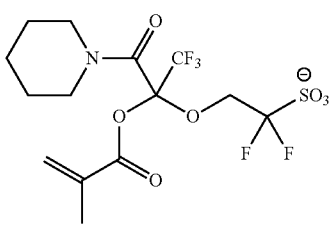
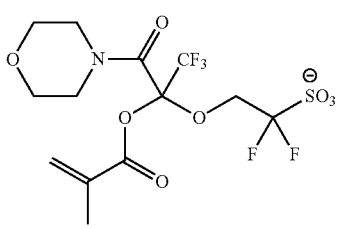
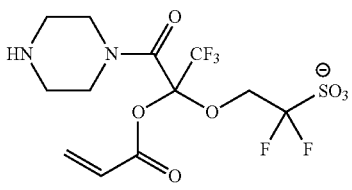
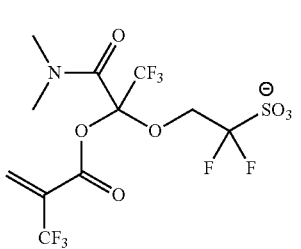
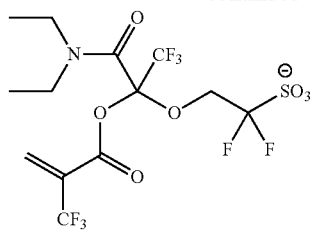
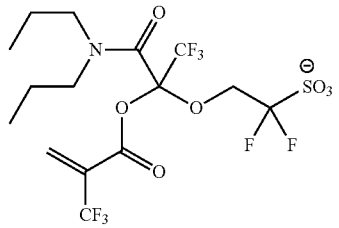
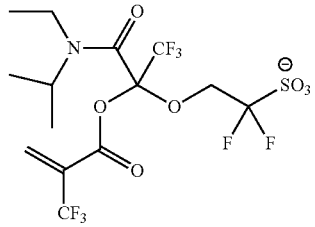
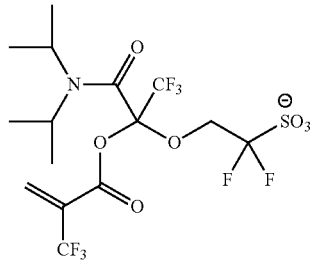
(E-5-10)
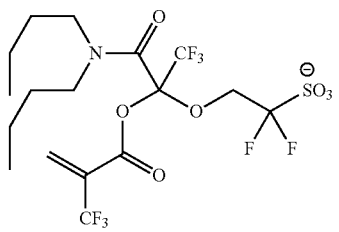
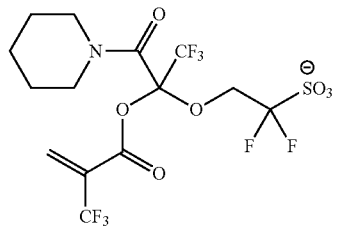
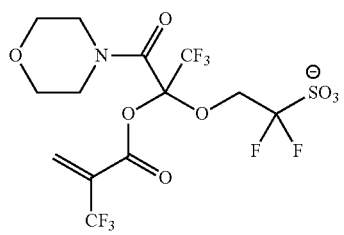

37
-continued
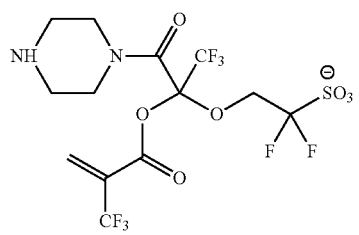
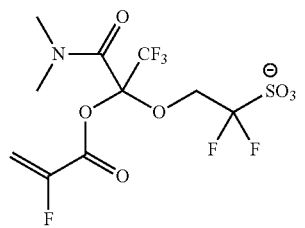
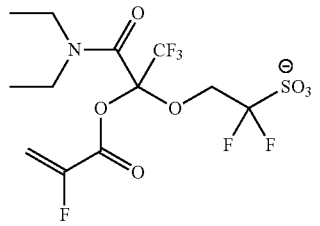
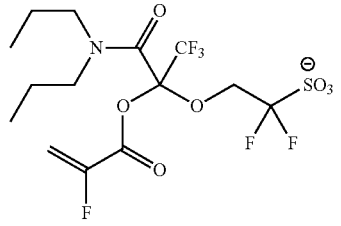
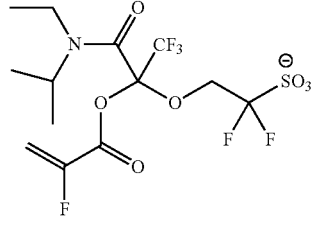
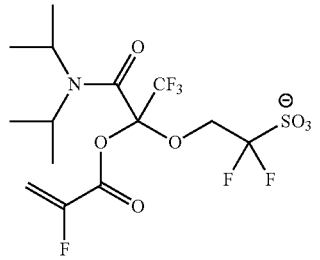
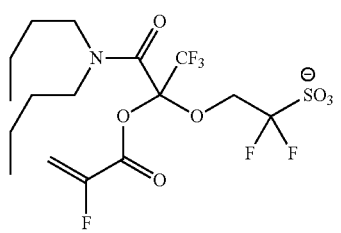
38
-continued
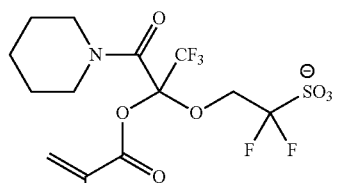
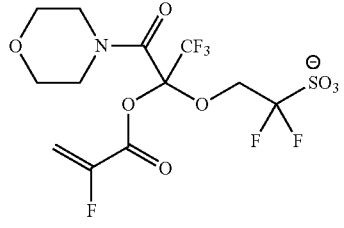
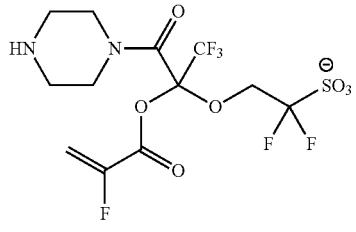
(E-5-11)
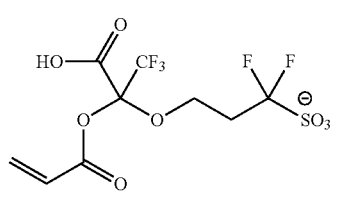
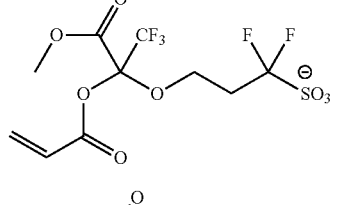
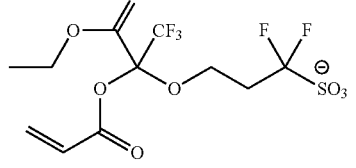
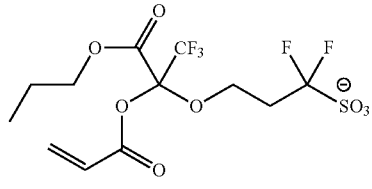
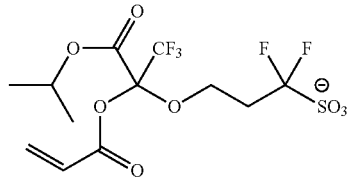

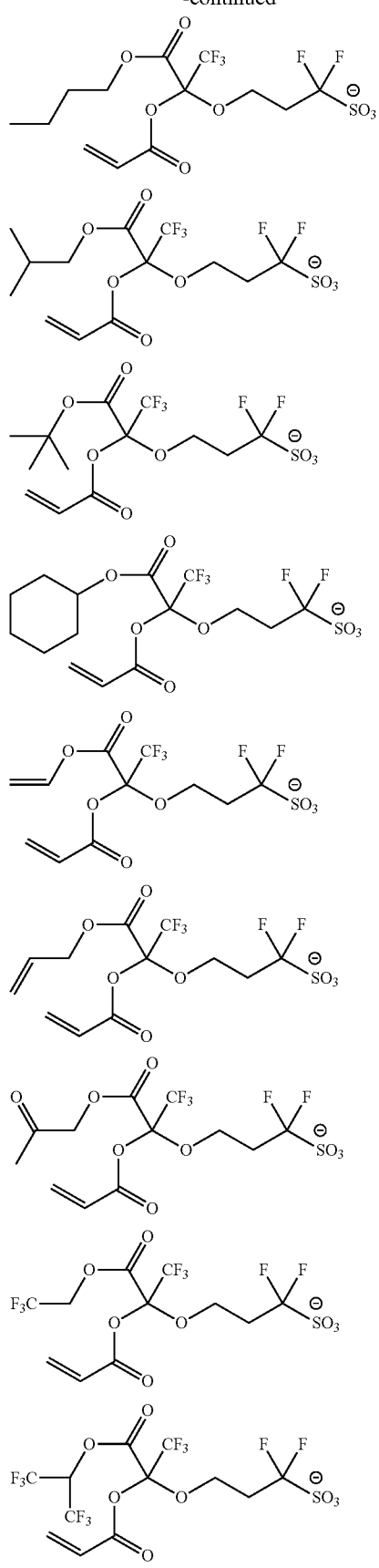
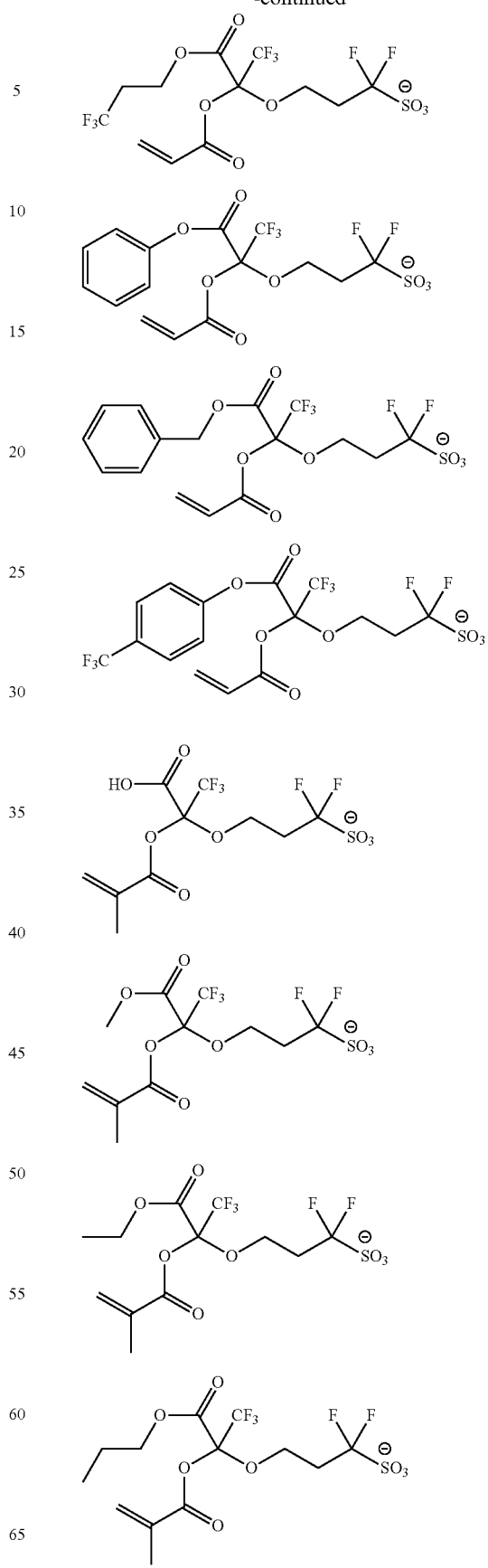
(E-5-12)

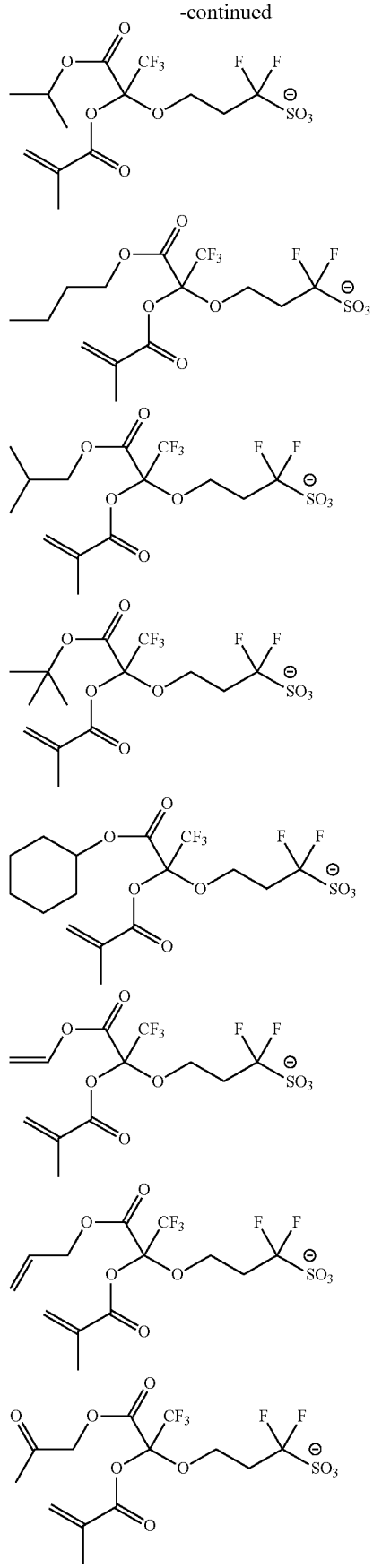
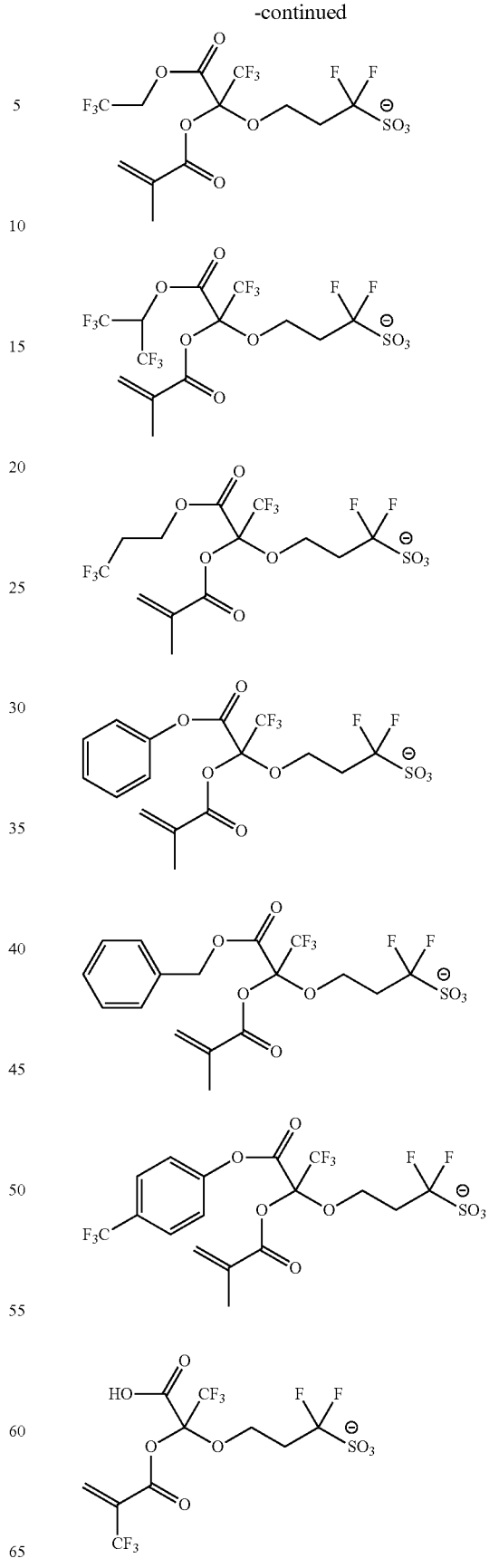
(E-5-13)

43
-continued
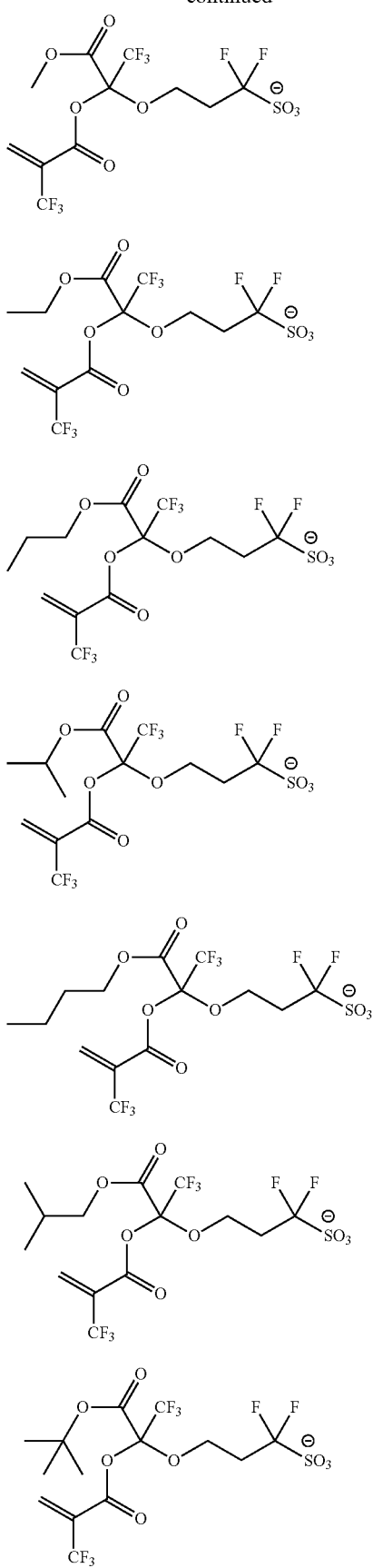
44
-continued
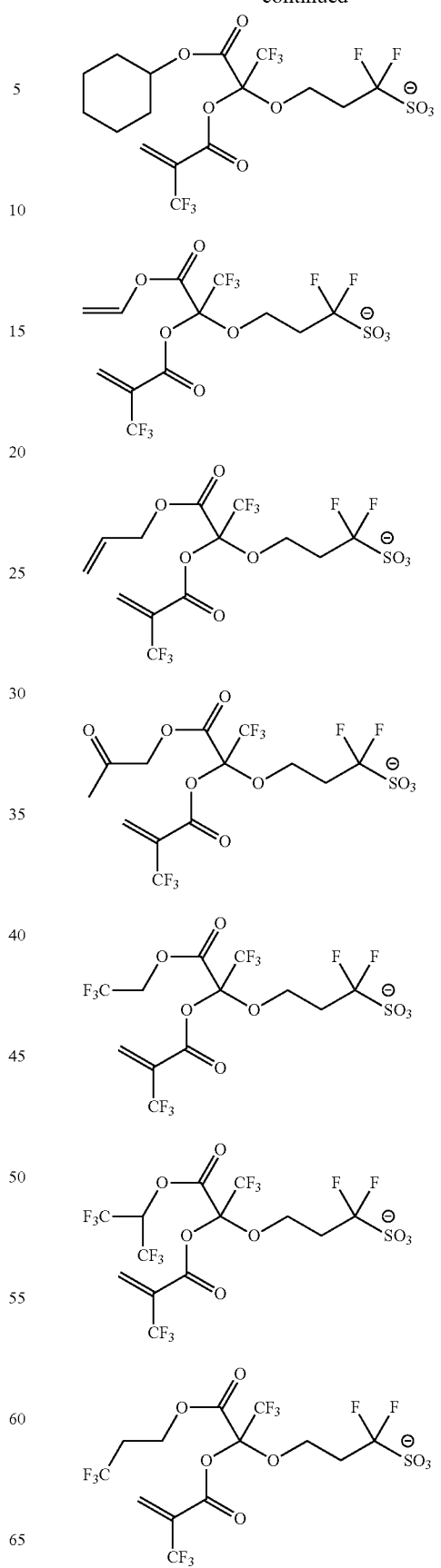

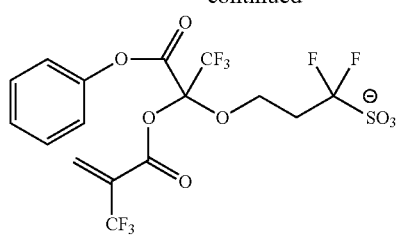
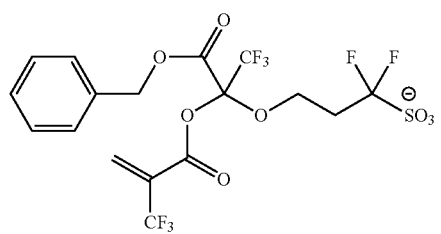
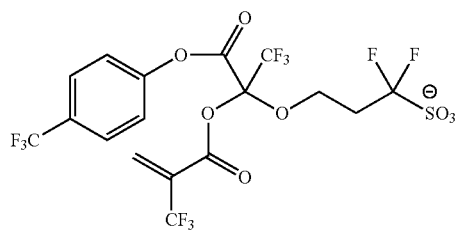
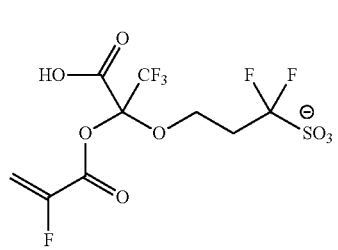
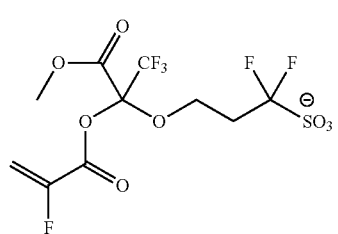
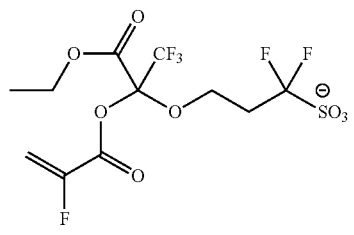
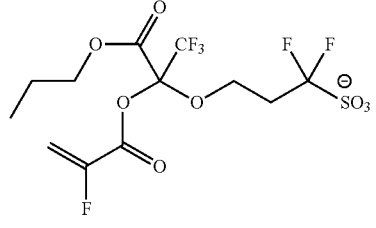
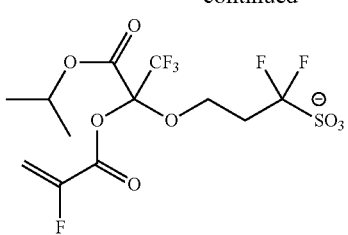
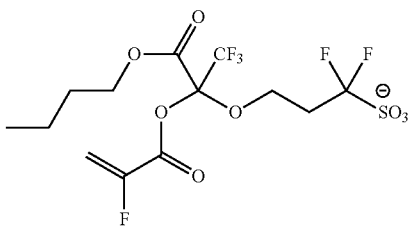
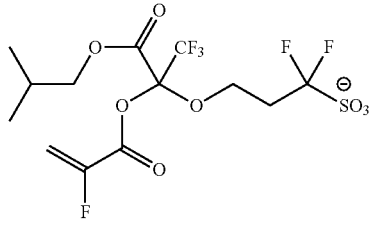
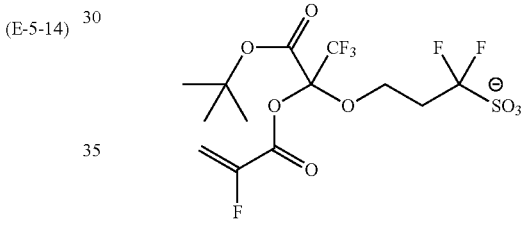
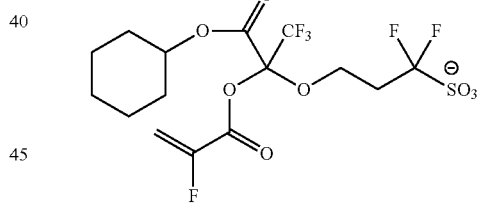
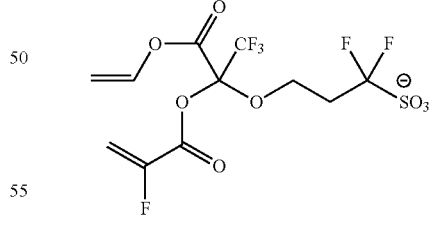
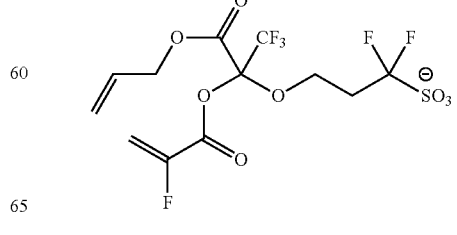
(E-5-14)

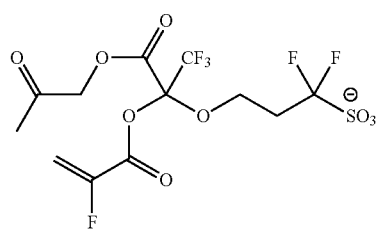
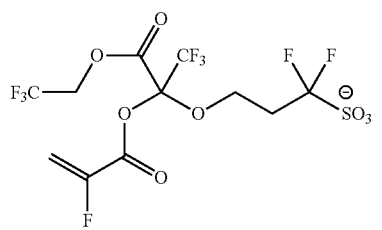
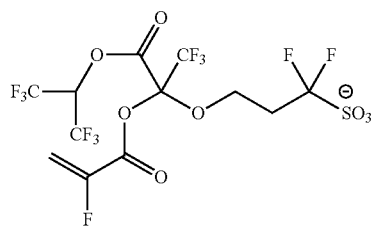
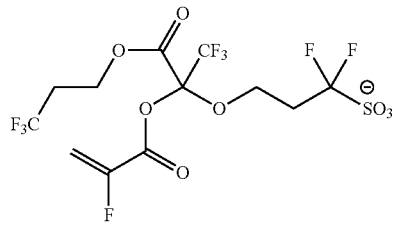
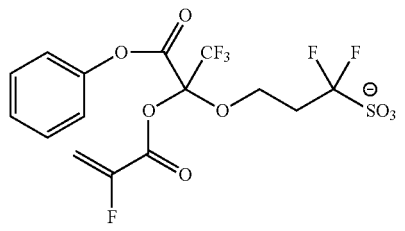
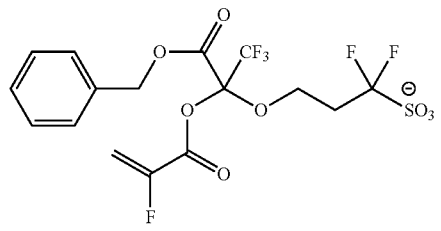
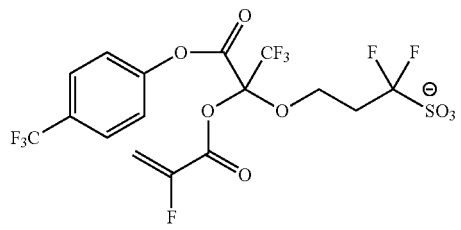
(E-5-15)
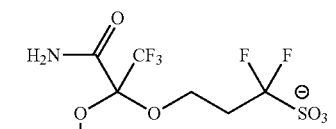
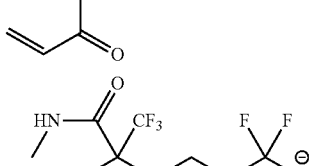
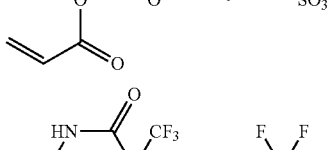
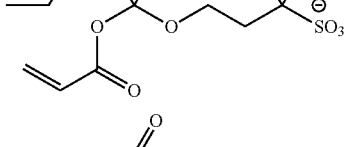
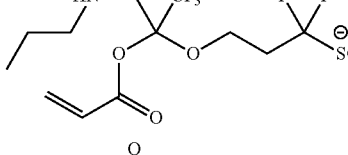
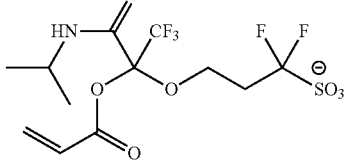
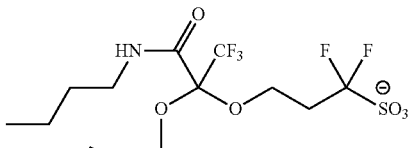
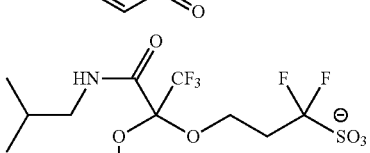
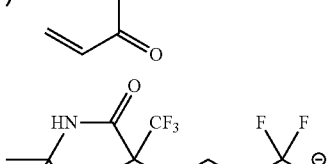
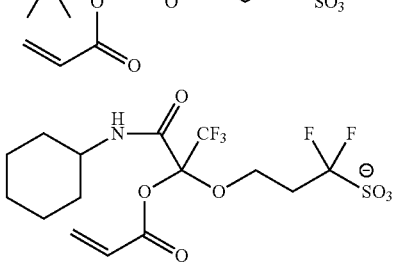

-continued
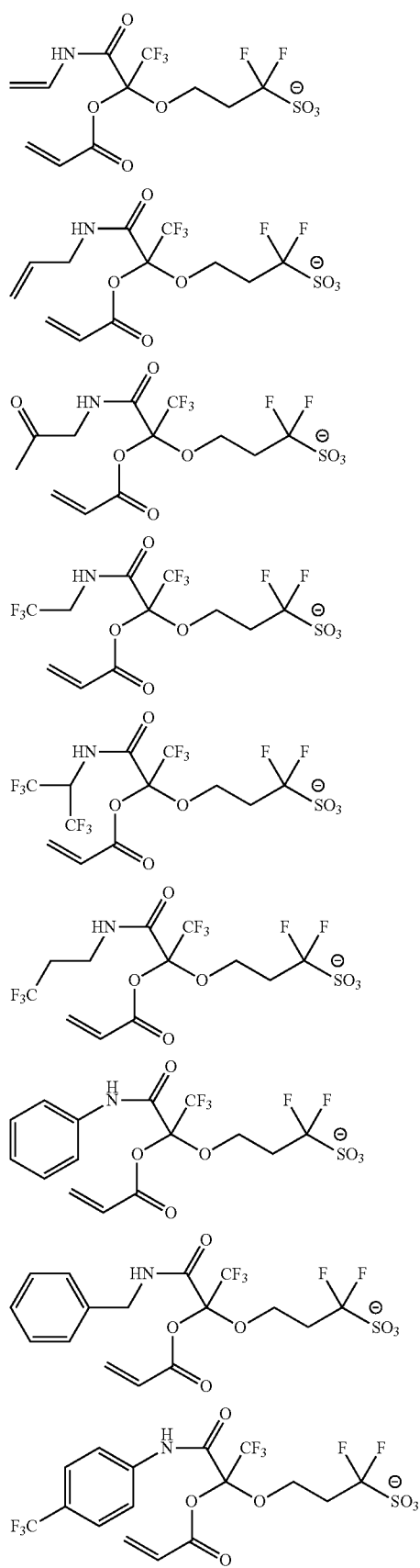
-continued
(E-5-16)
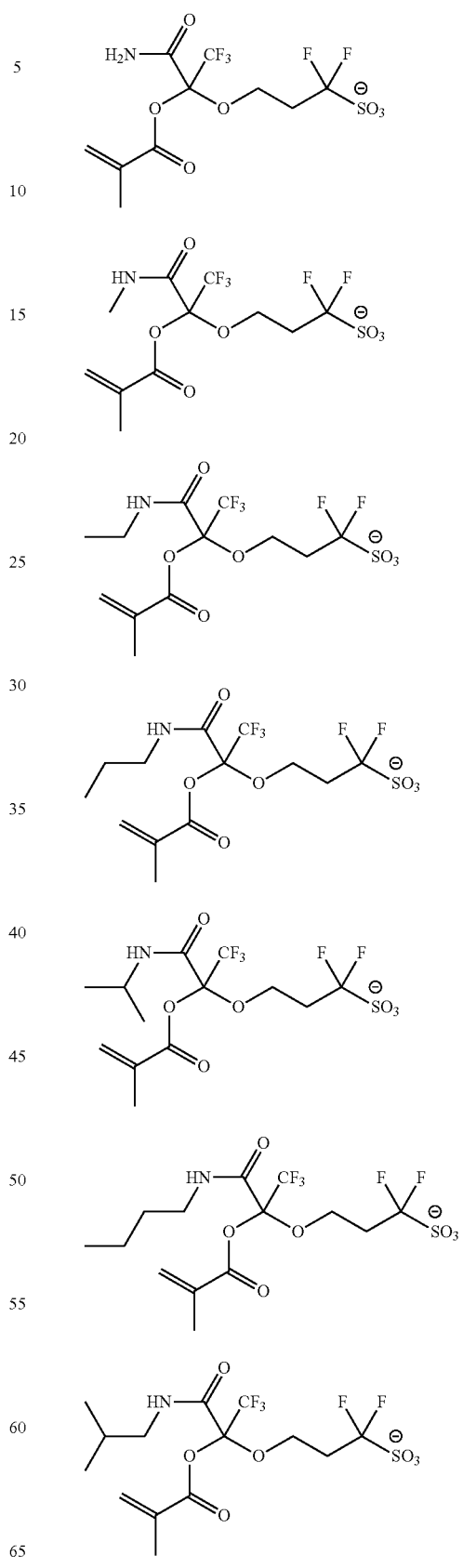

51
-continued
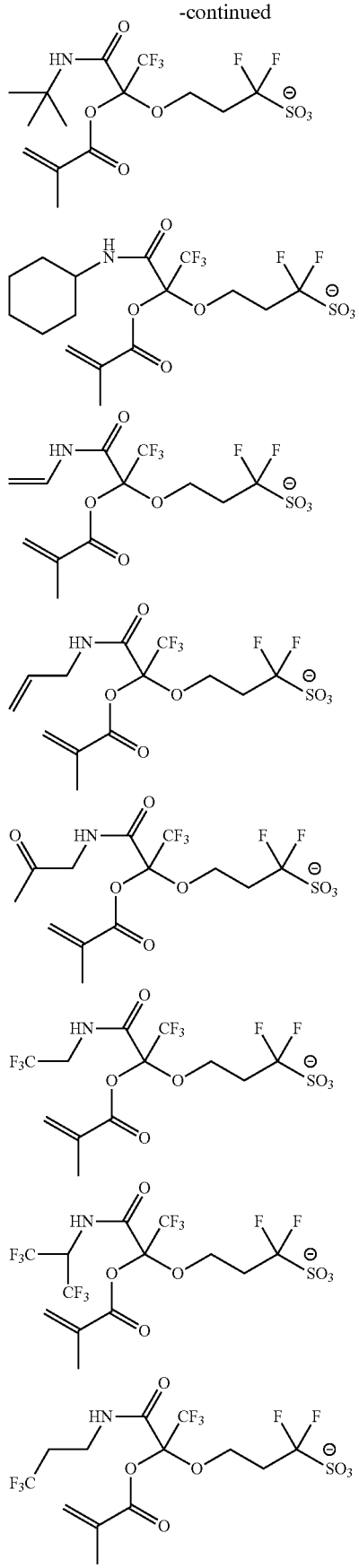
52
-continued
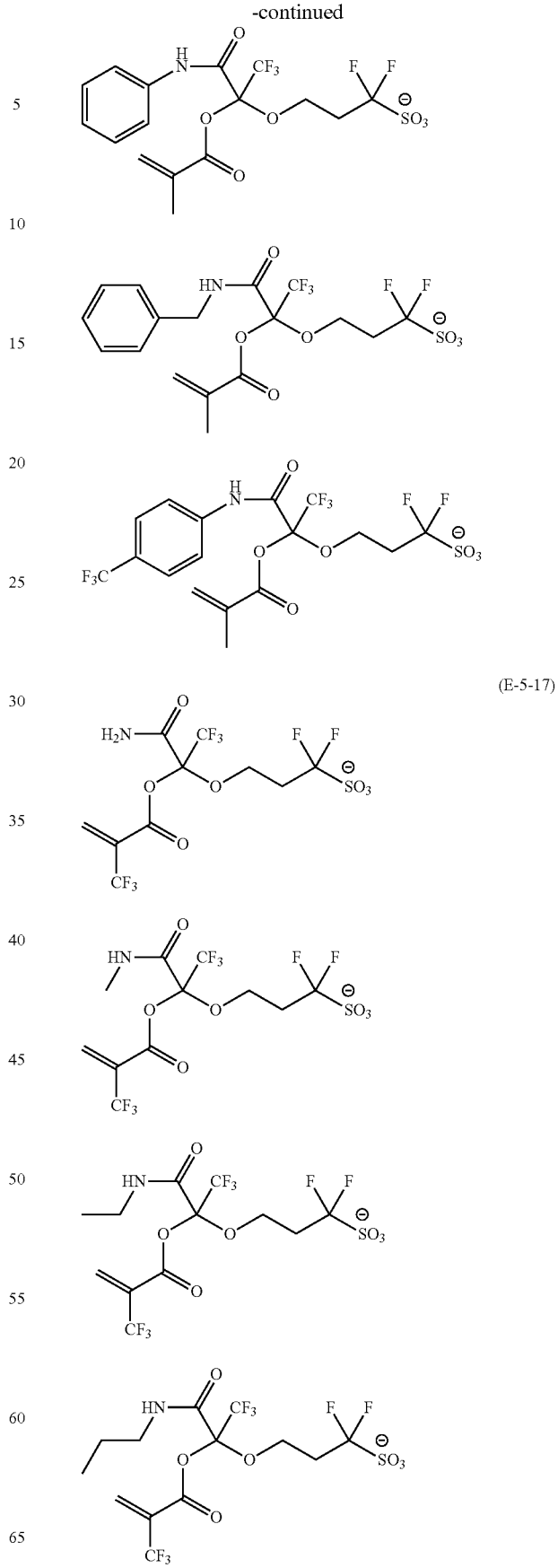
(E-5-17)

53
-continued
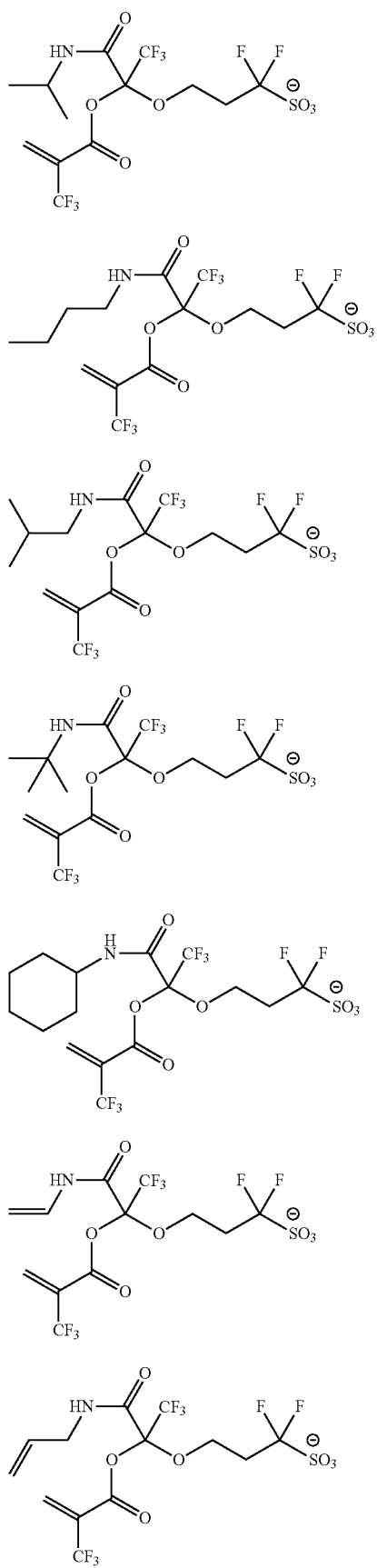
54
-continued
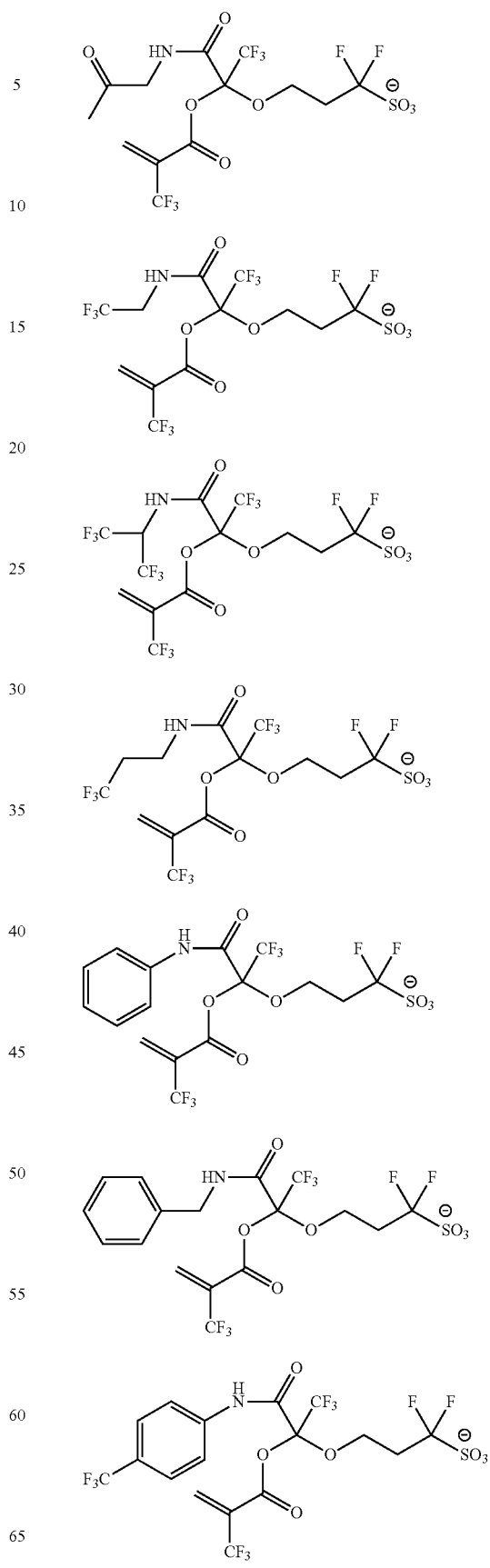

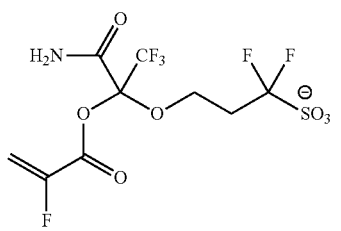
(E-5-18)
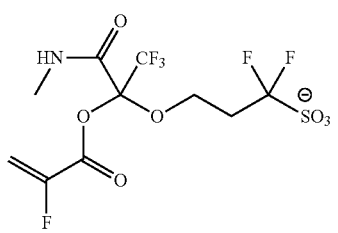
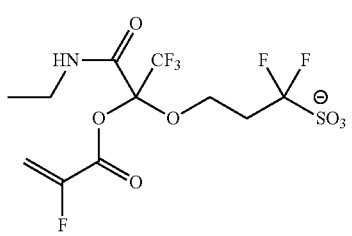
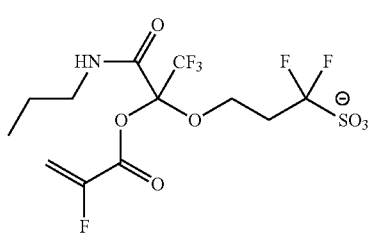
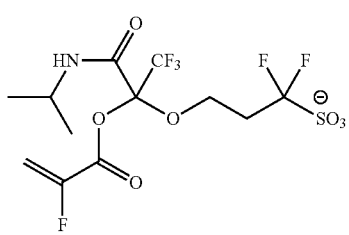
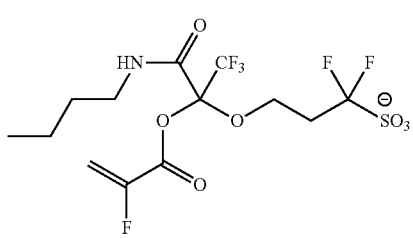
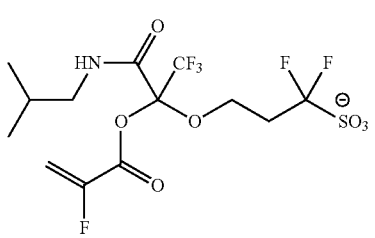
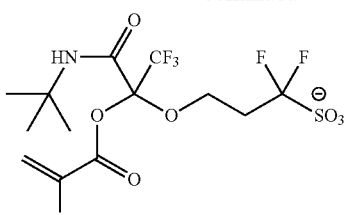
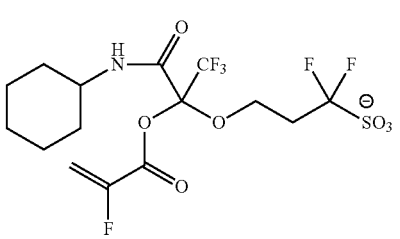
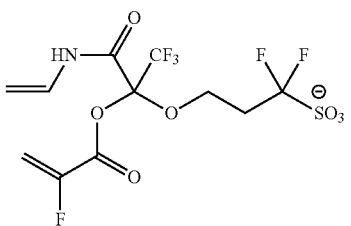
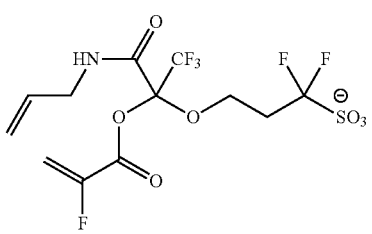
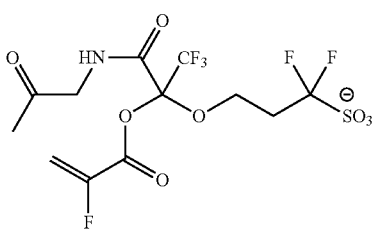
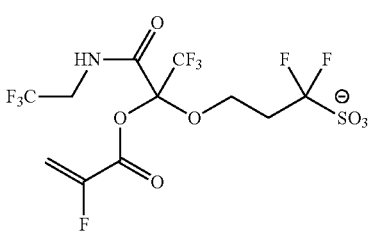
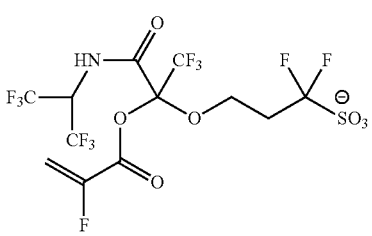

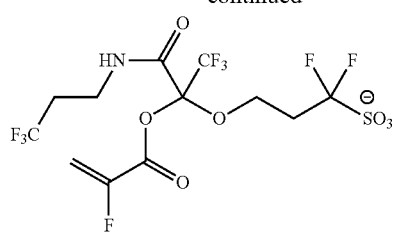
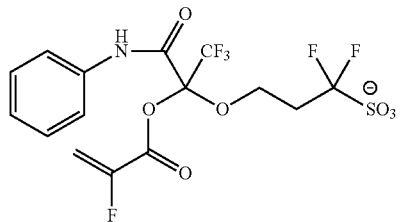
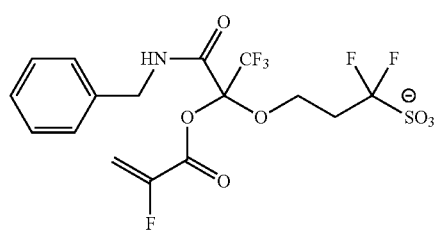
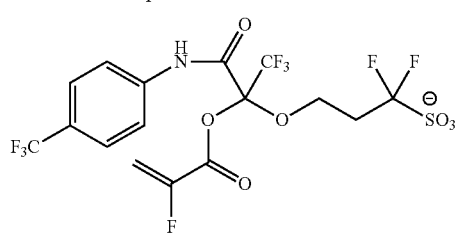
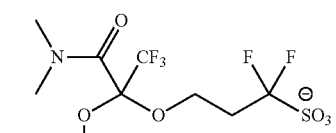
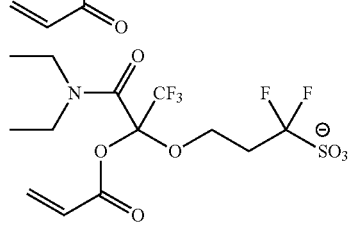
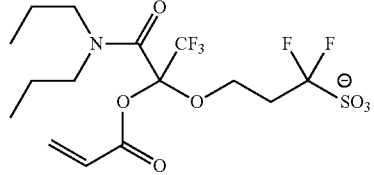
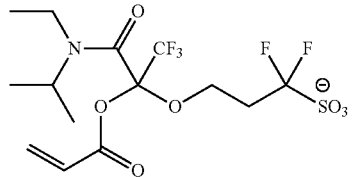
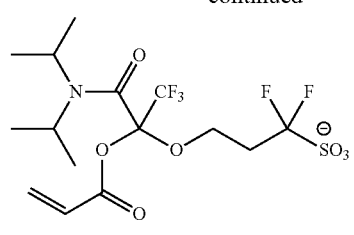
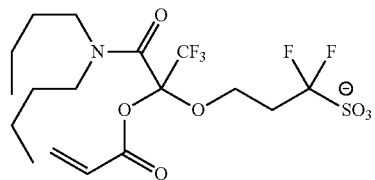
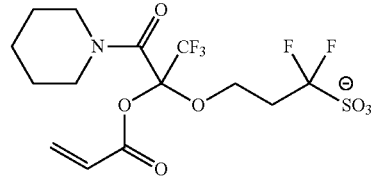
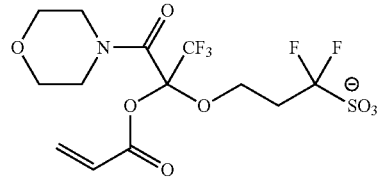
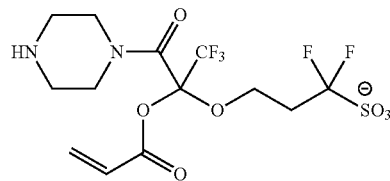
(E-5-19)
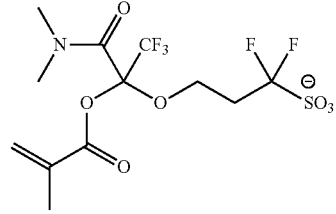
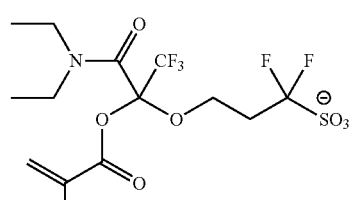
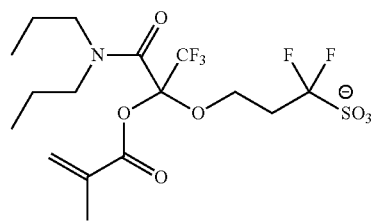

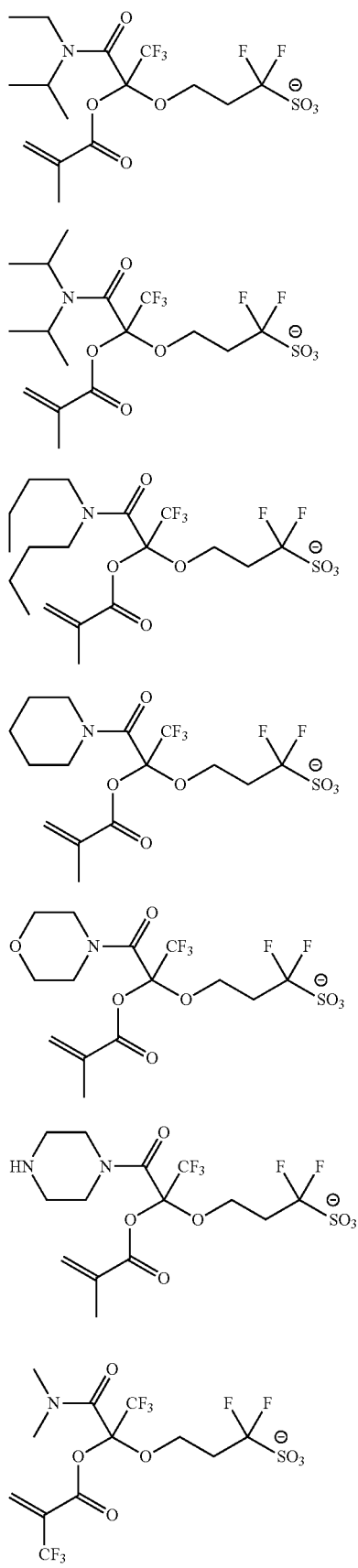
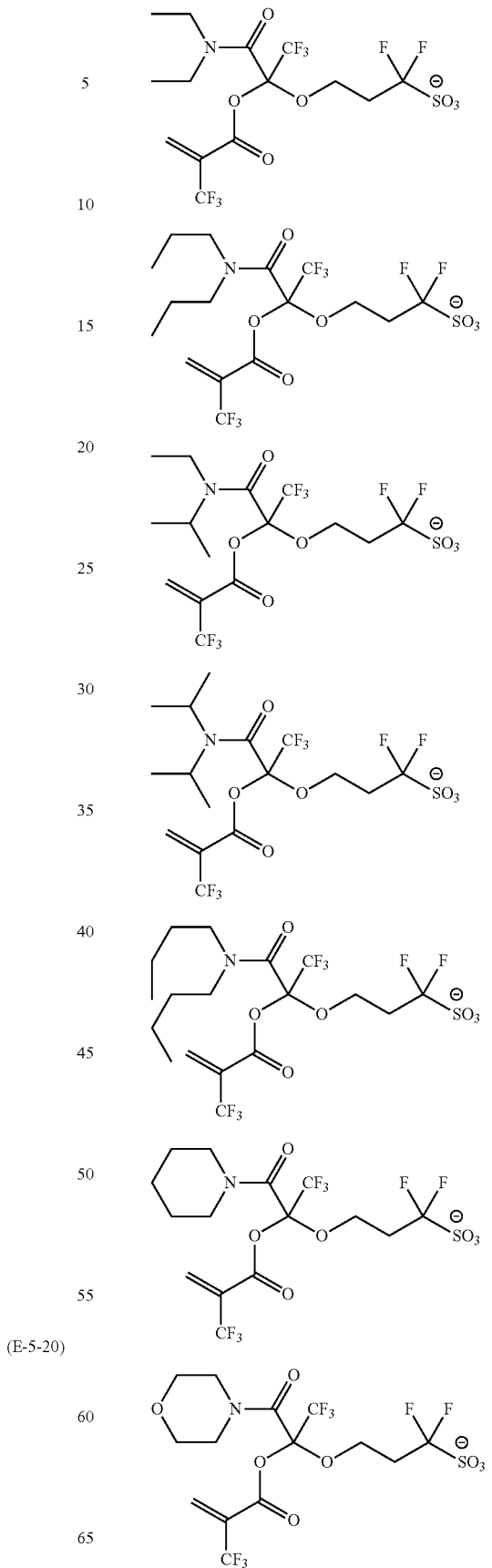
(E-5-20)

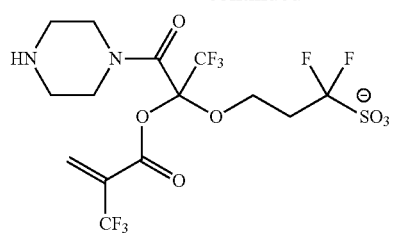
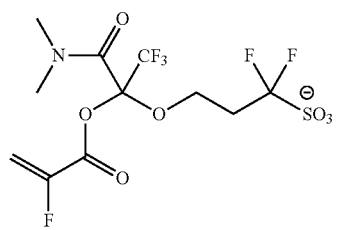
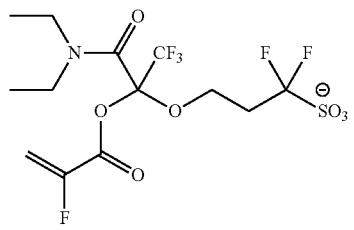
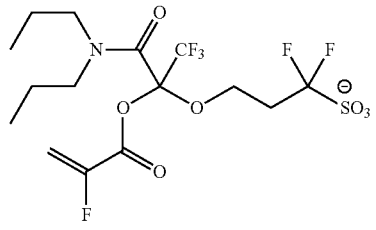
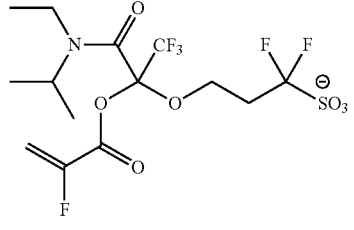
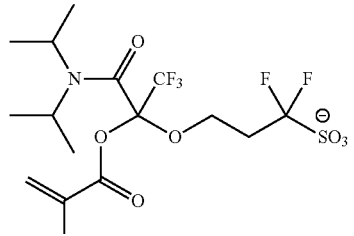
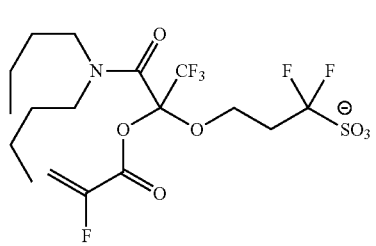
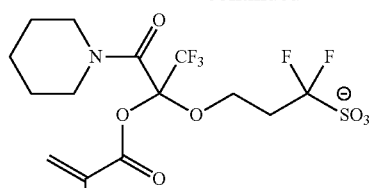
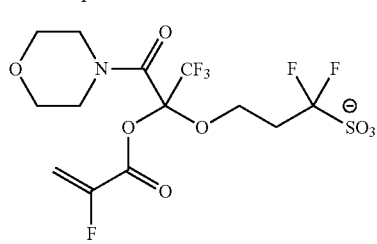
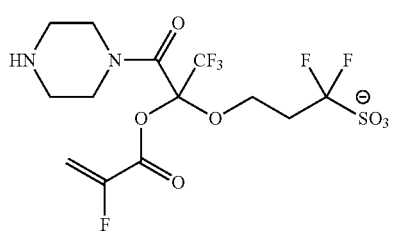
(E-5-21)
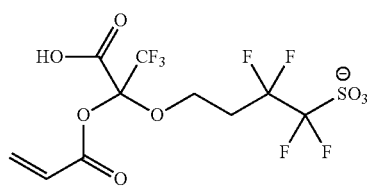
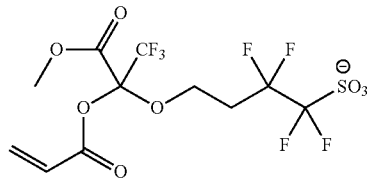
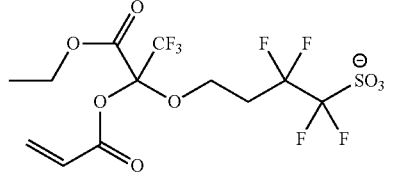
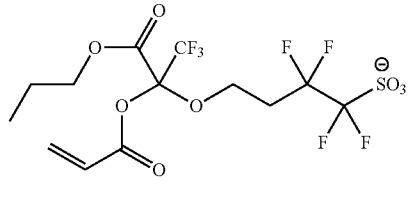
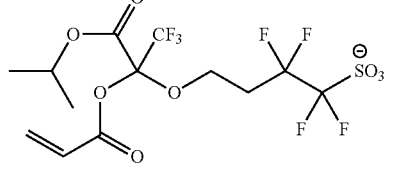

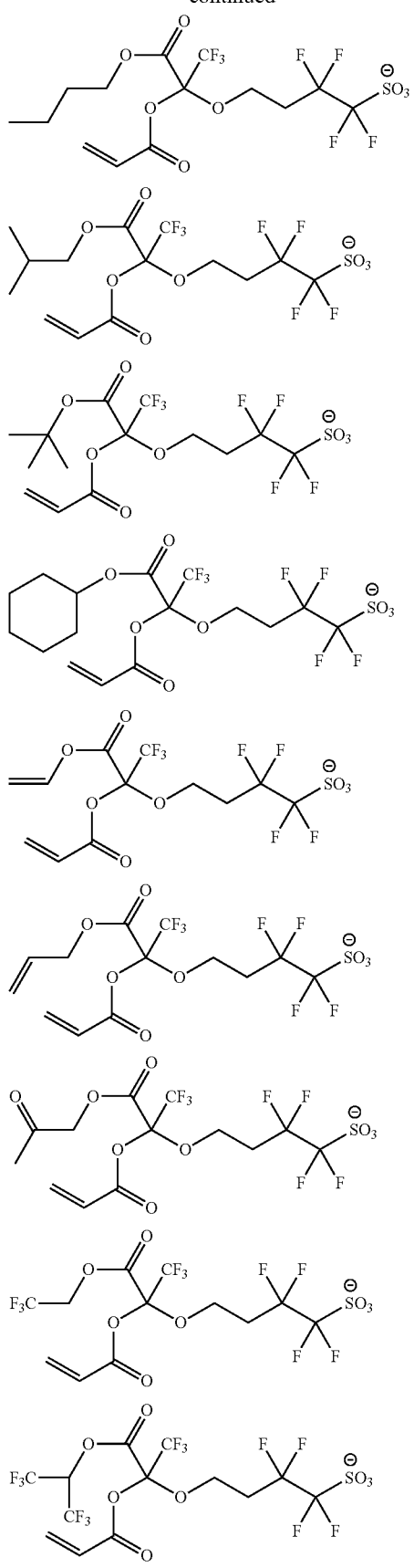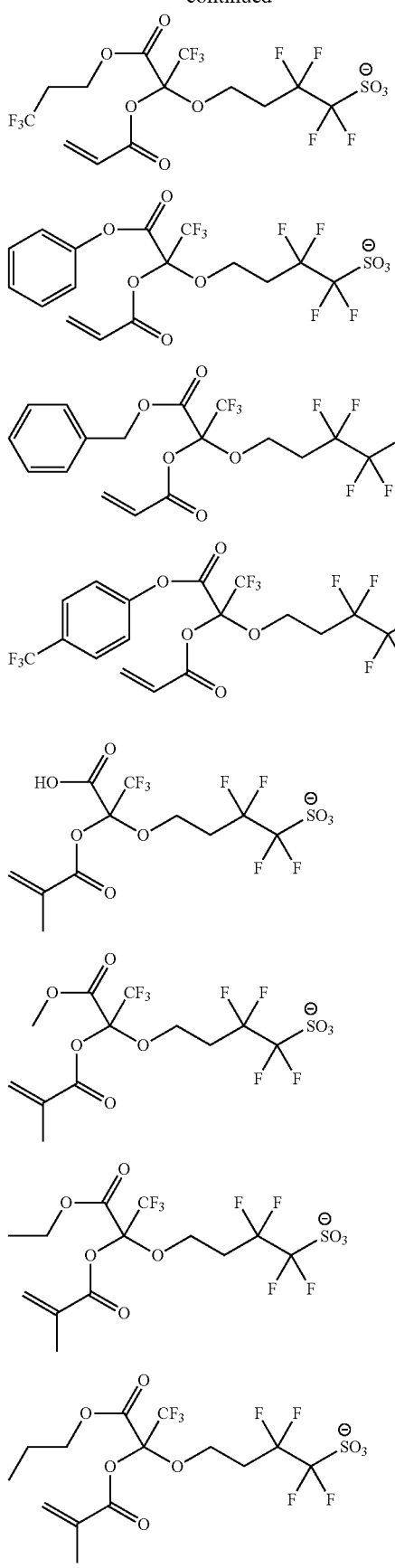
(E-5-22)

-continued
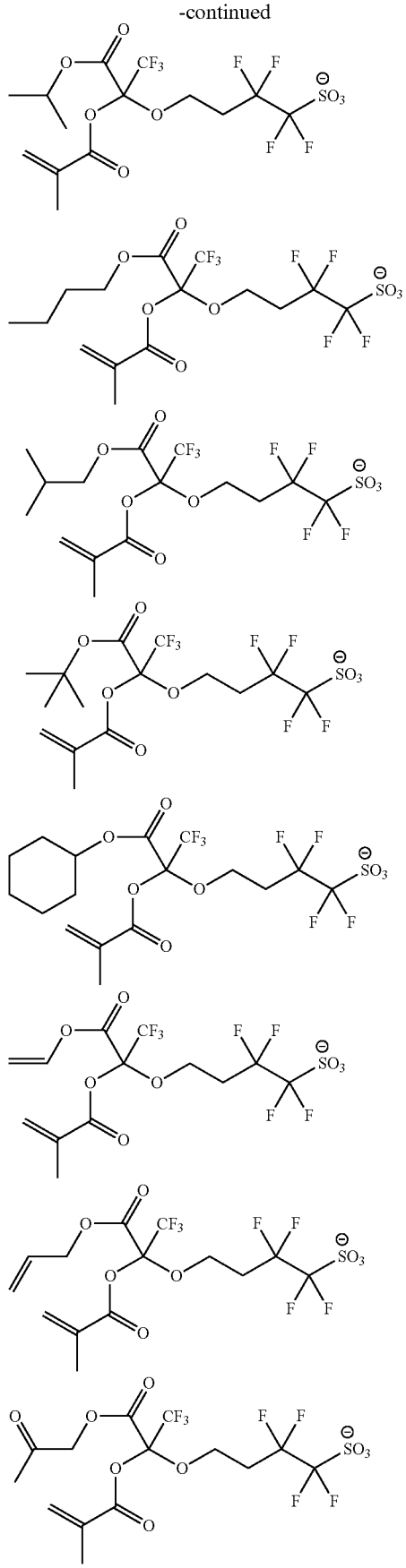
-continued
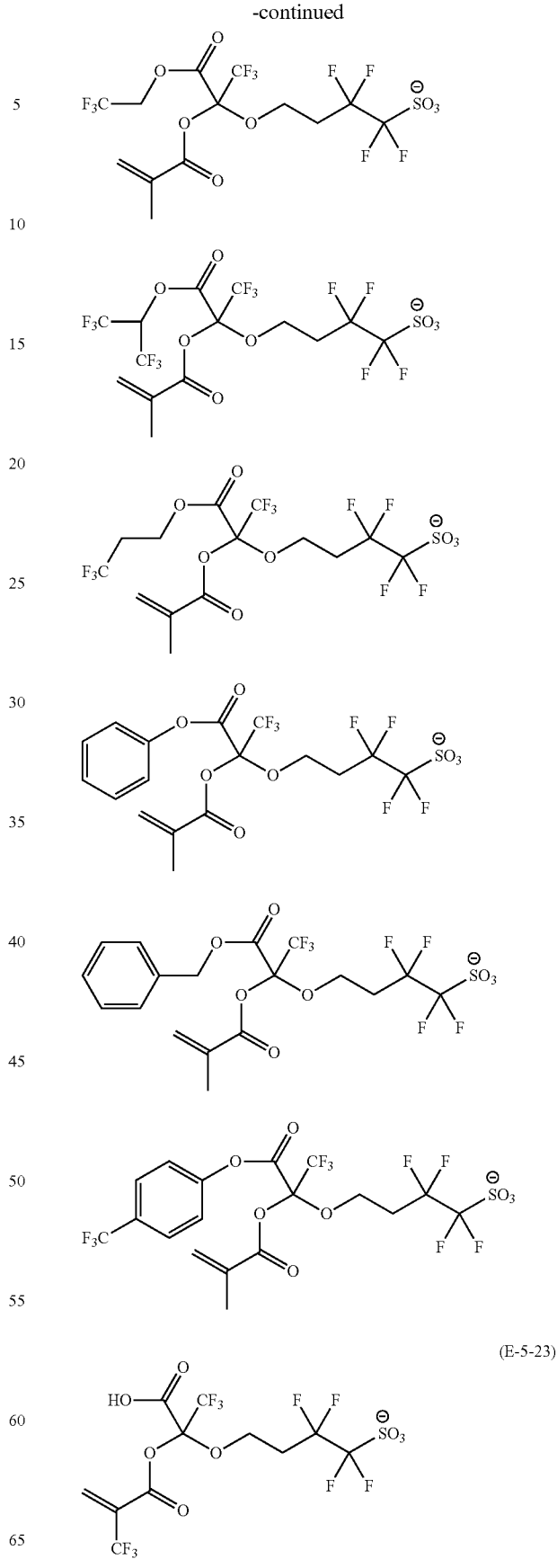
(E-5-23)

67
-continued
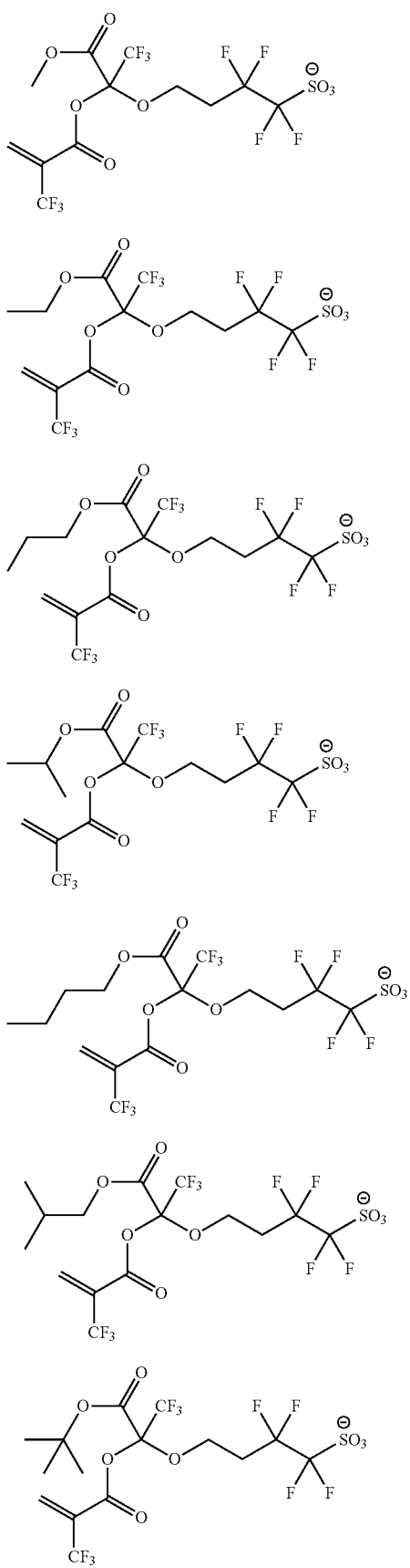
68
-continued
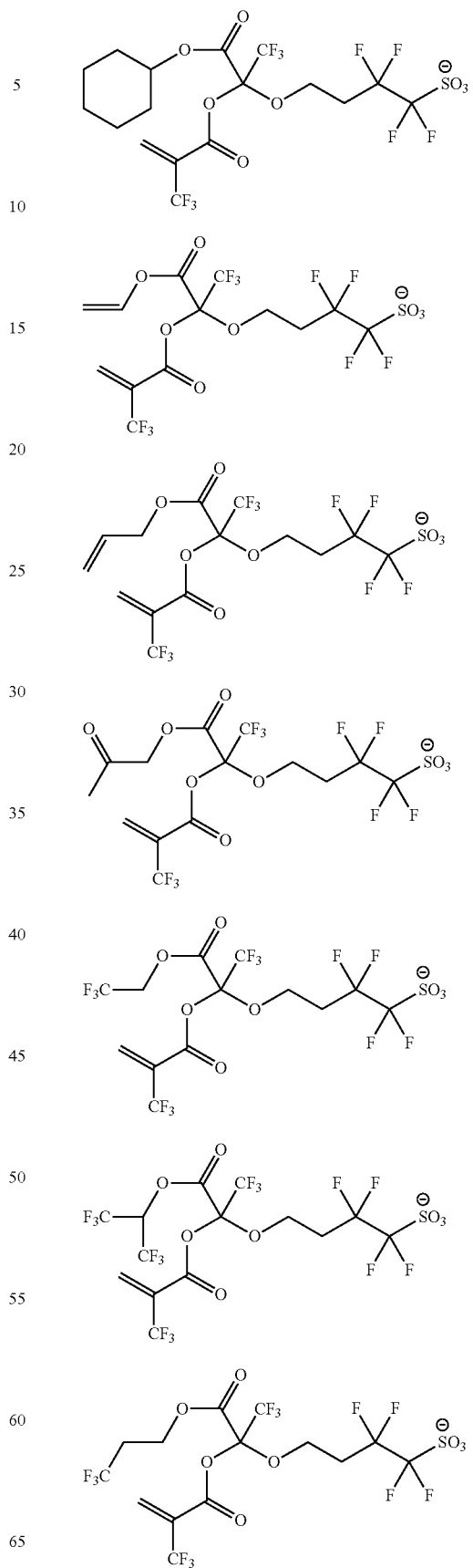

69
-continued
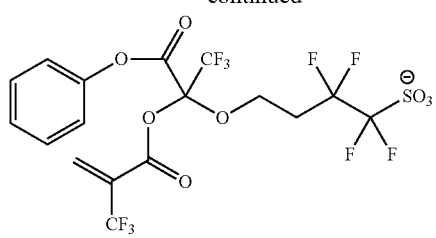
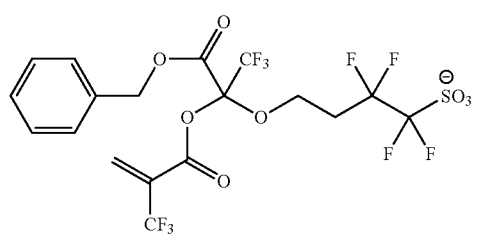
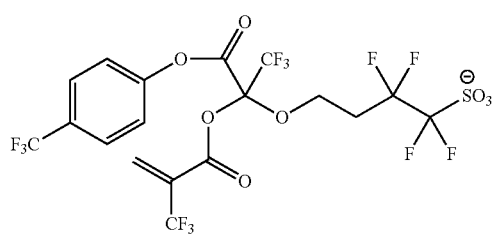
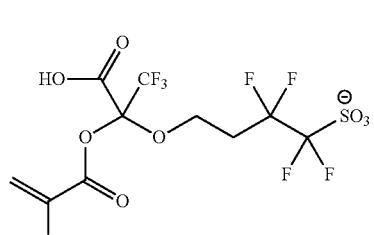
(E-5-24)
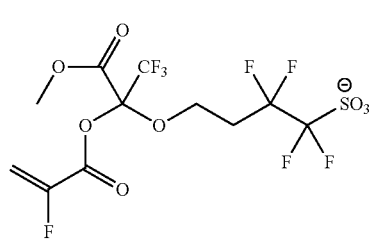
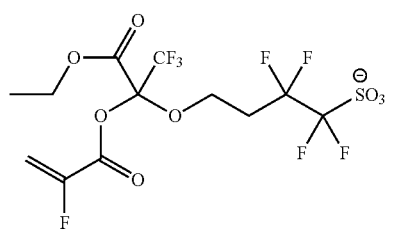
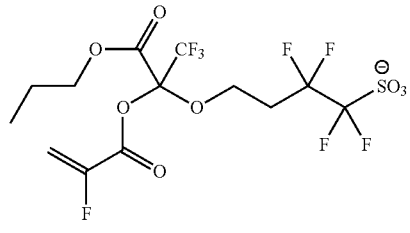
70
-continued
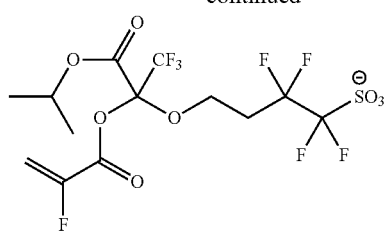
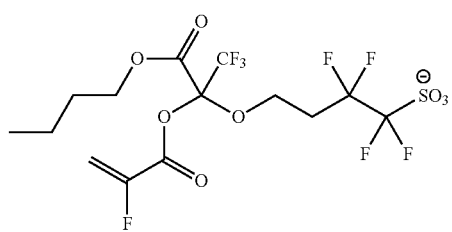
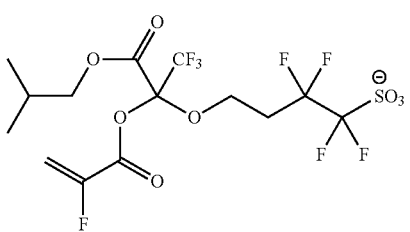
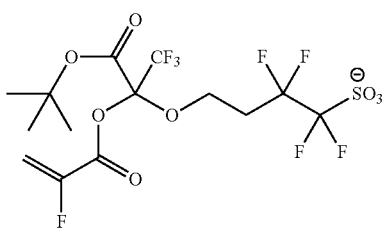
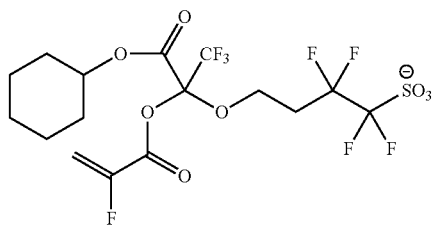
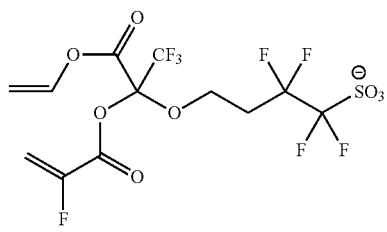
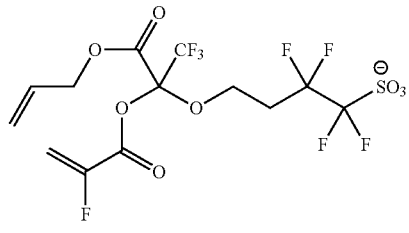

-continued
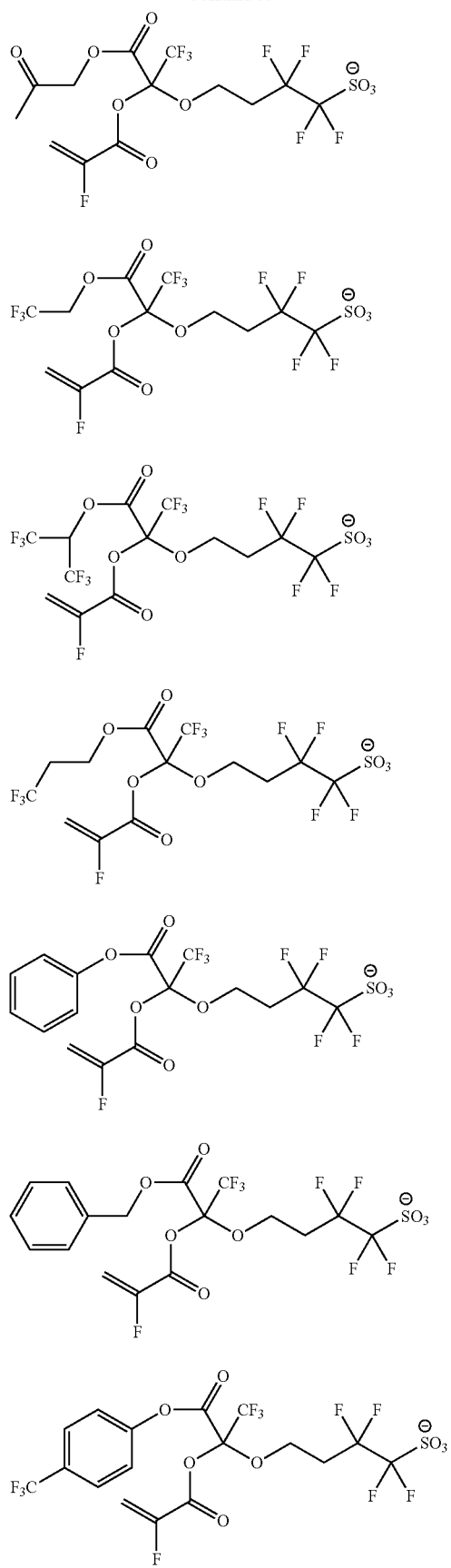
-continued
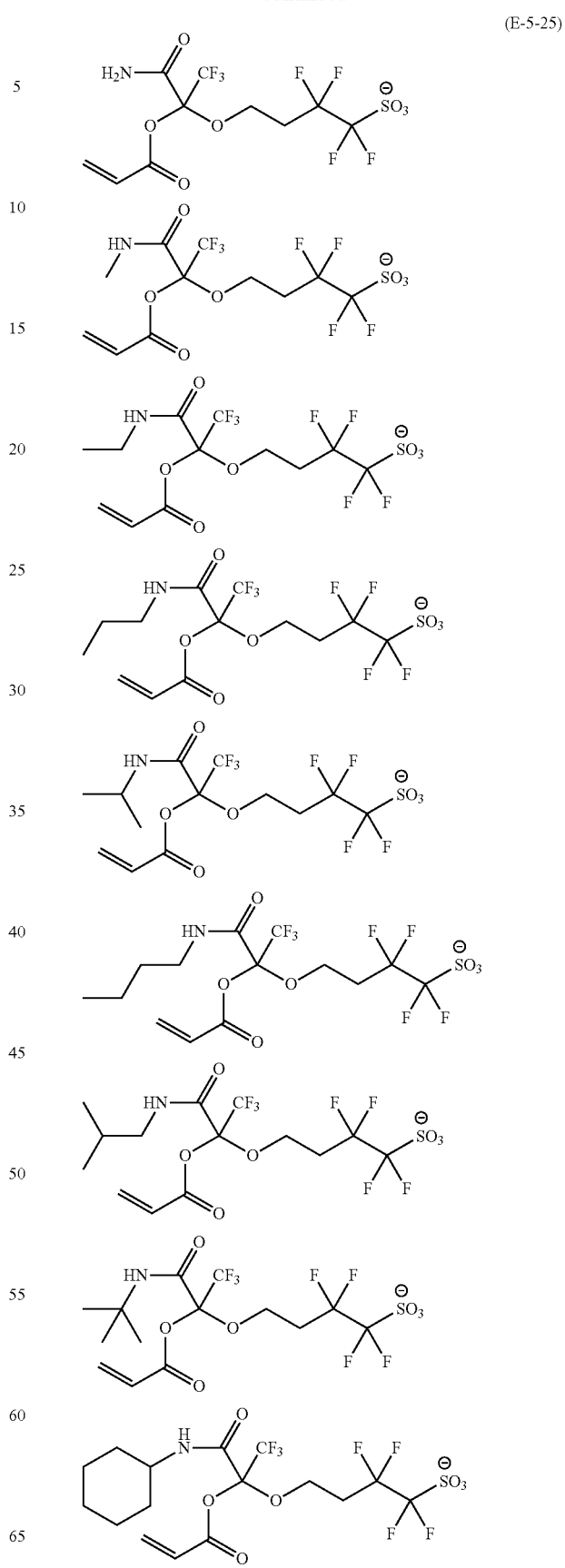
(E-5-25)

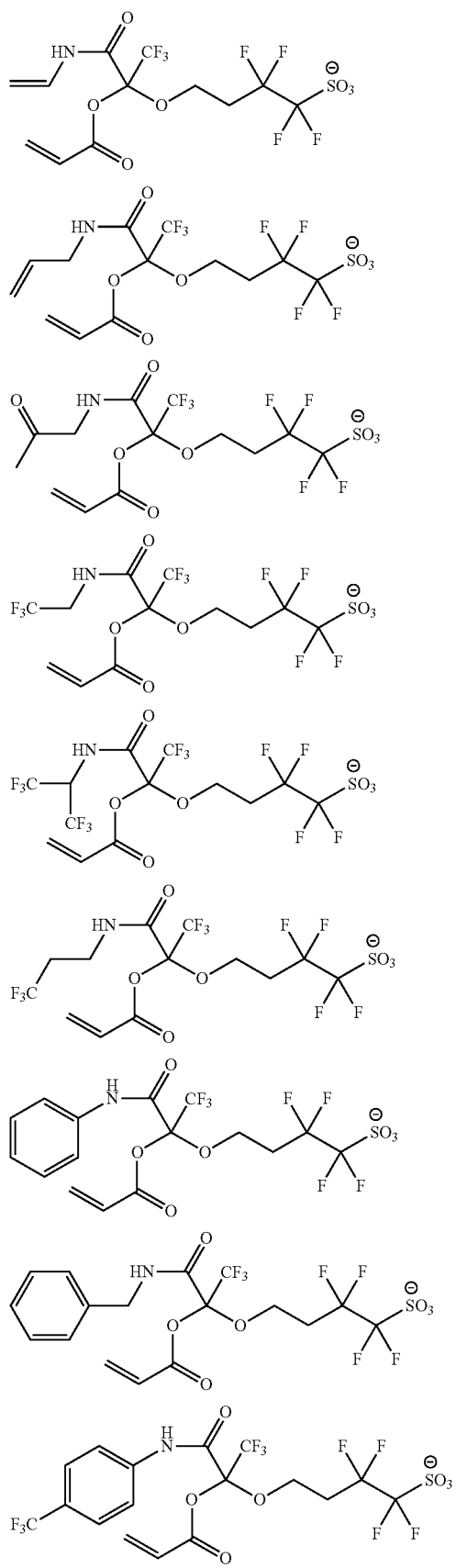
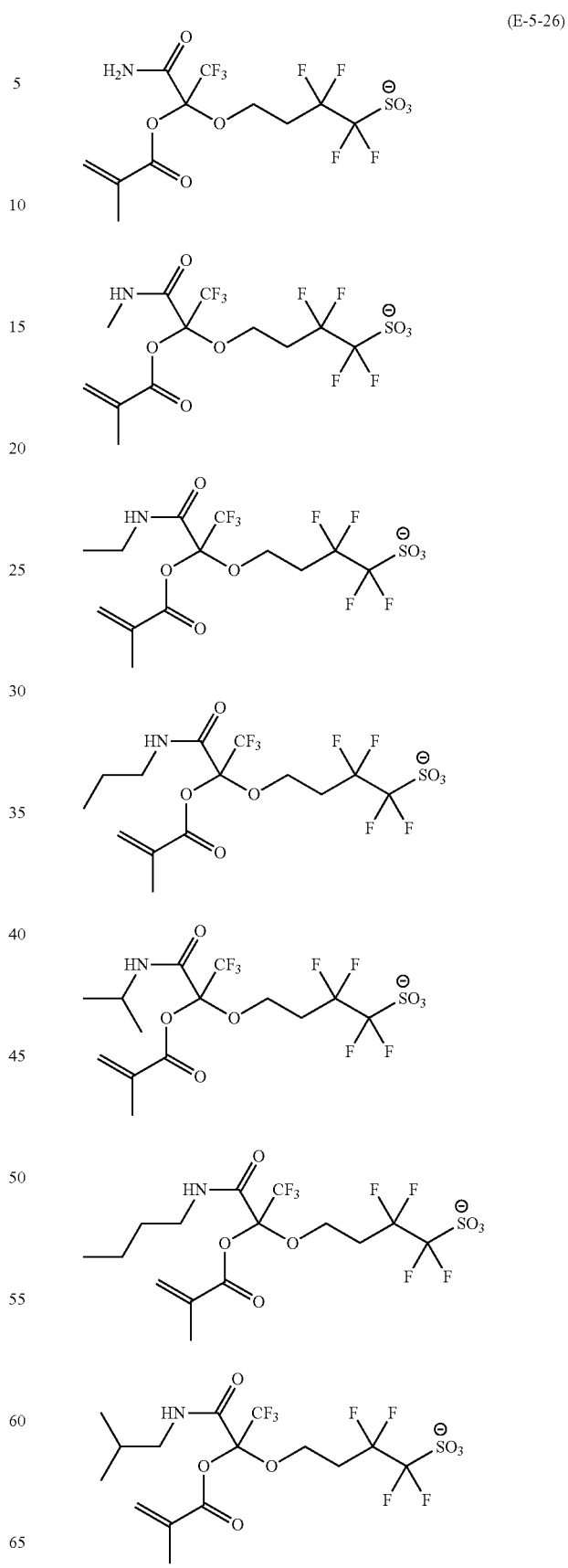
(E-5-26)

-continued
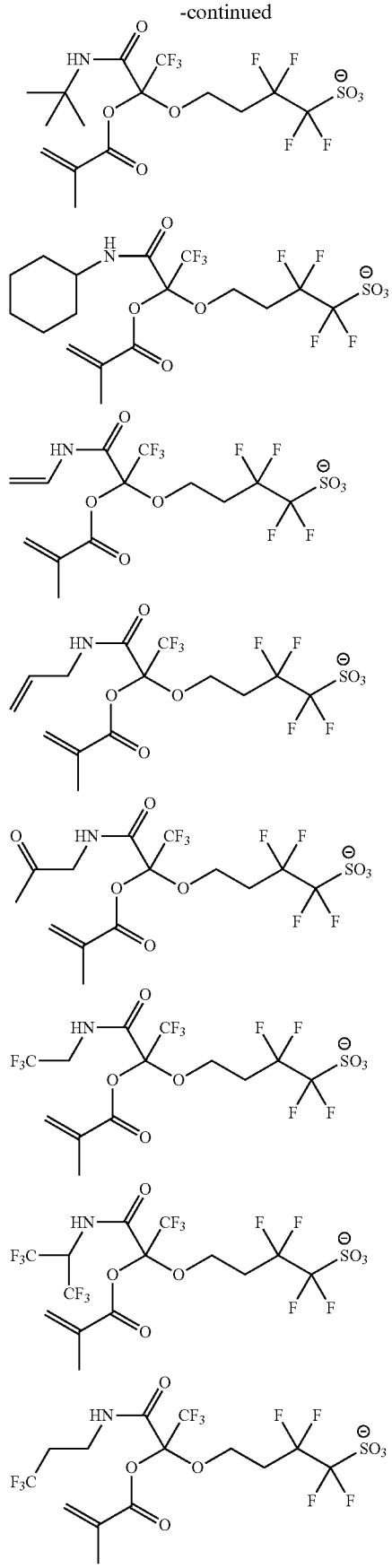
-continued
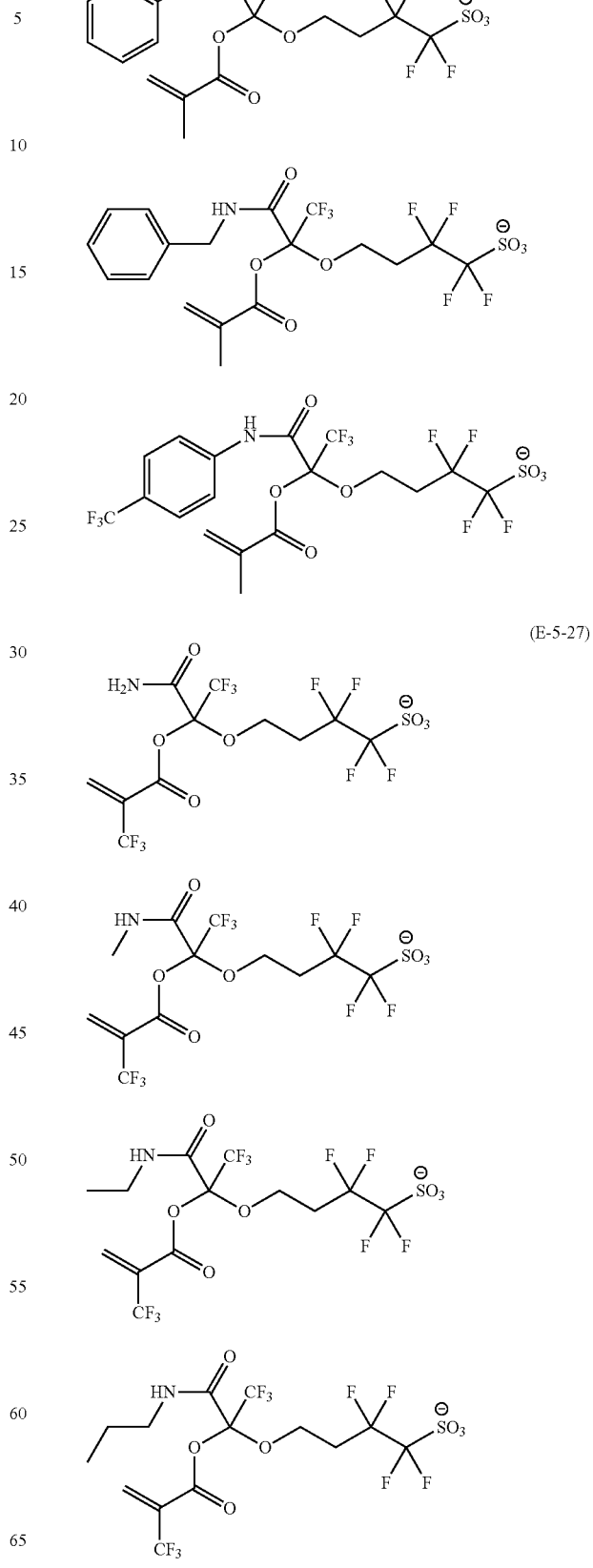
(E-5-27)

77
-continued
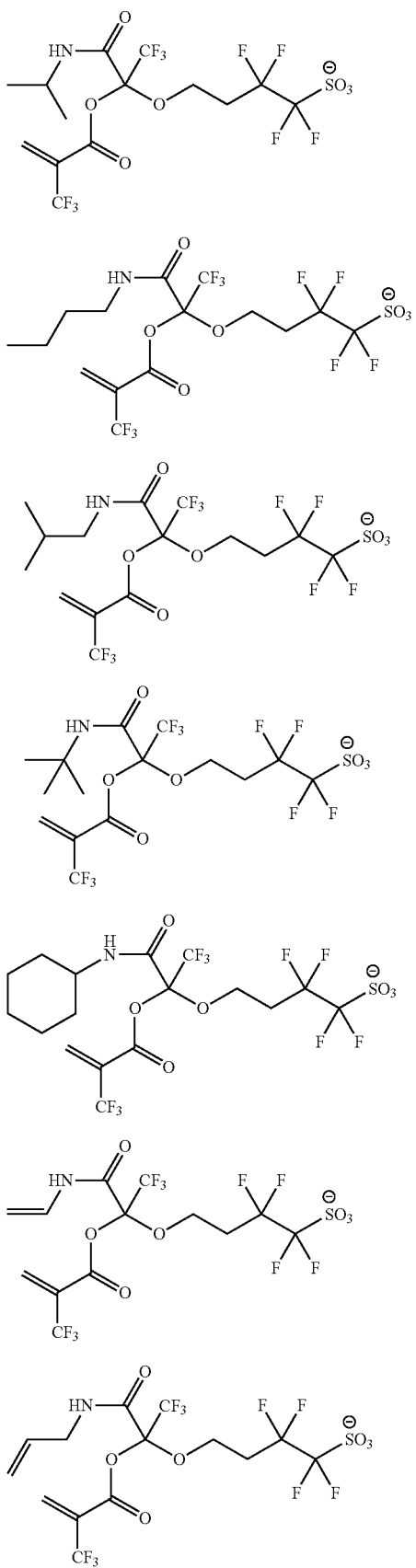
78
-continued
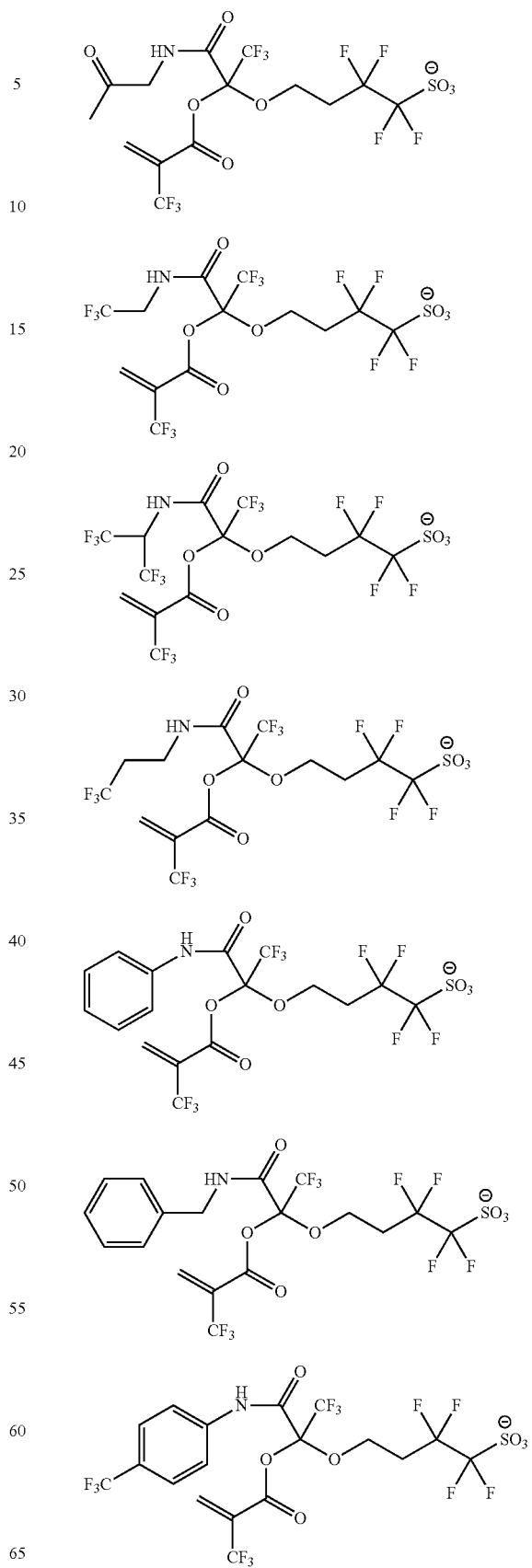

(E-5-28)
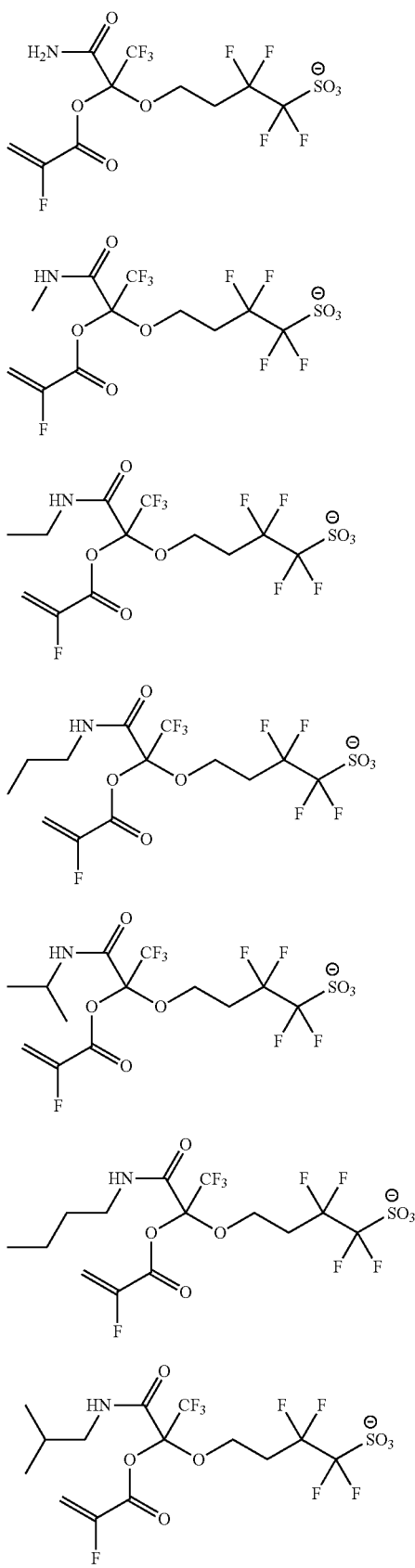
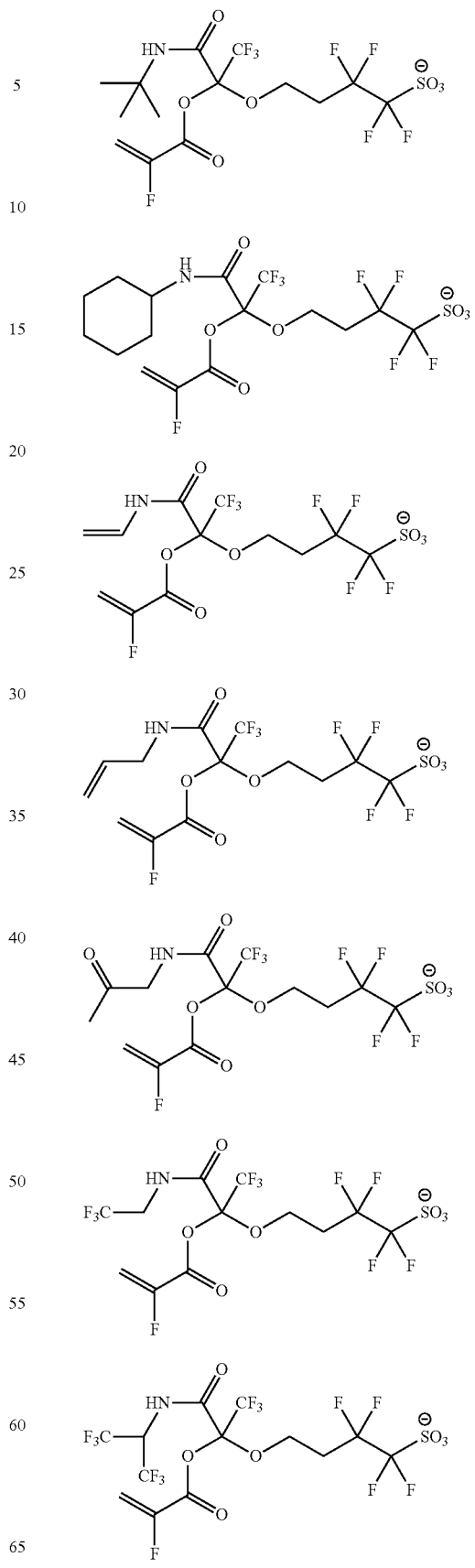

-continued
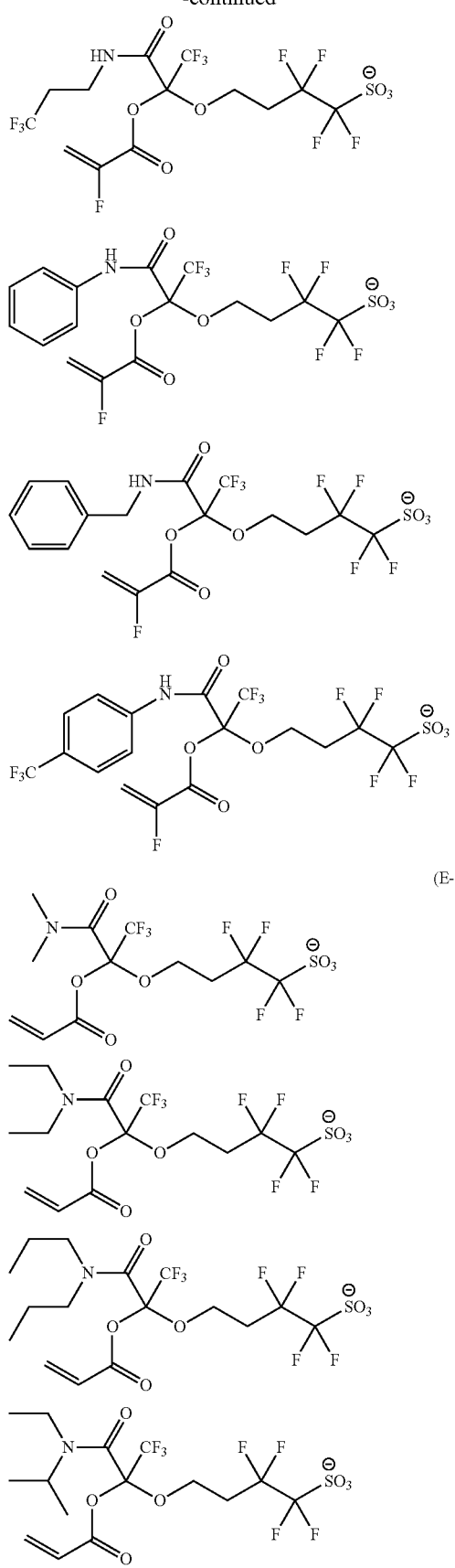
(E-5-29)
-continued
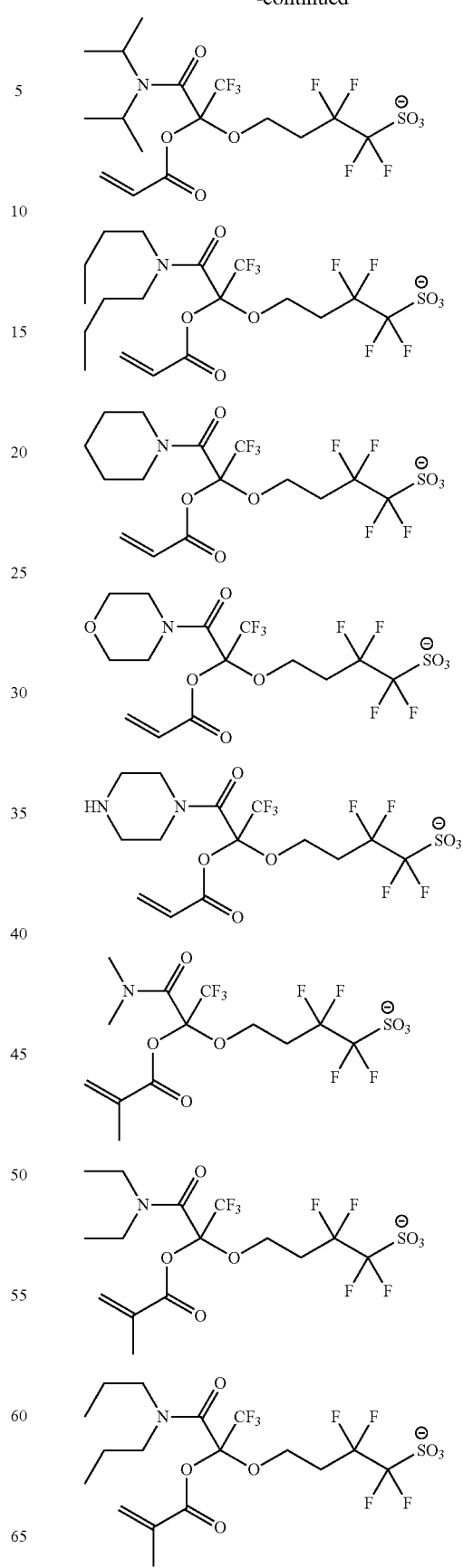

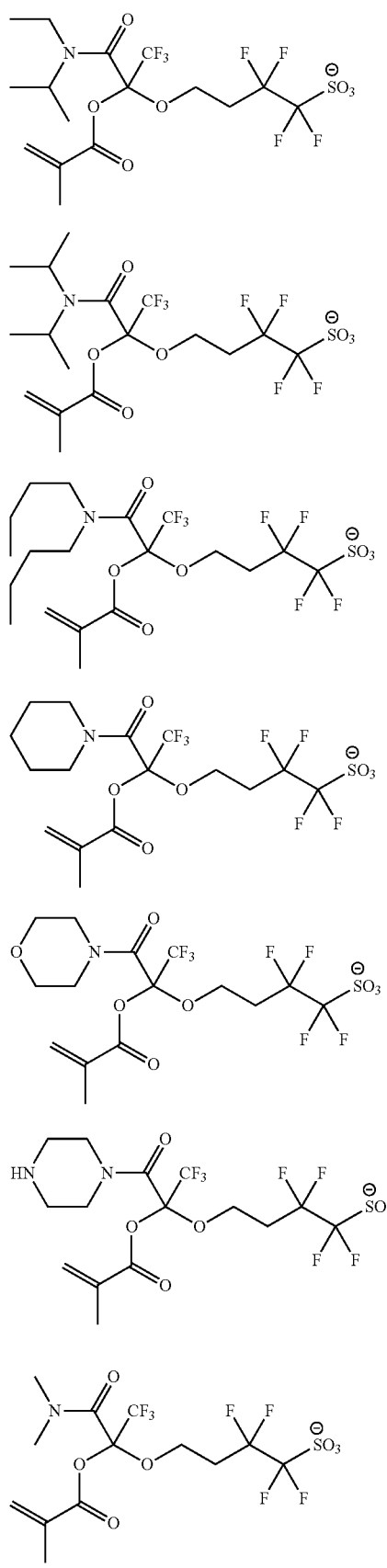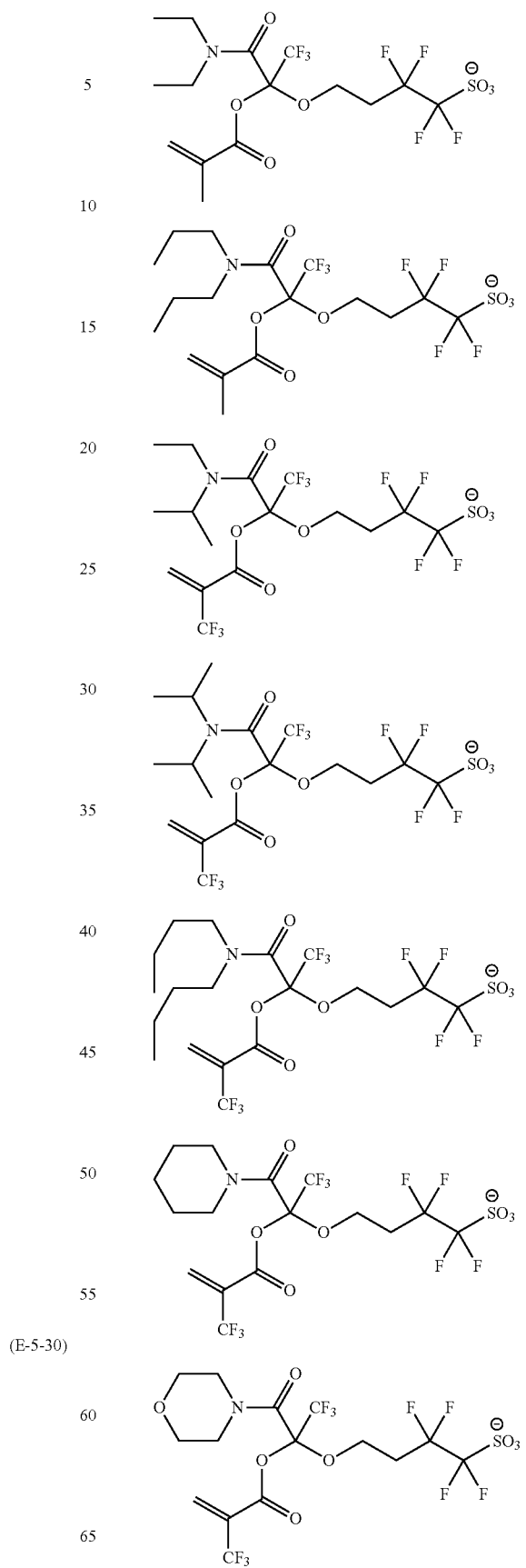
(E-5-30)

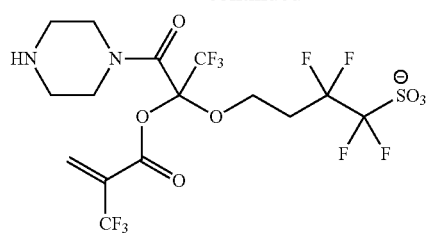
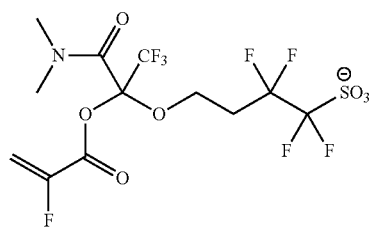
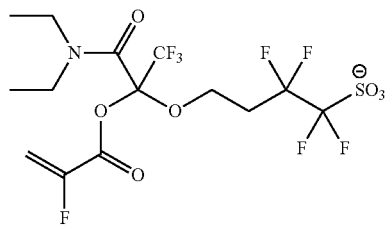
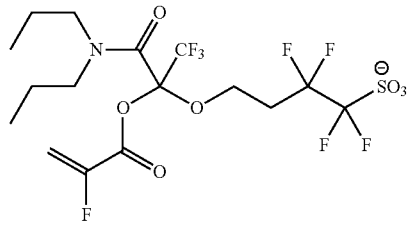
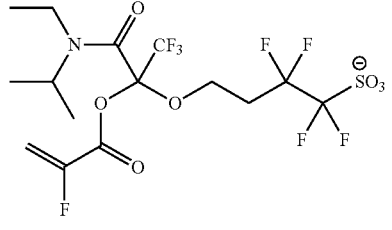
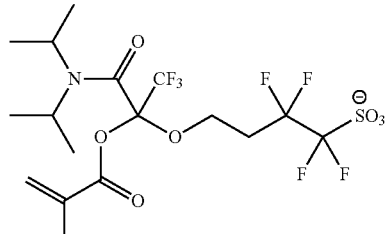
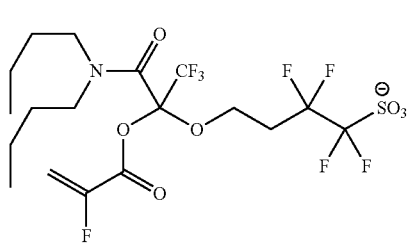
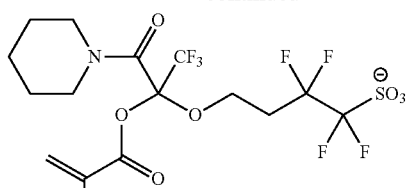
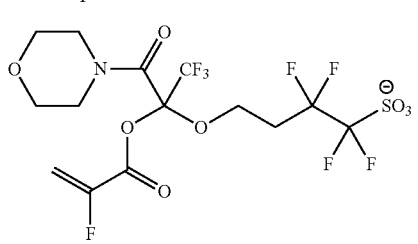
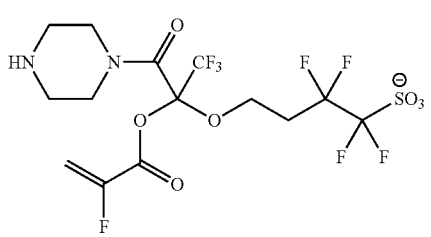
(E-5-31)
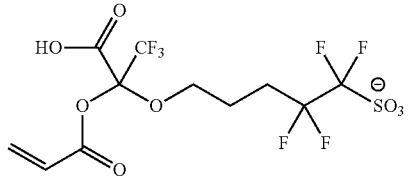
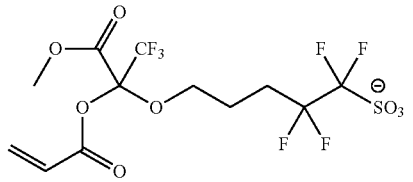
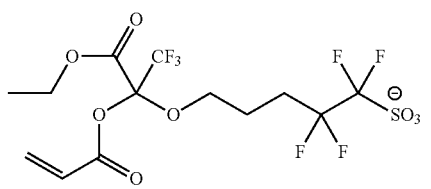
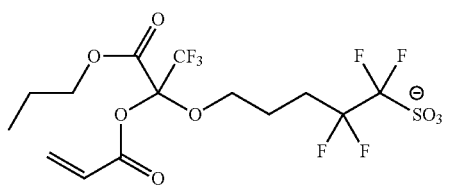
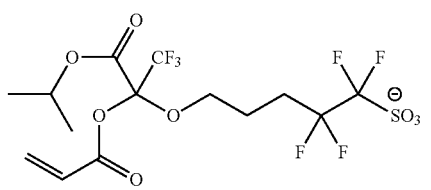

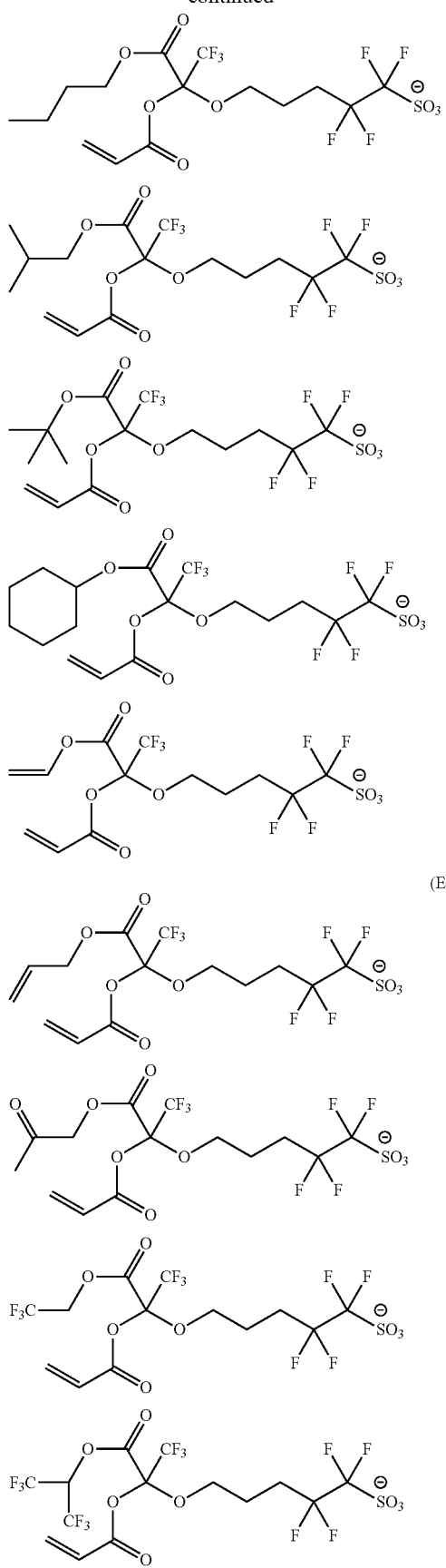
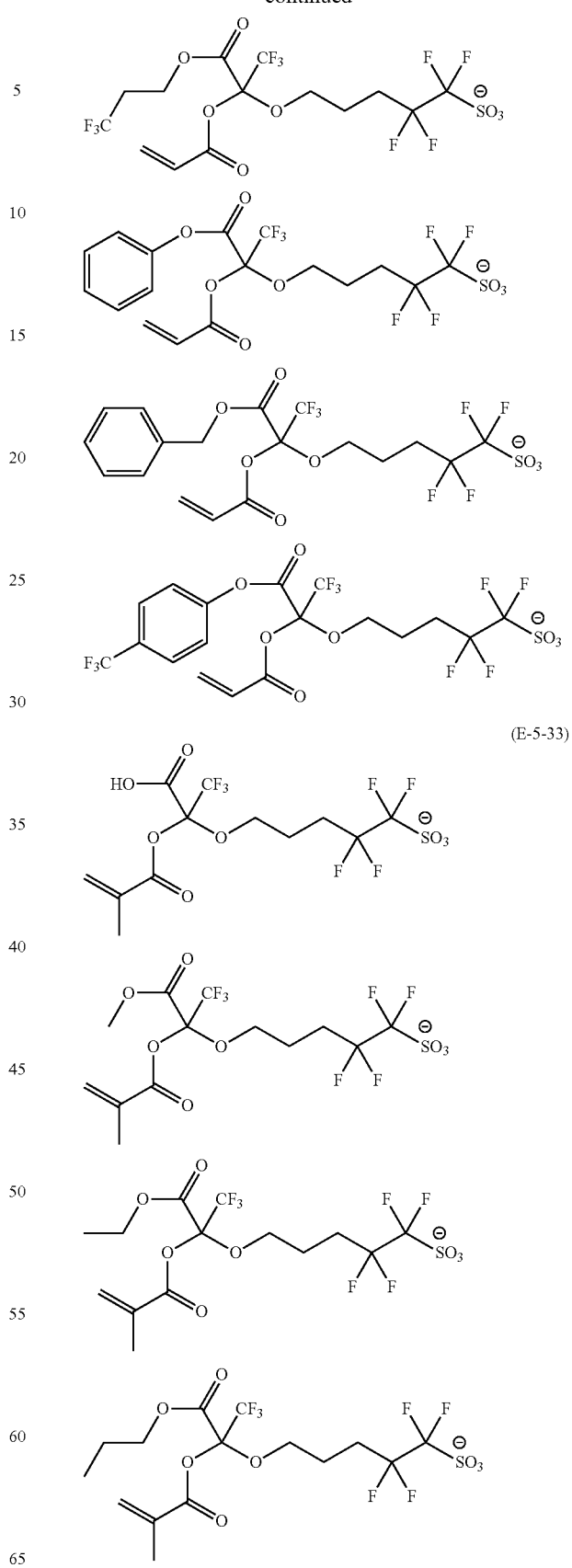
(E-5-32)
(E-5-33)

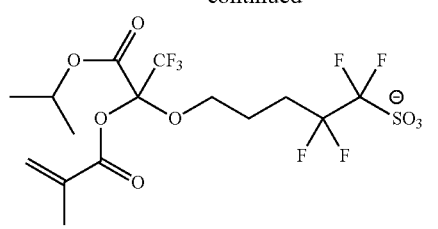
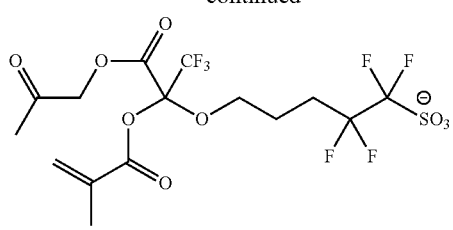
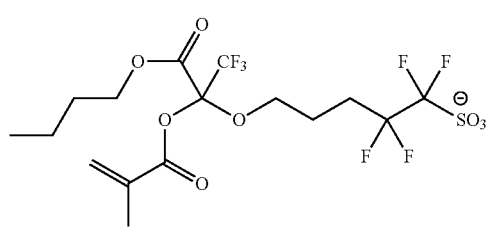
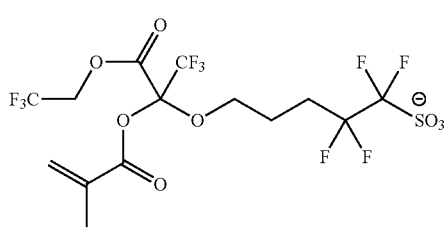
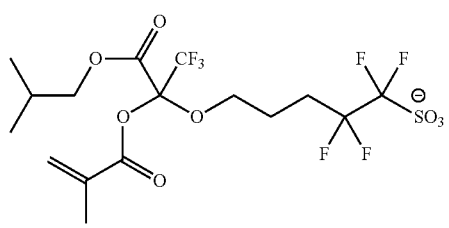
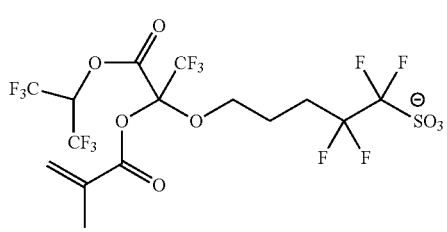
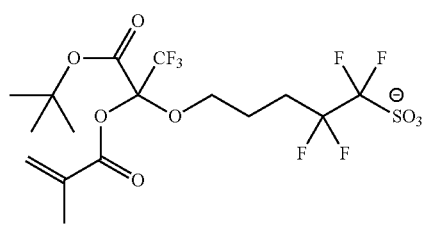
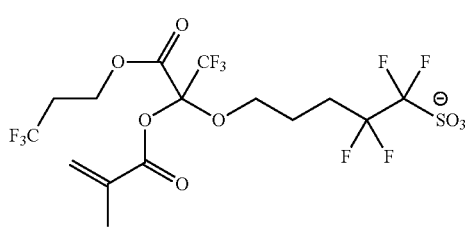
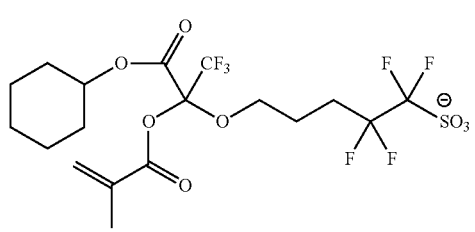
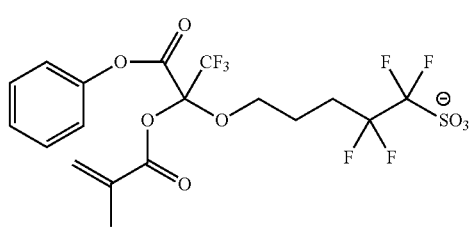
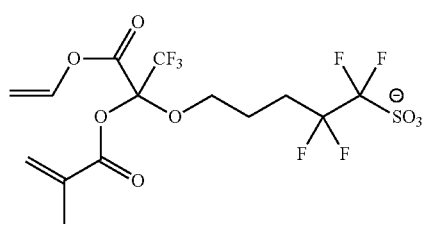
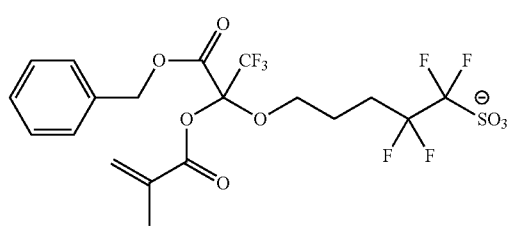
(E-5-34)
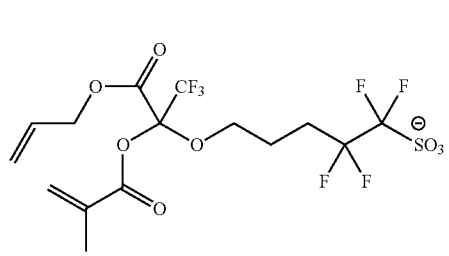
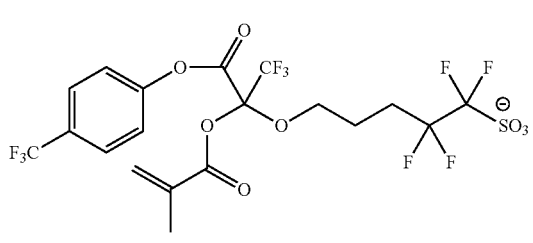

-continued
(E-5-35)
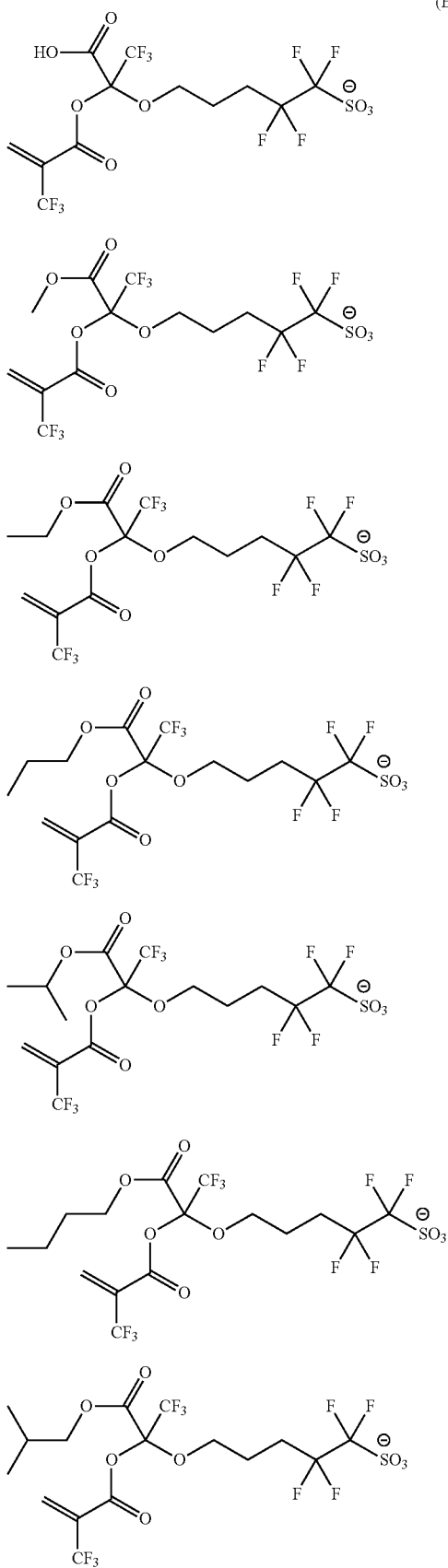
-continued
(E-5-36)
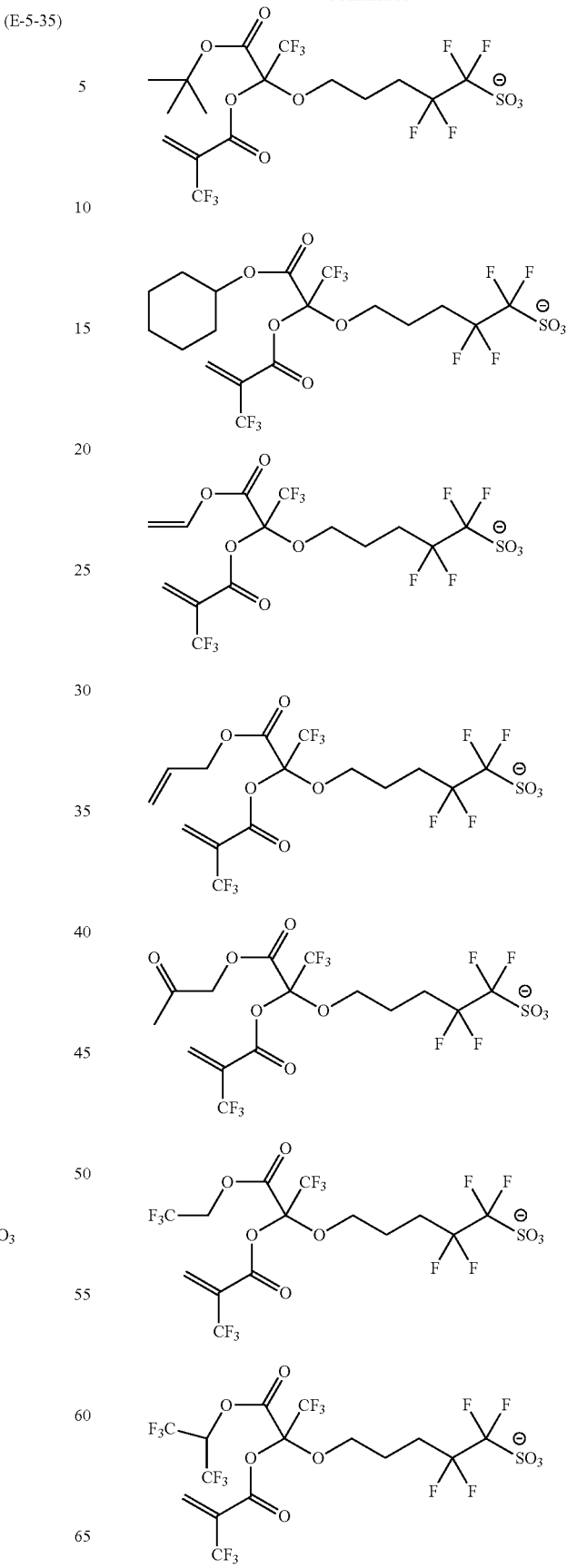

93
-continued
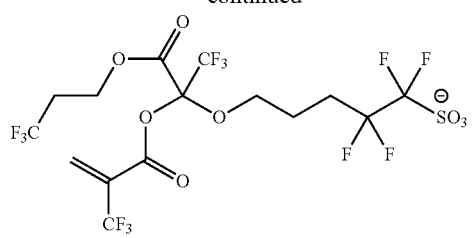
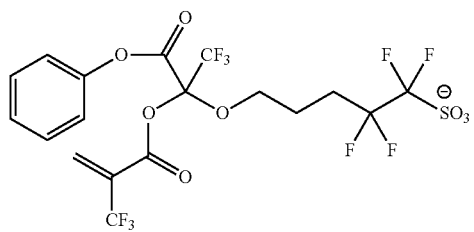
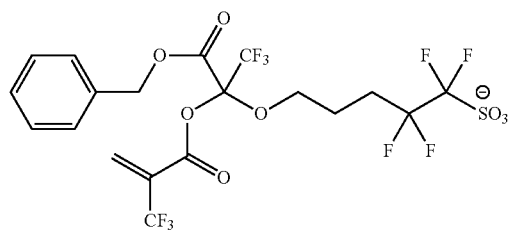
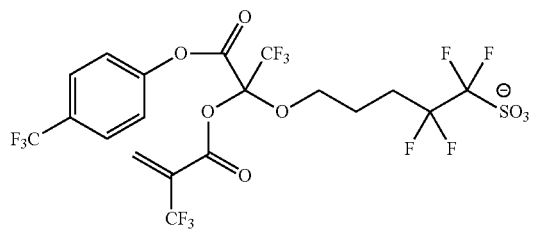
(E-5-37)
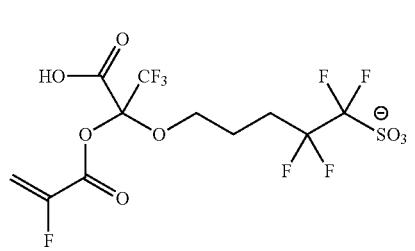
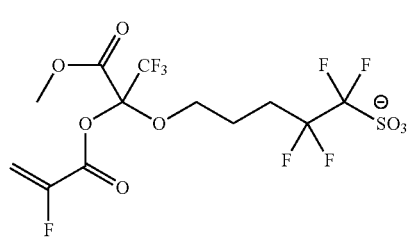
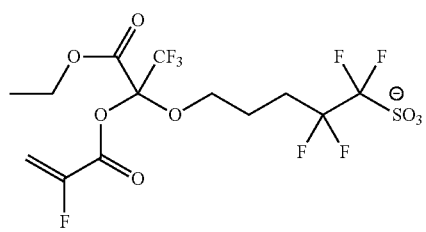
94
-continued
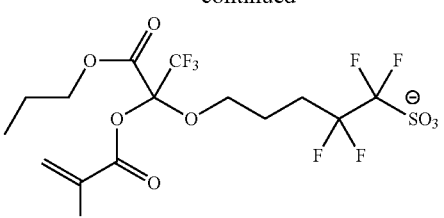
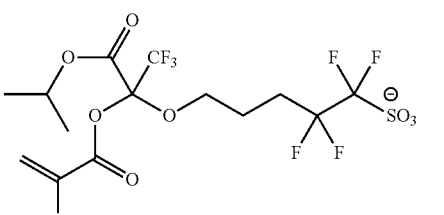
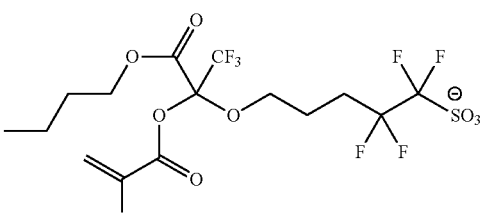
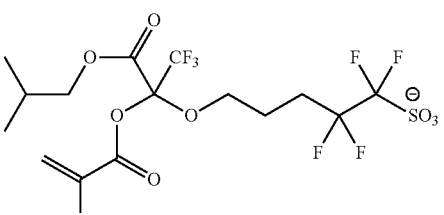
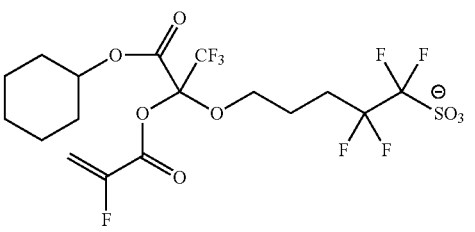
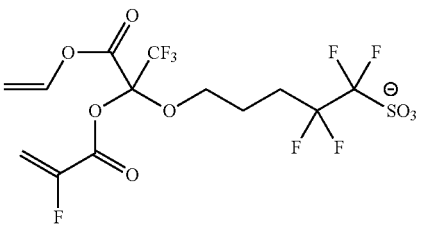

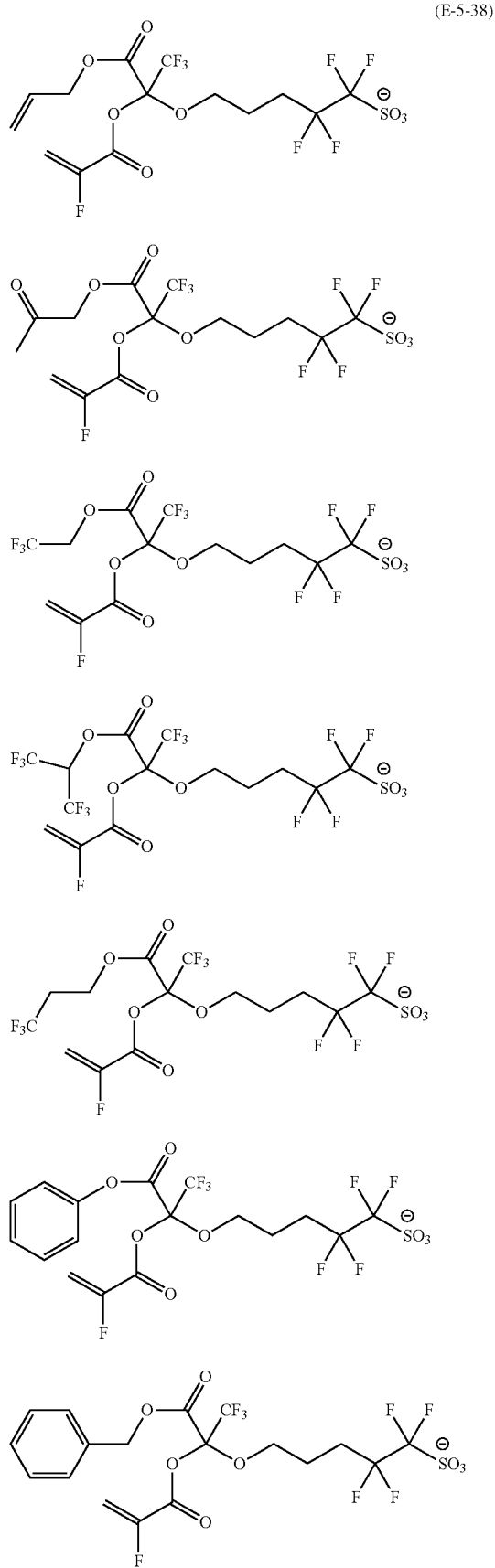
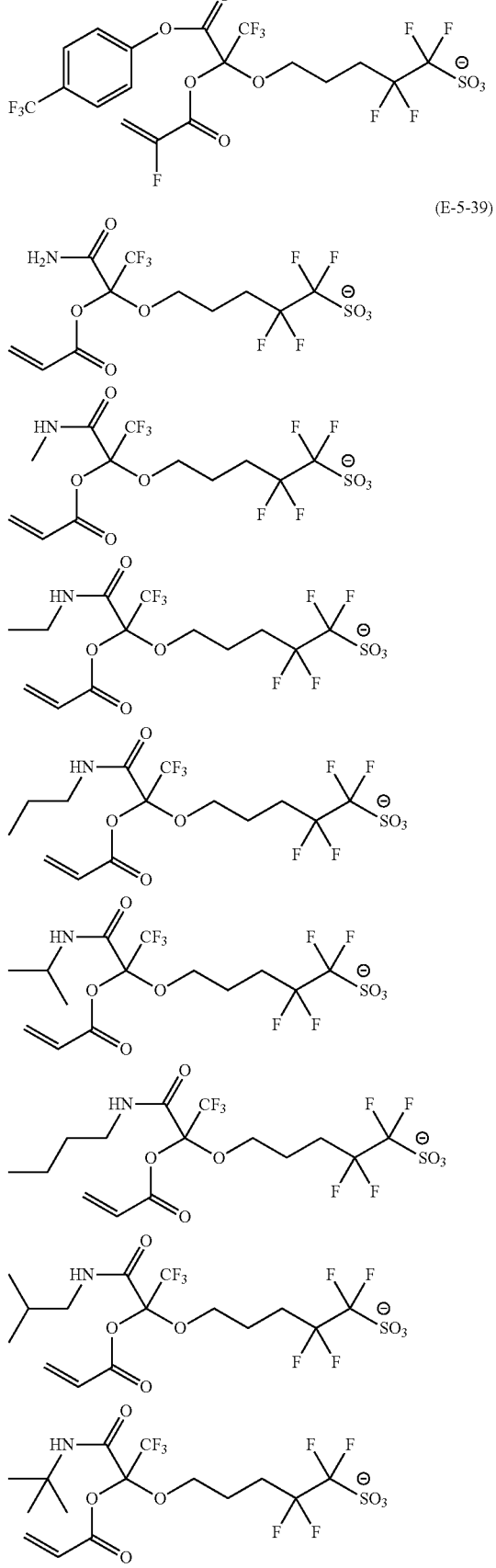

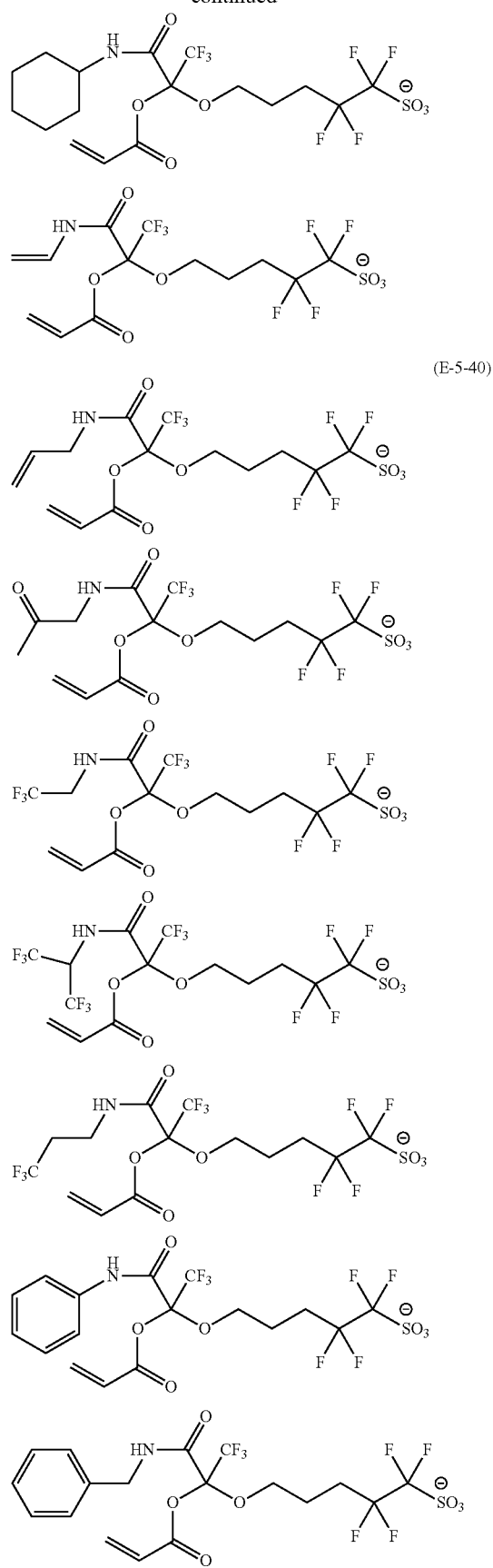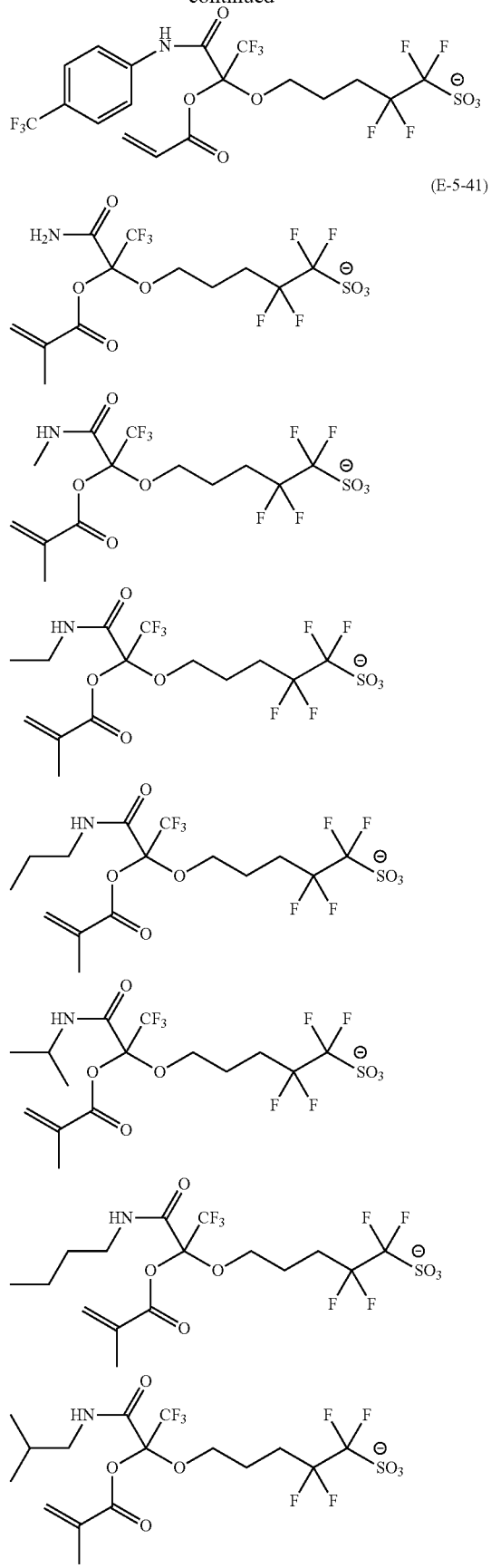
(E-5-40)
(E-5-41)

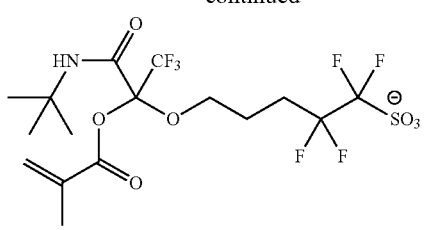
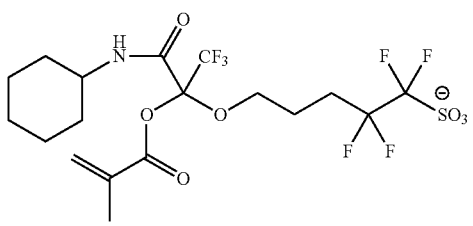
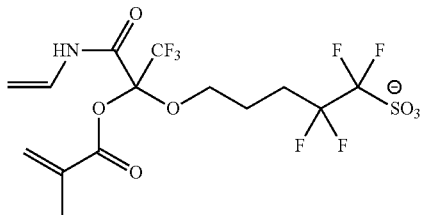
(E-5-42)
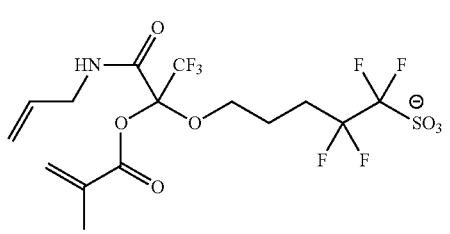
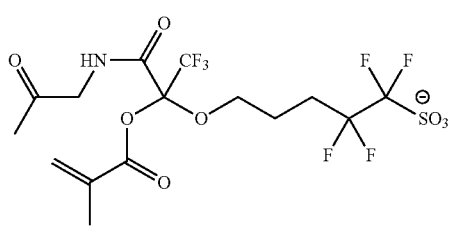
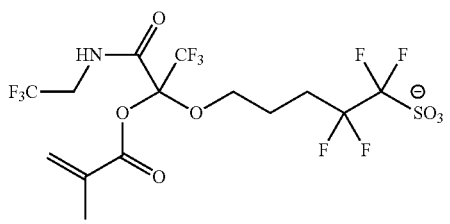
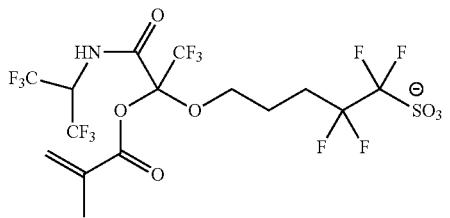
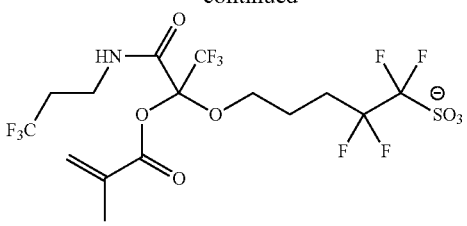
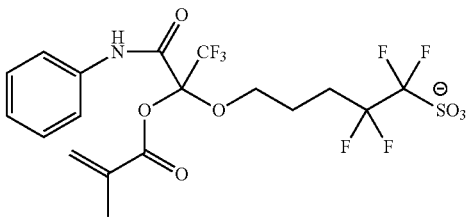
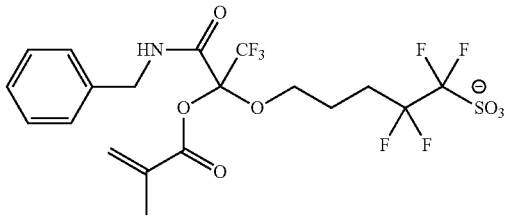
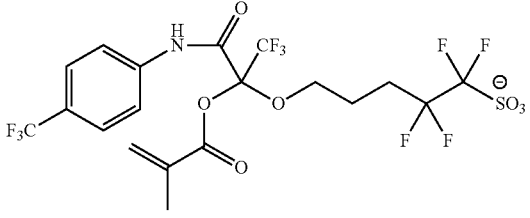
(E-5-43)
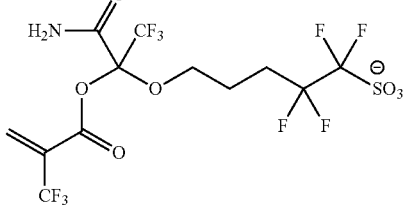
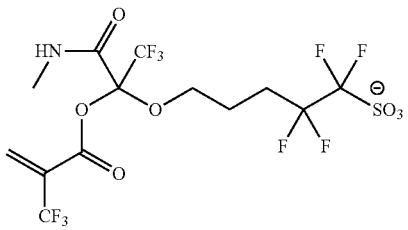
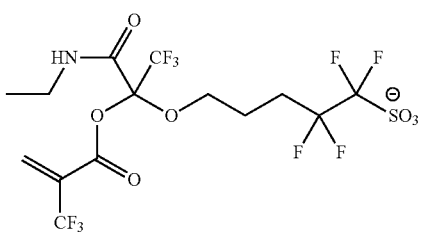

101
-continued
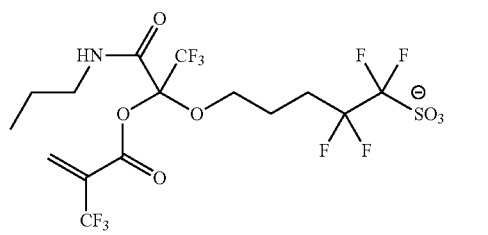
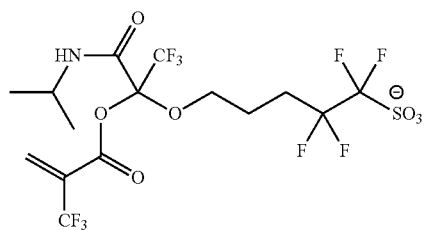
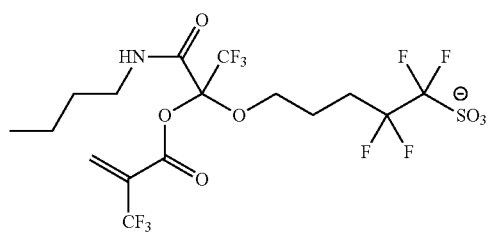
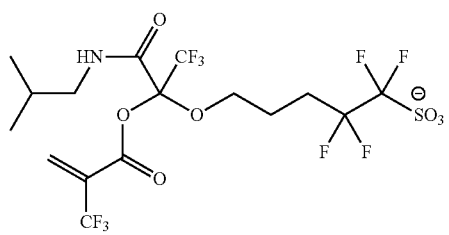
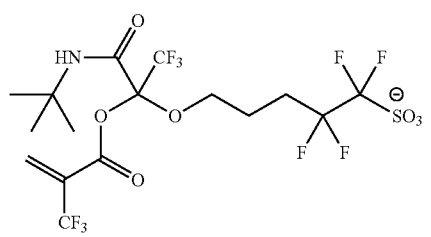
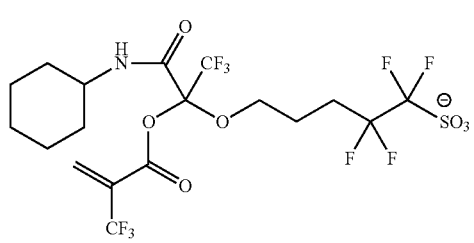
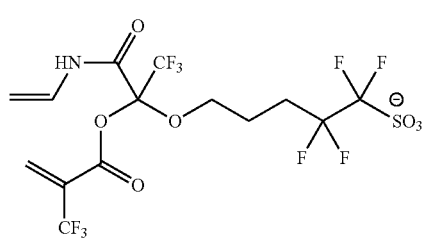
102
-continued
(E-5-44)
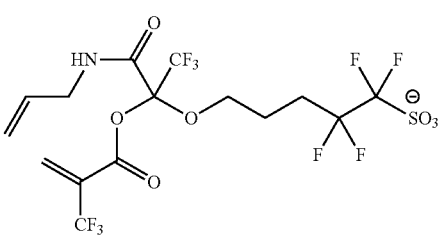
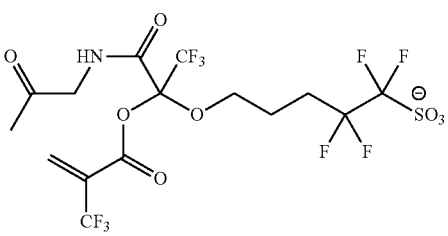
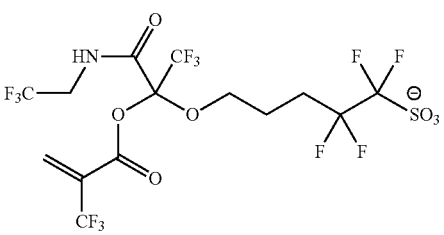
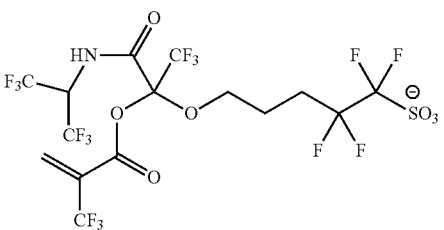
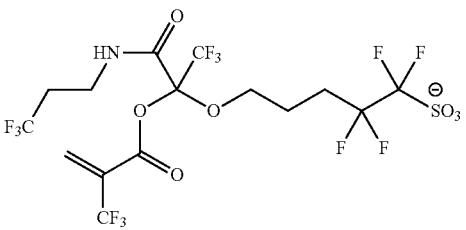
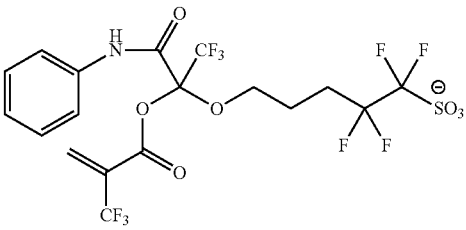
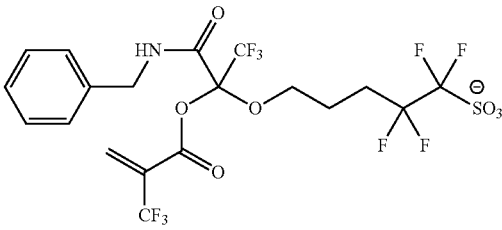

103
-continued
104
-continued
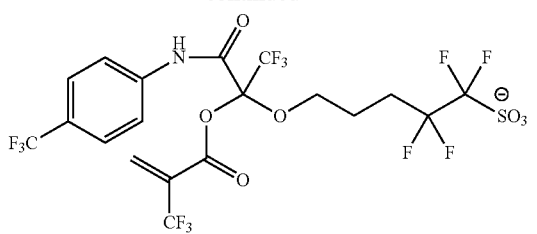
(E-5-45)
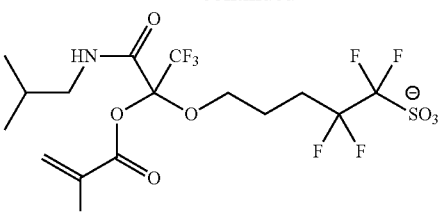
(E-5-46)
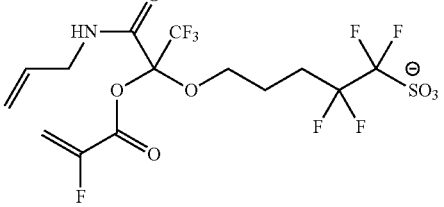
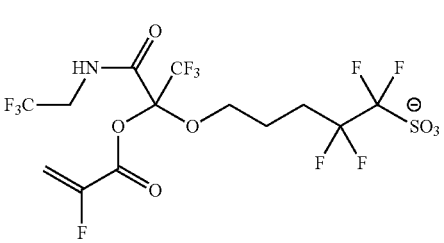

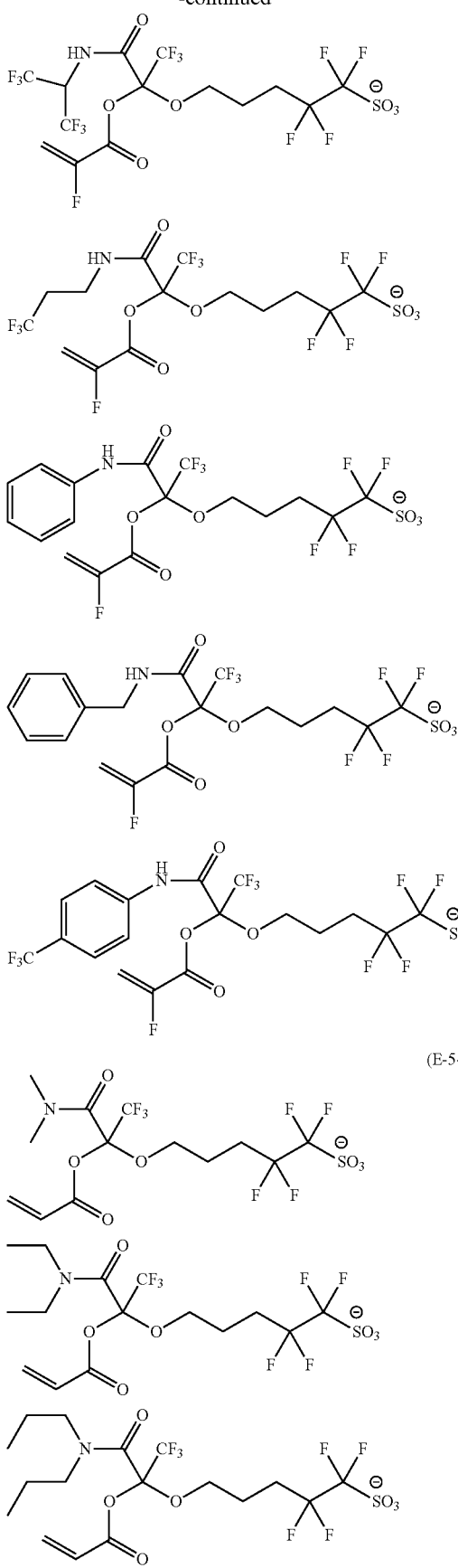
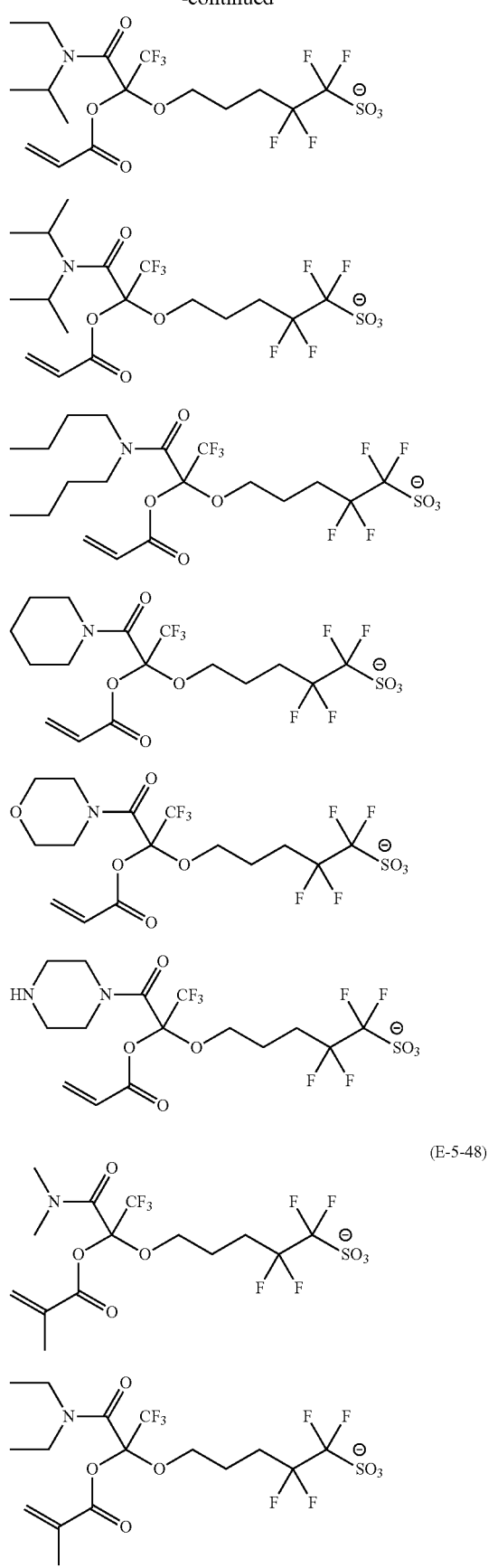

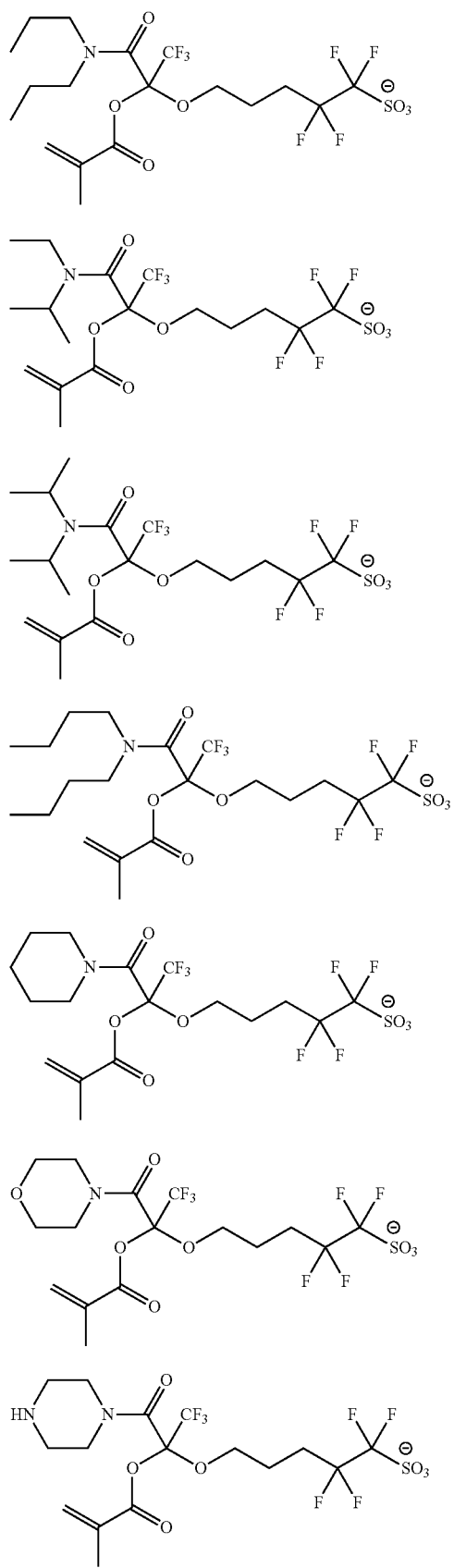
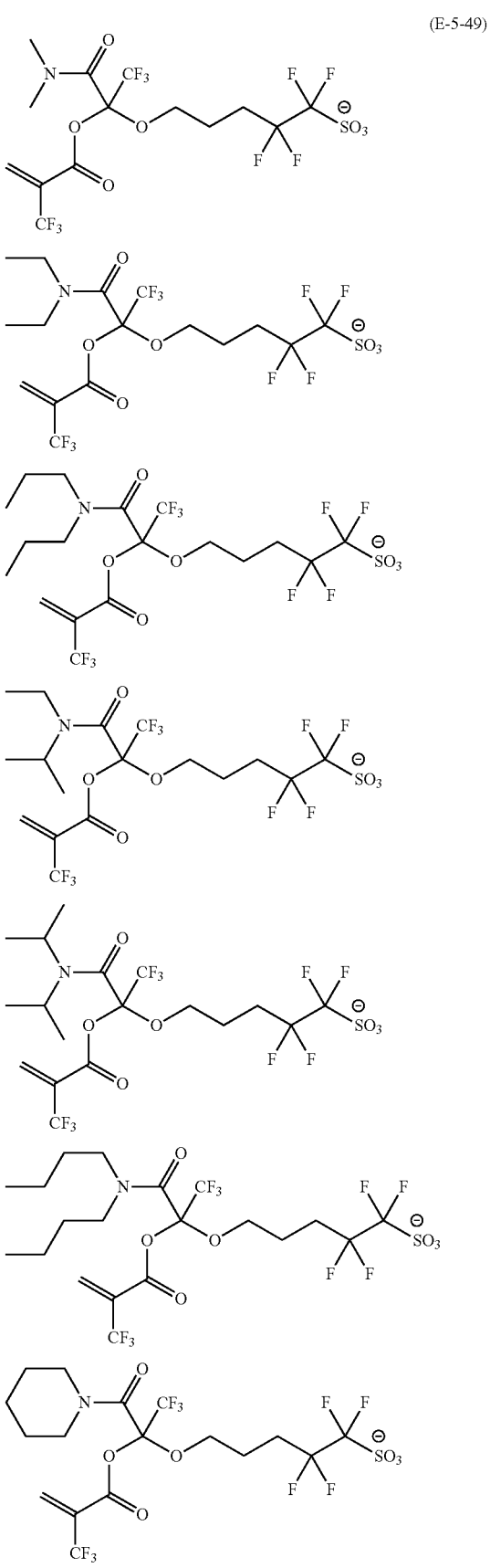
(E-5-49)

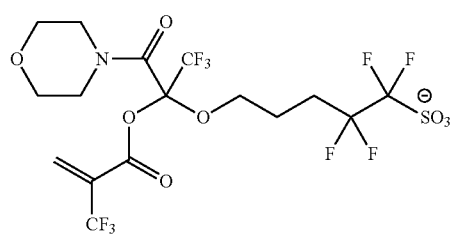
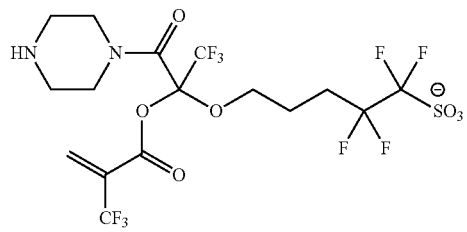
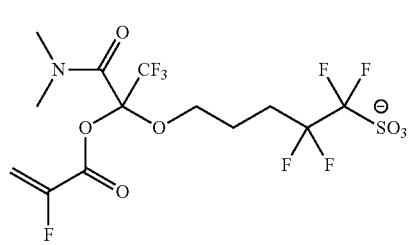
(E-5-50)
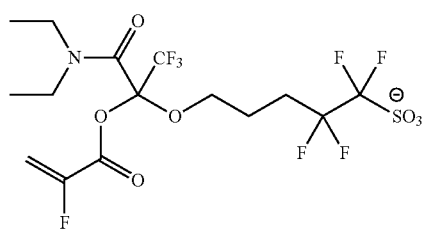
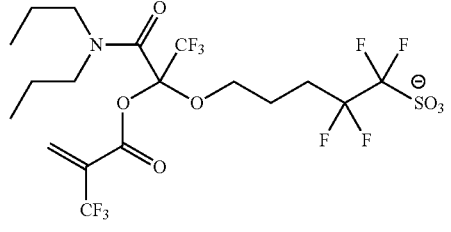
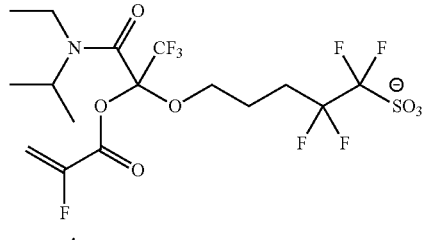
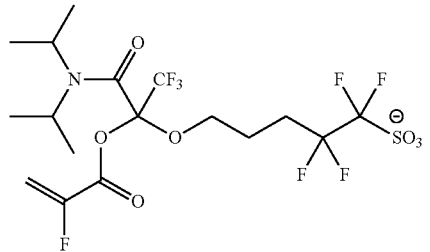
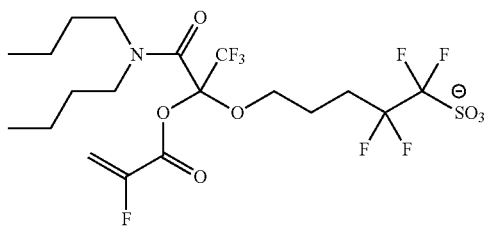
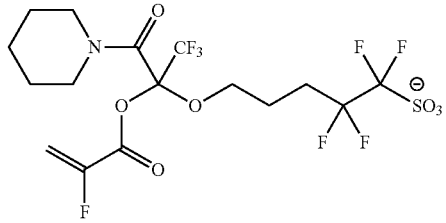
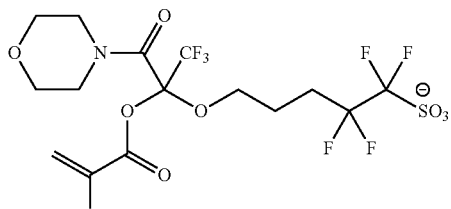
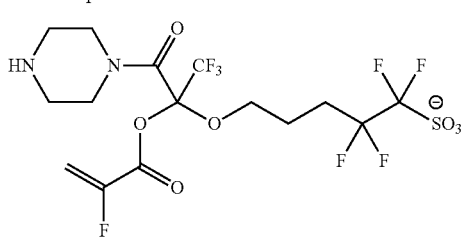
(E-5-51)
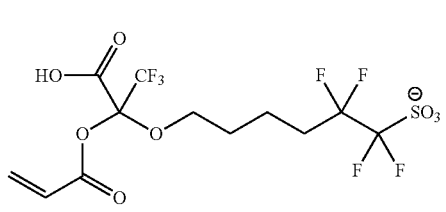
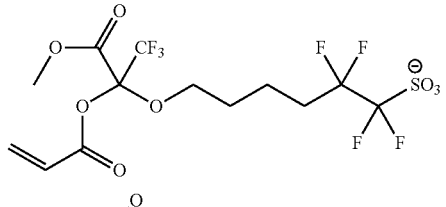
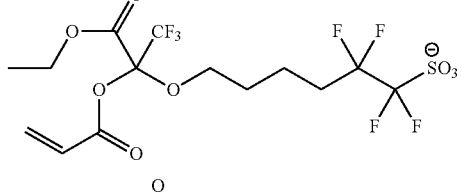
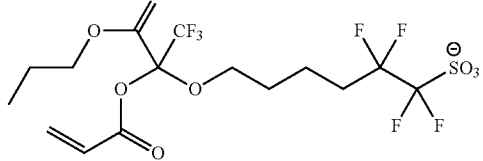

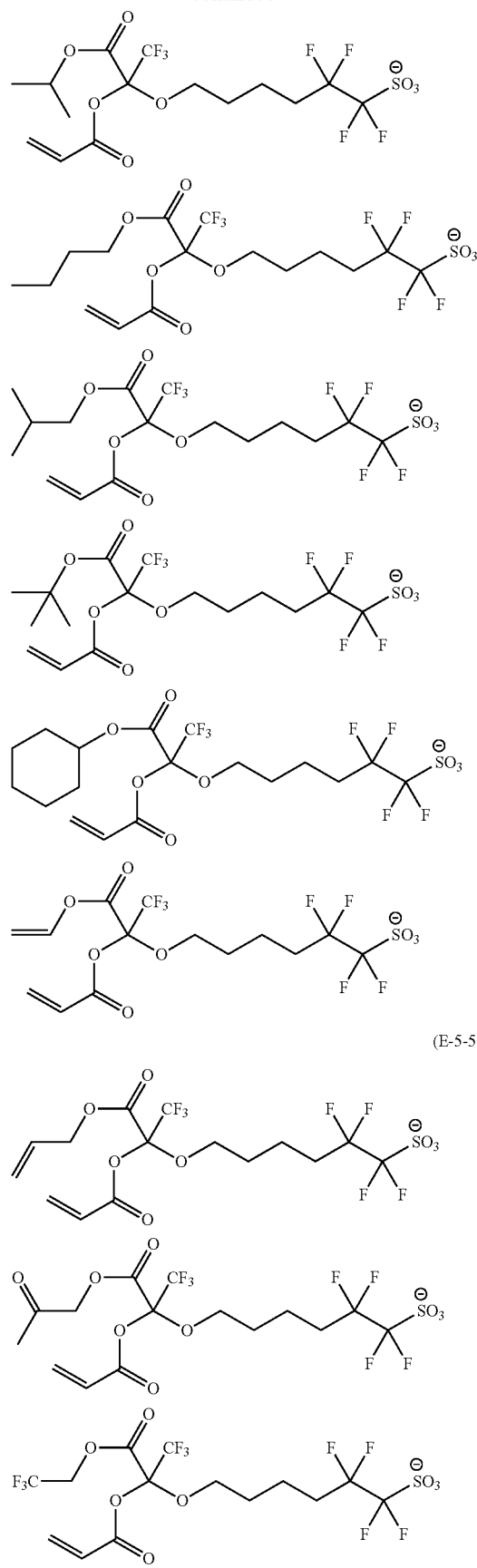
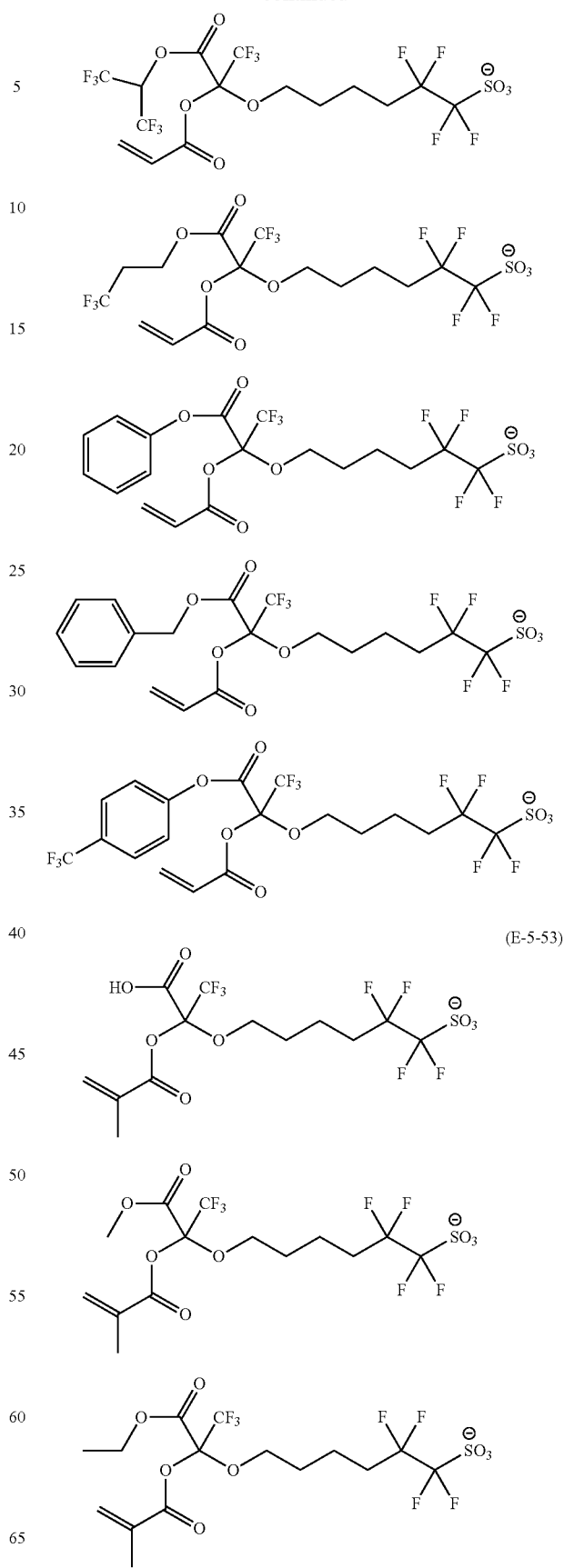

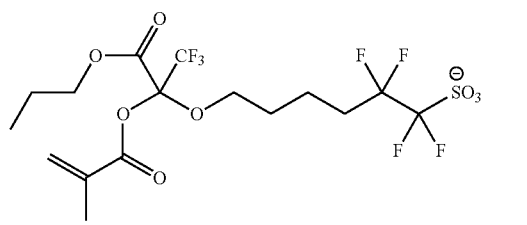
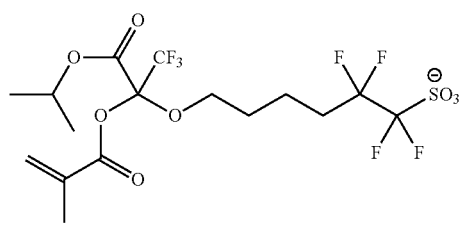
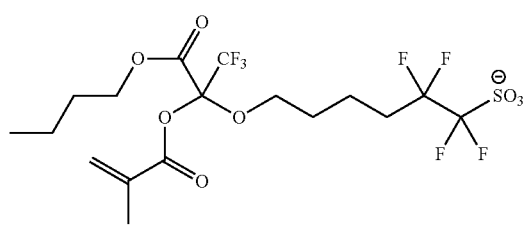
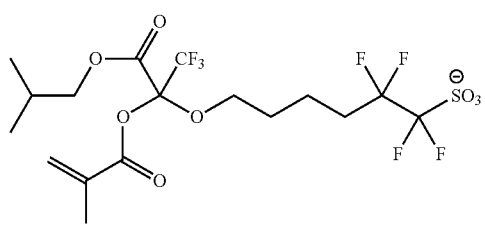
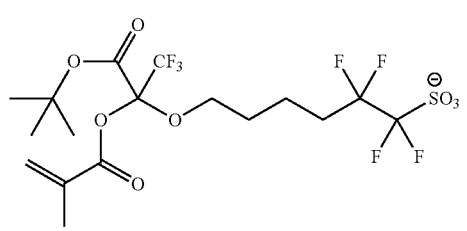
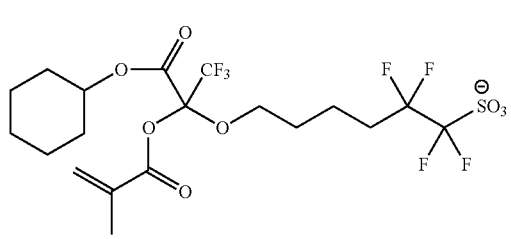
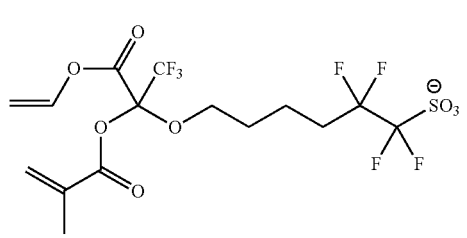
(E-5-54)
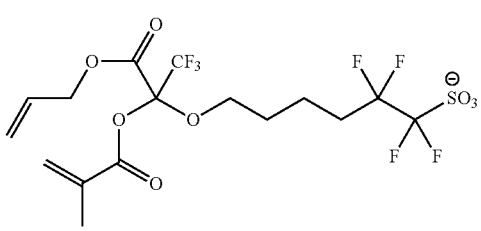
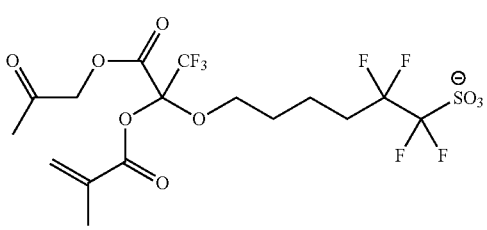
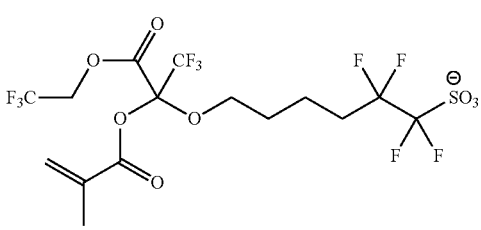
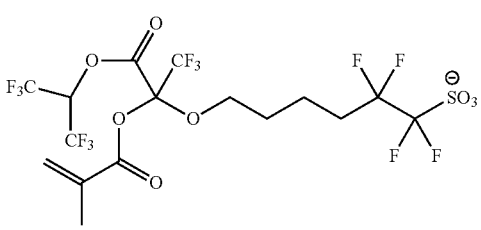
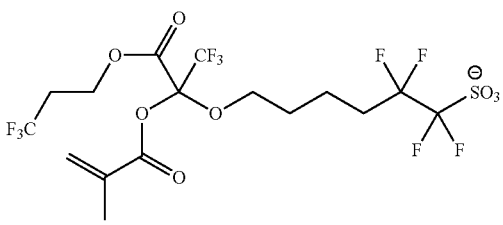
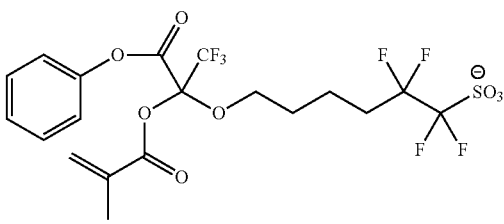
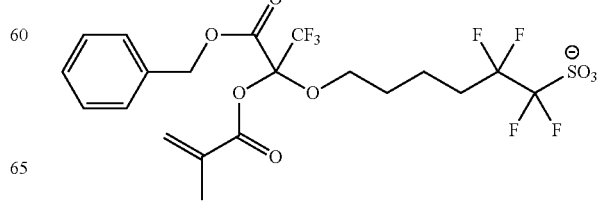

115
-continued
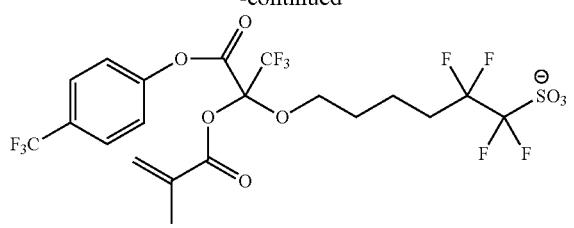
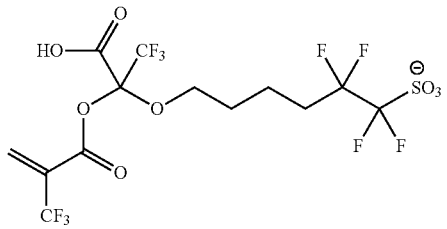
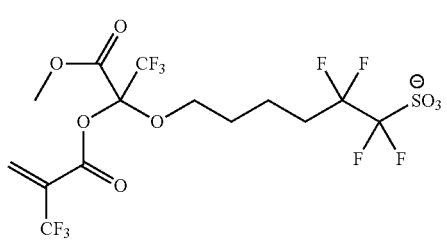
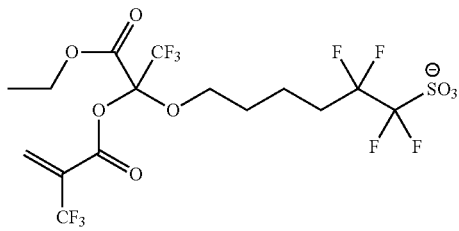
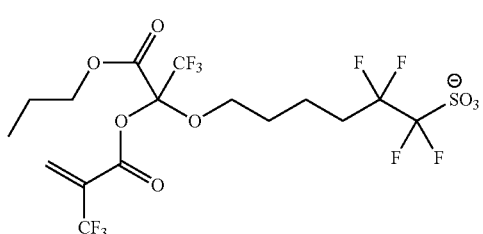
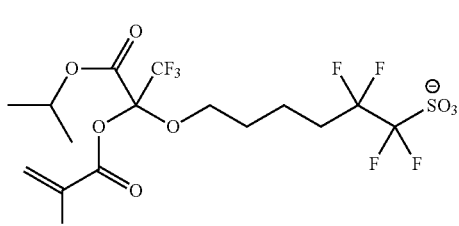
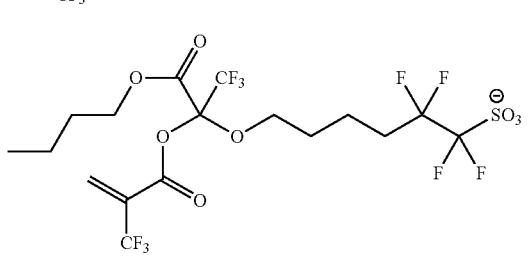
116
-continued
(E-5-55)
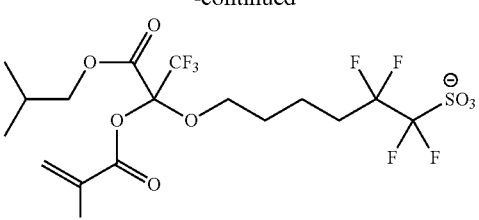
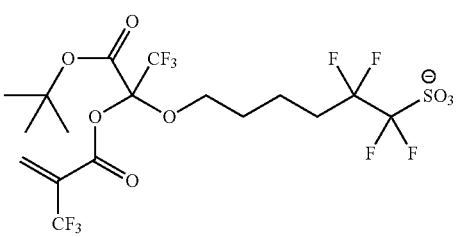
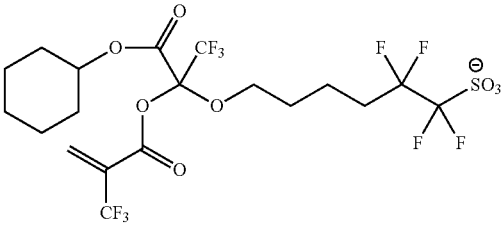
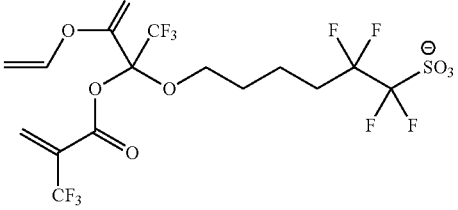
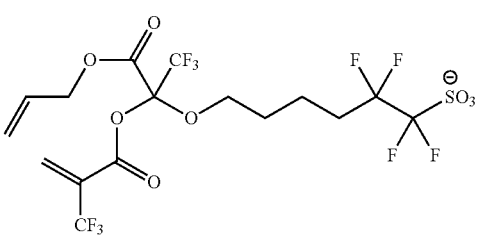
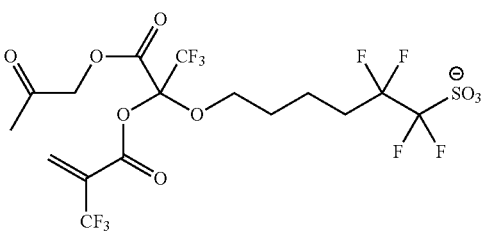
(E-5-56)
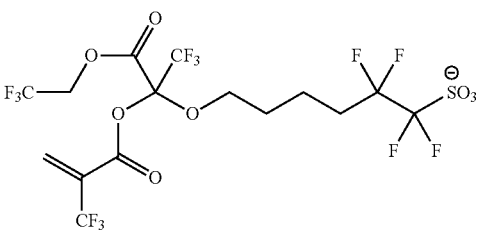

-continued
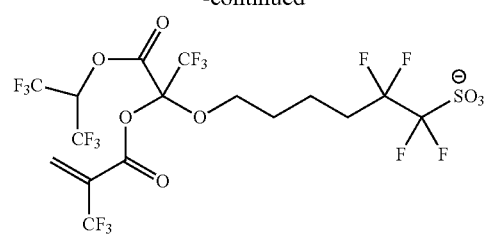
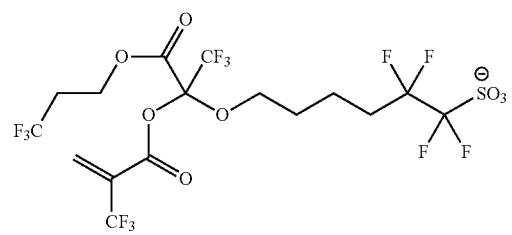
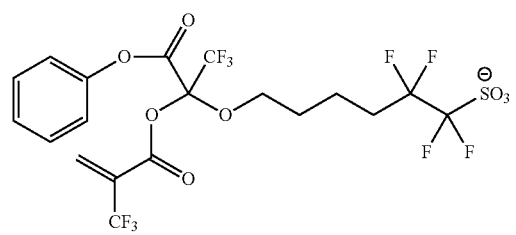
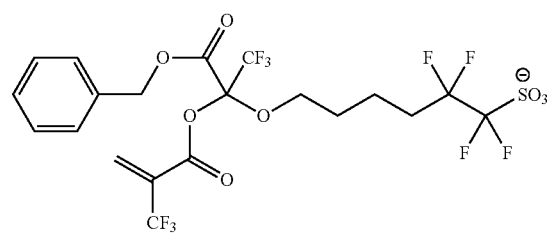
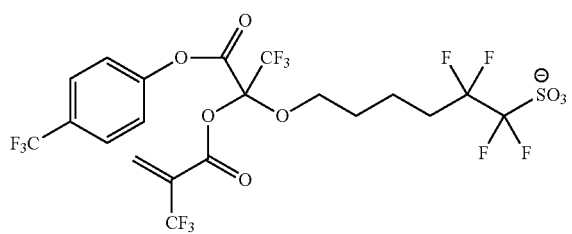
(E-5-57)
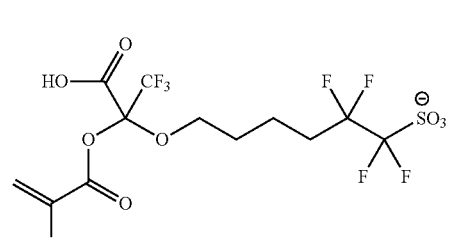
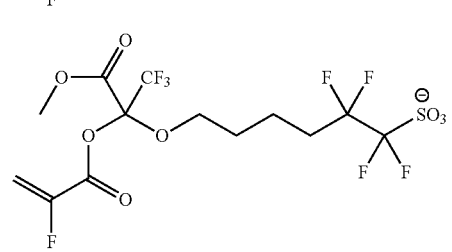
-continued
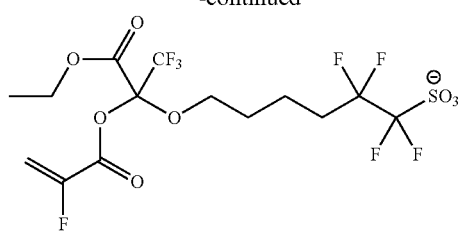
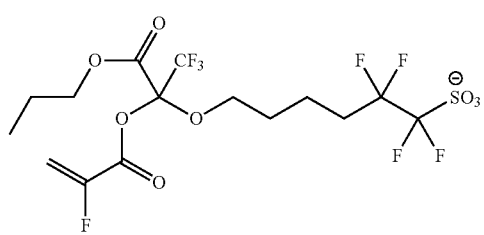
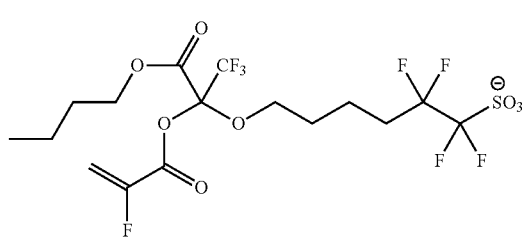
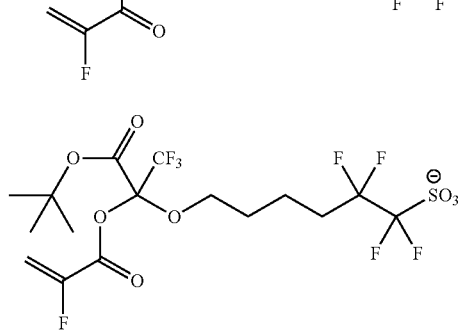
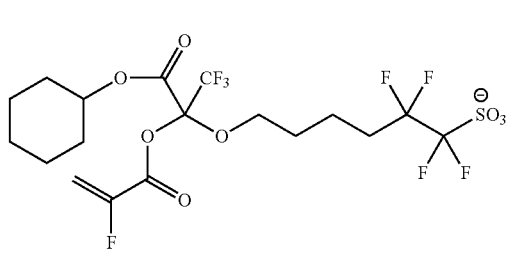

-continued
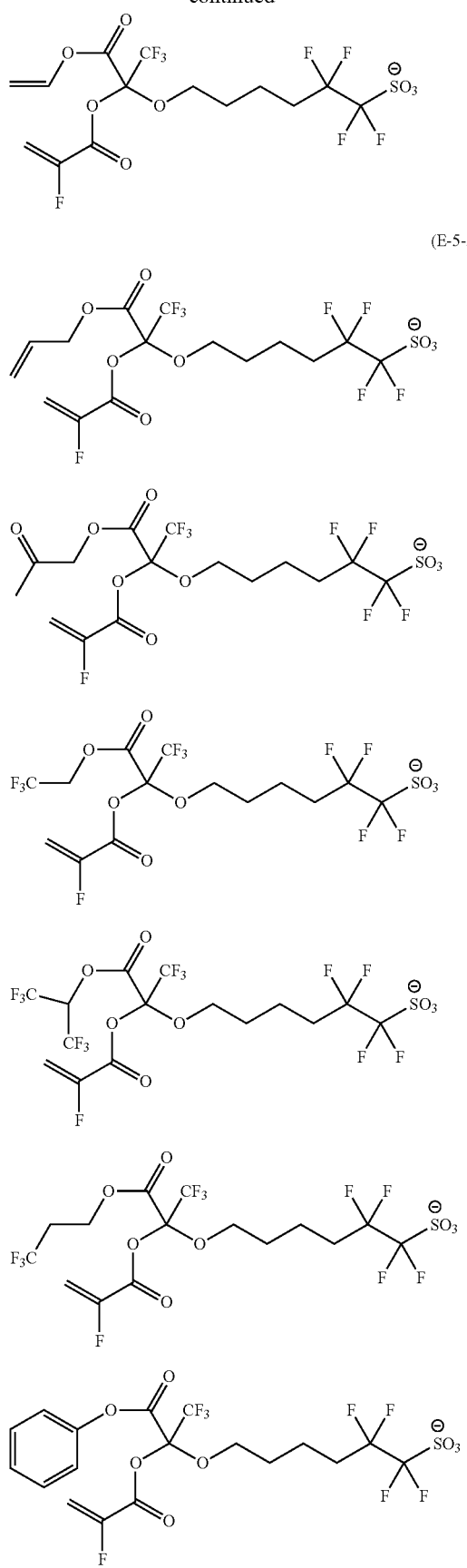
(E-5-58)
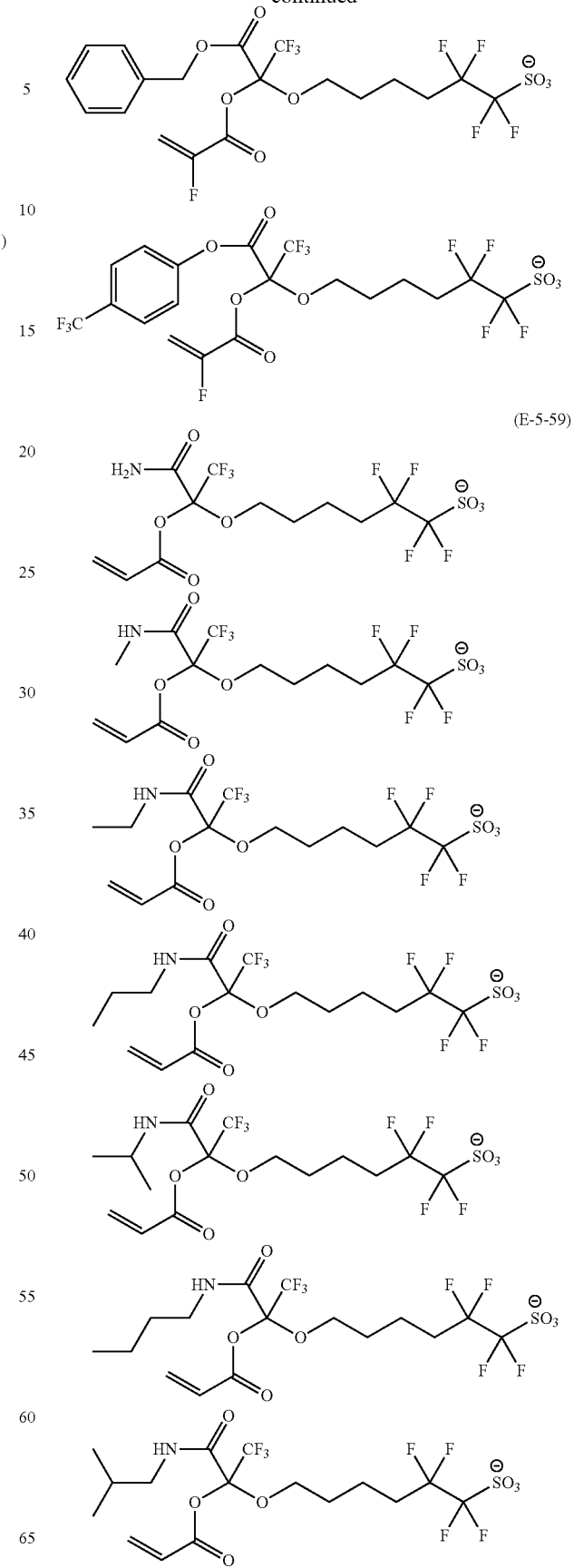
(E-5-59)

121
-continued
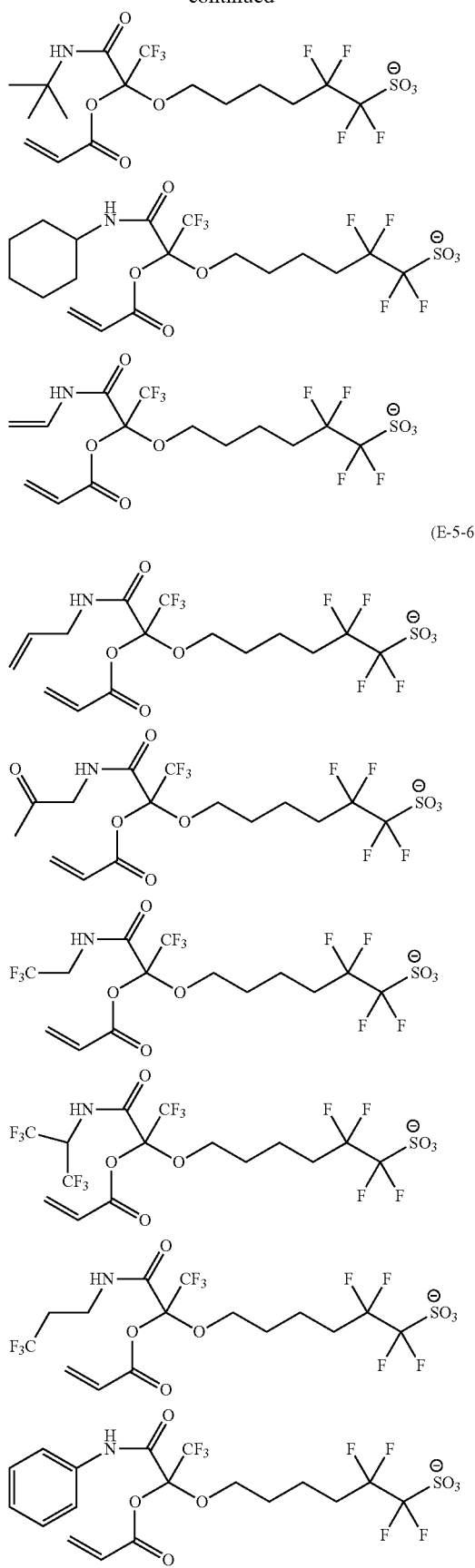
(E-5-60)
122
-continued
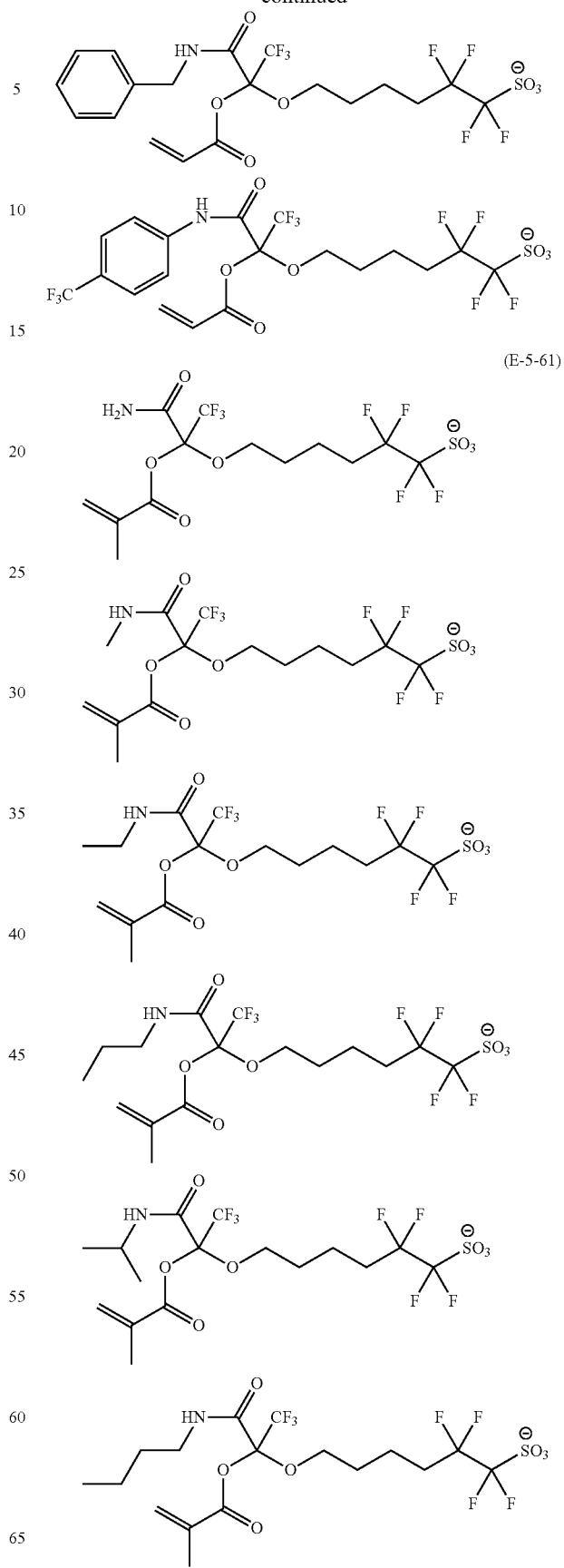
(E-5-61)

123
-continued
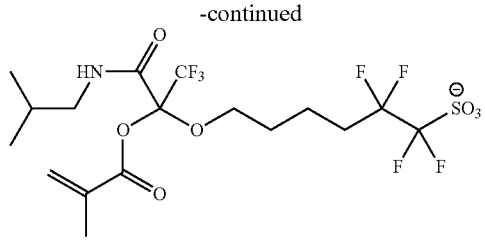
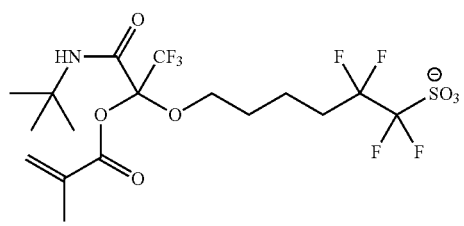
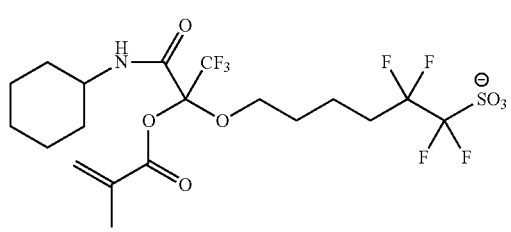
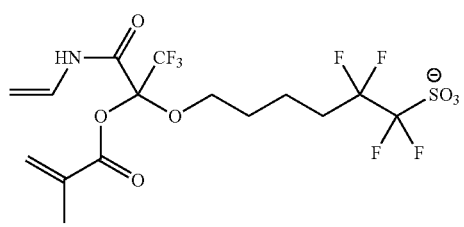
(E-5-62)
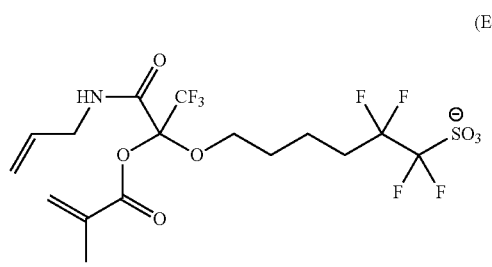
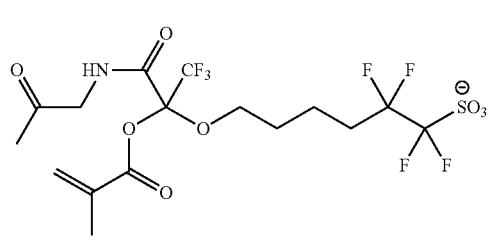
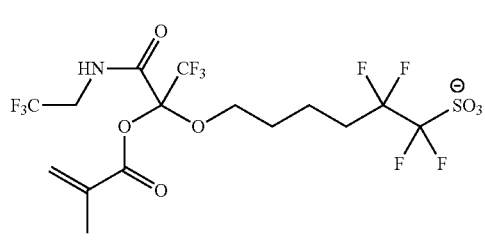
124
-continued
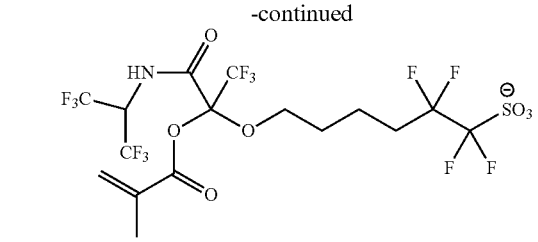
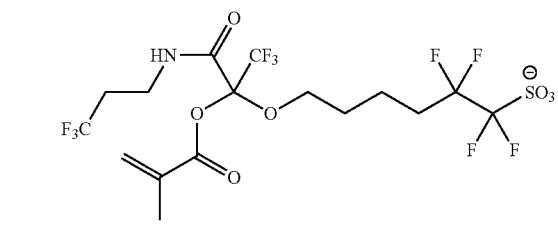
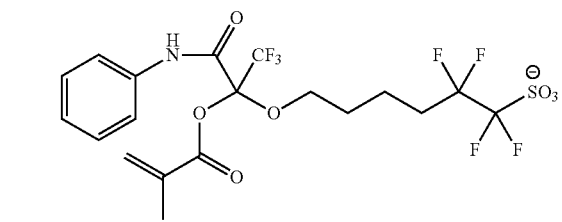
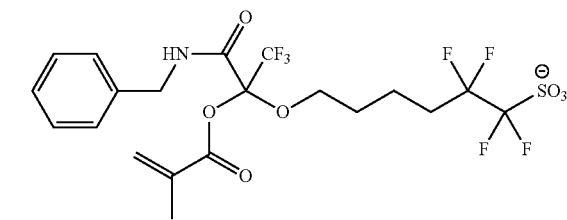
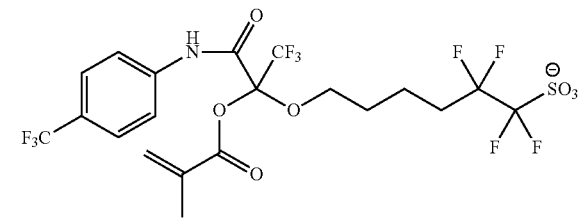
(E-5-63)
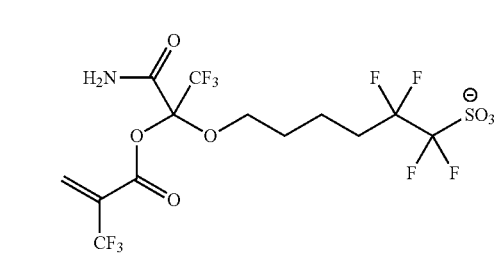
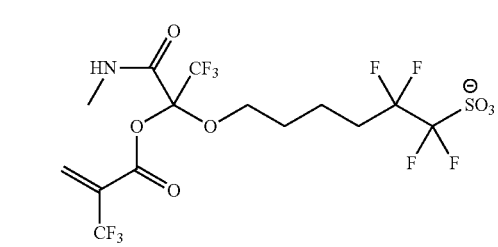

-continued
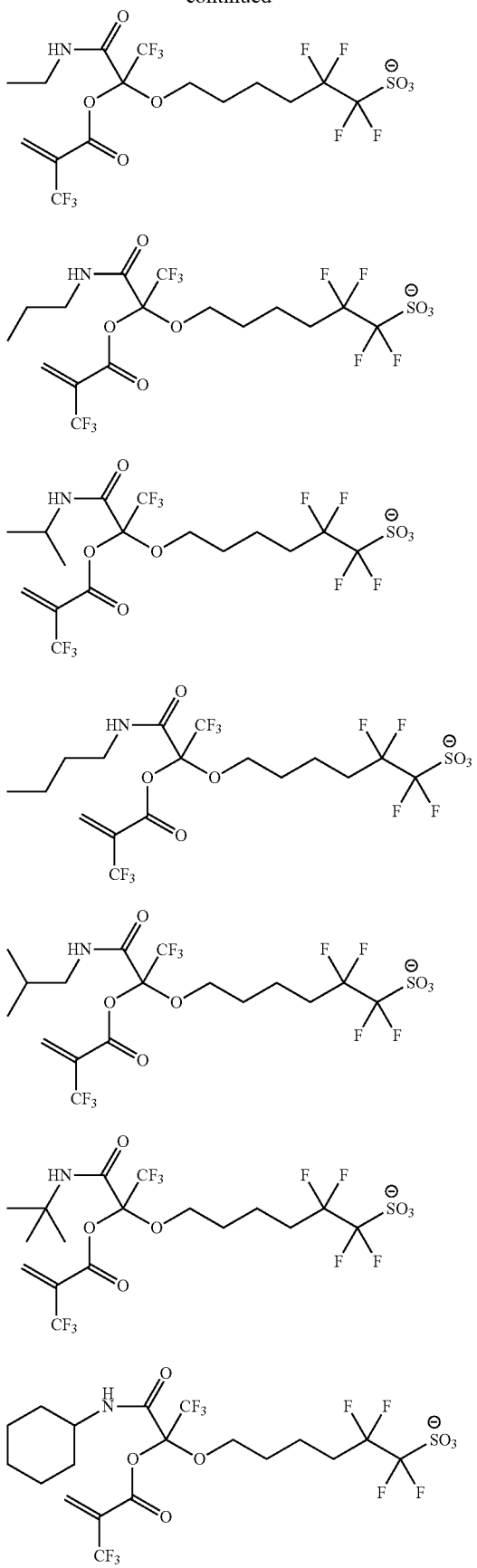
-continued
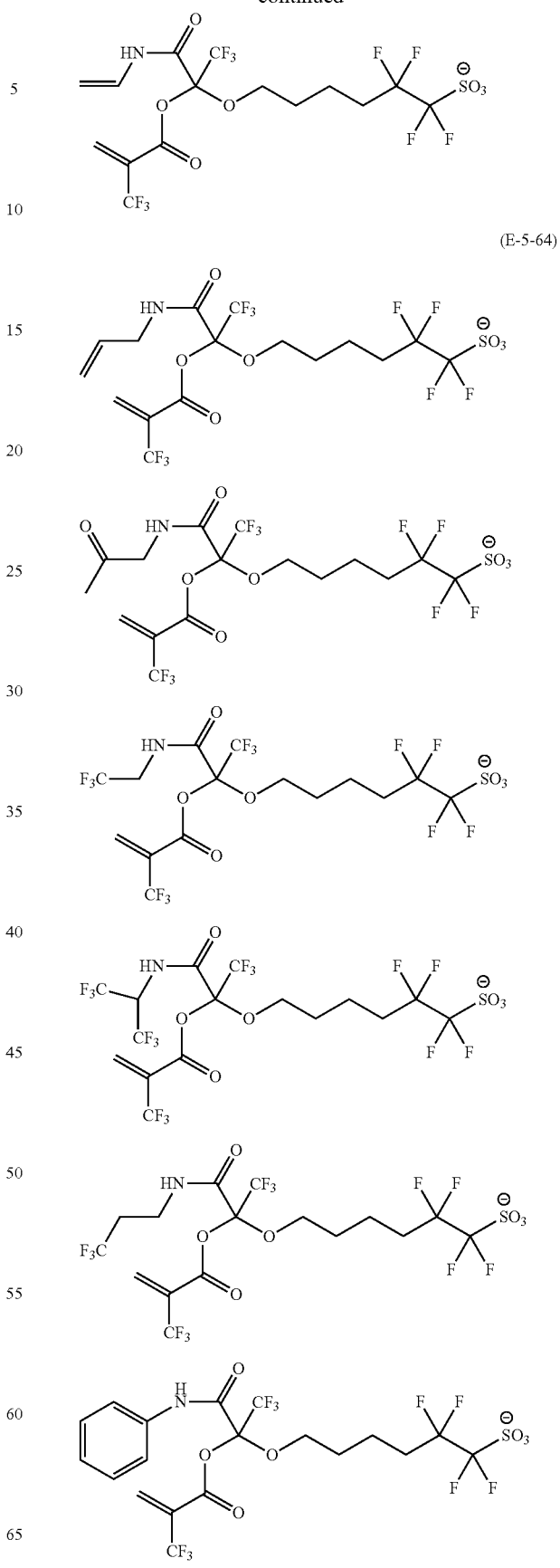
(E-5-64)

-continued
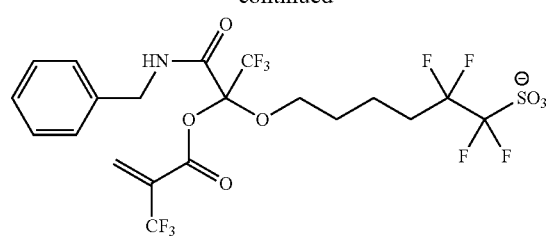
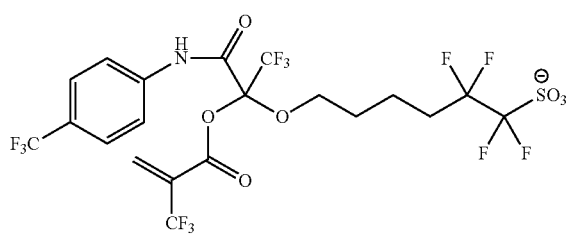
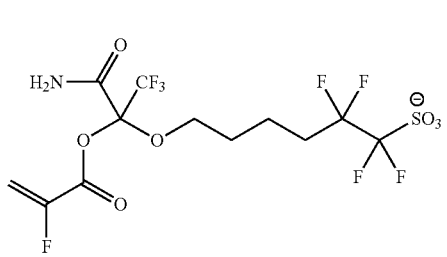
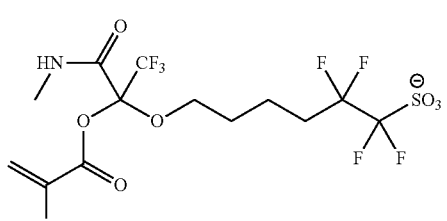
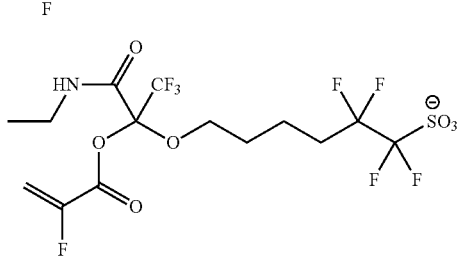
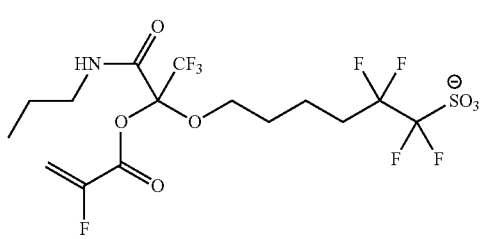
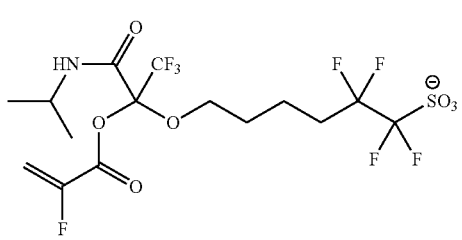
-continued
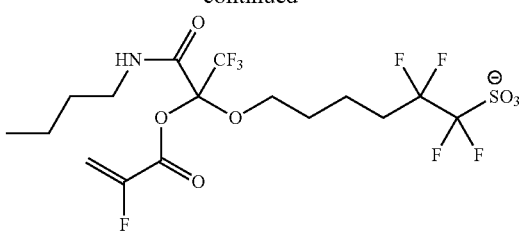
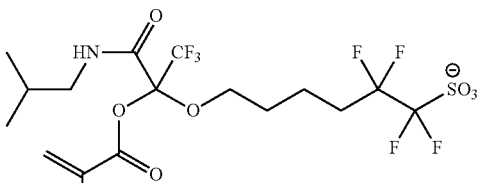
(E-5-65)
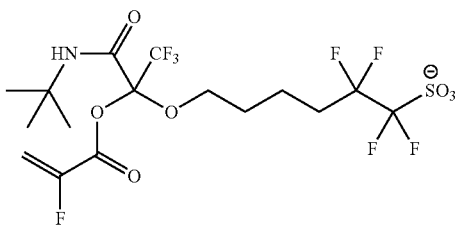
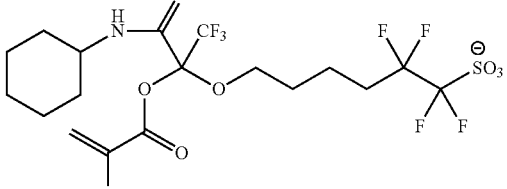
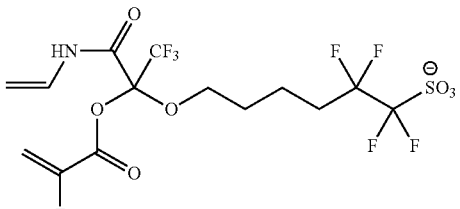
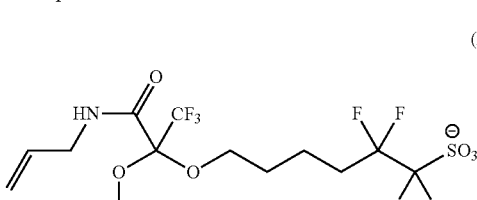
(E-5-66)
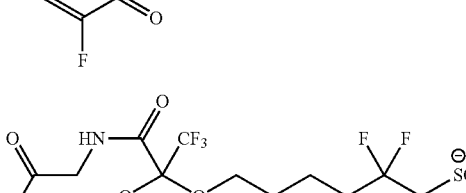
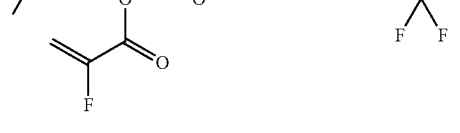

129
-continued
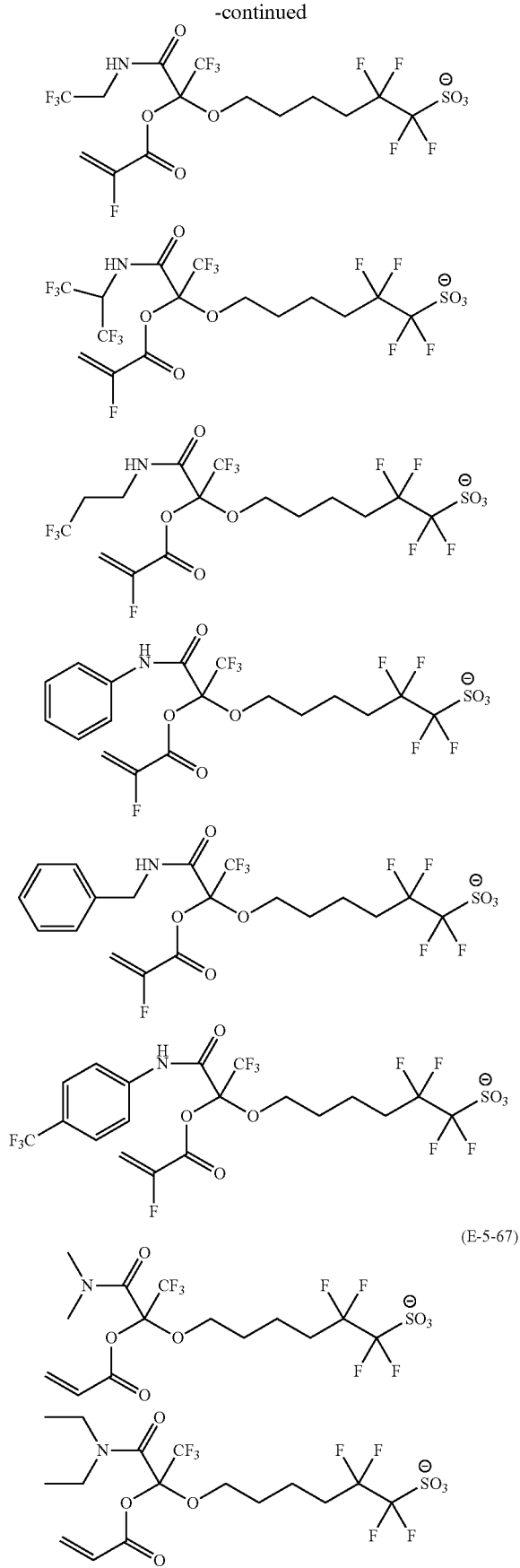
130
-continued
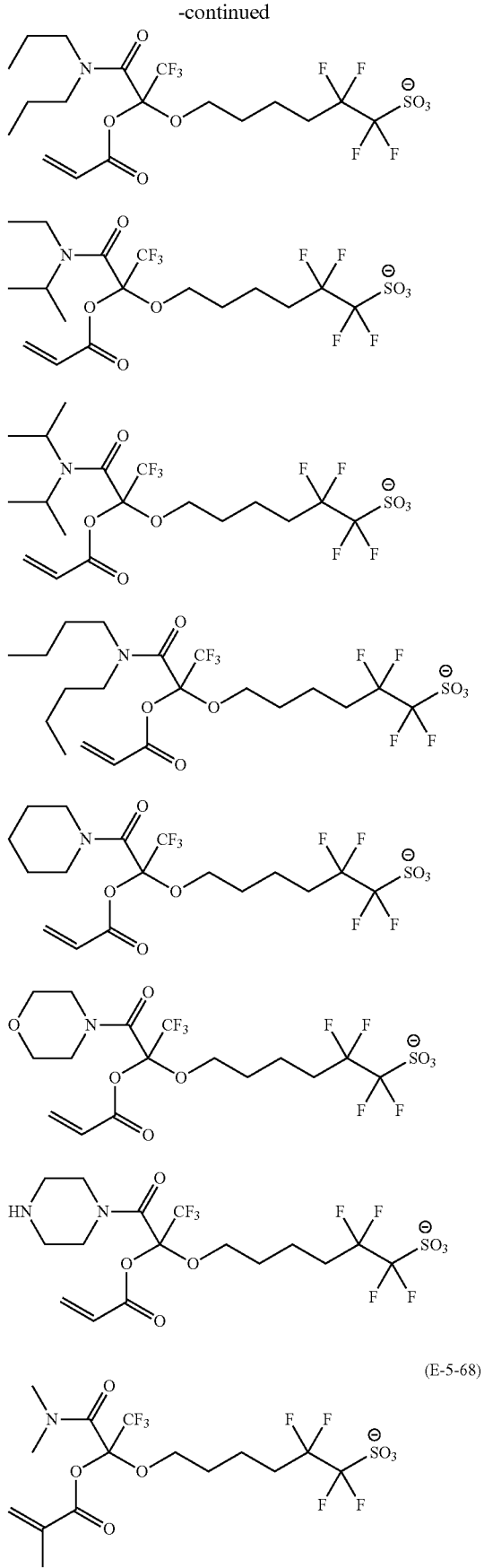
(E-5-67)
(E-5-68)

131
-continued
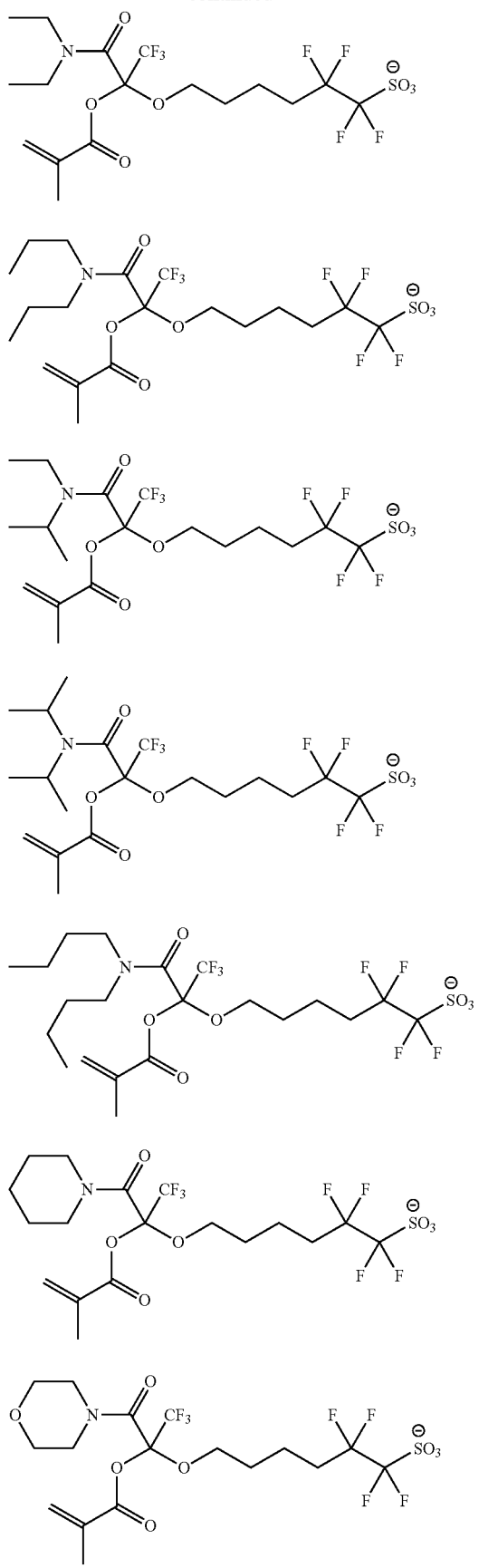
132
-continued
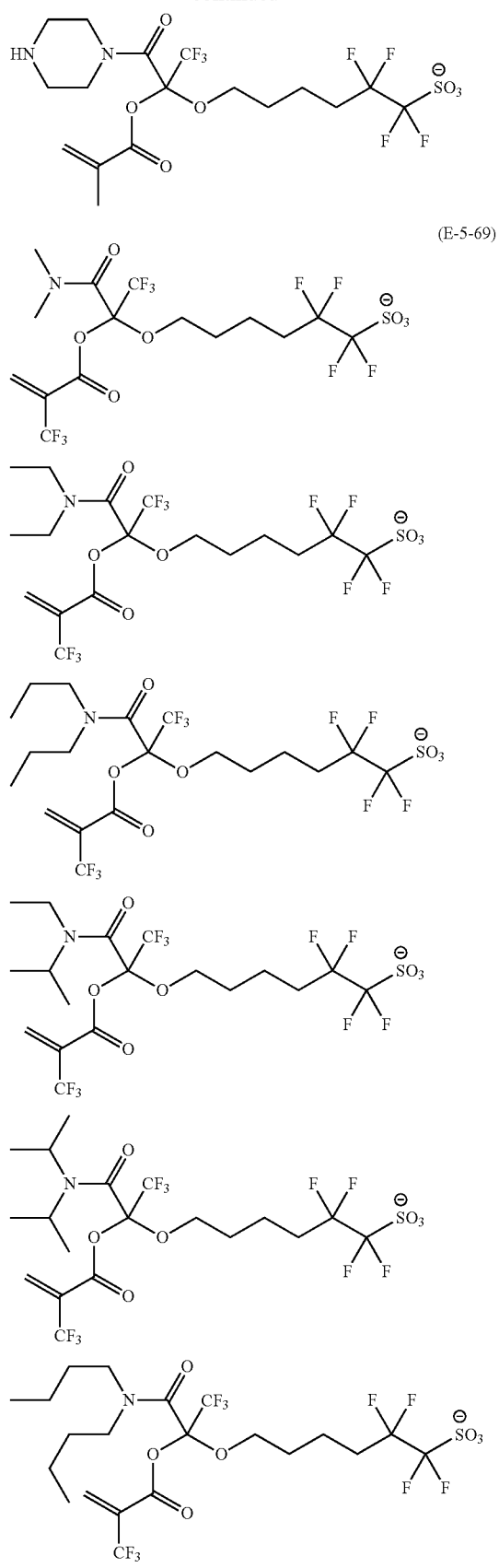
(E-5-69)

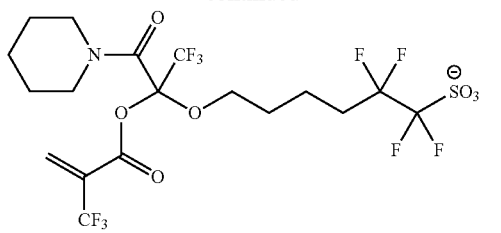

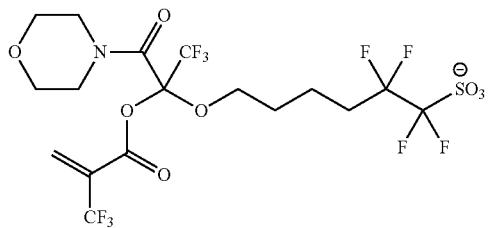

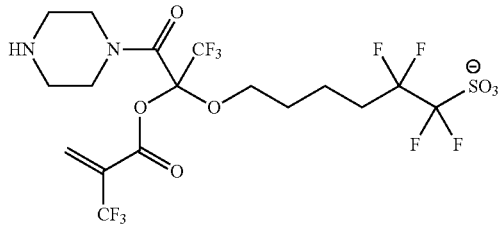

(E-5-70)

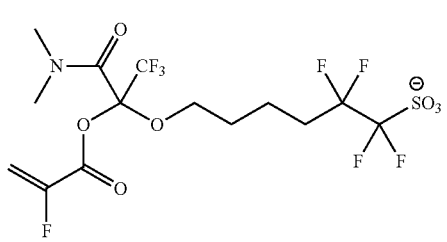

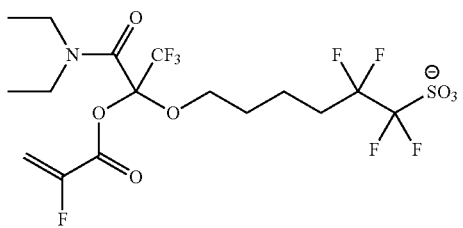

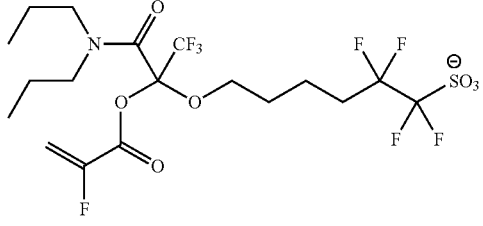

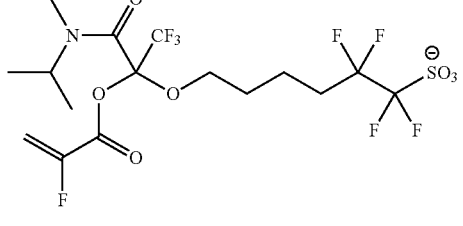

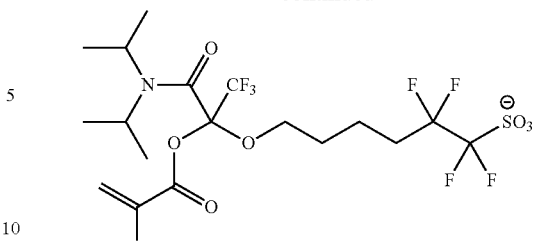

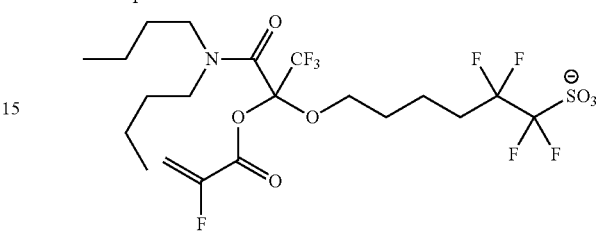

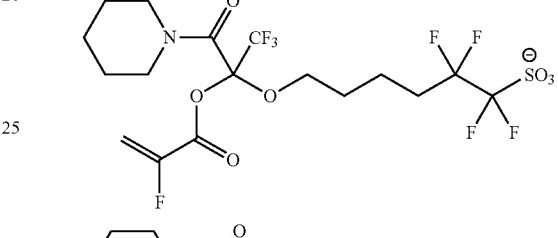

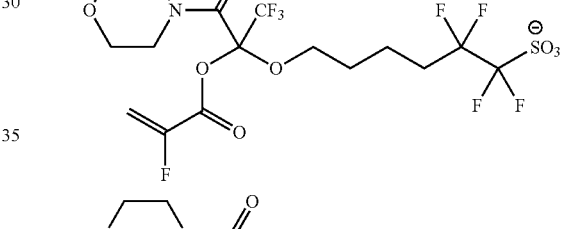

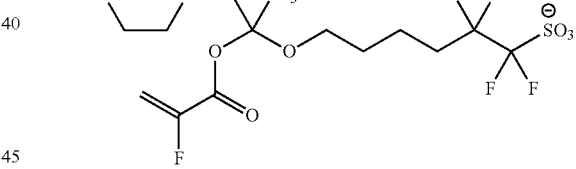

[Polymerizable Fluorine-Containing Sulfonic Acid Onium Salt]

The polymerizable fluorine-containing sulfonic acid onium salt of the general formula (2) is one preferred example of the polymerizable fluorine-containing sulfonate having the anion structure of the general formula (1) according to the present invention. This polymerizable fluorine-containing sulfonic acid onium salt, in the form of either a monomer or a resin obtained by homopolymerization or copolymerization thereof, is capable of sensing high-energy radiation and thereby generating a fluorine-containing sulfonic acid of high acidity. The polymerizable fluorine-containing sulfonic acid onium salt itself or the resin obtained therefrom can be thus suitably used as a photoacid generator. Further, the polymerizable fluorine-containing sulfonic acid onium salt is copolymerizable with a monomer having an acid labile group or a cross-linking site and thus can be also suitably used as a monomer for preparation of a base resin of a high-energy radiation resist composition.

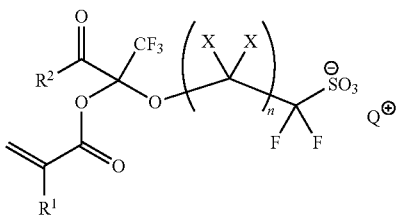
(2)

In the general formula (2), X, n, $R^1$ and $R^2$ have the same meanings as in the general formula (1); and $Q^+$ represents a sulfonium cation of the general formula (a) or an iodonium cation of the general formula (b).

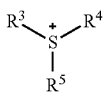
(a)

In the general formula (a), $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group. Two or more of $R^3$, $R^4$ and $R^5$ may be bonded together to form a ring with a sulfur atom in the formula.

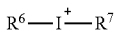
(b)

In the general formula (b), $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group. $R^6$ and $R^7$ may be bonded together to form a ring with an iodine atom in the formula. As specific structural examples of $Q^+$, the sulfonium cation of the general formula (a) and the iodonium cation of the general formula (b) will be described below in detail.

<Sulfonium Cation of General Formula (a)>

In the general formula (a), $R^3$, $R^4$ and $R^5$ are exemplified as follows. The substituted or unsubstituted $C_1$-$C_{20}$ alkyl group is a straight, branched or cyclic $C_1$-$C_{20}$ alkyl group that may have a substituent. Examples of the substituted or unsubstituted $C_1$-$C_{20}$ alkyl group are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl. The substituted or unsubstituted $C_1$-$C_{20}$ alkenyl group is a straight, branched or cyclic $C_1$-$C_{20}$ alkenyl group that may have a substituent. Examples of the substituted or unsubstituted $C_1$-$C_{20}$ alkenyl group are vinyl, allyl, propenyl, butenyl, hexenyl and cyclohexenyl. The substituted or unsubstituted $C_1$-$C_{20}$ oxoalkyl group is a straight, branched or cyclic $C_1$-$C_{20}$ oxoalkyl group that may have a substituent. Examples of the substituted or unsubstituted $C_1$-$C_{20}$ oxoalkyl group are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl. Examples of the substituted or unsubstituted $C_6$-$C_{18}$ aryl group are: phenyl; naphthyl; thienyl; alkoxylphenyl such as p-methoxyphenyl, m-methoxyphenyl, o-methoxyphenyl, p-ethoxypenyl, p-tert-butoxyphenyl or m-tert-butoxyphenyl; alkylphenyl such as 2-methylphenyl, 3-methylphenyl, 4-methylphenyl or ethylphenyl; alkylnaphthyl such as methylnaphthyl or ethylnaphthyl; dialkylnaphthyl such as diethylnaphthyl; and dialkoxynaphthyl such as dimethoxynaphthyl or diethoxynaphthyl. Examples of the substituted or unsubstituted $C_6$-$C_{18}$ aralkyl group are benzyl, 1-phenylethyl and 2-phenylethyl. Examples of the substituted or unsubstituted $C_6$-$C_{18}$ aryloxoalkyl group are 2-aryl-2-oxoethyl such as 2-phenyl-2-oxoethyl, 2-(1-naphthyl)-2-oxoethyl or 2-(2-naphthyl)-2-oxoethyl. In the case where two or more of $R^3$, $R^4$ and $R^5$ are bonded together to form a ring with the sulfur atom, there can be used divalent groups such as 1,4-butylene and 3-oxa-1,5-penthylene. There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general formula (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-buthylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are other specific examples of the sulfonium cation of the general formula (a). As such polymerizable sulfonium cations, there can be used those disclosed in Japanese Laid-Open Patent Publication No. 4-230645 and Japanese Laid-Open Patent Publication No. 2005-84365.

<Iodonium Cation of General Formula (b)>

Examples of $R^6$ and $R^7$ in the general formula (b) are the same as those of $R^3$, $R^4$ and $R^5$ in the general formula (a).

Specific examples of the iodonium cation of the general formula (b) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

More specifically, the polymerizable fluorine-containing sulfonic acid onium salt of the general formula (2) corresponds to any combination of the previously-exemplified polymerizable fluorine-containing sulfonate having the structure of the general formula (1) with either the sulfonium cation of the general formula (a) or the iodonium cation of the general formula (b) exemplified above.

Preferred examples of the polymerizable fluorine-containing sulfonic acid onium salt are those indicated below.

(E-6)

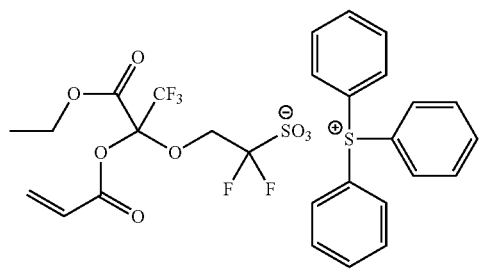

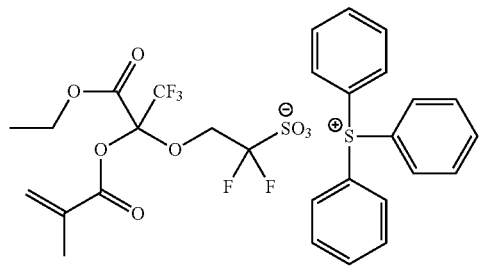

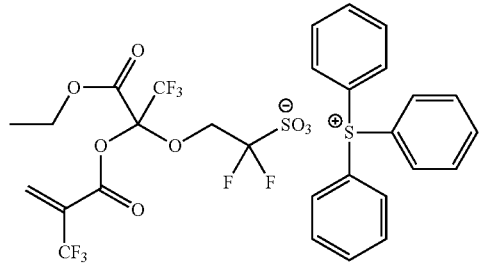

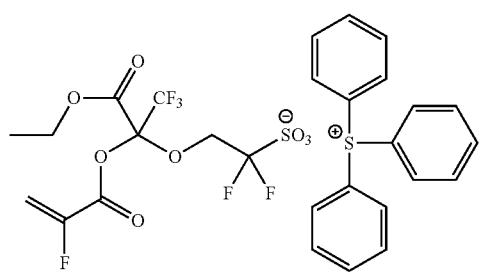

(E-7)

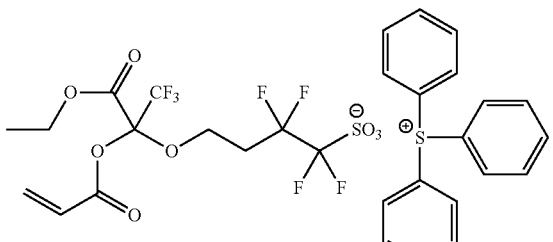

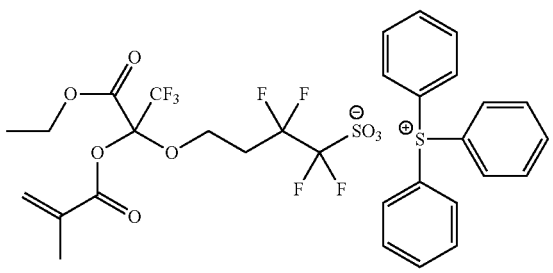

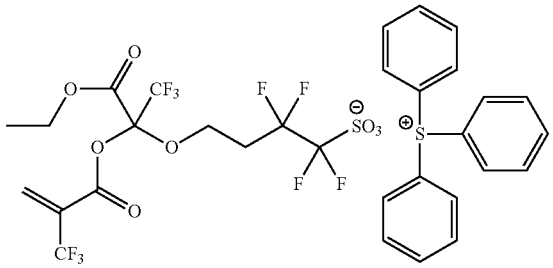

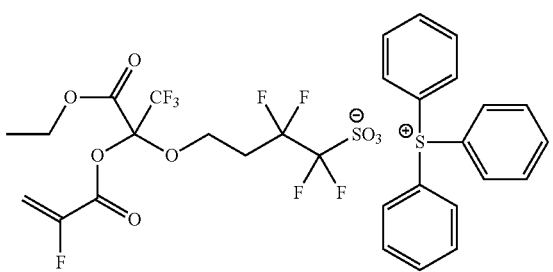

(E-8)

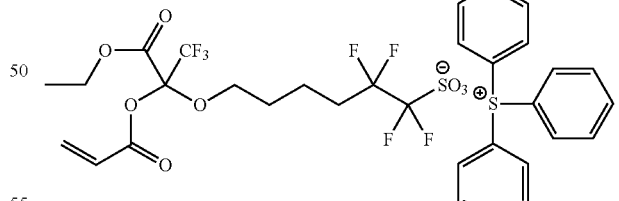

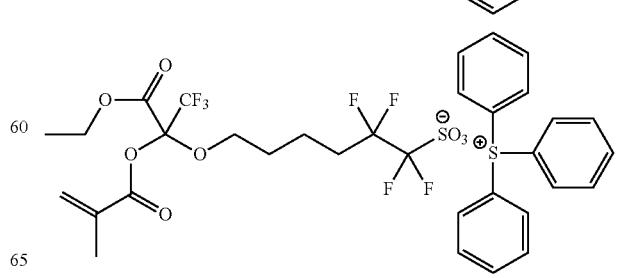

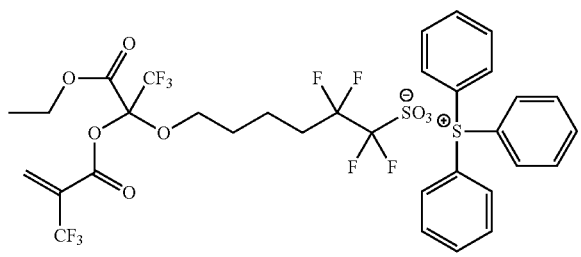

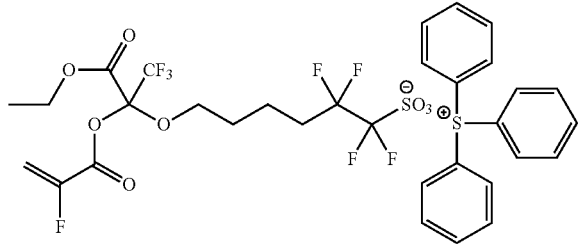

[Production Method of Polymerizable Fluorine-Containing Sulfonate]

Next, a production method of the above-mentioned polymerizable fluorine-containing sulfonate of the general formula (1-1) will be described below. As it is feasible to produce the polymerizable fluorine-containing sulfonate of the general formula (1-1) in the same manner as the polymerizable fluorine-containing sulfonic acid onium salt of the general formula (2), $Q^+$ can be read as $M^+$ in the following explanation.

The polymerizable fluorine-containing sulfonic acid onium salt of the general formula (2) can be produced in first and second steps from a compound of the general formula (13) as indicated in Scheme (2).

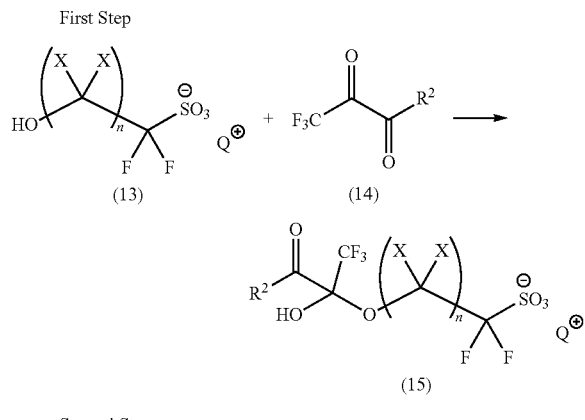

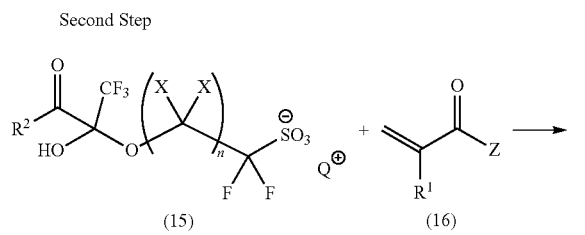

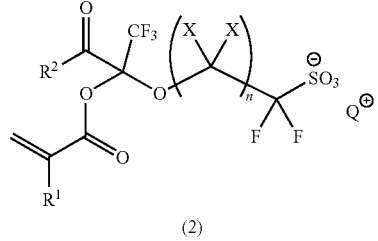

In Scheme (2), X, n, $R^1$, $R^2$ and $Q^+$ have the same meanings as in the general formula (1-1); and Z represents a hydroxyl group, a halogen atom or a —O(C=O)C($R^1$)=CH$_2$ group.

The general formula (13) represents a hydroxyfluoroalkanesulfonic acid onium salt. Herein, X is a hydrogen atom or a fluorine atom; n represents an integer of 1 to 10; and $Q^+$ is a sulfonium cation or an iodonium cation. Specific examples of the cation are the same as those in the explanation of the general formula (2).

As the compound of the general formula (13), there can be used 2-hydroxy-1,1-difluoroethanesulfonic acid triphenylsulfonium, 4-hydroxy-1,1,2,2-tetrafluorobutanesulfonic acid triphenylsulfonium, 5-hydroxy-1,1,2,2-tetrafluoropentanesulfonic acid triphenylsulfonium and 6-hydroxy-1,1,2,2-tetrafluorohexanesulfonic acid triphenylsulfonium. These compounds can be prepared by methods as disclosed in Japanese Laid-Open Patent Publication No. 2009-91351, International Application Publication No. WO 2008/56795, International Application Publication No. WO 2006/121096 and Japanese Laid-Open Patent Publication No. 2010-18573.

The general formula (14) represents a trifluoropyruvic acid derivative. Herein, $R^2$ is either $R^AO$ or $R^BR^CN$; and $R^A$, $R^B$ and $R^C$ are each independently a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group. $R^B$ and $R^C$ may be bonded to each other to form a 3- to 18-membered heterocyclic ring. Any of hydrogen atoms on carbons in $R^A$, $R^B$ and $R^C$ may be substituted with a substituent. Examples of $R^2$ are the same as those in the explanation of the general formula (1-1).

The compound of the general formula (14) can be commercially available and used as it is or can be prepared by known methods.

The general formula (16) represents a carboxylic acid derivative. In the case where Z is a hydroxyl group, the compound of the general formula (16) is a carboxylic acid. In the case where Z is a halogen group selected from fluorine, chlorine, bromine and iodine, the compound of the general formula (16) is an acid halide. The compound of the general formula (16) is an acid anhydride in the case where Z is —O(C=O)C($R^1$)=CH$_2$. Herein, $R^1$ is a hydrogen atom, a halogen atom or a $C_1$-$C_3$ alkyl or fluorine-containing alkyl group.

The compound of the general formula (16) can be commercially available and used as it is or can be prepared by known methods.

(First Step)

The first step will be next explained below. In the first step, the trifluoropyruvic acid derivative of the general formula (14) is added to the hydroxyfluoroalkanesulfonic acid onium salt of the general formula (13). This addition reaction can be performed by reacting the hydroxyfluoroalkanesulfonic acid onium salt of the general formula (13) with the trifluoropyruvic acid derivative of the general formula (14) in the presence of an acid catalyst or in the presence of no catalyst.

There is no particular limitation on the amount of the trifluoropyruvic acid derivative of the general formula (14) reacted with the hydroxyfluoroalkanesulfonic acid onium salt of the general formula (13). The amount of the trifluoropyruvic acid derivative is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

In general, it is preferable to perform the addition reaction with the use of an aprotic solvent although the addition reaction can be performed in the presence or absence of a solvent. Examples of the aprotic solvent are diisopropyl ether, dichloroethane, chloroform, toluene, ethylbenzene, monochlorobenzene, acetonitrile and N,N-dimethylformamide. These solvents can be used solely or in combination of two or more kinds thereof.

There is no particular limitation on the reaction temperature. The reaction temperature is generally 0 to 100° C., preferably 10 to 80° C. It is preferable to perform the reaction with stirring.

The reaction time is generally several minutes to 100 hours, preferably 30 minutes to 50 hours, more preferably 1 to 20 hours although the reaction time varies depending on the reaction temperature. It is preferable to determine the time at which the hydroxyfluoroalkanesulfonic acid onium salt raw material has been consumed as the end of the reaction while monitoring the progress of the reaction by any analytical means such as nuclear magnetic resonance (NMR).

Although the reaction is generally performed in the presence of no catalyst, the reaction proceeds in the same manner even in the presence of the acid catalyst. As the acid catalyst, an organic acid such as p-toluenesulfonic acid and/or an inorganic acids such as sulfuric acid can be used.

After the completion of the reaction, the target fluorine-containing sulfonic acid onium salt of the general formula (15) can be obtained by removing the solvent etc. under a reduced pressure.

The fluorine-containing sulfonic acid onium salt of the general formula (15) can be purified by ordinary means such as extraction or recrystallization after the completion of the reaction.

Alternatively, the reaction-completed solution may be used as it is, without removing the solvent, as raw material for production of the polymerizable fluorine-containing sulfonic acid onium salt of the general formula (2).

(Second Step)

The second step will be explained below. In the second step, the polymerizable fluorine-containing sulfonic acid onium salt of the general formula (2) is formed by esterification reaction of the fluorine-containing sulfonic acid onium salt of the general formula (15) and the carboxylic acid derivative of the general formula (16). This esterification reaction can be performed by any known process.

As the esterification reaction process, it is feasible to adopt dehydration condensation of the carboxylic acid of the general formula (16) (where Z is hydroxyl) with the fluorine-containing sulfonic acid onium salt in the presence of an acid catalyst (as is known as Fischer ester synthesis reaction), reaction of the carboxylic acid halide of the general formula (16) (where Z is halogen) or the carboxylic acid anhydride of the general formula (16) (where Z is —O(C=O)C($R^1$)=$CH_2$) with the fluorine-containing sulfonic acid onium salt or the like.

In the case of the carboxylic acid of the general formula (16) (where Z is hydroxyl), there is no particular limitation on the amount of the carboxylic acid reacted with the fluorine-containing sulfonic acid onium salt. The amount of the carboxylic acid is generally 0.1 to 5 mol, preferably 0.2 to 3 mol, more preferably 0.5 to 2 mol, most preferably 0.8 to 1.5 mol, per 1 mol of the fluorine-containing sulfonic acid onium salt.

In general, it is preferable to perform the esterification reaction with the use of an aprotic solvent although the esterification reaction can be performed in the presence or absence of a solvent. Examples of the aprotic solvent are dichloroethane, toluene, ethylbenzene, monochlorobenzene, acetonitrile and N,N-dimethylformamide. These solvents can be used solely or in combination of two or more kinds thereof.

As the fluorine-containing sulfonic acid onium salt is almost insoluble in an aromatic hydrocarbon solvent such as toluene, ethylbenzene or monochlorobenzene, the mixture of the fluorine-containing sulfonic acid onium salt and the aromatic hydrocarbon solvent is in slurry form. Even in such a state, the reaction proceeds sufficiently.

There is no particular limitation on the reaction temperature. The reaction temperature is generally 0 to 200° C., preferably 20 to 180° C., more preferably 50 to 150° C. It is preferable to perform the reaction with stirring.

The reaction time is generally several minutes to 100 hours, preferably 30 minutes to 50 hours, more preferably 1 to 20 hours although the reaction time varies depending on the reaction temperature. It is preferable to determine the time at which the fluorine-containing sulfonic acid onium salt raw material of the general formula (15) has been consumed as the end of the reaction while monitoring the progress of the reaction by any analytical means such as gas chromatography (GC) or nuclear magnetic resonance (NMR).

The reaction is generally performed in the presence of a catalyst, preferably an acid catalyst. It is feasible to select and use any known esterification reaction catalyst. For example, an organic acid such as p-toluenesulfonic acid and/or an inorganic acids such as sulfuric acid can be used as the acid catalyst. A dehydrating agent such as 1,1'-carbonyldiimidazole or N,N'-dicyclohexylcarbodiimide may be added to the reaction system. There is no particular limitation on the amount of the acid catalyst used. The amount of the acid catalyst is generally 0.0001 to 10 mol, preferably 0.001 to 5 mol, more preferably 0.01 to 1.5 mol, per 1 mol of the fluorine-containing sulfonic acid onium salt.

It is preferable to perform the esterification reaction using the acid catalyst while dehydrating the reaction system e.g. by means of a Dean-Stark apparatus for reduction of the reaction time.

After the completion of the reaction, the target fluorine-containing sulfonic acid onium salt of the general formula (2) can be obtained by any ordinary means such as extraction, reprecipitation or recrystallization. Further, the fluorine-containing sulfonic acid onium salt of the general formula (2) can be purified by recrystallization etc. as needed.

In the case of the carboxylic acid halide of the general formula (16) (where Z is halogen) or the carboxylic acid anhydride of the general formula (16) (where Z is —O(C=O)C($R^1$)=$CH_2$), there is no particular limitation on the amount of the carboxylic acid halide or acid anhydride reacted with the fluorine-containing sulfonic acid onium salt. The amount of the carboxylic acid halide or acid anhydride is generally 0.1 to 5 mol, preferably 0.2 to 3 mol, more preferably 0.5 to 2 mol, most preferably 0.8 to 1.5 mol, per 1 mol of the fluorine-containing sulfonic acid onium salt.

The reaction can be performed with the use of no solvent or any solvent inert to the reaction. There is no particular limitation on the solvent as long as the solvent is inert to the reaction. For example, it is feasible to perform the reaction in water, an organic solvent or a mixed solvent of water and an organic solvent. Example of the organic solvent are: ketone solvents such as acetone, methyl ethyl ketone and methyl isobutyl ketone; ester solvents such as ethyl acetate and butyl acetate; ether solvents such as diethyl ether, diethylene glycol dimethyl ether, tetrahydrofuran and dioxane; halogenated solvents such as dichloromethane, chloroform, carbon tetrachloride, 1,2-dichloroethane, tetrachloroethylene, chlorobenzene and oxochlorobenzene; and polar solvents such as acetonitrile, N,N-dimethylformamide, N,N-dimethylimidazolidinone, dimethyl sulfoxide and sulfolane. These organic solvents can be used solely or in combination of two or more thereof.

There is no particular limitation on the reaction temperature. The reaction temperature is generally −78 to 150° C., preferably −20 to 120° C., more preferably 0 to 100° C.

The reaction time is generally several minutes to 100 hours, preferably 30 minutes to 50 hours, more preferably 1 to 20 hours although the reaction time varies depending on the reaction temperature. It is preferable to determine the time at which the fluorine-containing sulfonic acid onium salt raw material has been consumed as the end of the reaction while monitoring the progress of the reaction by any analytical means such as gas chromatography (GC) or nuclear magnetic resonance (NMR).

It is feasible, in the case of using the carboxylic acid halide of the general formula (16) (where Z is halogen), to perform the reaction in the presence of no catalyst while removing a hydrogen halide by-product (such as hydrogen chloride) from the reaction system. It is alternatively feasible to perform the reaction with the use of a dehydrohalogenating agent (as an acid acceptor).

Examples of the acid acceptor are: organic bases such as triethylamine, pyridine, picoline, dimethylaniline, diethylaniline, 1,4-diazabicyclo[2.2.2]octane (DABCO) and 1,8-diazabicyclo[5.4.0]undeca-7-ene (DBU); and inorganic bases such as sodium hydrogen carbonate, sodium carbonate, potassium carbonate, lithium carbonate, sodium hydroxide, potassium hydroxide, calcium hydroxide and magnesium oxide. There is no particular limitation on the amount of the acid acceptor used. The amount of the acid acceptor is generally 0.05 to 10 mol, preferably 0.1 to 5 mol, more preferably 0.5 to 3 mol, per 1 mol of the fluorine-containing sulfonic acid onium salt.

After the completion of the reaction, the target fluorine-containing sulfonic acid onium salt of the general formula (2) can be obtained by any ordinary means such as extraction, distillation or recrystallization. Further, the fluorine-containing sulfonic acid onium salt of the general formula (2) can be purified by washing, recrystallization etc. as needed.

[Sulfonate Resin]

A resin having a repeating unit of the general formula (3) (also referred to as "sulfonate resin" in the present specification) is formed by cleavage of a polymerizable double bond of the polymerizable fluorine-containing sulfonate of the general formula (1-1). In the polymerization reaction, the original structure of any part of the fluorine-containing sulfonate, other than the polymerizable double bond, can be maintained with no structural changes.

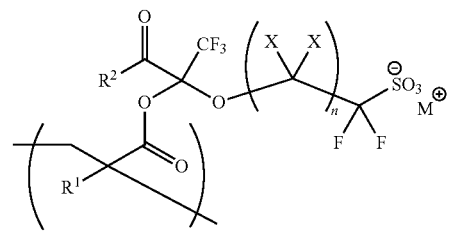

(3)

In the general formula (3), X, n, $R^1$ and $R^2$ have the same meanings as in the general formula (1-1); and $M^+$ represents a monovalent cation.

It is preferable to use the onium cation $Q^+$ as the cation $M^+$. Specific examples of the resin having the repeating unit formed by cleavage of the polymerizable double bond of the polymerizable fluorine-containing sulfonic acid onium salt of the general formula (2) are those having a repeating unit of the general formula (4).

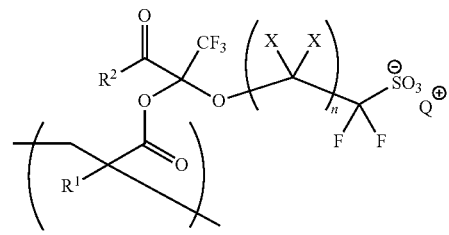

(4)

In the general formula (4), X, n, $R^1$ and $R^2$ have the same meanings as in the general formula (1-1); and $Q^+$ has the same meaning as in the general formula (2).

The resin having the repeating unit of the general formula (4) is converted to a resin having a repeating unit of the general formula (5) by exposure to high-energy radiation.

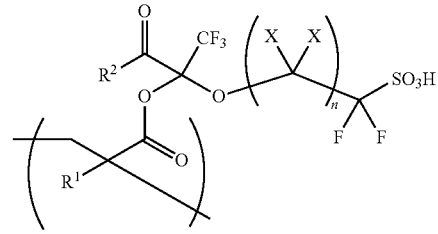

(5)

In the general formula (5), X, n, $R^1$ and $R^2$ have the same meanings as in the general formula (1-1).

There is no particular limitation on the high-energy radiation. Examples of the high-energy radiation are: an electromagnetic wave (light) generated by excimer laser e.g. KrF excimer laser, ArF excimer laser or $F_2$ excimer laser or by synchrotron radiation; and a charged particle beam such as electron beam. In the case of using the resin for fine patterning, it is particularly effective to use high-energy radiation of 300 nm or less wavelength generated by excimer laser e.g. KrF excimer laser, ArF excimer laser or $F_2$ excimer laser or by synchrotron radiation.

The repeating unit serves as a photoacid generator for a chemically amplified resist composition because, after the elimination of $Q^+$, the terminus of the repeating unit is a difluorosulfonic acid of high acidity. Namely, the resin having at least the repeating unit of the general formula (4) serves as a photoacid generator. A composition containing such a resin together with a positive or negative photosensitive solubility-changeable resin and a solvent can be thus suitably used as a resist composition.

Depending on the purpose of use of the sulfonate resin, the sulfonate resin can be formed from [I] the repeating unit of the general formula (4) formed from the polymerizable fluorine-containing sulfonic acid onium salt having the structure of the general formula (2) or [II] not only the repeating unit of the general formula (4) but also a repeating unit containing an acid labile group or a cross-linking site. In either case, any other repeating unit (referred to as "auxiliary repeating unit" in the present specification) may be included in the sulfonate resin. Herein, the term "auxiliary repeating unit" refers to a repeating unit that does not correspond to the repeating unit of the general formula (4) and the repeating unit containing the acid labile group or cross-linking site. Further, the term "auxiliary monomer" refers to a monomer capable of forming an auxiliary repeating unit by cleavage of a polymerizable double bond thereof.

In other words, the sulfonate resin can be in the form of a homopolymer having the repeating unit of the general formula (4) as obtained by homopolymerization of the polymerizable fluorine-containing sulfonic acid onium salt having the structure of the general formula (2) or in the form of a copolymer having the auxiliary repeating unit in addition to the repeating unit of the general formula (4). In these cases, the sulfonate resin itself cannot be used as a positive or negative resist resin but can be used as a photoacid generator in combination with a base resin to thereby form a resist composition. For such use, the sulfonate resin contains 0.1 to 100 mol %, preferably 1 to 100 mol %, more preferably 2 to 100 mol %, of the polymerizable fluorine-containing sulfonic acid onium salt monomer unit of the general formula (2), with the balance being the auxiliary repeating unit. If the amount of the polymerizable fluorine-containing sulfonic acid onium salt monomer unit is less than 0.1 mol %, the sulfonate resin unfavorably needs to be used as the acid generator in a large amount in order for the resist composition to maintain sufficient photosensitivity to high-energy radiation.

In the case where the sulfonate resin consists of the repeating unit containing the acid labile group or cross-linking site and the repeating unit of the general formula (4), the sulfonate resin contains 0.1 to 90 mol %, preferably 0.5 to 50 mol %, more preferably 1 to 30 mol %, of the repeating unit of the general formula (4), with the balance being the repeating unit containing the acid labile group or cross-linking site. If the amount of the repeating unit of the general formula (4) is less than 0.1 mol %, the sulfonate resin does not show sufficient photosensitivity as the photoacid generator so that it is unfavorably necessary to use another photoacid generator and is not possible to make sufficient use of the high performance of the sulfonate resin. Even if the amount of the repeating unit of the general formula (4) exceeds 90 mol %, the sulfonate resin can adequately serve as the photoacid generator. It is not however possible to take advantage of adding the repeating unit containing the acid labile group or cross-linking site in the resin. In the case where the sulfonate resin has the repeating unit containing the acid labile group or cross-linking site, the repeating unit of the general formula (4) and the auxiliary repeating unit, the sulfonate resin contains 0.1 to 70 mol %, preferably 1 to 60 mol %, more preferably 10 to 50 mol %, of the auxiliary repeating unit, with the balance being the repeating unit containing the acid labile group or cross-linking site and the repeating unit of the general formula (4).

If the amount of the auxiliary repeating unit is less than 0.1 mol %, it is unfavorably difficult to control the substrate adhesion and etching resistance of the resist resin. If the amount of the auxiliary repeating unit exceeds 70 mol %, it is unfavorably difficult to make sufficient use of the function of the sulfonate resin as the photoacid generator or the positive or negative resist resin in the present invention.

More specifically, in the case where the sulfonate resin has both of the photoacid generator function and the positive or negative resist function, the sulfonate resin contains 1 to 60 mol % of the repeating unit of the general formula (4) and 10 to 85 mol % of the repeating unit containing the acid labile group or cross-linking site, with the balance being the auxiliary repeating unit. It is preferable that the sulfonate resin contains 2 to 40 mol % of the repeating unit of the general formula (4) and 10 to 70% of the repeating unit containing the acid labile group or cross-linking site, more preferably 4 to 30 mol % of the repeating unit of the general formula (4) and 15 to 60% of the repeating unit containing the acid labile group or cross-linking site, with the balance being the auxiliary repeating unit. The composition of the sulfonate resin is not however limited to the above range as mentioned above.

In the present invention, the sulfonate resin generally has a mass-average molecular weight (MW) of 1,000 to 1,000,000, preferably 2,000 to 500,000, as measured by gel permeation chromatography (GPC). In the case of using the sulfonate resin in combination with any positive or negative photosensitive film-forming resin, the mass-average molecular weight of the sulfonate resin is generally 1,000 to 100,000, preferably 2,000 to 50,000. If the mass-average molecular weight of the sulfonate resin is less than 1,000, the acid generated from the sulfonate resin may diffuse and migrate in the resist film and reach the unexposed portion of the resist film during heat treatment after pattern exposure. This leads to deterioration in pattern resolution so that the effect of use of the sulfonate resin becomes low. If the mass-average molecular weight of the sulfonate resin, the solubility of the sulfonate resin in the solvent may become lowered so that it is unfavorably difficult to form a smooth resist film. The molecular weight distribution (Mw/Mn) of the sulfonate resin is preferably in the range of 1.01 to 5.00, more preferably 1.01 to 4.00, still more preferably 1.01 to 3.00, most preferably 1.10 to 2.50.

As mentioned above, the sulfonate resin can be in the form of a homopolymer or in the form of a copolymer with any other monomer in the present invention. When the acid labile group-containing monomer is used as the other monomer, the sulfonate resin attains a photosensitive solubility-changing function for use in a positive resist composition. When the cross-linking site-containing monomer is used as the other monomer, the sulfonate resin attains a photosensitive solubility-changing function for use in a negative resist composition. The copolymerization monomer used is not limited to the acid labile group-containing monomer or the cross-linking site-containing monomer. Various kinds of auxiliary monomers can be copolymerized in the sulfonate resin for control of dry etching resistance, standard developer compatibility, substrate adhesion, resist profile and other generally required resist characteristics such as resolution, heat resistance and sensitivity.

The sulfonate resin with the photoacid generator function and the positive or negative photosensitive solubility-changing function will be described in detail below.

The sulfonate resin having the repeating unit with the positive or negative photosensitive solubility-changing function can be obtained by copolymerization of any positive or negative photosensitive solubility-changeable monomer with the polymerizable fluorine-containing sulfonic acid onium salt of the general formula (2).

In order for the sulfonate resin to perform its photosensitive solubility-changing function as a positive resist resin, the sulfonate resin has a leaving moiety such as a carboxyl or hydroxyl group protected by an acid labile group on a side chain thereof. In this sulfonate resin, the main chain of repeating units is formed by cleavage of polymerizable double bond group such as vinyl group, 1-methylvinyl group, 1-fluorovinyl group, 1-trifluoromethylvinyl group, 1-cyanovinyl group or norbornenyl group and is bonded to the leaving moiety by a linking group W. In general, the linking group W provides a link as represented by (main chain)-W'—C(=O)-(acid labile group) or (main chain)-W'—O-(acid labile group) assuming the linking group as W'. The acid labile group refers to a group capable of leaving from the resin by the action of an acid generated from the photoacid generator etc. so as to serve as an acid and thereby increase the dissolution rate of the acid labile group-containing resin into an alkaline developer. The moiety containing such an acid labile group e.g. ester moiety (—(C=O)OR', alkoxycarbonyl group) or ether moiety (—O—R', alkoxy group) (where R' represents an acid labile group) is occasionally called "acid-decomposable site" or "leaving moiety".

In order for the sulfonate resin to perform its photosensitive solubility-changing function as a negative resist resin, the sulfonate resin has a cross-linking site such as a hydroxy or carboxyl group on a side chain thereof. In this sulfonate resin, the main chain of repeating units is formed by cleavage of polymerizable double bond group such as vinyl group, 1-methylvinyl group, 1-fluorovinyl group, 1-trifluoromethylvinyl group, 1-cyanovinyl group or norbornenyl group and is bonded to the cross-linking site via a linking group W. In general, the side chain has a structure represented by (main chain)-W'—C(=O)—OH or (main chain)-W'—OH assuming the linking group as W'. This hydroxyl group is an alcoholic hydroxyl group. The alcoholic hydroxyl group refers to a substantially neutral hydroxyl group that is not generally involved in the dissolution of the resin into an alkaline solution but is cross-linked with the after-mentioned cross-linking agent by hydroxyl-related reaction e.g. ester bonding, ether bonding, ureide bonding etc. so as to make the alkali-soluble resin component insoluble in an alkali solution.

The linking group W' will be next described below.

The linking group W', which links the leaving moiety to the main chain of the positive resist resin or links the cross-link moiety to the main chain of the negative resist resin, is a divalent linking group formed by one kind, or two or more kinds in combination, selected from the group consisting of a single bond, —$(CR^{21}R^{22})_n$— (where n is an integer of 1 to 10), —O—, —C(=O)—, —C(=O)O—, —O—C(=O)—, a divalent alicyclic hydrocarbon group, a divalent aromatic hydrocarbon group, a thioether group, an ester group, an amide group, a sulfonamide group, a urethane group and a urea group.

Examples of the combined linking group W' are:
—$(CR^{21}R^{22})_m$—C(=O)—O—$(CR^{21}R^{22})_n$—;
—$(CR^{21}R^{22})_m$—C(=O)—O—$(CR^{21}R^{22})_n$—B—$(CR^{21}R^{22})_l$—;
—$(CR^{21}R^{22})_m$—O—$(CR^{21}R^{22})_n$—;
—$(CR^{21}R^{22})_m$—O—$(CR^{21}R^{22})_n$—B—$(CR^{21}R^{22})_l$—;
—$(CR^{21}R^{22})_n$—B—$(CR^{21}R^{22})_l$—C(=O)—O—$(CR^{21}R^{22})_m$—; and
—$(CR^{21}R^{22})_n$—B—$(CR^{21}R^{22})_l$—O—$(CR^{21}R^{22})_m$—,
where B represents a cyclic group selected from divalent alicyclic and aromatic hydrocarbon groups; and l, m and n each independently represent an integer of 0 to 10. It is preferable that m is 0 and each of l and n is 0 or 1.

There is no particular limitation on the monovalent organic groups $R^{21}$ and $R^{22}$ in the above substituted methylene groups. $R^{21}$ and $R^{22}$ each independently represents a hydrogen atom, a hydroxyl group or a monovalent $C_1$-$C_{30}$ organic group selected from an alkyl group, an alicyclic hydrocarbon group, a substituted alkyl group, an alkoxy group, an aryl group, a condensed polycyclic aromatic group and a monocyclic or polycyclic heterocyclic group. The monovalent organic group may have a fluorine atom, an oxygen atom, a sulfur atom, a nitrogen atom or a carbon-carbon double bond. $R^{21}$ and $R^{22}$ can be the same or different. In the case where the methylene group contains a plurality of $R^{21}$ or $R^{22}$, $R^{21}$ or $R^{22}$ can be the same or different. Further, $R^{21}$ and $R^{22}$ may be bonded together to form a ring structure, preferably an alicyclic hydrocarbon structure.

Examples of the alkyl group are those of 1 to 30 carbon atoms, preferably 1 to 12 carbon atoms, such as methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl.

Examples of the substituted alkyl group are those obtained by substitution of one hydrogen atom or two or more hydrogen atoms of the alkyl group with a $C_1$-$C_4$ alkoxy group, a halogen atom, an acyl group, an acyloxy group, a cyano group, a hydroxyl group, a carboxyl group, an alkoxycarbonyl group, a nitro group etc. Among others, fluorine-substituted alkyl groups, i.e., fluoroalkyl groups are preferred. More specifically, there can be used lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

Examples of the alkoxy group are those of 1 to 4 carbon atoms, such as methoxy, ethoxy, propoxy and butoxy.

Examples of the aryl group are those of 1 to 30 carbon atoms. It is preferable that, when the aryl group is monocyclic, the monocyclic aryl group has 3 to 12 ring carbon atoms, more preferably 3 to 6 ring carbon atoms. As such aryl groups, there can be used phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the $C_1$-$C_{30}$ condensed polycyclic aromatic group are monovalent organic groups obtained by elimination of one hydrogen atom from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One hydrogen atom or two or more hydrogen atoms of the above condensed polycyclic aromatic group may preferably be substituted with a fluorine atom or a $C_1$-$C_4$ alkyl or fluorine-containing alkyl group.

Examples of the monocyclic or polycyclic heterocyclic group are those of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One hydrogen atom or two or more hydrogen atoms on the ring atoms of the above heterocyclic group may be substituted with an alkyl group, an alicyclic hydrocarbon group, an aryl group or a heterocyclic group. Among others, preferred are those having a monocyclic or polycyclic ether ring or lactone ring as exemplified as follows.

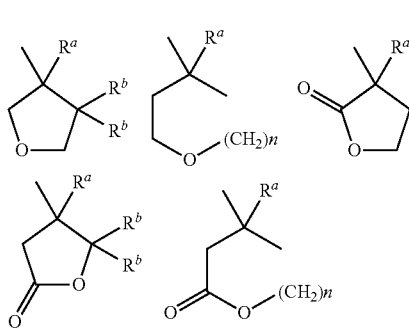

(E-9)

In the above formulas, $R^a$ and $R^b$ each independently represents a hydrogen atom or a $C_1$-$C_4$ alkyl group; and n represents an integer of 2 to 4.

The alicyclic hydrocarbon group as $R^{21}$, $R^{22}$ or the alicyclic hydrocarbon group formed by $R^{21}$ and $R^{22}$ together with the carbon atom bonded thereto in the linking group W' can be monocyclic or polycyclic. Examples of the alicyclic hydrocarbon group are those having a monocyclo, bicyclo, tricycle or tetracyclo structure of 3 or more carbon atoms, preferably 3 to 30 carbon atoms, more preferably 3 to 25 carbon atoms. The alicyclic hydrocarbon group may have a substituent.

As the monocyclic hydrocarbon group, there can preferably be used those having 3 to 12 ring carbon atoms, more preferably 3 to 7 ring carbon atoms. Examples of such a monocyclic hydrocarbon group are cyclopropyl, cyclobutyl, cyclopentyl, cyclohexyl, cycloheptyl, cyclooctyl, cyclodecanyl, cyclododecanyl, and 4-tert-butylcyclohexyl. As the polycyclic hydrocarbon group, there can preferably be used those having 7 to 15 ring carbon atoms. Examples of such a polycyclic hydrocarbon group are adamantyl, noradamantyl, decalin residue, tricyclodecanyl, tetracyclododecanyl, norbornyl and cedrol. The alicyclic hydrocarbon group can be a spiro ring of preferably 3 to 6 carbon atoms. Preferred examples of such a spiro ring are adamantyl, decalin residue, norbornyl, cedrol, cyclohexyl, cycloheptyl, cyclooctyl, cyclodecanyl, cyclododecanyl and tricyclodecanyl. One hydrogen atom or two or more hydrogen atoms on the ring carbons of the above organic group, or one hydrogen atom or two or more hydrogen atoms of the above linking group, may be each independently substituted with a substituent such as a $C_1$-$C_{25}$ alkyl or substituted alkyl group, a hydroxy group, an alkoxy group, a carboxyl group or an alkoxycarbonyl group. One hydrogen atom or two or more hydrogen atoms of the substituent may further be substituted with fluorine or trifluoromethyl.

Herein, the alkyl group is preferably a lower alkyl group, more preferably an alkyl group selected from the group consisting of methyl, ethyl, propyl and isopropyl. As the substituent of the substituted alkyl group, there can be used a hydroxyl group, a halogen atom, an alkoxy group etc. The alkoxy group is, for example, of 1 to 4 carbon atoms, such as methoxy, ethoxy, propoxy or butoxy. The alkoxycarbonyl group is, for example, methoxycarbonyl, ethoxycarbonyl or isopropoxycarbonyl.

Specific examples of the linking group W' are those indicated below:

— (single bond);
—$CH_2$—;
—$CH_2$—$CH_2$—;
—$CH_2$—B— (where B is a cyclic group selected from divalent alicyclic and aromatic hydrocarbon groups);
—B—$CH_2$—;
—$C_6H_4$—;
—O—$C_6H_4$—;
—C(=O)—O—;
—C(=O)—O—$CH_2$—$CH_2$—;
—$CH_2$—C(=O)—O—$CH_2$—;
—O—$CH_2$—;
—O—$CH_2$—$CH_2$—;
—$CH_2$—O—$CH_2$—;
—C(=O)—O—$(CR^{21}R^{22})_2$—; and
—$C_6H_4$—O—$(CR^{21}R^{22})_2$—.

It is preferable that $R^{21}$ and $R^{22}$ are each independently a hydrogen atom, a fluorine atom, an alkyl group, a substituted alkyl group or an alicyclic hydrocarbon group. One hydrogen atom or two or more hydrogen atoms of $R^{21}$, $R^{22}$ may be substituted with a fluorine atom. It is particularly preferable that the linking group W' is either —C(=O)—O—, —C(=O)—O—$CH_2$—, —$C_6H_4$— or —C(=O)—O—$(CR^{21}R^{22})_2$— where $R^{21}$ and $R^{22}$ are each independently a hydrogen atom, a fluorine atom, an alkyl group or a fluorine-containing alkyl group.

Further, there can be used a repeating unit of the general formula (11-1) where $R^{17-1}$ is an acid labile group; and the main chain is represented by —($CH_2$—C($R^8$))—.

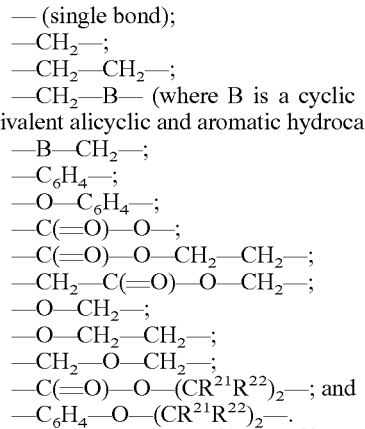

(11-1)

In the general formula (11-1), $R^8$ has the same meaning as in the after-mentioned general formula (6); $R^{18}$ represents a hydrogen atom, a fluorine atom or a fluorine-containing alkyl group; $R^{17-1}$ represents an acid labile group, preferably any one of the after-mentioned general formulas (d) to (h); and J represents a divalent linking group. As -J-CF($R^{18}$)— corresponds to the above-mentioned linking group W', the above explanation of the linking group W' can be applied to -J-CF($R^{18}$)—.

The acid labile group will be next described below.

In the photosensitive solubility-changeable sulfonate resin, the acid labile group is either one of acid labile groups of the following general formulas (d) to (h).

$R^{X1}$—O—C(=O)—                   (d)

$R^{X1}$—O—$CHR^{X2}$—                   (e)

CR$^{X3}$R$^{X4}$R$^{X5}$— (f)

SiR$^{X3}$R$^{X4}$R$^{X5}$— (g)

R$^{X1}$—C(=O)— (h)

In the above formulas, R$^{X1}$ represents an alkyl group, an alicyclic hydrocarbon group or an aryl group; R$^{X2}$ represents a hydrogen atom, an alkyl group, an alicyclic hydrocarbon group, an alkenyl group, an aralkyl group, an alkoxy group or an aryl group; and R$^{X3}$, R$^{X4}$ and R$^{X5}$ can be the same or different and each represents an alkyl group, an alicyclic hydrocarbon group, an alkenyl group, an aralkyl group or an aryl group. Two of R$^{X3}$, R$^{X4}$ and R$^{X5}$ may be bonded to each other to form a ring.

Preferred examples of the alkyl group are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, norbornane-epoxy, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, tolyl, cumenyl, naphthyl and anthracenyl. These groups may have substituents. Preferred examples of the aralkyl group are those of 7 to 20 carbon atoms, such as benzyl, phenethyl and cumyl, each of which may have a substituent.

As the substituents of the above organic groups, there can be used: a hydroxy group; a halogen atom (fluorine, chlorine, bromine, iodine); a nitro group; a cyano group; any of the above alkyl and alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (E-10) and (E-11).

(E-10)

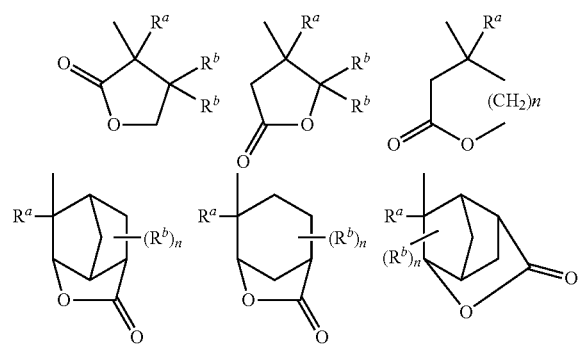

(E-11)

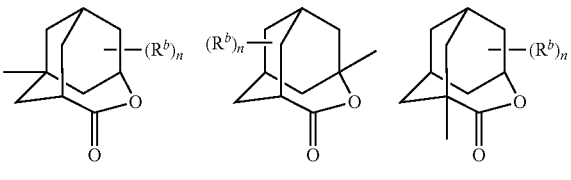

In the above formulas, R$^a$ represents a C$_1$-C$_4$ alkyl or perfluoroalkyl group; R$^b$ each independently represent a hydrogen atom, a C$_1$-C$_4$ alkyl or perfluoroalkyl group, a hydroxy group, a carbonic acid group, an alkyloxycarbonyl group or an alkoxy group; and n represents an integer of 1 to 4.

It is preferable to use the acid labile group of the general formula (d), (e) or (f) in the resist composition for pattern formation by exposure to high-energy radiation such as laser radiation or electron beam radiation because each of the acid labile groups of the general formulas (d), (e) and (0 has a chemical amplification function.

The acid labile group is more specifically exemplified as follows.

Specific examples of the alkoxycarbonyl group represented by the general formula (d): R$^{X1}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantanoxycarbonyl.

Specific examples of the acetal group represented by the general formula (e): R$^{X1}$—O—CHR$^{X2}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the tertiary hydrocarbon group represented by the general formula (f): CR$^{X3}$R$^{X4}$R$^{X5}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

The alicyclic hydrocarbon group or the alicyclic hydrocarbon-containing acid labile group can be exemplified by the following formulas (E-12) and (E-13).

(E-12)

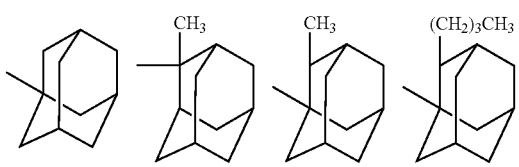

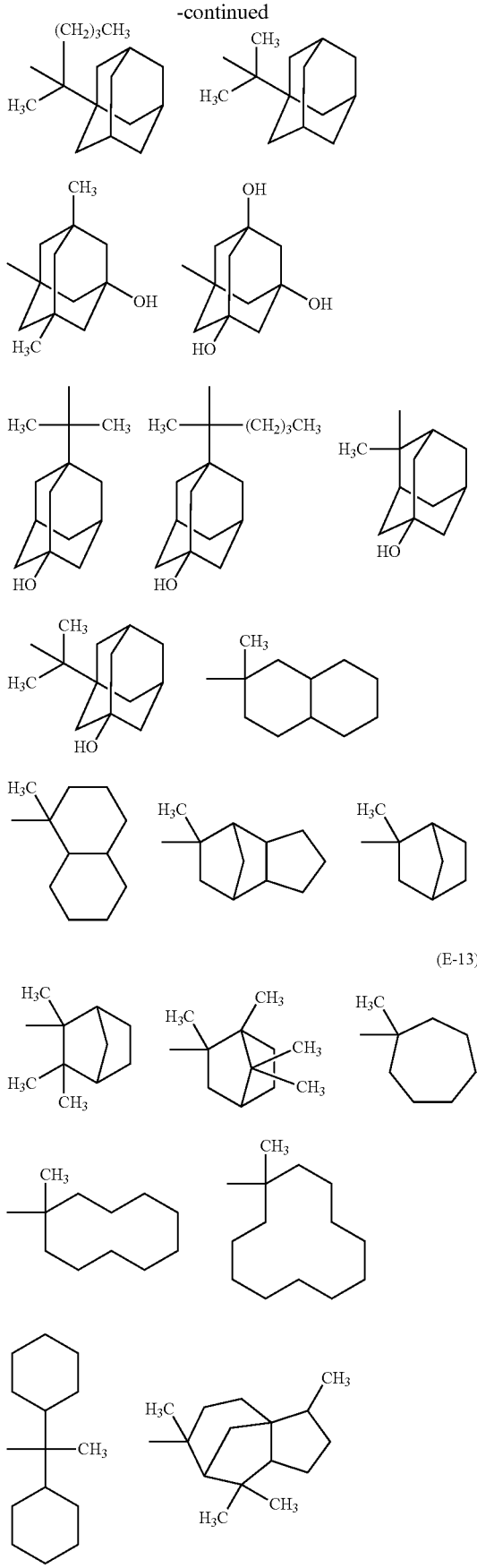
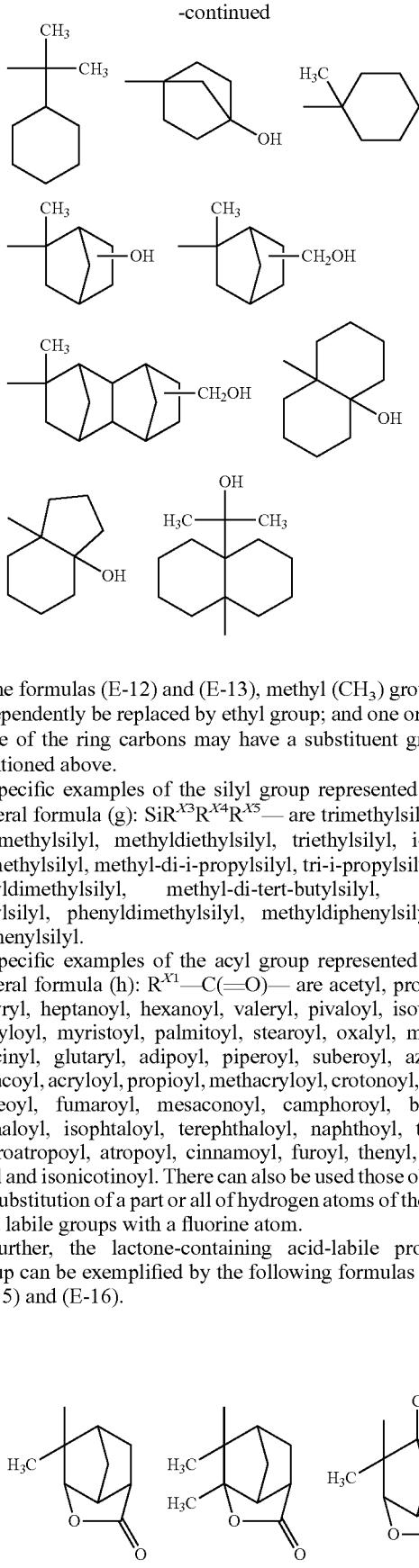

In the formulas (E-12) and (E-13), methyl (CH$_3$) group may independently be replaced by ethyl group; and one or two or more of the ring carbons may have a substituent group as mentioned above.

Specific examples of the silyl group represented by the general formula (g): SiR$^{X3}$R$^{X4}$R$^{X5}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (h): R$^{X1}$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydroatropoyl, atropoyl, cinnamoyl, furoyl, thenyl, nicotinoyl and isonicotinoyl. There can also be used those obtained by substitution of a part or all of hydrogen atoms of the above acid labile groups with a fluorine atom.

Further, the lactone-containing acid-labile protecting group can be exemplified by the following formulas (E-14), (E-15) and (E-16).

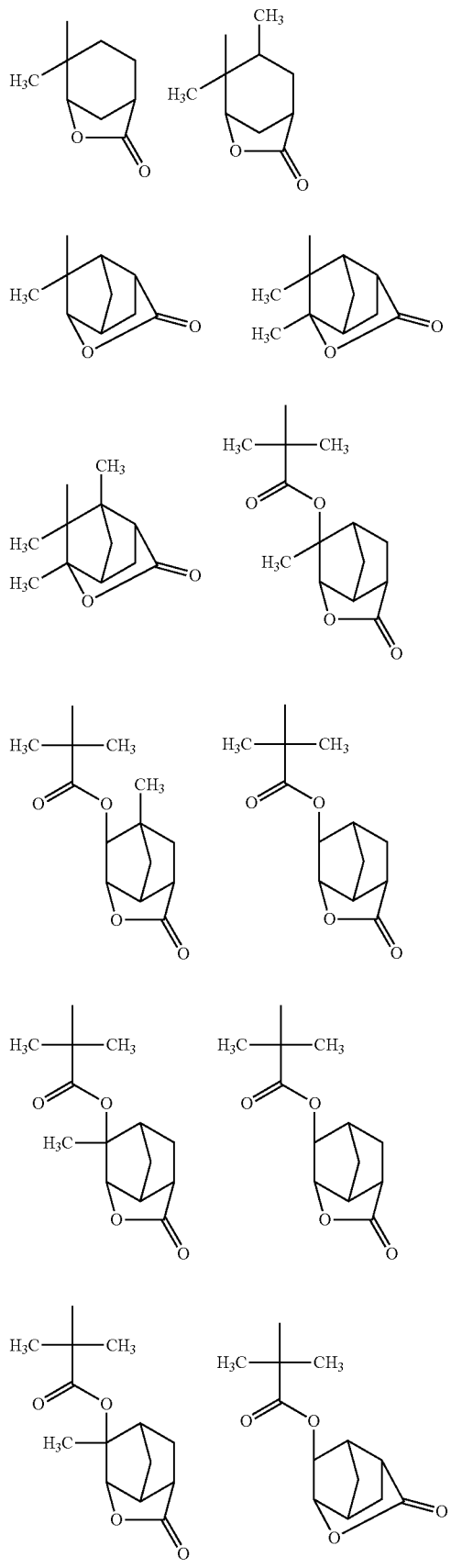
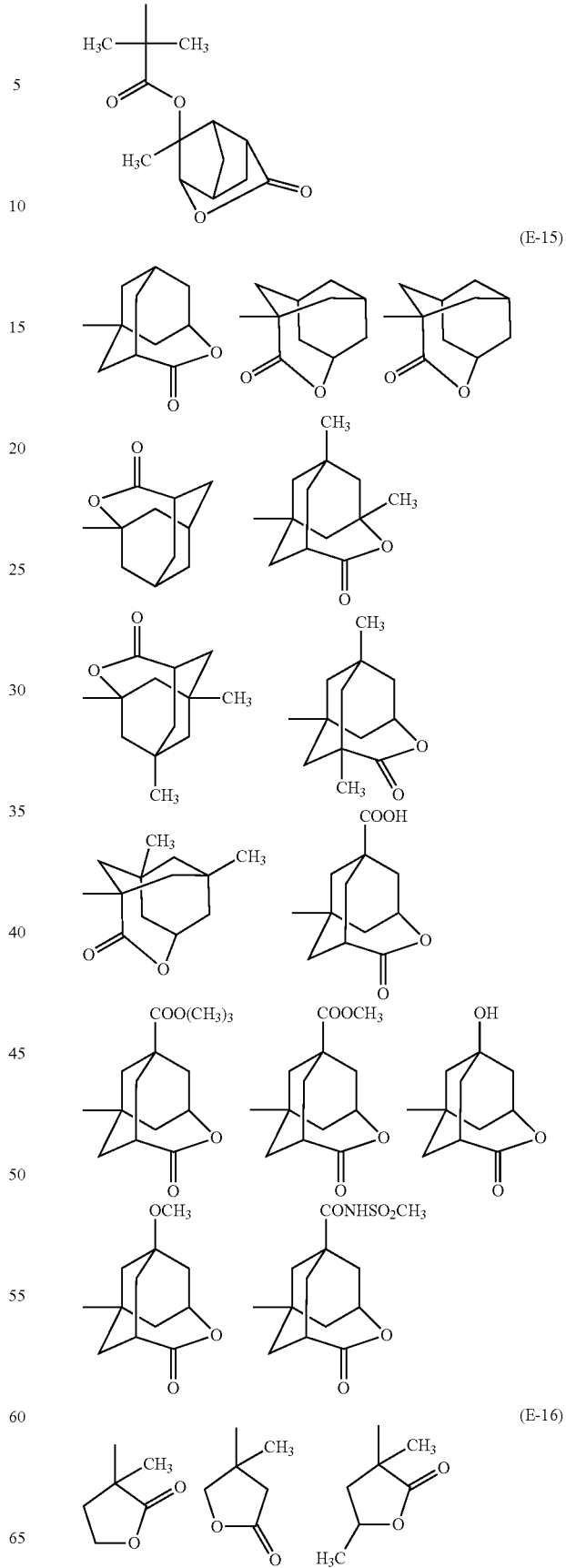

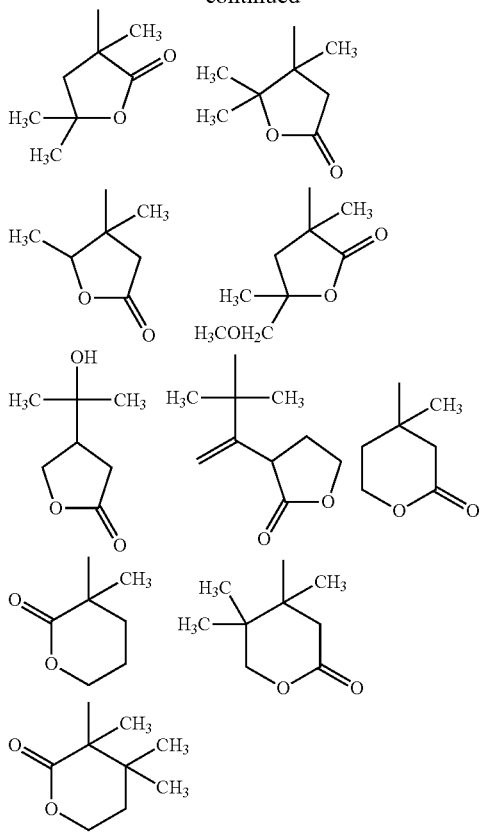

In the formulas (E-14), (E-15) and (E-16), methyl ($CH_3$) group may independently be replaced by ethyl group.

In the case of using ArF excimer laser as the exposure light source, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an alicyclic hydrocarbon group such as adamantyl or isobornyl, an alicyclic hydrocarbon-containing acid labile group or a lactone-containing acid labile group as exemplified above.

The other copolymerization component (auxiliary repeating unit) will be described below.

In the present invention, the sulfonate resin can be produced with the use of any auxiliary monomer as the other copolymerization component. One or more kinds selected from the after-mentioned monomers can be used as the auxiliary monomer for introduction into the sulfonate resin. There is no particular limitation on the other copolymerization component. As the other copolymerization component, there can be used any of olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. Among others, acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred as the other copolymerization component.

Specific examples of the olefins are ethylene and propylene. Specific examples of the fluoroolefins are vinyl fluoride, vinylidene fluoride, trifluoroethylene, chlorotrifluoroethylene, tetrafluoroethylene, hexafluoroethylene and hexafluoroisobutene.

There is no particular limitation on the ester side chain of the acrylic ester or methacrylic ester. Specific examples of the acrylic esters or methacrylic esters are known acrylic or methacrylic ester compounds: such as acrylic or methacrylic acid alkyl ester e.g. methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, or 2-hydroxypropyl acrylate or methacrylate; acrylate or methacrylate containing an ethylene glycol group, propylene glycol group or tetramethylene glycol group; alkoxysilyl-containing acrylic or methacrylic ester; t-butyl acrylate or methacrylate; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; and acrylate or methacrylate having a ring structure such as lactone ring or norbornene ring.

There can also be used: unsaturated amide e.g. acrylamide, methacrylamide, N-methylol acrylamide, N-methylol methacrylamide or diacetone acrylamide; acryloyl-containing compound e.g. acrylonitrile or methacrylonitrile; maleic acid; fumaric acid; and maleic anhydride.

Examples of the fluorine-containing acrylic esters or fluorine-containing methacrylic esters are acrylic or methacrylic ester monomers each having a fluorine atom or a fluorine-containing group at α-position of the acrylic acid group or in the ester moiety thereof. As the monomers having a fluorine-containing alkyl group at α-position, for example, there can suitably be used those obtained by addition of a trifluoromethyl group, a trifluoroethyl group, a nonafluoro-n-butyl group etc. to the α-position of the above non-fluorinated acrylic ester or methacrylic ester.

As the fluorine-containing acrylic or methacrylic ester with the fluorine-containing group, there can suitably be used those each having a perfluoroalkyl group, a fluoroalkyl group or a fluorine-containing cyclic group in which a fluorine atom or trifluoromethyl group is substituted on any number of ring carbons, such as a fluorine-containing benzene ring, a fluorine-containing cyclopentane ring, a fluorine-containing cyclohexane ring or a fluorine-containing cycloheptane ring, in the ester moiety. Examples of such fluorine-containing acrylic or methacrylic ester are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, and an acrylic ester or methacrylic ester having a fluorine-containing t-butyl ester group in the ester moiety.

Acrylate compounds, each obtained by bonding a cyano group to the α-position of any acrylic ester or fluorine-containing acrylic ester mentioned in the present specification, are also usable.

There is no particular limitation on the structure of the norbornene compound or fluorine-containing norbornene compound. The norbornene compounds or fluorine-containing norbornene compounds can have a mononuclear structure or a multinuclear structure. Suitable examples of the norbornene compounds are those each formed by Diels-Alder addition reaction of an unsaturated compound such as an allyl alcohol, a fluorine-containing allyl alcohol, an acrylic acid, an α-fluoroacrylic acid, a methacrylic acid or any of the acrylic esters, methacrylic esters, fluorine-containing acrylic esters and fluorine-containing methacrylic esters mentioned above in the present specification with cyclopentadiene or cyclohexadiene.

The styrenic compounds, fluorine-containing styrenic compounds, vinyl ethers, fluorine-containing vinyl ethers, allyl ethers, vinyl esters, vinyl silanes and the like can also be used. Examples of the styrenic compounds and fluorine-containing styrenic compounds are styrene, fluorinated styrene, hydroxystyrene, styrenic compounds in which hexafluoroacetone has been added to the benzene ring and monomers obtained by substituting any hydrogen atom on the benzene ring of styrene or hydroxystyrene with a trifluoromethyl group or by bonding a halogen atom, an alkyl group or a fluoroalkyl group to the α-position of the above styrene or fluorine-containing styrenic compound. Examples of the vinyl ethers and fluorine-containing vinyl ethers are: alkyl vinyl ethers having an alkyl group such as methyl or methyl or a hydroxyalkyl group such as hydroxyethyl or hydroxybutyl in which a part or all of hydrogen atoms may be substituted with fluorine; cyclic vinyl ethers such as those having an oxygen atom or carbonyl bond in the cyclic structure or those obtained by substitution of a part or all of hydrogen atoms with fluorine atom, e.g., cyclohexyl vinyl ether. The allyl ethers, vinyl esters and vinyl silanes can be used without particular limitation as long as they are known compounds.

As one preferred example of the repeating unit usable in combination with the repeating unit of the general formula (4) in the sulfonate resin or photosensitive solubility-changeable sulfonate resin, there can preferably be used a repeating unit of the following general formula (6).

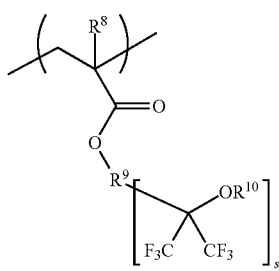

(6)

In the general formula (6), $R^8$ represents a hydrogen atom, a halogen atom or a $C_1$-$C_3$ alkyl or fluorine-containing alkyl group; $R^9$ represents a substituted or unsubstituted aliphatic hydrocarbon group, a substituted or unsubstituted aromatic hydrocarbon group or an organic group in which a plurality of substituted or unsubstituted aliphatic and/or aromatic hydrocarbon groups are bonded to each other; any number of hydrogen atoms in $R^9$ may be substituted with a fluorine atom; $R^{10}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms in $R^{10}$ may be substituted with a fluorine atom; $R^{10}$ may contain an ether bond or a carbonyl group; and s represents an integer of 1 or 2.

$R^8$ in the general formula (6) is exemplified as follows. Examples of the halogen atom are fluorine, chlorine and bromine. Examples of the $C_1$-$C_3$ alkyl group are methyl, ethyl, propyl and isopropyl. Examples of the $C_1$-$C_3$ fluorine-containing alkyl group as $R^1$ are those obtained by substitution of a part or all of hydrogen atoms of the above alkyl group with a fluorine atom, such as trifluoromethyl; —$CF_3$, trifluoroethyl; —$CH_2CF_3$, 1,1,1,3,3,3-hexafluoroisopropyl and heptafluoroisopropyl. Among others, preferred are a hydrogen atom, a fluorine atom, a methyl group and a trifluoromethyl group.

As mentioned above, $R^9$ is either a substituted or unsubstituted aliphatic hydrocarbon group, a substituted or unsubstituted aromatic hydrocarbon group or an organic group in which a plurality of substituted or unsubstituted aliphatic and/or aromatic hydrocarbon groups are bonded to each other; and any number of hydrogen atoms in $R^9$ may be substituted with a fluorine atom. The unsubstituted aliphatic hydrocarbon group can be straight, branched or cyclic. Examples of the unsubstituted divalent aliphatic hydrocarbon group are straight or branched alkylene groups such as methylene, ethylene, isopropylene and t-butylene and cyclic alkylene groups such as cyclobutylene, cyclohexylene, divalent norbornane and divalent adamantane. Examples of the unsubstituted aromatic group are divalent aromatic groups such as phenylene and naphthylene. There can also be used trivalent groups obtained by elimination of one hydrogen atom from these divalent groups. Examples of the substituted aliphatic hydrocarbon and aromatic groups are those obtained by substitution of any number of hydrogen atoms in the above unsubstituted aliphatic hydrocarbon and aromatic groups with any kind of substituent.

Particularly preferred examples of the repeating unit of the general formula (6) are those of the general formulas (7) to (9).

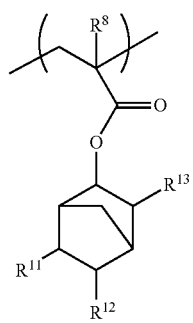

(7)

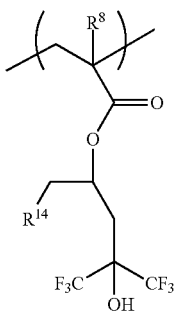

(8)

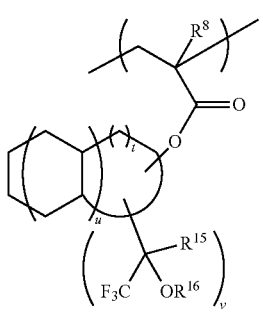

(9)

In the general formula (7), $R^8$ has the same meaning as in the general formula (6); one of $R^{11}$, $R^{12}$ and $R^{13}$ represents a $CF_3C(CF_3)(OH)CH_2$— group; and the other two of $R^{11}$, $R^{12}$ and $R^{13}$ each represent a hydrogen atom. In the general formula (8), $R^8$ has the same meaning as in the general formula (6); and $R^{14}$ represents a hydrogen atom or a $C_1$-$C_4$ alkyl or fluorine-containing alkyl group. Examples of the $C_1$-$C_4$ alkyl or fluorine-containing alkyl group as $R^{14}$ are methyl, ethyl, n-propyl, isopropyl, n-butyl, sec-butyl, tert-butyl, fluoromethyl, difluoromethyl, trifluoromethyl and perfluoroethyl. In the general formula (9), $R^8$ has the same meaning as in the general formula (6); $R^{15}$ represents a methyl group or a trifluoromethyl group; $R^{16}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an oxygen atom (ether bond) or a carbonyl group; u represents an integer of 0 to 2; t and v each independently represent an integer of 1 to 8 and satisfy a relationship of v≤t+2; and, when v is 2 to 8, $R^{15}$ and $R^{16}$ can be the same or different.

Examples of the substituted or unsubstituted $C_1$-$C_{25}$ aliphatic hydrocarbon group or substituted or unsubstituted $C_1$-$C_{25}$ aromatic hydrocarbon group as $R^{16}$ in the general formula (9) are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, in each of which a part or all of hydrogen atoms may be substituted with a fluorine atom. As the oxygen-containing hydrocarbon group, an alkoxycarbonyl group, an acetal group or an acyl group are usable. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above groups may be substituted with fluorine.

Further, there can suitably be used a repeating unit of the general formula (10) in combination with the repeating unit of the general formula (4).

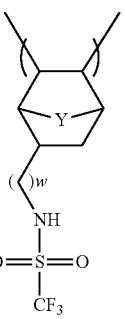

(10)

In the general formula (10), Y represents either —$CH_2$—, —O— or —S—; and w represents an integer of 2 to 6.

There can also suitably be used a repeating unit of the general formula (11) in combination with the repeating unit of the general formula (4).

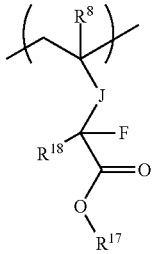

(11)

In the general formula (11), $R^8$ has the same meaning as in the general formula (6); and $R^{18}$ represents a hydrogen atom, a fluorine atom or a fluorine-containing alkyl group. The above explanation of $R^{16}$ in the general formula (16) can be applied to $R^{17}$. Further, J represents a linking group. As -J-CF($R^{18}$)— corresponds to the above-mentioned linking group W', the above explanation of the linking group W' can be applied to -J-CF($R^{18}$)—.

As mentioned above, $R^{18}$ is a hydrogen atom, a fluorine atom or a fluorine-containing alkyl group. There is no particular limitation on the fluorine-containing alkyl group as $R^{18}$. Examples of the fluorine-containing alkyl group are those of 1 to 12 carbon atoms, preferably 1 to 3 carbon atoms, such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl. Particularly preferred as $R^{18}$ are a fluorine atom and a trifluoromethyl.

There can also suitably be used a repeating unit of the general formula (12) in combination with the repeating unit of the general formula (4).

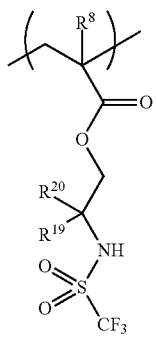

(12)

In the general formula (12), $R^8$ has the same meaning as in the general formula (6); $R^{19}$ and $R^{20}$ each independently represents a hydrogen atom, a substituted or unsubstituted $C_1$-$C_{25}$ straight, branched or cyclic aliphatic hydrocarbon group or a substituted or unsubstituted $C_1$-$C_{25}$ aromatic hydrocarbon group. Any number of hydrogen atoms in $R^{19}$, $R^{20}$ may be substituted with a fluorine atom. Further, $R^{19}$ and $R^{20}$ may contain an ether bond or a carbonyl group. Examples of $R^{19}$, $R^{20}$ are the same as those of $R^{16}$ in the general formula (9).

Next, a polymerization process for production of the sulfonate resin having the repeating unit of the general formula (4) will be described below.

There is no particular limitation on the polymerization process for production of the resin having the repeating unit of the general formula (4) in the present invention. It is preferable to adopt radical polymerization process or ionic polymerization process. In some cases, it is feasible to adopt coordination anionic polymerization process, living anionic polymerization process, cationic polymerization process, ring-opening metathesis polymerization process, vinylene polymerization process or vinyl addition process. The polymerization reaction can be performed by any ordinary known process.

The radical polymerization process can be conducted by a known polymerization technique such as bulk polymerization, solution polymerization, suspension polymerization or emulsion polymerization technique in a batch, semi-continuous or continuous system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Further, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents can also be used. These solvents can be used solely or in combination of two or more thereof. A molecular weight adjusting agent such as mercaptan may be used in combination. The reaction temperature of the copolymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained fluorine-containing polymer solution or dispersion, it is feasible to adopt reprecipitation, filtration, distillation by heating under a reduced pressure or the like.

[Resist Composition]

The resist composition will be next described below.

In the present invention, the resin having the repeating unit of the general formula (4) is used in a resist composition in the form of a solution mixed with other components. This sulfonate resin serves as a photoacid generator. In the case where the sulfonate resin has the repeating unit with the acid labile group or cross-linking site, the sulfonate resin can be used solely as a chemically amplified resist resin without the addition of any other resin having a repeating unit with an acid labile group or cross-linking site (as a base resin). In the case where the sulfonate resin has the repeating unit of the general formula (4) but does not have the repeating unit with the acid labile group or cross-linking site, the resist composition is prepared with the addition of a base resin as an essential component to the sulfonate resin. The resist composition includes not only a solvent but also various additives commonly used for resist compositions, such as an additive resin, a quencher, a dissolution inhibitor, a plasticizer, a stabilizer, a coloring agent, a surfactant, a viscosity improver, a leveling agent, an antifoaming agent, a compatibilizer, a primer and an antioxidant. In the case of the negative resist composition, other additives such as a cross-linking agent and a basic compound may further be added. As these additives, there can suitably be used any of known additives as well as the following compounds.

(Base Resin)

The base resin refers to a resin containing an acid labile group so as to perform a positive resist function or a resin containing a cross-linking site so as to perform a negative resist function. As mentioned above, the photosensitive solubility-changeable sulfonate resin is usable as the base resin.

Examples of the base resin for the positive resist composition are those having a leaving site such as carboxyl group or hydroxyl group protected by an acid labile group on a side chain thereof. In this base resin, the main chain of repeating units is formed by cleavage of polymerizable double bond group such as acrylic acid, methacrylic acid, α-trifloromethylacrylic acid, vinyl group, allyl group or norbornenyl group.

Examples of the base resin for the negative resist composition are those having a cross-linking site such as hydroxyl group or carboxyl group on a side chain thereof. In this base resin, the main chain of repeating units is formed by cleavage of polymerizable double bond group such as acrylic acid, methacrylic acid, α-trifloromethylacrylic acid, vinyl group, allyl group or norbornene group.

In many cases, the base resin is in the form of a copolymer for control of the resist characteristics. There are known various base resins. Herein, the above explanations of the copolymerization component, the acid labile group, cross-linking site and linking group (W or W') can be applied as they are to the base resin. The copolymerization component of the base resin is preferably a lactone ring-containing monomer for improvement in the substrate adhesion of the resist composition.

The repeating unit of the general formula (4) may be contained in the base resin. In this case, the base resin combines the function of the sulfonate resin as the photoacid generator. It is thus feasible to prepare the positive resist composition from only the acid labile group-containing base resin and the solvent. It is also feasible to prepare the negative resist composition from only the cross-linking site-containing base resin, the cross-linking agent and the solvent.

The base resin generally has a mass-average molecular weight of 1,000 to 1,000,000, preferably 2,000 to 500,000, as measured by gel permeation chromatography (GPC). If the mass-average molecular weight of the base resin is less than 1,000, the resulting resist film does not attain sufficient strength. If the mass-average molecular weight of the base resin exceeds 1,000,000, the solubility of the base resin in the solvent becomes lowered so that it is unfavorably difficult to form the resist composition into a smooth film. The molecular weight distribution (Mw/Mn) of the base resin is preferably in the range of 1.01 to 5.00, more preferably 1.01 to 4.00, still more preferably 1.01 to 3.00, most preferably 1.10 to 2.50.

(Additives)

In the case of the negative resist composition, there can be used any known cross-linking agent for chemically amplified negative resist compositions.

More specifically, the cross-linking agent can be any compound formed by reacting an amino-containing compound, such as melamine, acetoguanamine, benzoguanamine, urea, ethylene urea, propylene urea or glycoluril, with formaldehyde or a mixture of formaldehyde and lower alcohol and thereby substituting a hydrogen atom of the amino group with a hydroxymethyl group or a lower alkoxymethyl group.

Herein, the cross-linking agents using melamine, urea, alkylene urea e.g. ethylene urea, propylene urea etc. and glycoluril are referred to as "melamine-based cross-linking agent", "urea-based cross-linking agent", "alkylene urea-based cross-linking agent" and "glycoluril-based cross-linking agent", respectively. The cross-linking agent is preferably at least one kind selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Specific examples of the melamine-based cross-linking agent are hexamethoxymethylmelamine, hexaethoxymethylmelamine, hexapropoxymethylmelamine and hexabutoxymethylmelamine. Among others, hexamethoxymethylmelamine is preferred.

Specific examples of the urea-based cross-linking agent are bismethoxymethylurea, bisethoxymethylurea, bispropoxymethylurea and bisbutoxymethylurea. Among others, bismethoxymethylurea is preferred.

Specific examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Specific examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

One kind of cross-linking agent component, or two or more kinds of cross-linking agent components in combination, can be used. The total amount of the cross-linking agent used is preferably 3 to 30 parts by mass, more preferably 3 to 25 parts by mass, most preferably 5 to 20 parts by mass, per 100 parts by mass of the base resin in the negative resist composition. When the total amount of the cross-linking agent is larger than or equal to the above-specified lower limit value, the resist composition can form sufficient cross-linking for good resist pattern. The resist composition can show good storage stability and can be prevented from deteriorating in sensitivity with time when the total amount of the cross-linking agent is smaller than or equal to the above-specified upper limit value.

In the present invention, the basic compound is preferably contained as an optional component in the resist composition so as to serve as a quencher or to obtain improvements in resist pattern shape and post exposure stability.

There can be used any known basic compounds such as primary, secondary and tertiary aliphatic amines, aromatic amines, heterocyclic amines, nitrogen-containing compounds with hydroxyphenyl group, alcoholic nitrogen-containing compounds and amide derivatives. Among others, secondary and tertiary aliphatic amines, aromatic amines and heterocyclic amines are preferred.

The aliphatic amines can be alkylamines or alkylalcoholamines each obtained by replacing at least one hydrogen atom of ammonia ($NH_3$) with an alkyl or hydroxyalkyl group of up to 12 carbon atoms. Specific examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines such as aniline, aniline derivatives e.g. N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines e.g. 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines e.g. bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)

morpholine, 2-(2-hydroxyethyl)pyridine, 1-(2-hydroxyethyl)piperazine, and 1-[2-(2-hydroxyethoxy)ethyl]piperazine.

The above basic compounds can be used solely or in combination of two or more thereof.

The amount of the basic compound used is generally 0.01 to 5 parts by mass per 100 parts by mass of the base resin.

In the case of the negative resist resin, an organic carboxylic acid or a phosphorus oxo acid or derivative thereof may be added an optional component in order to prevent sensitivity deterioration caused by the addition of the basic compound and to obtain improvements in resist pattern shape and post exposure stability. The acid compound can be used solely or in combination with the basic compound.

Suitable examples of the organic carboxylic acid are malonic acid, citric acid, malic acid, succinic acid, benzoic acid and salicylic acid.

Suitable examples of the phosphorus oxo acid or its derivative are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Among others, phosphonic acid is particularly preferred.

(Solvent)

It is feasible, as one method of forming the fluorine-containing polymer compound into a thin film, to dissolve the fluorine-containing polymer compound etc. in an organic solvent, and then, apply and dry the resulting composition. There is no particular limitation on the organic solvent as long as the fluorine-containing polymer component can be dissolved in the organic solvent. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof.

(Surfactant)

The surfactant, preferably either one or two or more kinds of fluorine- and/or silicon-based surfactants (fluorine-based surfactant, silicon-based surfactants and surfactant containing both of fluorine and silicon atoms) can be contained in the resist composition.

The addition of such a surfactant into the resist composition is effective for use with an exposure light source of 250 nm or less wavelength, notably 220 nm or less wavelength, and for pattern formation with a narrower pattern line width. It is possible to attain good sensitivity and resolution and form good resist pattern with less adhesion/development failures.

(Acid Generator)

In the resist composition, any known photoacid generator can be used in combination with the sulfonate resin. It is feasible to select and use any one of acid generators for chemically amplified resist compositions. Examples of the acid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The total amount of the photoacid generators used, including the sulfonate resin according to the present invention, is generally in the range of 0.5 to 20 parts by mass per 100 parts by mass of the resist composition. If the total amount of the photoacid generators is less than 0.5 parts by mass, the resin composition unfavorably results in insufficient pattern formation. If the total amount of the photoacid generators exceeds 20 parts by mass, it is difficult to prepare the resin composition into a uniform solution. Further, the resin composition unfavorably tends to become low in storage stability if the amount of the photoacid generator exceeds 20 parts by mass. The fluorine-containing sulfonate resin according to the present invention is generally contained by 1 to 100 parts by mass, preferably 10 to 100 parts by mass, more preferably 30 to 100 parts by mass, in 100 parts by mass of the total photoacid generator content.

(Additive Resin)

There is no particular limitation on the additive resin as long as the additive resin can be dissolved in the solvent used and has compatibility with the other components of the resist composition. The additive resin functions as a plasticizer, a stabilizer, a viscosity improver, a leveling agent, an antifoaming agent, a compatibilizer, a primer etc.

[Pattern Forming Method]

Next, a pattern forming method will be described below.

In the present invention, the resist composition can be used for resist pattern formation by a conventional photoresist technique. For example, the resist composition is first prepared in solution form, applied to a substrate such as a silicon wafer by e.g. a spinner and dried to form a photosensitive film. The thus-formed photosensitive film is irradiated with high-energy radiation or electron beam by e.g. an exposure device through a desired mask pattern, and then, subjected to heating. Subsequently, the exposed photosensitive film is developed with an alkaline developer such as 0.1 to 10 mass % tetramethylammoniumhydroxide solution. It is possible by the above method to form a resist pattern according to the mask pattern. As mentioned above, various additives compatible with the resist composition, such as additive resin, quencher, plasticizer, stabilizer, coloring agent, surfactant, viscosity improver, leveling agent, antifoaming agent, compatibilizer, primer, antioxidant etc., can be contained as desired.

There is no particular limitation on the high-energy radiation used in the present invention. It is particularly effective to use high-energy radiation of 300 nm or less wavelength, such as near-ultraviolet radiation (wavelength: 380 to 200 nm) or vacuum-ultraviolet radiation (far-ultraviolet radiation, VUV, wavelength: 200 to 10 nm) e.g. $F_2$ excimer laser, KrF excimer laser or ArF excimer laser, extreme-ultraviolet radiation (EUV, wavelength: 10 nm or shorter) e.g. synchrotron radiation, soft X-ray, X-ray, γ-ray, or electron beam. The names of the above electromagnetic waves are only for the sake of convenience. The light source is selected according to the wavelength because the physical and chemical properties of the electromagnetic wave depend on the wavelength of the electromagnetic wave. It is thus effective in the present pattern forming method to use an exposure device having a light source capable of generating such high-energy radiation of 300 nm or less wavelength of electron beam. The vacuum-ultraviolet radiation of 10 to 14 nm wavelength (sometimes called EUV or soft X-ray in the field of lithography) is preferably used. Further, it is effective to adopt a liquid immersion exposure device which uses a medium causing less absorption of high-energy radiation, such as water or fluorinated solvent, in a part of optical path and enables more efficient fine processing in terms of numerical aperture and effective wavelength. The resist composition is suitable for use in even such an exposure device.

In liquid immersion lithography using the liquid immersion exposure device, it is feasible to perform an exposure step by applying ArF excimer laser of 193 nm wavelength and inserting water or any liquid medium other than water, having a higher refractive index than air, between the substrate to which the resist composition has been applied and projection lens.

EXAMPLES

Hereinafter, the present invention will be described in more detail below by way of the following synthesis examples, working examples and comparative examples. It should be noted that the following working examples are illustrative and are not intended to limit the present invention thereto.

Synthesis Example 1

Triphenylsulfonium 2-(1-Ethoxycarbonyl-1-methacryloyloxy-2,2,2-trifluoroethoxy)-1,1-difluoroethanesulfonate

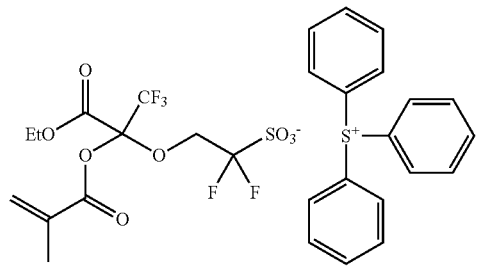

First, 5.0 g of triphenylsulfonium 2-hydroxy-1,1-difluoroethanesulfonate in white solid form (purity: 62.2%; equivalent to 7.3 mmol) was dissolved by stirring into 35 g of chloroform. The resulting solution was admixed with 1.46 g (8.55 mmol) of ethyltrifluoromethyl pyruvate and subjected to reaction for 3 hours at room temperature. The reaction solution was then concentrated under a reduced pressure. To the concentrated solution, 26.5 g of acetonitrile was added to dissolve the reaction intermediate by stirring.

The dissolved solution was admixed with 1.47 g (9.54 mmol) of methacrylic acid anhydride, 1.06 g (10.47 mmol) of triethylamine and 0.02 g (0.16 mmol) of 4-dimethylaminopyridine as a catalyst. The resulting mixture was stirred for 4 hours at 20 to 30° C. The organic layer was then separated with the addition of 30 g of chloroform and 50 g of ion-exchanged water. The separated organic layer was washed four times with 50 g of aqueous NaHCO$_3$ solution and washed four times with 50 g of ion-exchanged water.

After that, the organic layer was concentrated. To the concentrated organic layer, 8 g of 2-butanone and 30 g of diisopropyl ether were added. The resulting mixture was stirred. The 2-butanone layer (lower layer) was then separated from the mixture. The thus-obtained solution was concentrated under a reduced pressure, thereby yielding 7.2 g of the target compound in viscous liquid form (purity: 90%).

Properties of triphenylsulfonium 2-(1-ethoxycarbonyl-1-methacryloyloxy-2,2,2-trifluoroethoxy)-1,1-difluoroethanesulfonate $^1$H NMR (measurement solvent: deuterated chloroform, reference material: tetramethylsilane): δ=7.73-7.67 (m, 15H; Ph$_3$S$^+$), 6.22 (s, 1H; =CH$_2$), 5.71 (s, 1H; =CH$_2$), 4.64 (t, J=16.0 Hz, 2H), 4.26 (q, J=8.0 Hz, 2H), 1.96 (s, 3H), 1.25 (t, J=8.0 Hz, 3H).

$^{19}$F NMR (measurement solvent: deuterated chloroform, reference material: trichlorofluoromethane): δ=−79.0 (s, 3F), −115.7 (m, 2F).

Synthesis Example 2

Triphenylsulfonium 4-(1-Ethoxycarbonyl-1-methacryloyloxy-2,2,2-trifluoroethoxy)-1,1,2,2-tetrafluorobutanesulfonate

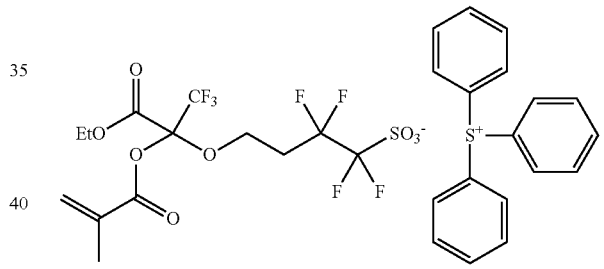

First, 14.4 g of triphenylsulfonium 4-hydroxy-1,1,2,2-tetrafluorobutanesulfonate in viscous liquid form (purity: 80%; equivalent to 23.6 mmol) was dissolved by stirring into 60 g of chloroform. The resulting solution was admixed with 7.5 g (43.8 mmol) of ethyltrifluoromethyl pyruvate and subjected to reaction for 3 hours at room temperature. The reaction solution was then concentrated under a reduced pressure. To the concentrated solution, 40 g of acetonitrile was added to dissolve the reaction intermediate by stirring.

The dissolved solution was admixed with 5.79 g (37.6 mmol) of methacrylic acid anhydride, 4.04 g (40.0 mmol) of triethylamine and 0.06 g (0.5 mmol) of 4-dimethylaminopyridine as a catalyst. The resulting mixture was stirred for 4 hours at 20 to 30° C. The organic layer was then separated with the addition of 40 g of chloroform and 30 g of ion-exchanged water. The separated organic layer was washed four times with 50 g of aqueous NaHCO$_3$ solution and washed four times with 30 g of ion-exchanged water.

After that, the organic layer was concentrated. To the concentrated organic layer, 15 g of 2-butanone and 60 g of diisopropyl ether were added. The resulting mixture was stirred. The 2-butanone layer (lower layer) was then separated from the mixture. The thus-obtained solution was concentrated under a reduced pressure, thereby yielding 11.2 g of the target compound in viscous liquid form (purity: 89%).

Properties of triphenylsulfonium 4-(1-ethoxycarbonyl-1-methacryloyloxy-2,2,2-trifluoroethoxy)-1,1,2,2-tetrafluorobutanesulfonate $^1$H NMR (measurement solvent: deuterated chloroform, reference material: tetramethylsilane): δ=7.73-7.67 (m, 15H; Ph$_3$S$^+$), 6.26 (s, 1H; =CH$_2$), 5.75 (s, 1H; =CH$_2$), 4.30 (q, J=8.0 Hz, 2H), 4.19 (m, 2H), 2.74 (m, 2H), 1.96 (s, 3H), 1.28 (t, J=8.0 Hz, 3H).

$^{19}$F NMR (measurement solvent: deuterated chloroform, reference material: trichlorofluoromethane): δ=−79.3 (s, 3F), −112.9 (s, 2F), −118.8 (s, 2F).

Synthesis Example 3

Triphenylsulfonium 6-(1-Ethoxycarbonyl-1-methacryloyloxy-2,2,2-trifluoroethoxy)-1,1,2,2-tetrafluorohexanesulfonate

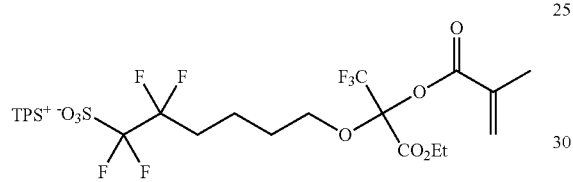

First, 20.0 g of triphenylsulfonium 6-hydroxy-1,1,2,2-tetrafluorohexanesulfonate in viscous liquid form (purity: 90%; equivalent to 35.8 mmol) was dissolved by stirring into 60 g of chloroform. The resulting solution was admixed with 7.31 g (43.0 mmol) of ethyltrifluoromethyl pyruvate and subjected to reaction for 3 hours at room temperature. The reaction solution was then concentrated under a reduced pressure. To the concentrated solution, 40 g of acetonitrile was added to dissolve the reaction intermediate by stirring.

The dissolved solution was admixed with 6.9 g (44.8 mmol) of methacrylic acid anhydride, 4.71 g (46.5 mmol) of triethylamine and 0.087 g (0.7 mmol) of 4-dimethylaminopyridine as a catalyst. The resulting mixture was stirred for 4 hours at 20 to 30° C. The organic layer was then separated with the addition of 40 g of chloroform and 30 g of ion-exchanged water. The separated organic layer was washed four times with 50 g of aqueous NaHCO$_3$ solution and washed four times with 30 g of ion-exchanged water.

After that, the organic layer was concentrated. To the concentrated organic layer, 20 g of 2-butanone and 80 g of diisopropyl ether were added. The resulting mixture was stirred. The 2-butanone layer (lower layer) was then separated from the mixture. The thus-obtained solution was concentrated under a reduced pressure, thereby yielding 22.8 g of the target compound in viscous liquid form (purity: 93%, yield: 80%).

Properties of triphenylsulfonium 6-(1-ethoxycarbonyl-1-methacryloyloxy-2,2,2-trifluoroethoxy)-1,1,2,2-tetrafluorohexanesulfonate $^1$H NMR (measurement solvent: deuterated chloroform, reference material: tetramethylsilane): δ=7.73-7.67 (m, 15H; Ph$_3$S$^+$), 6.28 (s, 1H; =CH$_2$), 5.77 (s, 1H; =CH$_2$), 4.34 (q, J=8.0 Hz, 2H), 4.05 (m, 2H), 2.23 (m, 2H), 2.00 (s, 3H), 1.58 (m, 2H), 1.30 (t, J=8.0 Hz, 3H).

$^{19}$F NMR (measurement solvent: deuterated chloroform, reference material: trichlorofluoromethane): δ=−79.4 (s, 3F), −112.0 (s, 2F), −117.5 (s, 2F).

Reference Example 1

As shown in TABLE 1, comparison was made on the solubility of polymerizable fluorine-containing sulfonic acid onium salts (polymerizable monomers) in propylene glycol monomethyl ether acetate (PGMEA). The structures and abbreviations of the polymerizable monomers used in this reference example are indicated below. Among others, the monomers PAG-1, PAG-2 and PAG-3 are the polymerizable fluorine-containing sulfonic acid onium salts according to the present invention.

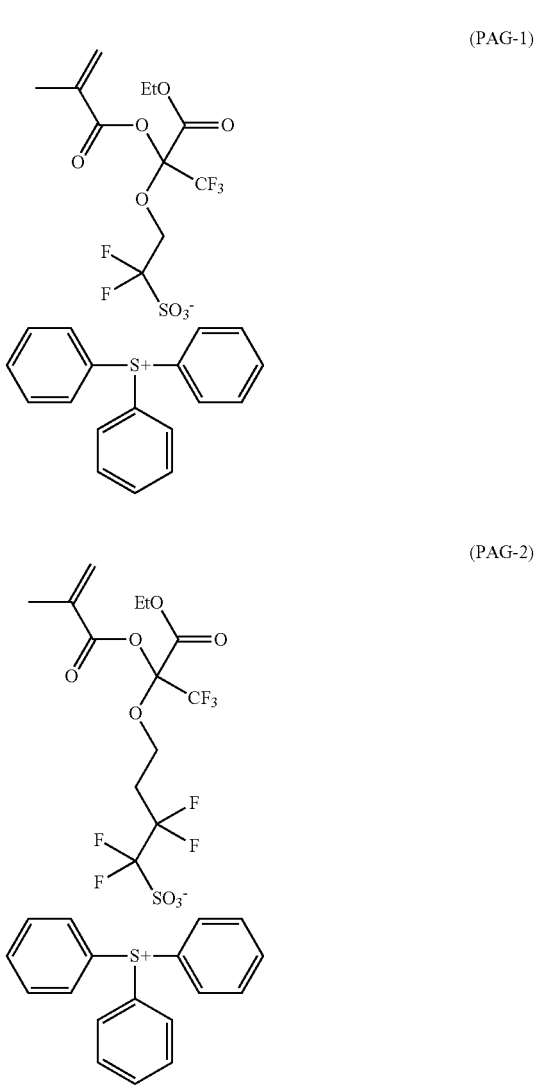

(PAG-3)

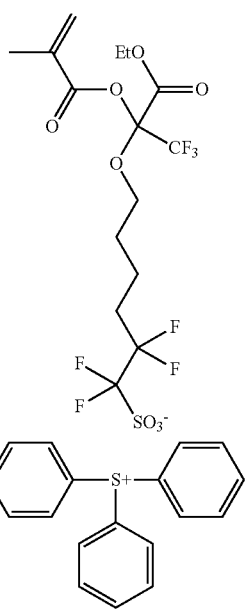

(PAG-C1)

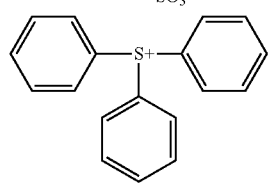

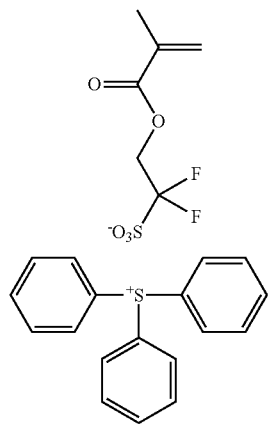

(PAG-C2)

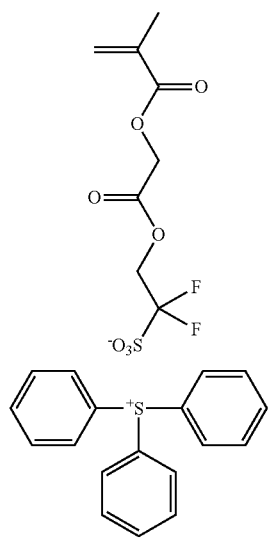

TABLE 1

| Polymerizable monomer | Solvent | Solubility (g/100 g) |
|---|---|---|
| PAG-1 | PGMEA | 45 |
| PAG-2 | PGMEA | 55 |
| PAG-3 | PGMEA | 90 |
| PAG-C1 | PGMEA | 10 |
| PAG-C2 | PGMEA | 11 |

Solubility: the amount of each polymerizable monomer in 100 g of PGMEA Polymerizable monomer: polymerizable fluorine-containing sulfonic acid onium salt It is apparent from the results of TABLE 1 that each of the polymerizable monomers according to the present invention had very high solubility than the conventional polymerizable monomers.

[Production of Resins]

The structures and abbreviations of polymerizable monomers used in the following polymerization examples, working examples and comparative examples are indicated below. (The polymerizable monomers PAG-1, PAG-2, PAG-3, PAG-C1 and PAG-C2 were the same as mentioned above.)

(A-1)

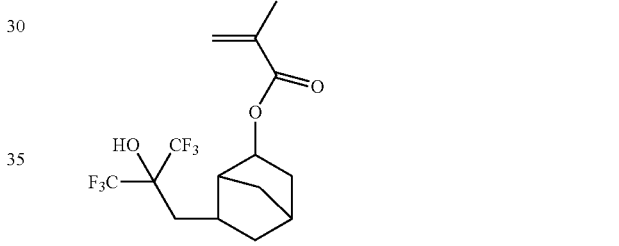

(A-2)

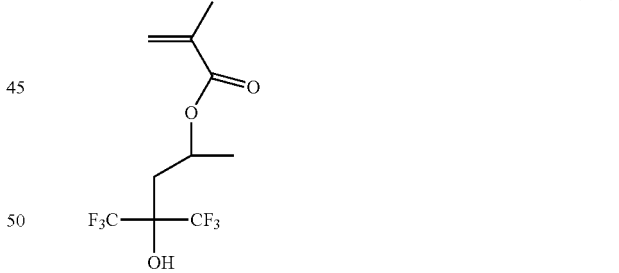

(A-3)

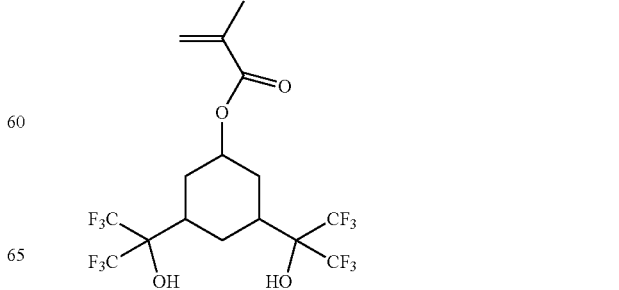

(A-4) 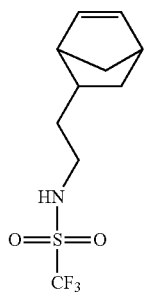
(A-5) 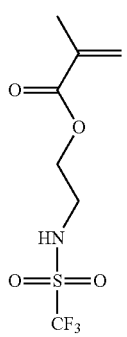
(A-6) 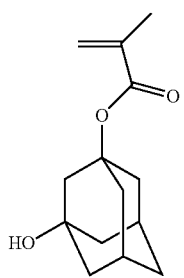
(A-7) 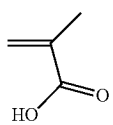
(B-1) 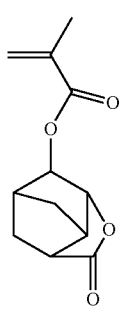
(B-2) 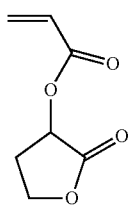
(C-1) 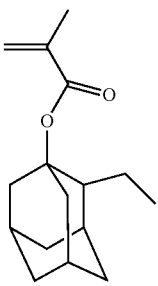
(C-2) 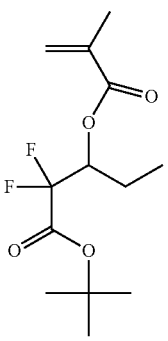
(D-1) 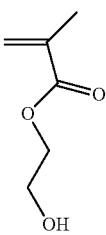
Polymerization Example P-1
(PAG-1) 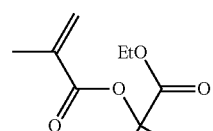 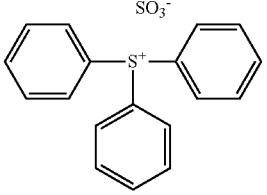

(B-1)

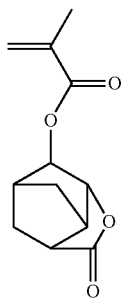

(C-1)

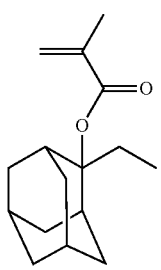

A monomer solution was prepared by dissolving 30.0 g (15 mol %) of compound (PAG-1), 30.2 g (45 mol %) of compound (B-1) and 30.0 g (40 mol %) of compound (C-1) in 300 g of 2-butanone and adding thereto 3.40 g of dimethyl 2,2'-azobis(2-methylpropionate). On the other hand, a 1000-ml three-neck flask was charged with 100 g of 2-butanone, purged with nitrogen for 30 minutes and heated to 80° C. while stirring the content of the flask. The previously prepared monomer solution was then dropped into the flask by means of a dropping funnel over 3 hours. Assuming the initiation of the dropping as a polymerization initiation time, the polymerization reaction was performed for 6 hours. After the completion of the polymerization reaction, the resulting polymerization solution was cooled by water to about 25° C. and put into 2 kg of methanol to precipitate a white powdery substance. The white powdery substance was filtered out of the solution.

The filtered white powdery substance was washed twice with 400 g of methanol in slurry form, filtered, and then, dried at 50° C. for 17 hours. With this, a polymer was obtained in white powder form (74.1 g). The mass-average molecular weight (Mw) of the polymer was 7,700. It was confirmed by $^{13}$C-NMR analysis that the polymer was in the form of a copolymer having repeating units derived from the compounds (PAG-1), (B-1) and (C-1) at a content ratio of 14.4:45.5:40.1 (mol %). The thus-obtained copolymer was named as "Resin (P-1)".

Polymerization Example P-2

(PAG-2)

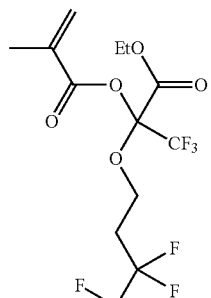

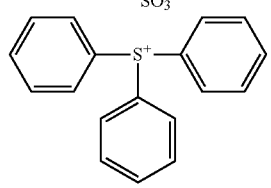

(B-1)

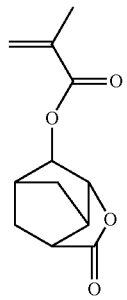

(C-1)

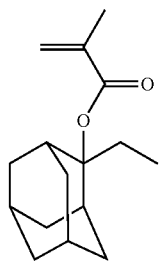

A monomer solution was prepared by dissolving 30.0 g (15 mol %) of compound (PAG-2), 27.5 g (45 mol %) of compound (B-1) and 27.3 g (40 mol %) of compound (C-1) in 300 g of 2-butanone and adding thereto 3.40 g of dimethyl 2,2'-azobis(2-methylpropionate). On the other hand, a 1000-ml three-neck flask was charged with 100 g of 2-butanone, purged with nitrogen for 30 minutes and heated to 80° C. while stirring the content of the flask. The previously prepared monomer solution was then dropped into the flask by means of a dropping funnel over 3 hours. Assuming the initiation of the dropping as a polymerization initiation time, the polymerization reaction was performed for 6 hours. After the completion of the polymerization reaction, the resulting polymerization solution was cooled by water to about 25° C. and put into 2 kg of methanol to precipitate a white powdery substance. The white powdery substance was filtered out of the solution.

The filtered white powdery substance was washed twice with 400 g of methanol in slurry form, filtered, and then, dried at 50° C. for 17 hours. With this, a polymer was obtained in white powder form (67.0 g). The mass-average molecular weight Mw of the polymer was 8,200. It was confirmed by $^{13}$C-NMR analysis that the polymer was in the form of a copolymer having repeating units derived from the compounds (PAG-2), (B-1) and (C-1) at a content ratio of 15.2:44.3:40.5 (mol %). The thus-obtained copolymer was named as "Resin P-2".

Polymerization Examples P-3 to P-27, X-1 to X-8 and N-1 to N-6

Resins (P-3 to P-27, X-1 to X-8 and N-1 to N-6) were produced in the same manner as in Polymerization Example P-1 or P-2. The kinds and contents of the copolymerization monomers, the mole ratio of the repeating units derived from the respective monomers and the mass-average molecular weight (Mw) of the produced resins are indicated in TABLES 2 and 3.

TABLE 2

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| P-1 | PAG-1 | 15 | — | — | B-1 | 45 | C-1 | 40 |
| P-2 | PAG-2 | 15 | — | — | B-1 | 45 | C-1 | 40 |
| P-3 | PAG-1 | 15 | A-1 | 15 | B-1 | 35 | C-1 | 35 |
| P-4 | PAG-1 | 15 | A-2 | 20 | B-1 | 35 | C-1 | 30 |
| P-5 | PAG-1 | 15 | A-3 | 15 | B-1 | 35 | C-1 | 35 |
| P-6 | PAG-1 | 15 | A-4 | 5 | B-1 | 35 | C-1 | 45 |
| P-7 | PAG-1 | 15 | A-5 | 20 | B-1 | 35 | C-1 | 30 |
| P-8 | PAG-1 | 15 | A-1 | 15 | B-1 | 35 | C-2 | 35 |
| P-9 | PAG-2 | 15 | A-1 | 15 | B-1 | 35 | C-1 | 35 |
| P-10 | PAG-2 | 15 | A-2 | 20 | B-1 | 35 | C-1 | 30 |
| P-11 | PAG-2 | 15 | A-3 | 15 | B-1 | 35 | C-1 | 35 |
| P-12 | PAG-2 | 15 | A-4 | 5 | B-1 | 35 | C-1 | 45 |
| P-13 | PAG-2 | 15 | A-5 | 20 | B-1 | 35 | C-1 | 30 |
| P-14 | PAG-2 | 15 | A-1 | 15 | B-1 | 35 | C-2 | 35 |
| P-15 | PAG-1 | 20 | A-6 | 30 | — | — | C-1 | 50 |
| P-16 | PAG-2 | 20 | A-6 | 25 | B-1 | 25 | C-1 | 30 |
| P-17 | PAG-2 | 15 | A-6 | 25 | B-1 | 25 | C-1 | 35 |
| P-18 | PAG-1 | 15 | A-6 | 25 | B-2 | 30 | C-1 | 30 |
| P-19 | PAG-1 | 20 | A-6 | 20 | B-2 | 30 | C-2 | 30 |
| P-20 | PAG-1 | 5 | — | — | B-1 | 50 | C-1 | 45 |
| P-21 | PAG-2 | 5 | — | — | B-1 | 50 | C-1 | 45 |
| P-22 | PAG-3 | 15 | — | — | B-1 | 45 | C-1 | 40 |
| P-23 | PAG-3 | 15 | A-1 | 15 | B-1 | 35 | C-1 | 35 |
| P-24 | PAG-3 | 15 | A-2 | 20 | B-1 | 35 | C-1 | 30 |
| P-25 | PAG-3 | 15 | A-3 | 15 | B-1 | 35 | C-1 | 35 |
| P-26 | PAG-3 | 15 | A-4 | 5 | B-1 | 35 | C-1 | 45 |
| P-27 | PAG-3 | 15 | A-5 | 20 | B-1 | 35 | C-1 | 30 |

| Polymerization Example Resin | Mole ratio of repeating units in resin | | | | Molecular weight Mw |
|---|---|---|---|---|---|
| | Monomer 1 | Monomer 2 | Monomer 3 | Monomer 4 | |
| P-1 | 14 | — | 46 | 40 | 7,700 |
| P-2 | 15 | — | 44 | 41 | 8,200 |
| P-3 | 15 | 14 | 35 | 36 | 7,500 |
| P-4 | 15 | 19 | 36 | 30 | 8,700 |
| P-5 | 15 | 15 | 35 | 35 | 8,200 |
| P-6 | 16 | 5 | 36 | 43 | 7,900 |
| P-7 | 15 | 20 | 36 | 29 | 8,000 |
| P-8 | 15 | 15 | 36 | 34 | 7,400 |
| P-9 | 15 | 14 | 35 | 36 | 7,300 |
| P-10 | 15 | 19 | 35 | 31 | 8,600 |
| P-11 | 15 | 14 | 34 | 37 | 8,200 |
| P-12 | 16 | 5 | 36 | 43 | 7,700 |
| P-13 | 15 | 20 | 35 | 30 | 7,500 |
| P-14 | 15 | 14 | 36 | 35 | 7,900 |
| P-15 | 18 | 30 | — | 52 | 9,700 |
| P-16 | 20 | 26 | 26 | 23 | 7,500 |
| P-17 | 15 | 25 | 26 | 34 | 9,200 |
| P-18 | 15 | 26 | 31 | 28 | 9,600 |
| P-19 | 19 | 21 | 32 | 28 | 8,200 |
| P-20 | 5 | — | 51 | 44 | 7,200 |

TABLE 2-continued

| | | | | | |
|---|---|---|---|---|---|
| P-21 | 5 | — | 52 | 43 | 6,900 |
| P-22 | 13 | — | 46 | 41 | 7,400 |
| P-23 | 13 | 14 | 37 | 36 | 7,500 |
| P-24 | 12 | 19 | 36 | 33 | 8,400 |
| P-25 | 13 | 15 | 36 | 36 | 8,000 |
| P-26 | 13 | 6 | 37 | 43 | 7,600 |
| P-27 | 13 | 20 | 36 | 31 | 7,900 |

Monomer 1: Polymerizable fluorine-containing sulfonic acid onium salt
Monomer 2, 3: Auxiliary monomer
Monomer 4: Monomer with acid labile group or cross-linking site

TABLE 3

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| X-1 | PAG-1 | 100 | — | — | — | — | — | — |
| X-2 | PAG-2 | 100 | — | — | — | — | — | — |
| X-3 | PAG-1 | 30 | A-2 | 70 | — | — | — | — |
| X-4 | PAG-1 | 30 | A-1 | 50 | B-1 | 20 | — | — |
| X-5 | PAG-2 | 50 | A-1 | 20 | B-1 | 30 | — | — |
| X-6 | PAG-1 | 5 | A-3 | 50 | B-1 | 45 | — | — |
| X-7 | PAG-3 | 100 | — | — | — | — | — | — |
| X-8 | PAG-3 | 50 | A-1 | 20 | B-1 | 30 | — | — |
| N-1 | PAG-1 | 15 | — | — | B-1 | 10 | A-7 | 40 |
| | | | | | | | D-1 | 35 |
| N-2 | PAG-2 | 15 | A-2 | 60 | B-2 | 5 | A-6 | 20 |
| N-3 | PAG-1 | 15 | A-2 | 40 | B-3 | 20 | D-1 | 25 |
| N-4 | PAG-2 | 15 | — | — | A-3 | 20 | A-6 | 35 |
| N-5 | PAG-3 | 15 | A-2 | 60 | B-2 | 5 | A-6 | 20 |
| N-6 | PAG-3 | 15 | — | — | A-3 | 50 | A-6 | 35 |

| Polymerization Example Resin | Mole ratio of repeating units in resin | | | | Molecular weight Mw |
|---|---|---|---|---|---|
| | Monomer 1 | Monomer 2 | Monomer 3 | Monomer 4 | |
| X-1 | 100 | — | — | — | 3,800 |
| X-2 | 100 | — | — | — | 4,500 |
| X-3 | 29 | 71 | — | — | 8,500 |
| X-4 | 29 | 52 | 19 | — | 9,000 |
| X-5 | 49 | 20 | 31 | — | 7,200 |
| X-6 | 5 | 53 | 42 | — | 9,900 |
| X-7 | 100 | — | — | — | 4,100 |
| X-8 | 47 | 21 | 32 | — | 6,900 |
| N-1 | 15 | — | 9 | 39 | 9,500 |
| | | | | 37 | |
| N-2 | 15 | 62 | 5 | 18 | 9,000 |
| N-3 | 15 | 41 | 21 | 33 | 7,800 |
| N-4 | 14 | — | 53 | 27 | 10,100 |
| N-5 | 13 | 62 | 6 | 19 | 8,700 |
| N-6 | 12 | — | 53 | 35 | 9,800 |

Monomer 1: Polymerizable fluorine-containing sulfonic acid onium salt
Monomer 2, 3: Auxiliary monomer
Monomer 4: Monomer with acid labile group or cross-linking site Examples 1 to 48

Resist compositions were each prepared by mixing the above-produced resin with a solvent and any other additive compound or compounds e.g. triphenylsulfonium nonafluorobutanesulfonate (PAG-C3) as conventional photoacid generator (PAG).

The component ratios of the prepared resist compositions are indicated in TABLES 4 and 5. Further, the resist compositions were filtrated with 0.2-μm membrane filters, respectively.

The kinds of the solvent, the additive (basic compound) and the cross-linking agent used in each example are indicated below.
(Solvent)
S-1: Propylene glycol monomethyl ether acetate (PGMEA)
S-2: γ-Butyrolactone
S-3: Ethyl lactate
S-4: Cyclohexanone
(Basic Compound)
O-1: N,N-Dibutylaniline
O-2: 2,6-Diisopropylaniline O-3: Diazabicyclo[4.3.0]nonene O-4: 2,4,5-Triphenylimidazole O-5: Ttrioctylamine (Cross-Linking Agent)

NIKALAC MX-270 (glycoluril-based cross-linking agent, manufactured by Sanwa Chemical Co., Ltd.)

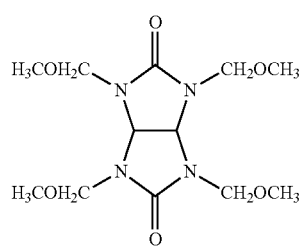

(PAG)

Triphenylsulfonium nonafluorobutanesulfonate (PAG-C3)

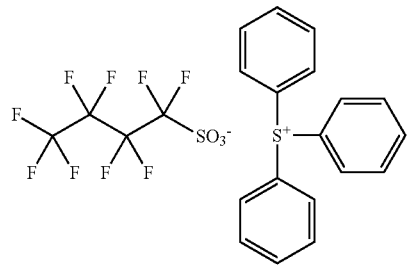

(PAG-C3)

[Pattern Formation]

Each of the above-obtained resist compositions was spin-coated on a silicon wafer substrate to form a resist film of 250 nm thickness. The resist film was prebaked at 110° C., exposed to 248-nm ultraviolet radiation through a photomask, and then, subjected to post exposure baking treatment at 120° C. After that, the resist film was developed with 2.38 mass % aqueous tetramethylammoniumhydroxide solution for 1 minute at 23° C. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLES 4 and 5.

TABLE 4

| Example | Resin 1 Kind | Resin 1 parts by mass | Resin 2 Kind | Resin 2 parts by mass |
|---|---|---|---|---|
| 1 | P-1 | 40 | none | — |
| 2 | P-3 | 40 | none | — |
| 3 | P-4 | 40 | none | — |
| 4 | P-5 | 14 | P'-3 | 26 |
| 5 | P-6 | 40 | none | — |
| 6 | P-7 | 40 | none | — |
| 7 | P-8 | 40 | none | — |
| 8 | P-2 | 40 | none | — |
| 9 | P-9 | 40 | none | — |
| 10 | P-10 | 14 | P'-3 | 26 |
| 11 | P-11 | 40 | none | — |
| 12 | P-12 | 40 | none | — |
| 13 | P-13 | 40 | none | — |
| 14 | P-14 | 40 | none | — |
| 15 | P-15 | 20 | P'-1 | 20 |
| 16 | P-16 | 20 | P'-2 | 20 |
| 17 | P-17 | 20 | P'-1 | 20 |
| 18 | P-18 | 20 | P'-2 | 20 |
| 19 | P-19 | 20 | P'-2 | 20 |
| 20 | P-20 | 40 | none | — |
| 21 | P-21 | 40 | none | — |
| 22 | P-22 | 40 | none | — |
| 23 | P-23 | 40 | none | — |
| 24 | P-24 | 40 | none | — |
| 25 | P-25 | 40 | none | — |
| 26 | P-26 | 40 | none | — |
| 27 | P-27 | 40 | none | — |

| Example | Basic compound | Solvent Kind | Solvent parts by mass | Pattern shape |
|---|---|---|---|---|
| 1 | O-1 | S-1 | 400 | clean rectangular shape |
| 2 | O-1 | S-2 | 400 | clean rectangular shape |
| 3 | O-2 | S-1 | 400 | clean rectangular shape |
| 4 | O-3 | S-1 | 400 | clean rectangular shape |
| 5 | O-3 | S-1 | 400 | clean rectangular shape |
| 6 | O-3 | S-1 | 400 | clean rectangular shape |
| 7 | O-1 | S-1 | 400 | clean rectangular shape |
| 8 | O-1 | S-1 | 400 | clean rectangular shape |
| 9 | O-1 | S-3 | 400 | clean rectangular shape |
| 10 | O-4 | S-4 | 400 | clean rectangular shape |
| 11 | O-5 | S-1 | 400 | clean rectangular shape |
| 12 | O-5 | S-1 | 400 | clean rectangular shape |
| 13 | O-5 | S-1 | 400 | clean rectangular shape |
| 14 | O-5 | S-1 | 400 | clean rectangular shape |
| 15 | O-1 | S-1 | 400 | clean rectangular shape |
| 16 | O-1 | S-1 | 400 | clean rectangular shape |
| 17 | O-5 | S-1 | 400 | clean rectangular shape |
| 18 | O-3 | S-2 | 400 | clean rectangular shape |
| 19 | O-5 | S-1 | 400 | clean rectangular shape |
| 20 | O-5 | S-3 | 400 | clean rectangular shape |
| 21 | O-2 | S-1 | 400 | clean rectangular shape |
| 22 | O-1 | S-1 | 400 | clean rectangular shape |
| 23 | O-1 | S-1 | 400 | clean rectangular shape |
| 24 | O-1 | S-1 | 400 | clean rectangular shape |
| 25 | O-1 | S-1 | 400 | clean rectangular shape |
| 26 | O-1 | S-1 | 400 | clean rectangular shape |
| 27 | O-1 | S-1 | 400 | clean rectangular shape |

Basic compound (0.15 parts by mass)
O-1: N,N-Dibutylaniline,
O-2: 2,6-Diisopropylaniline,
O-3: Diazabicyclo[4.3.0]nonene
O-4: 2,4,5-Triphenylimidazole,
O-5: Trioctylamine Solvent
S-1: Propylene glycol monomethyl ether acetate (PGMEA),
S-2: γ-Butyrolactone
S-3: Ethyl lactate,
S-4: Cyclohexanone

TABLE 5

| Example | Resin 1 Kind | Resin 1 parts by mass | Resin 2 Kind | Resin 2 parts by mass |
|---|---|---|---|---|
| 28 | P-1 | 40 | none | — |
| 29 | P-2 | 40 | none | — |
| 30 | P-22 | 40 | none | — |
| 31 | X-1 | 2 | P'-1 | 40 |
| 32 | X-1 | 4 | P'-2 | 40 |
| 33 | X-2 | 6 | P'-1 | 40 |
| 34 | X-2 | 1 | P'-2 | 40 |
| 35 | X-3 | 12 | P'-3 | 32 |
| 36 | X-4 | 30 | P'-4 | 19 |
| 37 | X-5 | 30 | P'-5 | 25 |
| 38 | X-6 | 30 | P'-1 | 13 |
| 39 | X-7 | 2 | P'-1 | 40 |
| 40 | X-8 | 30 | P'-5 | 25 |
| 41 | X-2 | 6 | P'-5 | 40 |
| 42 | N-1 | 40 | none | — |
| 43 | N-1 | 20 | N-4 | 20 |
| 44 | N-2 | 40 | none | — |
| 45 | N-3 | 40 | none | — |
| 46 | N-4 | 40 | none | — |
| 47 | N-5 | 40 | none | — |
| 48 | N-6 | 40 | none | — |

| Example | Cross-linking agent Basic compound etc. | Solvent Kind | Solvent parts by mass | Pattern shape |
|---|---|---|---|---|
| 28 | acid generator, O-1 | S-1 | 400 | clean rectangular shape |
| 29 | acid generator, O-1 | S-1 | 400 | clean rectangular shape |
| 30 | acid generator, O-1 | S-1 | 400 | clean rectangular shape |
| 31 | O-5 | S-1 | 400 | clean rectangular shape |
| 32 | O-5 | S-1 | 400 | clean rectangular shape |
| 33 | O-2 | S-4 | 400 | clean rectangular shape |
| 34 | O-5 | S-1 | 400 | clean rectangular shape |
| 35 | O-1 | S-1 | 400 | clean rectangular shape |
| 36 | O-1 | S-1 | 400 | clean rectangular shape |
| 37 | O-5 | S-1 | 400 | clean rectangular shape |
| 38 | O-5 | S-1 | 400 | clean rectangular shape |
| 39 | O-5 | S-1 | 400 | clean rectangular shape |
| 40 | O-5 | S-1 | 400 | clean rectangular shape |
| 41 | cross-linking agent, O-5 | S-1 | 400 | clean rectangular shape |
| 42 | cross-linking agent, O-5 | S-1 | 400 | clean rectangular shape |
| 43 | cross-linking agent, O-5 | S-1 | 400 | clean rectangular shape |
| 44 | cross-linking agent, O-1 | S-1 | 400 | clean rectangular shape |
| 45 | cross-linking agent, O-4 | S-2 | 400 | clean rectangular shape |
| 46 | cross-linking agent, O-5 | S-3 | 400 | clean rectangular shape |
| 47 | cross-linking agent, O-1 | S-1 | 400 | clean rectangular shape |
| 48 | cross-linking agent, O-5 | S-3 | 400 | clean rectangular shape |

Cross-linking agent (3 parts by mass)
NIKALAC MX-270 (glycoluril-based cross-linking agent available from Sanwa Chemical Co., Ltd.)
Acid generator (2 parts by mass)
Triphenylsulfonium nonafluorobutanesulfonate
Basic compound (15 parts by mass)
O-1: N,N-Dibutylaniline,
O-2: 2,6-Diisopropylaniline,
O-3: Diazabicyclo[4.3.0]nonene
O-4: 2,4,5-Triphenylimidazole,
O-5: Trioctylamine
Solvent
S-1: Propylene glycol monomethyl ether acetate (PGMEA),
S-2: γ-Butyrolactone,
S-3: Ethyl lactate,
S-4: Cyclohexanone Reference Polymerization Example 1

Sulfonate-free resins (P-1' to P-5') were produced in the same manner as in Polymerization Example 1 or 2 using various monomers as shown in Figure 6. The mole ratio of the repeating units and the weight-average molecular weight (Mw) of the produced resins are indicated in TABLE 6.

TABLE 6

| Polymerization Example Resin | Raw material composition Monomer 1 Kind | Monomer 1 mol % | Monomer 2 Kind | Monomer 2 mol % | Monomer 3 Kind | Monomer 3 mol % |
|---|---|---|---|---|---|---|
| P-1' | A-1 | 20 | B-1 | 45 | C-1 | 35 |
| P-2' | A-2 | 25 | B-1 | 45 | C-1 | 30 |
| P-3' | A-3 | 20 | B-1 | 45 | C-1 | 35 |
| P-4' | A-4 | 10 | B-1 | 45 | C-1 | 45 |
| P-5' | A-1 | 20 | B-1 | 45 | C-2 | 35 |

| Polymerization Example Resin | Mole ratio of repeating units in resin Monomer 1 | Monomer 2 | Monomer 3 | Molecular weight Mw |
|---|---|---|---|---|
| P-1' | 22 | 44 | 34 | 8,000 |
| P-2' | 26 | 44 | 30 | 8,800 |
| P-3' | 20 | 45 | 35 | 8,700 |
| P-4' | 10 | 46 | 44 | 8,100 |
| P-5' | 21 | 44 | 35 | 8,900 |

Monomer 1, 2: Auxiliary monomer
Monomer 3: Monomer with acid labile group

Reference Polymerization Example 2

Resins (P-C1 to P-C4) were produced in the same manner as in Polymerization Example 1 or 2 using conventional onium salt monomers (PAG-C1, PAG-C2), in place of the polymerizable fluorine-containing sulfonic acid onium salts (polymerizable monomers) according to the present invention, as shown in TABLE 7. The mole ratio of the repeating units and the weight-average molecular weight (Mw) of the produced resins are indicated in TABLE 7.

TABLE 7

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| P-C1 | PAG-C1 | 15 | — | — | B-1 | 45 | C-1 | 40 |
| P-C2 | PAG-C2 | 15 | — | — | B-1 | 45 | C-1 | 40 |
| P-C3 | PAG-C1 | 20 | A-6 | 30 | — | — | C-1 | 50 |
| P-C4 | PAG-C2 | 20 | A-6 | 25 | B-1 | 25 | C-1 | 30 |

| Polymerization Example Resin | Mole ratio of repeating units in resin | | | | Molecular weight Mw |
|---|---|---|---|---|---|
| | Monomer 1 | Monomer 2 | Monomer 3 | Monomer 3 | |
| P-C1 | 13 | — | 46 | 41 | 7,500 |
| P-C2 | 14 | — | 45 | 41 | 7,900 |
| P-C3 | 18 | 28 | — | 54 | 9,300 |
| P-C4 | 17 | 27 | 26 | 30 | 7,100 |

Monomer 1: Polymerizable fluorine-containing sulfonic acid onium salt
Monomer 2, 3: Auxiliary monomer
Monomer 4: Monomer with acid labile group or cross-linking site Comparative Examples Resist compositions were prepared, in the same manner as in Examples 1 to 48, by mixing the conventional onium salt monomer resins (P-C1 to P-C4) with a solvent and other additive compound. However, many of the resins were difficult to dissolve in propylene glycol monomethyl ether acetate (PGMEA) so that it was impossible to completely dissolve these resins even in twice as much volume of PGMEA. Some of the resins were dissolved in the cyclohexanone solvent. The thus-prepared resist compositions were subjected to pattern formation in the same manner as in Examples 1 to 48. The component ratio and evaluation results of the resist compositions are indicated in TABLE 8.

TABLE 8

| Comparative Example | Resin 1 | | Basic compound | Solvent | | Pattern shape |
|---|---|---|---|---|---|---|
| | Kind | Parts by mass | | Kind | Parts by mass | |
| 1 | P-C1 | 40 | O-1 | S-1 | 400 | difficult to dissolve resin and impossible to prepare resist composition |
| 2 | P-C1 | 40 | O-1 | S-1 | 800 | difficult to dissolve resin and impossible to prepare resist composition |
| 3 | P-C1 | 40 | O-1 | S-4 | 400 | slightly distorted rectangular shape |
| 4 | P-C2 | 40 | O-1 | S-1 | 400 | difficult to dissolve resin and impossible to prepare resist composition |
| 5 | P-C2 | 40 | O-1 | S-1 | 800 | difficult to dissolve resin and impossible to prepare resist composition |
| 6 | P-C2 | 40 | O-1 | S-4 | 400 | slightly distorted rectangular shape |
| 7 | P-C3 | 40 | O-1 | S-1 | 400 | difficult to dissolve resin and impossible to prepare resist composition |
| 8 | P-C3 | 40 | O-1 | S-1 | 800 | difficult to dissolve resin and impossible to prepare resist composition |
| 9 | P-C3 | 40 | O-1 | S-4 | 400 | difficult to dissolve resin and impossible to prepare resist composition |
| 10 | P-C4 | 40 | O-1 | S-1 | 400 | difficult to dissolve resin and impossible to prepare resist composition |
| 11 | P-C4 | 40 | O-1 | S-1 | 800 | difficult to dissolve resin and impossible to prepare resist composition |
| 12 | P-C4 | 40 | O-1 | S-4 | 400 | difficult to dissolve resin and impossible to prepare resist composition |

Basic compound (0.15 parts by mass)
O-1: N,N-Dibutylaniline Solvent
S-1: Propylene glycol monomethyl ether acetate (PGMEA)
S-4: Cyclohexanone

Examples 49 and 51

Using the resin P'-1 produced in Reference Polymerization Example 1 as a base resin and the polymerizable fluorine-containing sulfonic acid onium salt according to the present invention as an acid generator, resist compositions were prepared in the same manner as in Example 1 etc. The prepared resist compositions were subjected to pattern formation and observed in the same manner as above. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLE 9.

TABLE 9

| Example | Resin Kind | Resin parts by mass | PAG Kind | PAG parts by mass | Basic compound | Solvent Kind | Solvent parts by mass | Pattern shape |
|---|---|---|---|---|---|---|---|---|
| 49 | P'-1 | 40 | PAG-1 | 2 | O-1 | S-1 | 400 | clean rectangular shape |
| 50 | P'-1 | 40 | PAG-2 | 2 | O-1 | S-1 | 400 | clean rectangular shape |
| 51 | P'-1 | 40 | PAG-3 | 2 | O-1 | S-1 | 400 | clean rectangular shape |

Basic compound (0.15 parts by mass)
0-1: N,N-Dibutylaniline Solvent
S-1: Propylene glycol monomethyl ether acetate (PGMEA)

INDUSTRIAL APPLICABILITY

The resin according to the present invention can be used as a photoacid generator for a photoresist material and can also be used by itself as a positive or negative resist resin. The monomer for synthesis of this resin can be used as an acid generator and as a raw material for production of other compounds.

The invention claimed is:

1. A sulfonate resin having a repeating unit of the following general formula (3):

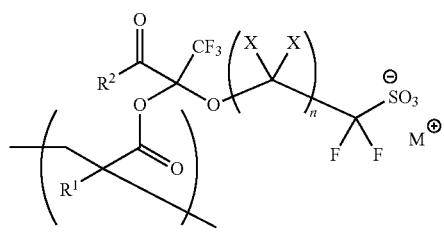

(3)

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^A O$ or $R^B R^C N$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with a nitrogen atom in $R^B R^C N$; any of hydrogen atoms on carbons in $R^A$, $R^B$ and $R^C$ may be substituted with a substituent; and $M^+$ represents a monovalent cation.

2. The sulfonate resin according to claim 1, wherein the repeating unit is of the following general formula (4):

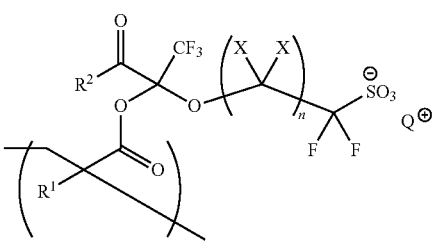

(4)

where X, n, $R^1$ and $R^2$ have the same meanings as in the general formula (3); and $Q^+$ represents a sulfonium cation of the general formula (a) or an iodonium cation of the general formula (b):

(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

3. The sulfonate resin according to claim 1, further comprising at least one selected from the group consisting of repeating units formed by cleavage of polymerizable double bonds of olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

4. The sulfonate resin according to claim 1, further comprising a repeating unit of the following general formula (6):

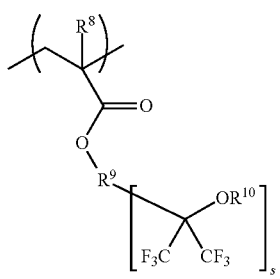
(6)

where $R^8$ represents a hydrogen atom, a halogen atom or a $C_1$-$C_3$ alkyl or fluorine-containing alkyl group; $R^9$ represents a substituted or unsubstituted aliphatic hydrocarbon group, a substituted or unsubstituted aromatic group or an organic group in which a plurality of substituted or unsubstituted aliphatic hydrocarbon and/or aromatic groups are bonded to each other; any number of hydrogen atoms in $R^9$ may be substituted with a fluorine atom; $R^{10}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms in $R^{10}$ may be substituted with a fluorine atom; $R^{10}$ may contain an ether bond or a carbonyl group; and s represents an integer of 1 or 2.

5. The sulfonate resin according to claim 4, wherein the repeating unit of the general formula (6) is at least one selected from the group consisting of repeating units of the following general formula (7), the following general formula (8) and the following general formula (9):

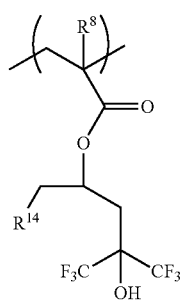
(7)

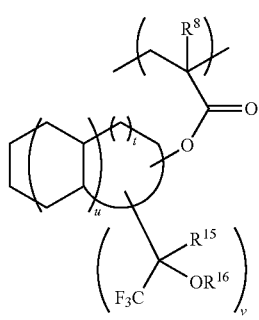
(8)

(9)

where $R^8$ represents a hydrogen atom, a halogen atom or a $C_1$-$C_3$ alkyl or fluorine-containing alkyl group; one of $R^{11}$, $R^{12}$ and $R^{13}$ represents a $CF_3C(CF_3)(OH)CH_2$— group; the other two of $R^{11}$, $R^{12}$ and $R^{13}$ each represents a hydrogen atom; $R^{14}$ represents a hydrogen atom or a $C_1$-$C_4$ alkyl or fluorine-containing alkyl group; $R^{15}$ represents a trifluoromethyl group; $R^{16}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; u represents an integer of 0 to 2; t and v each independently represent an integer of 1 to 8 and satisfy a relationship of v≤t+2; and, when v is 2 to 8, $R^{15}$ and $R^{16}$ can be the same or different.

6. The sulfonate resin according to claim 1, further comprising a repeating unit of the following general formula (10):

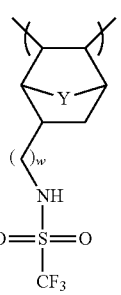
(10)

where Y represents either —$CH_2$—, —O— or —S—; and w represents an integer of 2 to 6.

7. The sulfonate resin according to claim 1, further comprising a repeating unit of the following general formula (11) or the following general formula (11-1):

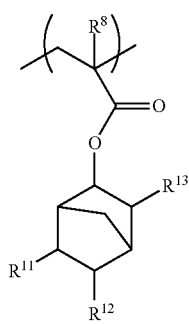

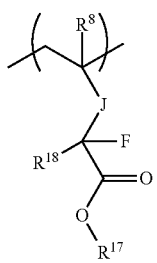

(11)

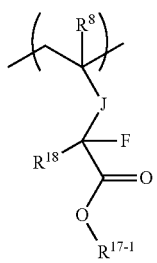

(11-1)

where $R^8$ represents a hydrogen atom, a halogen atom or a $C_1$-$C_3$ alkyl or fluorine-containing alkyl group; $R^{18}$ represents a hydrogen atom, a fluorine atom or a fluorine-containing alkyl group; J represents a divalent linking group; $R^{17}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; and $R^{17-1}$ represents an acid labile group.

8. The sulfonate resin according to claim 1, further comprising a repeating unit of the following general formula (12):

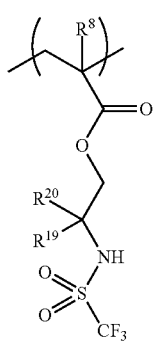

(12)

where $R^8$ represents a hydrogen atom, a halogen atom or a $C_1$-$C_3$ alkyl or fluorine-containing alkyl group; $R^{19}$ and $R^{20}$ each independently represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group.

9. The sulfonate resin according to claim 1, wherein, in the formula, —$(CX_2)_n$— is represented by —$(CH_2)_p$—$(CF_2)_q$— where p is an integer of 0 to 10; q is an integer of 0 to 8; and p and q satisfy a relationship of $1 \leq p+q \leq 10$.

10. The sulfonate resin according to claim 9, wherein, in the formula, —$(CX_2)_n$— is represented by —$(CH_2)_p$—$(CF_2)_q$— where p is an integer of 0 to 4; q is 0 or 1; and p and q satisfy a relationship of $1 \leq p+q \leq 5$.

11. The sulfonate resin according to claim 1, wherein, in the general formula (3), $R^1$ represents a fluorine atom, a chlorine atom, a bromine atom, an iodine atom, a methyl group, an ethyl group, a n-propyl group, an i-propyl group, a fluoromethyl group, a difluoromethyl group, a trifluoromethyl group, a 2-fluoroethyl group, a 2,2-difluoroethyl group, a 2,2,2-trifluoroethyl group, a pentafluoroethyl group, a 1-methyl-2,2,2-trifluoroethyl group, a 1-(trifluoromethyl)-2,2,2-trifluoroethyl group or a 1-(trifluoromethyl)-1,2,2,2-tetrafluoroethyl group.

12. The sulfonate resin according to claim 1, wherein, in the general formula (3), $R^2$ represents any one of groups of the following general formulas (E-3) and (E-4):

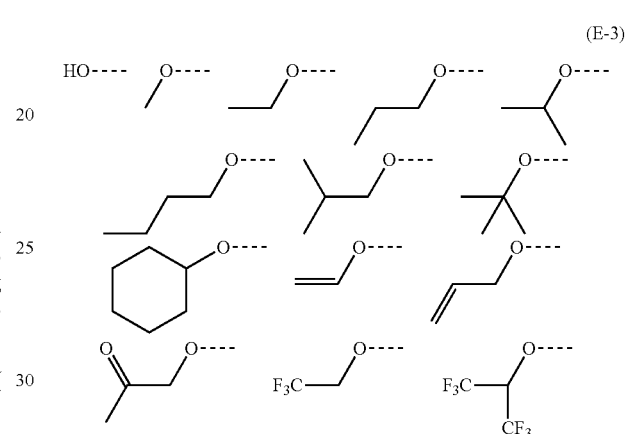

(E-3)

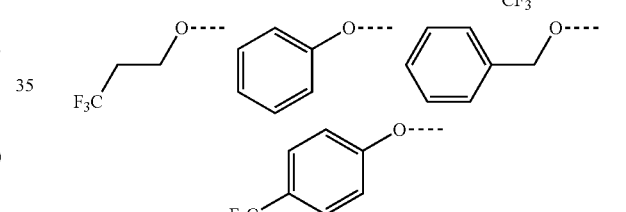

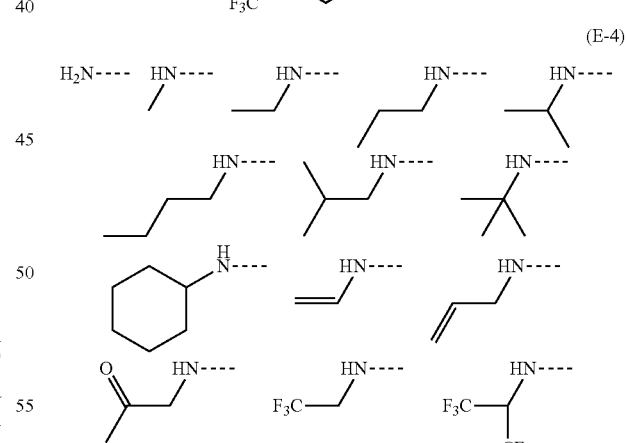

(E-4)

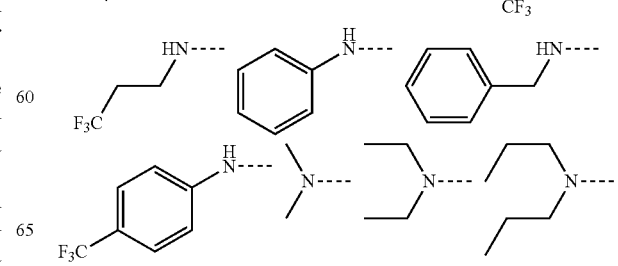

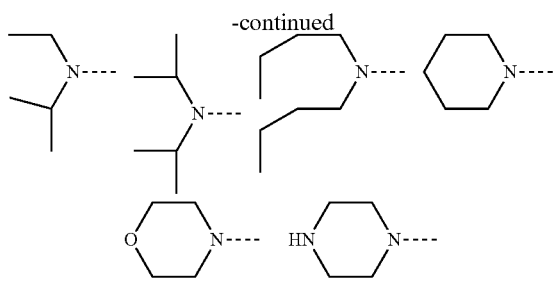

where dotted lines each indicate a bonding position.

13. A resist composition comprising at least the sulfonate resin according to claim 1 and a solvent.

14. The resist composition according to claim 13, wherein the sulfonate resin has an acid labile group so that the resist composition serves as a chemically amplified positive resist composition.

15. The resist composition according to claim 13, further comprising a resin having an acid labile group.

16. The resist composition according to claim 13, wherein the sulfonate resin has an alcoholic hydroxyl group or a carboxyl group so that the resist composition serves as a chemically amplified negative resist composition.

17. The resist composition according to claim 13, further comprising a resin having an alcoholic hydroxyl group or a carboxyl group.

18. A pattern forming method, comprising: applying the resist composition according to claim 13 to a substrate; heat-treating the applied resist composition; exposing the heat-treated applied resist composition to high-energy radiation of 300 nm or less wavelength through a photomask; heat-treating the exposed resist composition; and developing the heat-treated exposed resist composition with a developer.

19. The pattern forming method according to claim 18, wherein said exposing is performed by liquid immersion lithography with ArF excimer laser radiation of 193 nm wavelength and containing water or any other liquid of higher refractive index than that of the air between the substrate to which the resist composition has been applied and projector lens.

20. The pattern forming method according to claim 18, wherein the exposing is performed with soft X-ray radiation of 10 to 14 nm wavelength.

21. A sulfonate resin having a repeating unit of the following general formula (5):

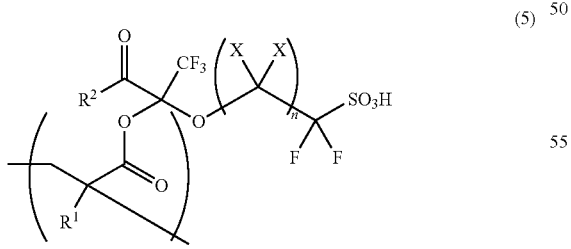

(5)

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^AO$ or $R^BR^CN$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with a nitrogen atom in $R^BR^CN$; and any of hydrogen atoms on carbons in $R^A$, $R^B$ and $R^C$ may be substituted with a substituent.

22. A resist composition comprising at least the sulfonate resin according to claim 21 and a solvent.

23. A pattern forming method, comprising: applying the resist composition according to claim 22 to a substrate; heat-treating the applied resist composition; exposing the heat-treated applied resist composition to high-energy radiation of 300 nm or less wavelength through a photomask; heat-treating the exposed resist composition; and developing the heat-treated exposed resist composition with a developer.

24. A polymerizable fluorine-containing sulfonate having an anion structure of the following general formula (1):

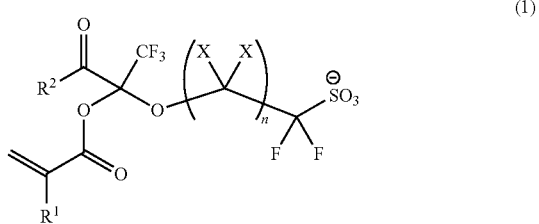

(1)

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^AO$ or $R^BR^CN$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with a nitrogen atom in $R^BR^CN$; and any of hydrogen atoms on carbons in $R^A$, $R^B$ and $R^C$ may be substituted with a substituent.

25. A polymerizable fluorine-containing sulfonic acid having a structure of the following general formula (1-1):

(1-)

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^AO$ or $R^BR^CN$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with a nitrogen atom in $R^BR^CN$; and any of hydrogen atoms on carbons in $R^A$, $R^B$ and $R^C$ may be substituted with a substituent.

26. A polymerizable fluorine-containing sulfonic acid onium salt of the general formula (2):

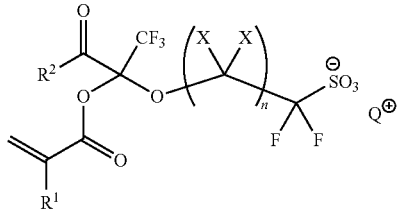
(2)

where X each independently represents a hydrogen atom or a fluorine atom; n represents an integer of 1 to 10; $R^1$ represents a hydrogen atom, a halogen atom, a $C_1$-$C_3$ alkyl group or a $C_1$-$C_3$ fluorine-containing alkyl group; $R^2$ represents either $R^A O$ or $R^B R^C N$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group; $R^B$ and $R^C$ may be bonded to each other to form a 3- to 18-membered heterocyclic ring with a nitrogen atom in $R^B R^C N$; any of hydrogen atoms on carbons in $R^A$, $R^B$ and $R^C$ may be substituted with a substituent; and $Q^+$ represents a sulfonium cation of the general formula (a) or an iodonium cation of the general formula (b):

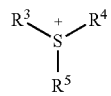
(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

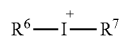
(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

* * * * *